(12) United States Patent
Woychik et al.

(10) Patent No.: US 6,310,034 B1
(45) Date of Patent: Oct. 30, 2001

(54) AGOUTI POLYPEPTIDE COMPOSITIONS

(75) Inventors: Richard P. Woychik, Orinda, CA (US); Scott J. Bultman, Lakewood, OH (US); Edward J. Michaud, Kingston, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/034,088

(22) Filed: Mar. 3, 1998

Related U.S. Application Data

(63) Continuation-in-part of application No. 08/064,385, filed on May 21, 1993, now abandoned.

(51) Int. Cl.[7] .................................................. C07K 14/435
(52) U.S. Cl. ............................... 514/2; 530/350; 530/300
(58) Field of Search .................................... 530/350, 300; 514/2; 435/69.1

(56) References Cited

U.S. PATENT DOCUMENTS

| | | | |
|---|---|---|---|
| 4,736,866 | 4/1988 | Leder et al. | 800/1 |
| 5,175,385 | 12/1992 | Wagner et al. | 800/2 |

FOREIGN PATENT DOCUMENTS

| | | |
|---|---|---|
| 0247494 A2 | 2/1987 | (EP) . |
| 0247494 B1 | 2/1987 | (EP) . |
| WO 96/05309 | 2/1996 | (WO) . |
| WO 97/00319 | 1/1997 | (WO) . |
| WO 97/00892 | 1/1997 | (WO) . |
| WO 97/11192 | 3/1997 | (WO) . |
| WO 97/26335 | 7/1997 | (WO) . |
| WO 97/40380 | 10/1997 | (WO) . |
| WO 97/43412 | 11/1997 | (WO) . |

OTHER PUBLICATIONS

Abel and Zemel, "Impaired recovery of vascular smooth muscle intracellular calcium following agonist stimulation in insulin resistant (Zucker Obese) rats," *Am. J. Hypertens.*, 6:500–504, 1993.

Ahmad et al., "Obesity–associated decrease in growth hormone–releasing hormone gene expression: a mechanism for reduced growth hormone mRNA levels in genetically obese Zucker rats," *Neuroendocrinol.*, 58:332–337, 1993.

Argeson et al., "Molecular basis of the pleiotropic phenotype of mice carrying the hypervariable yellow ($A^{hvy}$) mutation at the agouti locus," *Genetics*, 142:557–567, 1996.

Balling, "Craniofacial abnormalities induced by ectopic expression of the homeobox gene Hox–1. 1 in transgenic mice," *Cell*, 58:337–347, 1989.

Barsh et al., "Effects of the lethal yellow ($A^y$) mutation in mouse aggregation chimeras," *Development*, 109:683–690, 1990.

Barsh and Epstein, "Physical and genetic characterization of a 75–kilobase deletion associated with a/, a recessive lethal allele at the mouse agouti locus," *Genetics*, 121:811–818, 1989a.

Barsh and Epstein, "The long–range restriction map surrounding the mouse agouti locus reveals a disparity between physical and genetic distances," *Genomics*, 5:9–18, 1989b.

Bultman et al., "Molecular analysis of reverse mutations from nonagouti (a) to black–and–tan ($a^t$) and white–bellied agouti ($A^w$) reveals alternative forms of agouti transcripts," *Genes Dev.*, 8:481–490, 1994.

Bultman et al., "Molecular characterization of the mouse agouti locus," *Cell*, 71:1195–1204, 1992.

Bultman et al., "Molecular characterization of a region of DNA associated with mutations at the agouti locus in the mouse," *Proc. Natl. Acad. Sci. USA*, 88:8062–8066, 1991.

Duhl et al., "Pleiotropic effects of the mouse lethal yellow ($A^y$) mutation explained by deletion of a maternally expressed gene and the simultaneous production of agouti fusion RNAs," *Develop.*, 120:1695–1708, 1994a.

Enser, "The role of insulin in the regulation of stearic acid desaturase activity in liver and adipose tissue from obese––hyperglycaemic (ob/ob) and lean mice," *Biochem. J.*, 180:551–558, 1979.

Fan et al., "Role of melanocortinergic neurons in feeding and the agouti obesity syndrome," *Nature* (Lond.), 385:165–168, 1997.

Frigeri et al., "Impairment of glucose tolerance in yellow ($A^{vy}$/A) (BALB/c X VY) F–1 hybrid mice by hyperglycemic peptide(s) from human pituitary glands," *Endocrinol.*, 113:2097–2105, 1983.

Frigeri et al., "Differential responses of yellow $A^{vy}$/A and agouti A/a (BALB/c X VY) F1 hybrid mice to the same diets: glucose tolerance, weight gain, and adipocyte cellularity," *Int. J. Obes.*, 12:305–320, 1988.

Gantz et al., "Molecular cloning of a novel melanocortin receptor," *J. Biol. Chem.*, 268:8246–8250, 1993a.

Gantz et al., "Molecular cloning, expression, and characterization of a fifth melanocortin receptor," *Biochem. Biophys. Res. Commun.*, 200:1214–1220, 1994.

(List continued on next page.)

Primary Examiner—Elyabik C. Kammerer
(74) Attorney, Agent, or Firm—Williams, Morgan & Amerson

(57) ABSTRACT

Disclosed are methods and compositions comprising novel agouti polypeptides and the polynucleotides which encode them. Also disclosed are DNA segments encoding these proteins derived from human and murine cell lines, and the use of these polynucleotides and polypeptides in a variety of diagnostic and therapeutic applications. Methods, compositions, kits, and devices are also provided for identifying compounds which are inhibitors of agouti activity, and for altering fatty acid synthetase activity and intracellular calcium levels in transformed cells.

34 Claims, 41 Drawing Sheets

OTHER PUBLICATIONS

Gill and Yen, "Effects of ciglitazone on endogenous plasma islet amyloid polypeptide and insulin sensitivity in obese-–diabetic viable yellow mice," *Life Sci.*, 48:703–710, 1991.

Hustad et al., "Molecular genetic characterization of six recessive viable alleles of the mouse agouti locus," *Genetics*, 140:255–265, 1995.

Huszar et al., "Targeted disruption of the melanocortin–4 receptor results in obesity in mice," *Cell*, 88:131–141, 1997.

Izawa et al., Increase in cytosolic free $Ca^{2+}$ in corticotropin–stimulated white adipocytes. *Am. J. Physiol.*, 266 (*Endocrinol. Metab.* 29):E418–E426, 1994.

Jackson, "Molecular and developmental genetics of mouse coat color," *Annu. Rev. Genet.*, 28:189–217, 1994.

Jackson, "Mouse coat colour mutations: a molecular genetic resource which spans the centuries," *BioEssays*, 13:439–446, 1991.

Jones et al., "Dietary polyunsaturated fatty acids suppress stearoyl–CoA desaturase gene expression in adipose tissue," Abstract, *FASEB J.*, 9:A722, 1995.

Jones et al., "Upregulation of adipocyte metabolism by agouti protein: possible paracrine actions in yellow mouse obesity," *Am. J. Physiol.* 270(*Endocrinol. Metab.* 33):E192–E196, 1996.

Kiefer et al., "Mutations in the carboxyl terminus of the agouti protein decrease agouti inhibition of ligand binding to the melanocortin receptors," *Biochem.*, 36:2084–2090, 1997.

Kim et al., "Agouti regulation of intercellular calcium: role of melanocortin receptors," *Am. J. Physiol.*, 272:E379–E384, 1997.

Kim and Zemel, "Insulin increases vascular smooth muscle recovery from intracellular calcium loads," *Hypertension*, 22:74–77, 1993.

Kim et al., "The effects of calcium channel blockade on agouti–induced obesity," *FASEB J.*, 10:1646–1652, 1996.

Klebig et al., "Molecular analysis of the mouse agouti gene and the role of dominant agouti–locus mutations in obesity and insulin resistance," In: *Molecular and Genetic Aspects of Obesity*, ed. Bray, G., Baton Rouge, Louisiana State Univ. Press, Baton Rouge, LA, 1994.

Klebig et al., "Ectopic expression of the agouti gene in transgenic mice causes obesity, features of type II diabetes, and yellow fur," *Proc. Natl. Acad. Sci. USA*, 92:4728–4732, 1995.

Kucera et al., "Overexpression of an agouti cDNA in the skin of transgenic mice recapitulates dominant coat color phenotypes of spontaneous mutants," *Dev. Biol.*, 173:162–173, 1996.

Kwoh et al., "Transcription–based amplification system and detection of amplified human immunodeficiency virus type 1 with a bead–based samdwich hybridization format," *Proc. Natl. Acad. Sci*, USA, 86(4):1173–1177, 1989.

Kwon et al., "Molecular structure and chromosomal mapping of the human homolog of the agouti gene," *Proc. Natl. Acad. Sci. USA*, 91:9760–9764, 1994.

Lewin, "When does homology mean something else?," *Science*, 237:1570, 1987.

Lu et al., "Agouti protein is an antagonist of the melanocyte–stimulating–hormone receptor," *Nature* (Lond.), 371:799–802, 1994.

Manne et al., "Mechanisms for the pleitropic effects of the agouti gene," *Proc. Natl. Acad. Sci. USA*, 92:4721–4724, 1995.

Michaud et al., "Differential expression of a new dominant agouti allele ($A^{iapy}$) is correlated with methylation state and is influenced by parental lineage," *Genes Dev.*, 8:1463–1472, 1994c.

Michaud et al., "A molecular model for the genetic and phenotypic characteristics of the mouse lethal yellow ($A^y$) mutation," *Proc. Natl. Acad. Sci. USA*, 91:2562–2566, 1994a.

Michaud et al., "Role of the agouti gene in obesity," *J Endocrinology*, 155:207–209, 1997.

Michaud et al., "The embryonic lethality of homozygous lethal yellow mice ($A^y/A^y$) is associated with the disruption of a novel RNA–binding protein," *Genes Dev.*, 7:1203–1213, 1993.

Millar et al., "Expression and transgenic studies of the mouse agouti gene provide insight into the mechanisms by which mammalian coat color patterns are generated," *Develop.*, 121:3223–3232, 1995.

Miller et al., "Cloning of the mouse agouti gene predicts a secreted protein ubiquitously expressed in mice carrying the lethal yellow mutation," *Genes & Dev.*, 7:454–467, 1993.

Miltenberger et al., "The role of the agouti gene in the yellow obese syndrome," *J. Nutr.*, 127:1902S–1907S, 1997.

Mynatt et al., "Combined effects of insulin treatment and adipose tissue–specific agouti expression on the development of obesity," *Proc. Natl. Acad. Sci. USA*, 94:919–922, 1997.

Nishi et al., "Conservation of the sequence od islet amyloid polypeptide in five mammals is consistent with its putative role as an islet hormone," *Proc. Natl. Acad. Sci. USA*, 86:5738–5742, 1989.

Perry et al., "A transgenic mouse assay for agouti protein activity," *Genetics*, 140:267–274, 1995.

Perry et al., "Couple site–directed mutagenesis/transgenesis identifies important functional domains of the mouse agouti protein," *Genetics*, 144:255–264, 1996.

Reeck et al., "Homology in proteins and nucleic acids: A terminology muddle and a way out of it," *Cell*, 50:667, 1987.

Rolland et al., "Evidence of increased glyceraldehyde–3–phosphate dehydrogenase and fatty acid synthetase promoter activities in transiently transfected adipocytes from genetically obese rats," *J. Biol. Chem.*, 270:1102–1106, 1995.

Rosenthal, "Myosin light chain enhancer activities muscle–specific, developmentally regulated gene expression in transgenic mice," *Proc. Natl. Acad. Sci. USA*, 86:7780–7784, 1989.

Salem et al., "Effects of hypophysectomy and the insulin-–like and anti–insulin pituitary peptides on carbohydrate metabolism in yellow $A^{vy}/A$ (BALB/c x VY)$F_1$, hybrid mice," *Proc. Soc. Exp. Biol. Med.*, 191:408–419, 1989.

Shillabeer et al., "Fatty acid synthase and adipsin mRNA levels in obese and lean JCR:LA–cp rats:effect of diet," J. LipidRes., 33:31–39, 1992.

Shimizu et al., "Adrenalectomy and response to corticosterone and MSH in the genetically obese yellow monse," *Am. J. Physiol.*, 256:R494–R500, 1989.

Siracusa et al., "Genetic organization of the agouti region of the mouse," *Genetics*, 117:93–100, 1987.

Siracusa, "Genomic organization and molecular genetics of the agouti locus in the mouse," *Ann. N.Y. Acad. Sci.*, 642:419–430, 1991.

Siracusa et al., "Recombinant inbred strain and interspecific backcross analysis of molecular markers flanking the murine agouti coat color locus," Genetics, 122:669–679, 1989.

Siracusa et al., "Allelic variation within the Emv–15 locus defines genomic sequences closely linked to the agouti locus on mouse chromosome 2," Genetics, 117:85–92, 1987.

Warbritton et al., "Pancreatic, islet cells in preobese yellow $A^{vy}$/–mice: relation to adult hyperinsulinemia and obesity," Proc. Soc. Exp. Biol. Mod., 206:145–151, 1994.

Willard et al., "Agouti structure and function: characterization of a potent alpha–melanocyte stimulating hormone receptor antagonist," Biochem., 34:12341–12346, 1995.

Wilson et al., "Structure and function of ASP, the human homolog of the mouse agouti gene," Human Mol. Genet., 4:223–230, 1995.

Wolff et al., "Phaeomelanin synthesis and obesity in mice. Interaction of the viable yellow ($A^{vy}$) and sombre ($E^{so}$) mutations," J. Hered., 69:295–298, 1978.

Wolff et al., "Prenatal determination of obesity, tumor susceptibility, and coat color pattern in viable yellow $A^{vy}$/a) mice. The yellow mouse syndrome," J. Hered., 77:151–158, 1986.

Woychik et al., "Molecular and genetic characterization of a radiation–induced structural rearrangement in mouse chromosome 2 causing mutations at the limb deformity and agouti loci," Proc. Natl. Acad. Sci. USA, 87:2588–2592, 1990.

Woychik et al., "An inherited limb deformity created by insertional mutagenesis in a transgenic mouse," Nature (Lond.), 318:36–40, 1985.

Yen et al., "Obesity, diabetes, and neoplasia in yellow $A^{vy}$/–mice: ectopic expression of the agouti gene," FASEB J., 8:479–488, 1994.

Zemel, Insulin resistance vs. hyperinsulinemia in hyper–tension: insulin regulation of $Ca^{2+}$ transport and $Ca^{2+}$ regulation of insulin sensitivity, J. Nutr., 125:17385–17435, 1995.

Zemel et al., "Effects of diltiazem on vascular resistance and insulin receptor function in isolated systolic hypertension," Am. J. Hypertens., 4:121A, Abstract #382, 1991.

Zemel et al., "Role of insulin in regulating vascular smooth muscle $Ca^{2+}$ –ATPase expression," J. Vasc. Biol. Med., 4:79–84, 1993.

Zemel et al., "Agouti gene product regulation of adipocyte intracellular free calcium ($Ca^{2+}$) results in stimulation of fatty acid synthase," Obes. Res., 3:338s, Abstract $O_{54}$, 1995.

Zemel et al., "Agouti regulation of intracellular calcium: role in the insulin resistance of viable yellow mice," Proc. Natl. Acad. Sci. USA, 92:4733–4737, 1995.

Zhang et al., "Positional cloning of the mouse obese gene and its human homologue," Nature (London), 372:425–432, 1994.

Swart et al. Biochem. J. 133:641–654, 1973.*

Northwood et al., The Journal of Biological Chemistry, 266, 15266–15276, Aug. 15, 1991.*

Sambrook et al, Molecular Cloning, A laboratory Manual, Second Edition, vol. 3, pp. 16.2–16.30 and pp. 17.3–17.28, 1989, Cold Spring Harbor Laboratory Press.*

* cited by examiner

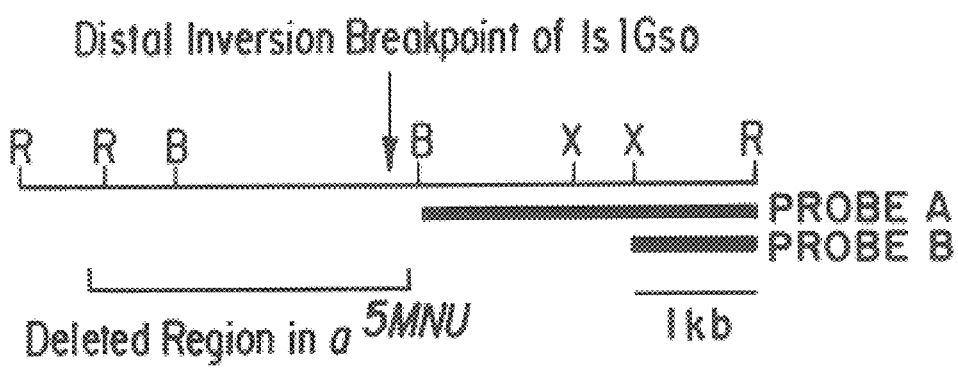
FIG.1A
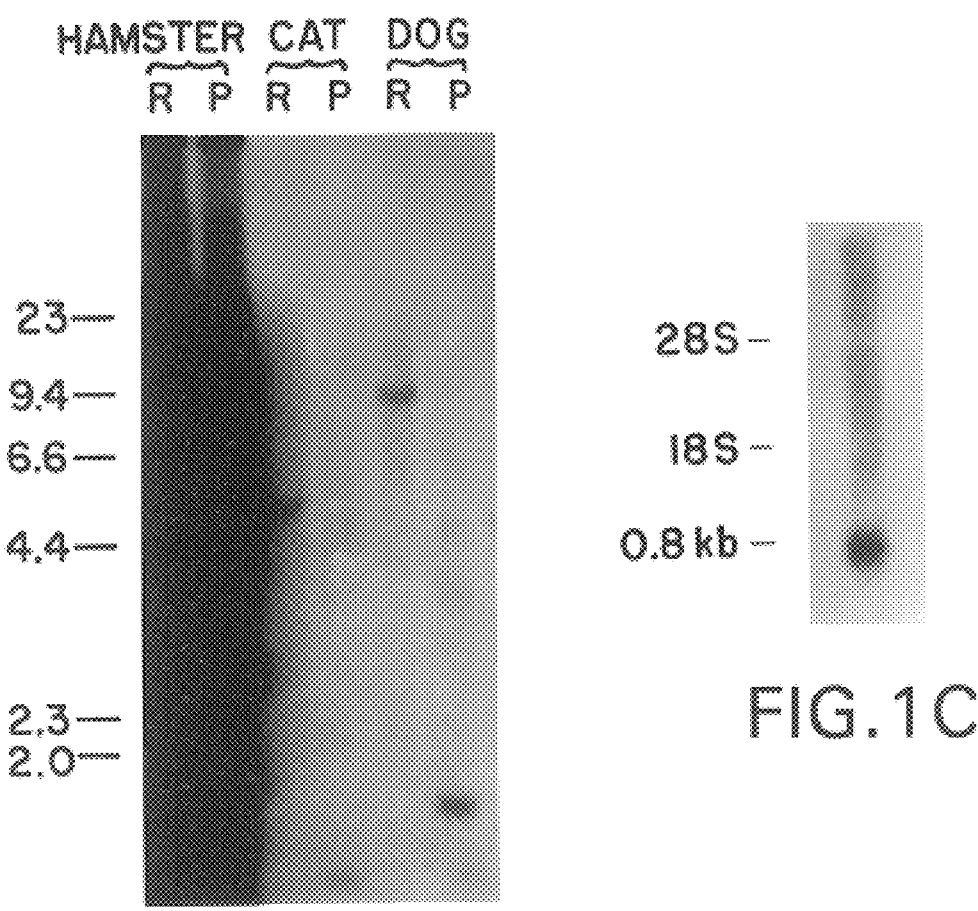
FIG.1B
FIG.1C

```
(SEQ ID: 1)  TTCAAGGACAGGAAAGACATTCTGGCCTGGCTTCCCTTAGGGGAGCTGATGCGGAATAGAGTC                    63
                                  →
(SEQ ID: 2)  ACTTGTGCTGCTTCTCAGG ATG GAT GTC ACC CGC CTA CTC CTG GCC ACC CTA              115
                                 Met Asp Val Thr Arg Leu Leu Leu Ala Thr Leu              11

GTG AGC TTC CTG TGC TTC TTC ACC GTC CAC AGC CAC CTG GCA CTC GAG              163
             Val Ser Phe Leu Cys Phe Phe Thr Val His Ser His Leu Ala Leu Glu               27
                              PO₄     ●
             GAG ACG CTT GGA GAT GAC AGG AGT CTG CGG AGT CTG CGG AGT CTG CGG AGT

GAG ACG CTT GGA GAT GAC AGG AGT CTG CGG AGT AAC TCC TCC ATG AAC              211
             Glu Thr Leu Gly Asp Asp Arg Ser Leu Arg Ser Asn Ser Ser Met Asn               43
                                                          *
                                          →
             TCG CTG GAT TTC TCC TCT GTT TCT ATC GTG GCA CTG AAC AAG AAA TCC              259
             Ser Leu Asp Phe Ser Ser Val Ser Ile Val Ala Leu Asn Lys Lys Ser               59
                                                                    PO₄
             AAG AAG ATC AGC AGA AAA GAA GCC GAG AAG CGG AAG AGG TCT TCC AAG              307
             Lys Lys Ile Ser Arg Lys Glu Ala Glu Lys Arg Lys Arg Ser Ser Lys               75
              PO₄                                                  PO₄ PO₄
             AAA AAG GCT TCG ATG AAG AAG GTG GCA AGG CCC CCG CCA CCT TCG CCC              355
             Lys Lys Ala Ser Met Lys Lys Val Ala Arg Pro Pro Pro Pro Ser Pro               91

FIG. 2A
```

```
                                                               PO4
TGC GTG GCC ACC CGC GAC AGC TGC AAG CCA CCC GCA CCC GCC TGC       403
Cys Val Ala Thr Arg Asp Ser Cys Lys Pro Pro Ala Pro Ala Cys Cys● 107
 ●                                                             PO4
GAC CCG TGC GCC TCC TGC CAG TGC CGT TTC TTC GGC AGC GCC TGC ACC   451
Asp Pro Cys Ala Ser Cys Gln Cys Arg Phe Phe Gly Ser Ala Cys Thr  123
         ●                       ●                             ●

TGT CGA GTA CTC AAC CCC AAC TGC TGA CGCAGCTTCTTCGCTGCCGCGCAGCT   505
Cys Arg Val Leu Asn Pro Asn Cys End                              131
 ●                               ●

TCGGGAACGGGGTGATTGGGGCGGGGCTTCAGGGTCCCGCGCTTCTAGGCTGAGGGGCGGGTCTC  568

TGTGGGTGGGGCTTGTGGGTGGGGCGTGGTCAGTGGTTGTGACTTGTGGGCGCTTTCAAAAAAC  631

CGGTTTTCTAGGAAACCTAGTGGAAGCTAAAATCAGAATACAATAATATTTTTAGGCTGCC(A)  692
```

FIG. 2B

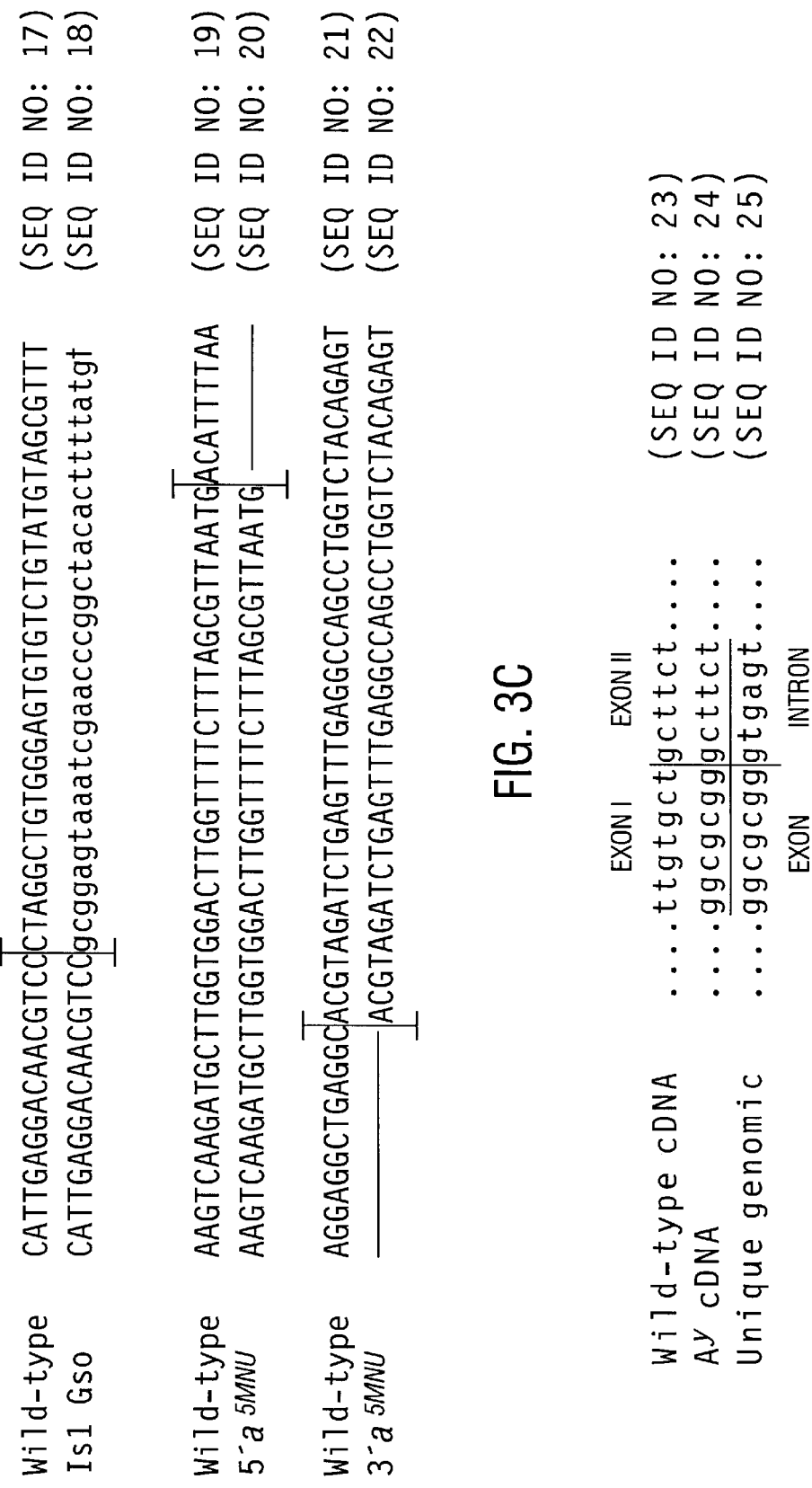

II | gcttctcaggatggatgtcacccgcctactcctggccaccctagtgagcttcctgtgcttcttcaccgtccacagc
.c... | ..c...ctg........................t.......gc..gt.....c........t.c.a......

cacctggcactcgaggagacgcttggagatgacaggagtctgcggagtaactcctccatgaactgctgatttctcctctgt
.......c....ct........a....cc.............c...a..c.........tg.....cta.......g...c.t......

ttctatcgtgg | gtaa
c......t..... | gtaa

III gaag | cactgaacaagaaatccaagagatcagcagaaagaagccgagaagcggaagaggtcttccaag | gtaa
.... | ..........................ac......g.........c...a..a.....a..a....t... | ........

IV acag | aaaaaggcttcgatgaagaaggtgcaaggcccccgccaccttcg-----ccctgctgtggccaccccgcgacagct
.... | ..gg........................a....tgc......g.a.c...cctatctgcg................a.........

gcaagccaccccgccaccgcctgctgcgaccgtgcctcctgccagtgccgtttcttcggcagcgctgcacctgtcgagta
........g..g.......................................c.............c.........t...c..c..g ctcaacccccaactgctgacgcagctcttcgctgcgcgcagcttcgggaacgggtgattgggcggggcttcagggtcccgc
....g...t..........gcgcc..ccac..c..g..cgcgagcaggca...cttc..g..cgc..g..c..ct..ctc...cgggtg

FIG. 10B-1 gcttctaggctgaggggcgggtctctgtgggtgggcttgtgggtgggcgtggtcagtggttgtgggcgtggtcagtggttgtgactgttgtgggcgctttcaa
atcc...acag.gc..cttcccagggc..cag.c..gcg.a..t.ccag.a.a.gg.act.cag.gagacct...ttggg.t.

aaaaccggttttctaggaaacctagtgtggaagctaaaatcagaatacaataatattttttaggctgcc mouse (SEQ ID NO:26)
...t.gaaa.acaatat.t.taggc..ctc.aaggtg.gc.gctgtttctg..aagg.cccgaaag human (SEQ ID NO:27)

FIG. 10B-2

```
Met Asp Val Thr Arg Leu Leu Leu Ala Thr Leu Val Ser Phe Leu Cys
 ·   ·   ·   ·   ·   ·   ·   ·   ·   ·   ·  Leu Val  ·   ·   ·

Phe Phe Thr Val His Ser His Leu Ala Leu Glu Glu Thr Leu Gly Asp
 ·   ·   ·  Ala Asn  ·   ·   ·  Pro Pro  ·   ·  Lys  ·  Arg  ·

Asp Arg Ser Leu Arg Ser Asn Ser Ser Met Asn Ser Leu Asp Phe Ser
 ·   ·   ·   ·   ·   ·   ·   ·   ·  Val  ·  Leu  ·   ·  Val Pro

Ser Val Ser Ile Val Ala Leu Asn Lys Lys Ser Lys Lys Ile Ser Arg
 ·   ·   ·   ·   ·   ·   ·   ·   ·   ·   ·   ·  Gln  ·  Gly  ·

Lys Glu Ala Glu Lys Arg Lys Arg Ser Ser Lys Lys Lys Ala Ser Met
 ·  Ala  ·   ·   ·   ·   ·   ·   ·   ·   ·   ·  Glu  ·   ·   ·

Lys Lys Val Ala Arg Pro Pro Pro Pro Ser  -   -  Pro Cys Val Ala
 ·   ·   ·  Val  ·   ·  Arg Thr  ·  Leu Ser Ala  ·   ·   ·   ·

Thr Arg Asp Ser Cys Lys Pro Pro Ala Pro Ala Cys Cys Asp Pro Cys
 ·   ·  Asn  ·   ·   ·   ·   ·   ·   ·   ·   ·   ·   ·   ·   ·

Ala Ser Cys Gln Cys Arg Phe Phe Gly Ser Ala Cys Thr Cys Arg Val
 ·   ·   ·   ·   ·   ·   ·   ·  Arg  ·   ·   ·  Ser  ·   ·   ·

Leu Asn Pro Asn Cys mouse (SEQ ID NO:2)
 ·  Ser Leu  ·   ·  human (SEQ ID NO:4)
```

FIG. 11

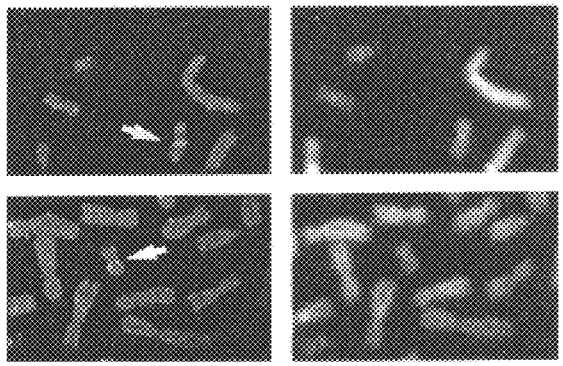

FIG.12A

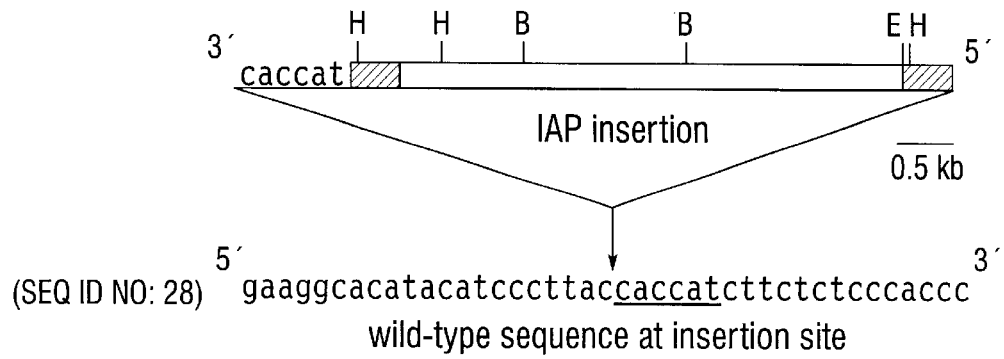

(SEQ ID NO: 28) 5′ gaaggcacatacatcccttaccaccatcttctctcccaccc 3′
wild-type sequence at insertion site

FIG. 19A tgtgggaagccgcccccacattcgccgtcacaagatggcgctgacatcctgtgttctaag ttggtaaacaaataatctgcgcatgagccaagggtatttacgaccacttgtactctgttt ttcccgtgaacgtcagctcggccatgggctgcagccaatcagggagtgatgcgccctagg
                                                U3 ←—|—→ R
caatggttgttctctttaaagagggaaggggttttcgttttctctctcttgcttcttgct ctctcttgcttcttgctctctcttgcttccctctcttgcttcttgctctctcttgcttct
                                        R ←—|—→ US
tgctctcttttcctgaagatgtaagaataaagctttgtcgcagaagattctggtctgtgg tgttcttcctggccggtcgtgagaacgcgtcgaataaca     (SEQ ID NO: 29)

FIG. 19B tgtgggaagccgcccccacattcgccgtcacaagatggcgctgacatcctgtgttctaag ttggtaaacaaataatctgcgcatgagccaagggtatttacgaccacttgtactctgttt ttcccgtgaacgtcagctcggccatgggctgcagccaatcagggagtgatgcgccctagg
                            U3 ←—|—→ R
caatggttgttctctttaaaatagaaggggtttcgttttctctctcttgcttcttgc tctctcttgcttccctctcttgcttcgctctctcttgcttcttacactctggcccccaaa
                    R ←—|—→ US
aagatgtaagcaataaagctttgccgtagaagattctggttgttgtgttcttcctggccg gtcgtgagaacgcgacgaataaca  (SEQ ID NO: 30)

FIG. 19C

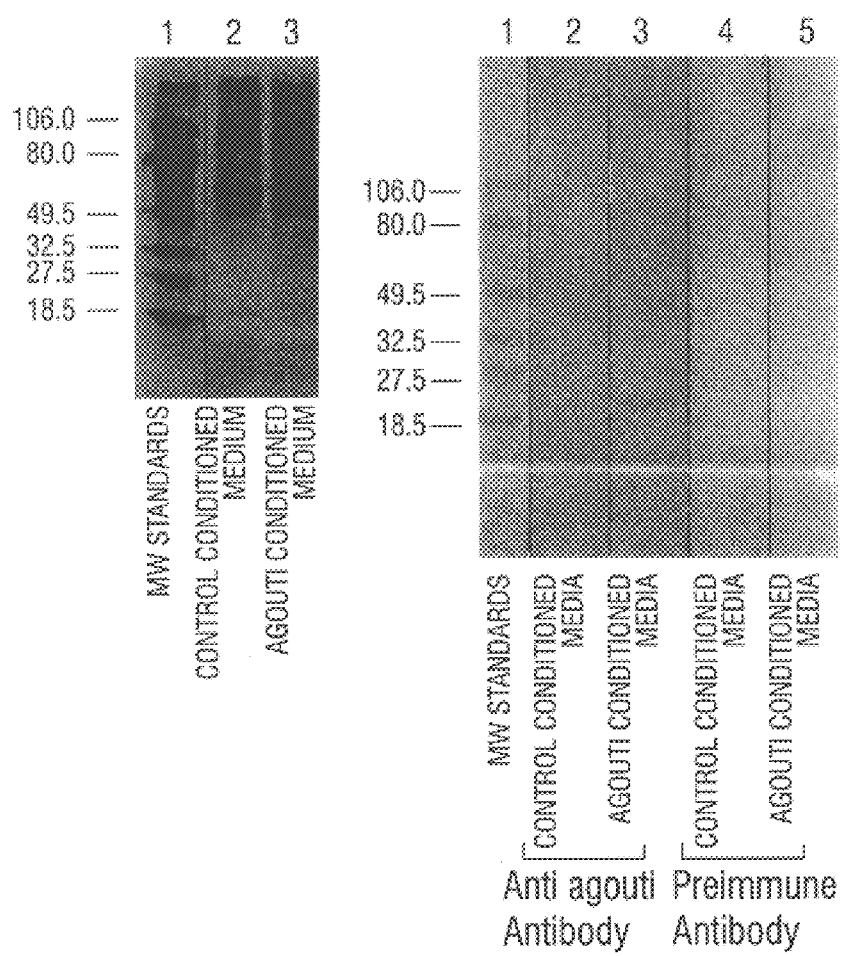
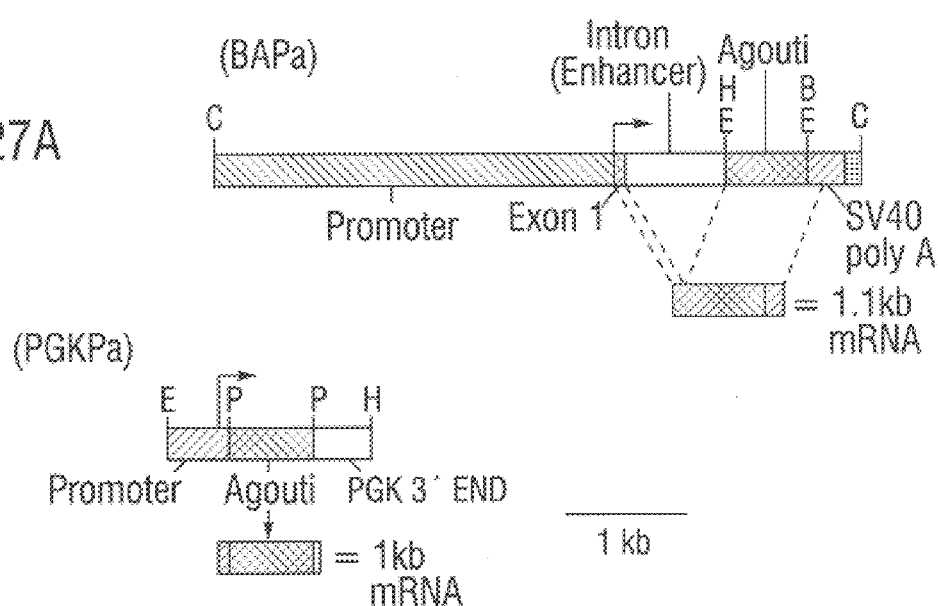
FIG. 26
FIG. 27A
FIG. 27B

SEQUENCE LISTING

<160> NUMBER OF SEQ ID NOS: 30

<210> SEQ ID NO: 1
<211> LENGTH: 692
<212> TYPE: DNA
<213> ORGANISM: Mus musculus

<400> SEQUENCE: 1

```
ttcaaggaca ggaaagacat tctggcctgg cttcccttag gggagctgat gcggaataga      60
gtcacttgtg ctgcttctca ggatggatgt cacccgccta ctcctggcca ccctagtgag     120
cttcctgtgc ttcttcaccg tccacagcca cctggcactc gaggagacgc ttggagatga     180
caggagtctg cggagtaact cctccatgaa ctcgctggat ttctcctctg tttctatcgt     240
ggcactgaac aagaaatcca agaagatcag cagaaaagaa gccgagaagc ggaagaggtc     300
ttccaagaaa aaggcttcga tgaagaaggt ggcaaggccc ccgccacctt cgccctgcgt     360
ggccacccgc gacagctgca agccacccgc acccgcctgc tgcgacccgt gcgcctcctg     420
ccagtgccgt ttcttcggca gcgcctgcac ctgtcgagta ctcaacccca actgctgacg     480
cagcttcttc gctgcgcgcg cagcttcggg aacgggtgat tgggcgggc ttcagggtcc     540
cgcgcttcta ggctgagggg cgggtctctg tgggtggggc ttgtgggtgg gcgtggtcag     600
tggttgtgac ttgtgggcgc tttcaaaaaa ccggttttct aggaaaccta gtggaagcta     660
aaatcagaat acaataatat ttttaggctg cc                                    692
```

<210> SEQ ID NO: 2
<211> LENGTH: 131
<212> TYPE: PRT
<213> ORGANISM: Mus musculus

<400> SEQUENCE: 2

```
Met Asp Val Thr Arg Leu Leu Leu Ala Thr Leu Val Ser Phe Leu Cys
  1               5                  10                  15

Phe Phe Thr Val His Ser His Leu Ala Leu Glu Glu Thr Leu Gly Asp
                 20                  25                  30

Asp Arg Ser Leu Arg Ser Asn Ser Ser Met Asn Ser Leu Asp Phe Ser
             35                  40                  45

Ser Val Ser Ile Val Ala Leu Asn Lys Lys Ser Lys Lys Ile Ser Arg
         50                  55                  60

Lys Glu Ala Glu Lys Arg Lys Arg Ser Ser Lys Lys Lys Ala Ser Met
 65                  70                  75                  80

Lys Lys Val Ala Arg Pro Pro Pro Ser Pro Cys Val Ala Thr Arg
                 85                  90                  95

Asp Ser Cys Lys Pro Pro Ala Pro Ala Cys Cys Asp Pro Cys Ala Ser
```

```
                    100                 105                 110
Cys Gln Cys Arg Phe Phe Gly Ser Ala Cys Thr Cys Arg Val Leu Asn
            115                 120                 125

Pro Asn Cys
    130

<210> SEQ ID NO: 3
<211> LENGTH: 395
<212> TYPE: DNA
<213> ORGANISM: Homo sapien

<400> SEQUENCE: 3
gcagaaggag gcttcgatga agaaagtggt gcggccccgg accccctat  ctgcgccctg      60 cgtggccacc cgcaacagct gcaagccgcc ggcacccgcc tgctgcgacc cgtgcgcctc     120
ctgccagtgc cgcttcttcc gcagcgcctg ctcctgccgc gtgctcagcc tcaactgctg     180
agcgccccca ctcccggccg cgagcaggca gggcttcggg gacgcggggc gcttctcggg     240
cgggtgatcc ctaacagggc ggcttcccag ggctgcaggc gggcggaggt tccaggagat     300
gggacttcag ggagacctgg cttgggctaa atcgaaata  caatatatat aggctgctcg     360
aaggtgtgcg gctgtttctg taaaggtccc gaaag                                395

<210> SEQ ID NO: 4
<211> LENGTH: 132
<212> TYPE: PRT
<213> ORGANISM: Homo sapien

<400> SEQUENCE: 4

Met Asp Val Thr Arg Leu Leu Leu Ala Thr Leu Leu Val Phe Leu Cys
  1               5                  10                  15

Phe Phe Thr Ala Asn Ser His Leu Pro Pro Glu Glu Lys Leu Arg Asp
                 20                  25                  30

Asp Arg Ser Leu Arg Ser Asn Ser Ser Val Asn Leu Leu Asp Val Pro
             35                  40                  45

Ser Val Ser Ile Val Ala Leu Asn Lys Lys Ser Lys Gln Ile Gly Arg
 50                  55                  60

Lys Ala Ala Glu Lys Lys Arg Ser Ser Lys Lys Glu Ala Ser Met Lys
 65                  70                  75                  80

Lys Val Val Arg Pro Arg Thr Pro Leu Ser Ala Pro Cys Val Ala Thr
                 85                  90                  95

Arg Asn Ser Cys Lys Pro Pro Ala Pro Ala Cys Cys Asp Pro Cys Ala
                100                 105                 110

Ser Cys Gln Cys Arg Phe Phe Arg Ser Ala Cys Ser Cys Arg Val Leu
            115                 120                 125

Ser Leu Asn Cys
    130

<210> SEQ ID NO: 5
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 5
cactgaacaa gaaatccaag aagatcagca gaaaagaagc cg                         42
```

```
<210> SEQ ID NO: 6
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 6
ttggaagacc tcttccgctt ctcggcttct tttctgctga tc                          42

<210> SEQ ID NO: 7
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 7
cctcttacca ttacccctga                                                    20

<210> SEQ ID NO: 8
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 8
ctaggtgact tacccacaat                                                    20

<210> SEQ ID NO: 9
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 9
atggatgtca cccgcttact cctggcc                                            27

<210> SEQ ID NO: 10
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 10
gcgctcagca gttgaggctg agcacgc                                            27

<210> SEQ ID NO: 11
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 11
gaactggcat caaagtacca                                                    20

<210> SEQ ID NO: 12
```

```
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 12
caatgctcct gcctctgcca                                                    20

<210> SEQ ID NO: 13
<211> LENGTH: 19
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 13
cctggctcat gcgcagatt                                                     19

<210> SEQ ID NO: 14
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 14
ttccgcttct cggcttcttt                                                    20

<210> SEQ ID NO: 15
<211> LENGTH: 24
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 15
acaggaaaga cattctggcc tggc                                               24

<210> SEQ ID NO: 16
<211> LENGTH: 21
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 16
tttagcttcc actaggtttc c                                                  21

<210> SEQ ID NO: 17
<211> LENGTH: 51
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 17
cattgaggac aacgtcccta ggctgtggga gtgtgtctgt atgtagcgtt t                 51

<210> SEQ ID NO: 18
<211> LENGTH: 51
```

```
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 18
cattgaggac aacgtccgcg gagtaaatcg aacccggcta cacttttatg t          51

<210> SEQ ID NO: 19
<211> LENGTH: 52
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 19
aagtcaagat gcttggtgga cttggttttc tttagcgtta atgacatttt aa         52

<210> SEQ ID NO: 20
<211> LENGTH: 43
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 20
aagtcaagat gcttggtgga cttggttttc tttagcgtta atg                   43

<210> SEQ ID NO: 21
<211> LENGTH: 52
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 21
aggaggctga ggcacgtaga tctgagtttg aggccagcct ggtctacaga gt         52

<210> SEQ ID NO: 22
<211> LENGTH: 39
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 22
acgtagatct gagtttgagg ccagcctggt ctacagagt                        39

<210> SEQ ID NO: 23
<211> LENGTH: 13
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 23
ttgtgctgct tct                                                    13

<210> SEQ ID NO: 24
<211> LENGTH: 13
<212> TYPE: DNA
```

```
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 24
ggcgcgggct tct                                                          13

<210> SEQ ID NO: 25
<211> LENGTH: 13
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 25
ggcgcgggtg agt                                                          13

<210> SEQ ID NO: 26
<211> LENGTH: 640
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 26
ttaggcttct caggatggat gtcacccgcc tactcctggc caccctagtg agcttcctgt        60
gcttcttcac cgtccacagc cacctggcac tcgaggagac gcttggagat gacaggagtc       120
tgcggagtaa ctcctccatg aactcgctgg atttctcctc tgtttctatc gtgggtaaga       180
agcactgaac aagaaatcca agaagatcag cagaaaagaa gccgagaagc ggaagaggtc       240
ttccaaggta aacagaaaaa ggcttcgatg aagaaggtgg caaggccccc gccaccttcg       300
ccctgcgtgg ccacccgcga cagctgcaag ccaccccgcac ccgcctgctg cgacccgtgc      360
gcctcctgcc agtgccgttt cttcggcagc gcctgcacct gtcgagtact caaccccaac       420
tgctgacgca gcttcttcgc tgcgcgcgca gcttcgggaa cgggtgattg ggcggggctt       480
cagggtcccg cgcttctagg ctgaggggcg ggtctctgtg ggtggggctt gtgggtgggc       540
gtggtcagtg gttgtgactt gtgggcgctt tcaaaaaacc ggttttctag gaaacctagt      600
ggaagctaaa atcagaatac aataatattt ttaggctgcc                            640

<210> SEQ ID NO: 27
<211> LENGTH: 643
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 27
tcaggcctcc tgggatggat gtcacccgct tactcctggc caccctgctg gtcttcctct        60
gcttcttcac tgccaacagc cacctgccac ctgaggagaa gctccgagat gacaggagcc       120
tgagaagcaa ctcctctgtg aacctactgg atgtcccttc tgtctctatt gtgggtaaga       180
agcgctgaac aagaaatcca aacagatcgg cagaaaagca gcagaaaaga aagatcttc        240 taaggtaagc agaaggaggc ttcgatgaag aaagtggtgc ggccccggac cccctatct       300 gcgccctgcg tggccacccg caacagctgc aagccgccgg caccc
```

-continued

```
aactgctgag cgcccccact cccggccgcg agcaggcagg gcttcgggga cgcggggcgc    480
ttctcgggcg ggtgatccct aacagggcgg cttcccaggg ctgcaggcgg gcggaggttc    540
caggagatgg gacttcaggg agacctggct tgggctaaaa tcgaaataca atatatatag    600
gctgctcgaa ggtgtgcggc tgtttctgta aaggtcccga aag                      643
```

<210> SEQ ID NO: 28
<211> LENGTH: 41
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 28

```
gaaggcacat acatccctta ccaccatctt ctctcccacc c                         41
```

<210> SEQ ID NO: 29
<211> LENGTH: 399
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 29

```
tgtgggaagc cgcccccaca ttcgccgtca caagatggcg ctgacatcct gtgttctaag     60
ttggtaaaca aataatctgc gcatgagcca agggtattta cgaccacttg tactctgttt    120
ttcccgtgaa cgtcagctcg gccatgggct gcagccaatc agggagtgat gcgccctagg   180
caatggttgt tctctttaaa gagggaaggg gttttcgttt tctctctctt gcttcttgct   240
ctctcttgct tcttgctctc tcttgcttcc ctctcttgct tcttgctctc tcttgcttct   300
tgctctcttt tcctgaagat gtaagaataa agctttgtcg cagaagattc tggtctgtgg   360
tgttcttcct ggccggtcgt gagaacgcgt cgaataaca                           399
```

<210> SEQ ID NO: 30
<211> LENGTH: 384
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 30

```
tgtgggaagc cgcccccaca ttcgccgtca caagatggcg ctgacatcct gtgttctaag     60
ttggtaaaca aataatctgc gcatgagcca agggtattta cgaccacttg tactctgttt    120
ttcccgtgaa cgtcagctcg gccatgggct gcagccaatc agggagtgat gcgccctagg   180
caatggttgt tctctttaaa atagaagggg tttcgttttt ctctctctct tgcttcttgc   240
tctctcttgc ttccctctct tgcttcgctc tctcttgctt cttacactct ggcccccaaa   300
aagatgtaag caataaagct tgccgtaga agattctggt tgttgtgttc ttcctggccg   360
gtcgtgagaa cgcgacgaat aaca                                          384
```

AGOUTI POLYPEPTIDE COMPOSITIONS

The present application is a continuation-in-part application of U.S. Ser. No. 08/064,385 filed May 21, 1993, now abandoned the entire contents of which is specifically incorporated herein by reference in its entirety.

The United States government has rights in the present invention pursuant to a grant from the Department of Energy.

BACKGROUND OF THE INVENTION

1. Field of the Invention

The present invention relates generally to the field of molecular biology, and in particular, methods and compositions for the detection and treatment of diabetes, neoplasms, hyperinsulinemia, and obesity. More particularly, certain embodiments concern the DNA segments encoding novel murine- and human-derived polypeptides comprising agouti and agouti-related proteins. In certain examples, the invention concerns the use of these nucleic acids to regulate fatty acid metabolism and treat various forms of cancer, including tumors. Methods, compositions, kits and devices are also provided for identifying compounds which are inhibitors of agouti activity in vitro and in vivo.

2. Description of Related Art

The agouti locus (a) in chromosome 2 regulates the differential production of black and yellow pigment granules that give rise the agouti coat color of the mouse. Agouti coloration, which is the true wild-type coat color of mice, is unusual in that it arises not from a homogenous pigmentation of the pelage, but rather from a banded coloration pattern in which each hair is black with a subapical band of yellow. One of the most interesting aspects of the agouti locus is that it functions within the microenvironment of the hair follicle (Silver and Russell, 1955; Silvers, 1958a, 1958b, Silvers, 1961, Silvers, 1979), unlike may other coat color genes, which act in a cell-autonomous manner within the melanocytes. Therefore, agouti must be regulating coat pigmentation by some direct or indirect form of intercellular signaling within the follicular environment.

Like many other genes that play a role in the regulation of coat pigmentation in the mouse, the agouti locus contributes to essential developmental processes unrelated to pigmentation (Geissler et al., 1988; Witte, 1990; Epstein et al., 1991; Mercer et al., 1991). For example, some of the individual alleles at the agouti locus are associated with embryonic lethality, obesity, diabetes, and the development of tumors in a wide variety of tissues. In fact, the lethal yellow ($A^y$) mutation at agouti was the first embryonic lethal mutation to be characterized in the mouse (Cuenot, 1905). Embryos homozygous for $A^y$ die very early in development, around the time of implantation, possibly owing to a defect in trophectoderm differentiation (Eaton and Green, 1963; Calarco and Pederson, 1976; Papaioannou and Gardner, 1979).

Genetic analyses of numerous a locus mutants have been ongoing for nearly a century, and have led to the identification of at least 18 dominant and recessive alleles and pseudoalleles of agouti (Silvers, 1979; Green, 1989). Different combinations of alleles account for an array of different phenotypes, ranging from subtle differences in coat color as compared with the wild type, to drastic changes in the distribution of pigmentation in different regions of the animal, particularly across the dorso-ventral surface. An intricate dominance hierarchy exists in which alleles associated with phaeomelanin (yellow) production are generally dominant over alleles associated with eumelanin (Black or brown, depending on alleles at other loci) production. This relationship is exemplified by several alleles that date back to the mouse fancy: lethal yellow ($A^y$), which confers an all-yellow phenotype in the heterozygous condition, black-and-tan($a^t$), which gives rise to an all-black dorsum and an all-yellow ventrum (Dunn, 1928), nonagouti (a), which gives rise to a predominantly black phenotype, except for small amounts of phaeomelanin around the pinnae, nipples, and perineum, and extreme nonagouti ($a^e$), which confers a completely black phenotype (Hollander and Gowen, 1956).

The large number of alleles and the wide range of phenotypes associated with the agouti locus have been used as evidence by some investigators to propose that the agouti locus is comprised of multiple "mini-loci" and not a single gene. According to this hypothesis, each gene of the mini-locus plays a role in regulating pigmentation in different parts of the body, particularly over the dorsal and ventral surfaces, and around the pinnae, nipples, and perineum. Support for this assertion stems from the finding that changes from yellow to black pigmentation proceed from the dorsal to the ventral regions as one progresses from the most dominant to the most recessive mutation of the agouti allelic series. For example, phaeomelanin progressively disappears from the mid-dorsum with $A^i$/a ($A^i$, intermediate yellow), from the lateral dorsum with $a^t/a^t$, from the ventral surface with a/a, and from the pinnae, nipples, and perineum with $a^e$. With the mini-locus hypothesis, different genes should be affected by mutations associated with the individual alleles in the hierarchy. The present invention demonstrates that the structure and expression of the same gene is affected by mutations at the top ($A^y$), middle ($a^t$ and a), and bottom ($a^e$) of the allelic series. These results disprove the mini-locus hypothesis.

Although the agouti alleles have been extensively characterized with classical genetic techniques, the structure of the gene(s) responsible for a locus function had not been determined until the present invention. Attempts by others to isolate the gene using positional cloning techniques, failed to isolate the gene (Barsh and Epstein, 1989a; Siracusa et al., 1987a; Siracusa et al., 1989; Siracusa, 1991).

A radiation-induced inversion mutation, called Is(17;In2)Id,aJGso (abbreviated IslGso), which contains DNA breakpoints in the limb deformity (Id) and agouti loci, two regions that are normally separated by 22 cM on chromosome 2 (Woychik et al., 1990a; Bultman et al., 1991) was previously described. Utilizing a DNA probe from the $Id^{Hd}$ insertional mutant (Woychik et al., 1985), 22 cM were jumped with the inversion which allowed a region of DNA that maps to the agouti locus to be identified (Woychik et al., 1990a). Moreover, this region also hybridizes to sequences that are rearranged in several agent-induced a locus mutations (Bultman et al., 1991).

DEFICIENCIES IN THE PRIOR ART

Little is known about the molecular mechanisms involved in obesity in animals. Likewise, little is known about the molecular events which lead to diabetes in humans. Prior to the present invention, the only genes involved in obesity which had been characterized were those encoding leptin. This polypeptide, which is unrelated to polypeptides disclosed herein, was found to be associated with obesity and diabetes in mice. The isolation and characterization of the gene encoding leptin and the leptin receptor along with methods of use of both molecules have been described in Intl. Pat. Appl. Publ. No. WO 96/05309, Intl. Pat. Appl. Publ. No. WO 97/11192, Intl. Pat. Appl. Publ. No. WO 97/00319, Intl. Pat. Appl. Publ. No. WO 97/40280, and Intl. Pat. Appl. Publ. No. WO 97/26335 (each of which is specifically incorporated herein by reference in its entirety). Studies have shown that leptin is not functionally equivalent to the agouti polypeptides disclosed herein. Whereas overexpression of agouti is associated with obesity, administration of leptin to obese (ob/ob) mice leads to leaner mice.

Obesity and non-insulin dependent diabetes are genetically inherited disorders in humans and mice. The obesity-associated diabetes of the $A^y$ and $A^{vy}$ mutant animals bears remarkable similarity to non-insulin dependent diabetes in obese humans. To date no genes involved in genetic obesity has been cloned.

SUMMARY OF THE INVENTION

The present invention overcomes deficiencies in the prior art by providing gene and polypeptide compositions in which expression of the agouti gene product correlates with the development of insulin independent diabetes, hyperamylinemia, neoplasms and obesity in animals. Another aspect of the invention is the use of the gene in transgenic animals as an animal model for such diseases as insulin independent diabetes, obesity, hyperamylinemia, and neoplasms. The invention also relates to the gene product, antibodies to the gene product and their use as diagnostics and therapeutics. The present invention relates to nucleic acid sequences in which expression of the agouti gene product is associated with the development of diabetes, obesity, hyperamylinemia and the development of tumors in a wide variety of tissues in animals. Such nucleic acid sequences may be synthetic DNA or RNA sequences or isolated natural DNA or RNA sequences, or any functionally equivalent nucleic acid sequences, analogs and portions thereof. Such DNA sequences may be complementary DNA (cDNA) or genomic DNA. The present invention also relates to anti-sense nucleic acid sequences, and mRNA sequences.

In an important embodiment, the invention discloses and claims a transgenic non-human vertebrate animal (preferably a mammal, e.g., a cow, horse, pig, goat, monkey, hamster, mouse, rabbit, rat and the like) that contains germ cells and somatic cells which comprise one or more genes which are identical to, or substantially homologous with, a vertebrate agouti gene or a portion thereof, which is capable of promoting (i.e. increases the probability of developing) a disease such as non-insulin-dependent diabetes, obesity, neoplasm or hyperamylinemia.

The agouti gene composition (e.g, an agouti transgene, an agouti gene cassette, or an isolated agouti gene comprised within a vector) is preferably introduced into the animal, or an ancestor (i e., an ascendant) of the animal, at an early embryonic stage (i.e. preferably the one-cell, or fertilized oocyte, stage, and generally not later than about the 8-cell stage). The agouti gene preferably is a mammalian gene, and is identical to, or substantially homologous with (i.e. greater than 50% homologous in terms of encoded amino acid sequence) a naturally occurring vertebrate agouti gene or portion thereof or their vertebrate counterparts, preferably the murine agouti gene or the human agouti gene homolog (i.e. counterpart). Alternatively, the gene composition may be a vertebrate-derived gene or sequence thereof, or even a substantially homologous gene isolated from non-vertebrate sources such as invertebrates, plants, virus, protozoas, bacteria or the like, so long as the gene functions in an equivalent manner to the mammalian agouti genes disclosed herein, and so long as the gene comprises a nucleotide sequence which is substantially homologous to, one or more of the nucleotide sequences disclosed in SEQ ID NO:1 or SEQ ID NO:3, herein. Likewise, preferred polypeptides of the invention are those which are identical to, or substantially homologous to, one or more of the polypeptides disclosed in SEQ ID NO:2 or SEQ ID NO:4.

In another embodiment, the invention provides novel DNA and protein compositions comprising a mammalian agouti protein or peptide. Also provided are methods for the preparation, detection and use of these proteins and nucleic acid segments encoding them.

The present invention relates to isolated agouti protein. Preferably, the agouti protein of the present invention are substantially homologous to, and most preferably functionally equivalent to, the native agouti protein. By "functionally equivalent" as used throughout the specification and claims, it is meant that the compositions are capable of promoting the development of diabetes, hyperamylinemia, tumors and obesity in animals. By "substantially homologous" as used throughout the ensuing specification and claims, is meant a degree of homology in the amino acid sequence to the native agouti protein. Preferably the degree of homology is in excess of 50%, preferably in excess of 70%, of particular interest are proteins being at least of 90% homologous with the native agouti protein.

In one embodiment the proteins or fragment thereof or analogs are those proteins or fragments thereof that are encoded by the agouti gene. Of particular interest are proteins encoded by an agouti gene having the sequence of SEQ ID NO:1 or SEQ ID NO:3.

It is contemplated that additions, substitutions or deletions of discrete amino acids or of discrete sequences of amino acids may be made to alter the biological activity of the agouti proteins. The proteins may be naturally occurring or may be made by recombinant methods or chemically synthesized using methods known in the art for peptide synthesis.

Another embodiment of the invention concerns a method of detecting a nucleic acid segment comprising an agouti or agouti-related gene. This method generally involves contacting a population of nucleic acid segments suspected of containing an agouti or agouti-related gene with an agouti composition described herein under conditions effective to allow binding of the agouti composition to the gene, and detecting the bound complex.

Another embodiment of the invention relates to a method of identifying an agouti or agouti-related protein or peptide. This method generally involves contacting a sample suspected of containing an agouti or agouti-related protein or peptide with an agouti-specific antibody composition under conditions effective to allow binding of the protein or peptide and the antibody, and detecting the bound complex.

In yet another embodiment, there is provided a method for the production of an antibody that binds immunologically to a mammalian agouti or agouti-related protein or peptide. This method generally comprises administering to an animal an immunologically-effective amount of an agouti protein or peptide composition. In one such method, coadministration of an adjuvant to the animal is contemplated to be particularly useful in producing an immune response in the animal, and the formation of antibodies specific for an agouti protein or peptide.

Methods Employing Agouti Compositions

The polynucleotides and proteins of the present invention may be used to identify molecules that control agouti. This can be achieved by ectopic expression (i.e., expression of the gene where it is normally not expressed) in cell culture studies and in transgenic mice. Moreover, the gene may also be used to screen (using a yeast two hybrid system, protein-protein interactions, or by immunoassay) for the proteins that interact with agouti or that regulate agouti expression or function. The nucleic acid compositions of the invention may also be used to identify regulatory sequences that control agouti expression in cells by DNA transfection studies and generation of transgenic mammal lines such as transgenic mice.

Another aspect of the invention is a method for the manufacture of a recombinant protein which is encoded by a DNA sequence in which expression of the gene product is associated with the development of diabetes, obesity, hyperamylinemia and neoplasms in animals. In particular, this invention relates to a method for the manufacture of a recombinant protein encoded by the agouti gene, counterpart genes, or by its functionally equivalent nucleic acid sequences, or analogs. It is a further object of this invention to provide a method for the manufacture of analogs of the protein which is encoded by DNA sequences in which expression of the gene product is associated with the development of diabetes, obesity, hyperamylinemia and neoplasms in animals.

Agouti-Encoding Nucleic Acid Compositions

The invention provides nucleic acid sequences encoding an agouti protein. As used herein, an "agouti gene" means a nucleic acid sequence encoding an agouti protein or peptide. Preferred agouti genes include mammalian agouti genes, and in particular those from humans. A preferred nucleic acid sequence encoding an agouti gene is the nucleotide sequence of SEQ ID NO:1 or variants or active fragments thereof.

It is expected that the genes encoding agouti proteins will vary in nucleic acid sequence from species to species, and even from strain to strain or cell line to cell line within a species, but that the variation in nucleic acid sequence will not preclude hybridization between sequences encoding the agouti proteins of various species, cell lines, and strains under moderate to strict hybridization conditions. It is also contemplated that the genes encoding agouti proteins from various species may vary in nucleic acid sequences, but that the variation will not preclude hybridization between sequences encoding an agouti protein from various species, cell lines and strains under moderate to stringent hybridization conditions.

As used herein, a variant of an agouti protein means any polypeptide encoded, in whole or in part, by a nucleic acid sequence which hybridizes under moderate to stringent hybridization conditions to the nucleic acid sequence of SEQ ID NO:1 or SEQ ID NO:3, which encodes the agouti protein isolated from murine and human cell lines, respectively.

One of skill in the art will understand that variants of agouti proteins include those proteins encoded by nucleic acid sequences which may be amplified using one or more of the agouti nucleic acid sequences disclosed herein, and particularly the sequences in SEQ ID NO:1 and SEQ ID NO:3.

In related embodiments, the invention also comprises variants of agouti proteins and nucleic acid segments encoding agouti proteins, in particular, the agouti genes from mammalian species including human and murine agouti and agouti-related proteins.

Aspects of the invention concern the identification of such protein and peptide variants using diagnostic methods and kits described herein. In particular, methods utilizing agouti gene sequences as nucleic acid hybridization probes and/or anti-agouti antibodies in western blots or related analyses are useful for the identification of other agouti and agouti-related polypeptides and polynucleotides which encode them. The identity of potential variants of agouti proteins may also be confirmed by transcriptional assays as described herein. In preferred embodiments, an agouti protein is encoded by a nucleic acid sequence having the sequence of SEQ ID NO:1 or SEQ ID NO:3, or a sequence which hybridizes to the sequence of SEQ ID NO:1 or SEQ ID NO:3

An agouti polypeptide may be defined as a protein or peptide which comprises a contiguous amino acid sequence from SEQ ID NO:2 or SEQ ID NO:4, or which protein comprises the entire amino acid sequence of SEQ ID NO:2 or SEQ ID NO:4, or a polypeptide encoded by a sequence identical to, or substantially homologous to the polynucleotide sequence of SEQ ID NO:1or SEQ ID NO:3, or a polypeptide that is encoded by a nucleotide sequence which hybridizes to the sequence of SEQ ID NO:1 or SEQ ID NO:3 under conditions of high to moderate stringency. Preferably, an agouti or agouti-related polypeptide will have at least about 65% or greater sequence homology with the sequence of SEQ ID NO:2 or SEQ ID NO:4, and more preferably, will have at least about 75% or greater sequence homology with the sequence of SEQ ID NO:2 or SEQ ID NO:4, and more preferably still, will have at least about 85% or greater sequence homology with the sequence of SEQ ID NO:2 or SEQ ID NO:4. In all cases, however, the agouti and agouti-related polypeptides of the present invention will comprise amino acid sequences which are at least about 70% homologous with the sequence of SEQ ID NO:2 or SEQ ID NO:4, and more preferably, are at least about 80% homologous with the sequence of SEQ ID NO:2 or SEQ ID NO:4, and more preferably still, are at least about 90% homologous with the sequence of SEQ ID NO:2 or SEQ ID NO:4.

Likewise, a gene which encodes an agouti or agouti-related polypeptide will have at least about 65% or greater sequence homology with the nucleotide sequence of SEQ ID NO:1 or SEQ ID NO:3, and more preferably, will have at least about 75% or greater sequence homology with the nucleotide sequence of SEQ ID NO:1 or SEQ ID NO:3, and more preferably still, will have at least about 85% or greater sequence homology with the nucleotide sequence of SEQ ID NO:1 or SEQ ID NO:3. In all cases, it is contemplated that genes encoding agouti or agouti-related polypeptides of the present invention will comprise nucleotide sequences which are at least about 70% homologous with the sequence of SEQ ID NO:1 or SEQ ID NO:3, and more preferably, are at least about 80% homologous with the nucleotide sequence of SEQ ID NO:1 or SEQ ID NO:3, and more preferably still, are at least about 90% homologous with the nucleotide sequence of SEQ ID NO:1 or SEQ ID NO:3.

In the present invention, an agouti protein composition is also understood to comprise one or more polypeptides that are immunologically reactive with antibodies generated against an agouti protein, particularly a protein having the amino acid sequence disclosed in SEQ ID NO:2 or SEQ ID NO:4; or the protein encoded by the agouti nucleic acid sequence disclosed in SEQ ID NO:1 or SEQ ID NO:3, or to active fragments, or to variants thereof.

Likewise, an agouti protein composition of the present invention is understood to comprise one or more polypeptides that are capable of eliciting antibodies that are immunologically reactive with one or more agouti proteins encoded by one or more contiguous agouti nucleic acid sequences contained in SEQ ID NO:1 or SEQ ID NO:3, or to active fragments, or to strain variants thereof, or to one or more nucleic acid sequences which hybridize to one or more of these sequences under conditions of moderate to high stringency. Particularly preferred polypeptides comprise at least a ten or more contiguous amino acid sequence from SEQ ID NO:2 or SEQ ID NO:4.

As used herein, an active fragment of an agouti protein includes a whole or a portion of an agouti protein which is modified by conventional techniques, e.g., mutagenesis, or by addition, deletion, or substitution, but which active fragment exhibits substantially the same structure and function as a native agouti protein as described herein.

Other aspects of the present invention concern isolated nucleic acid segments and recombinant vectors encoding one or more agouti proteins, in particular, the agouti protein from mammalian, and preferably, human or murine sources, and the creation and use of recombinant host cells through the application of DNA technology, that express one or more agouti-derived gene products. As such, the invention concerns nucleic acid segments comprising an isolated gene that encodes an agouti protein or peptide that includes an amino acid sequence essentially as set forth by a contiguous sequence from SEQ ID NO:2 or SEQ ID NO:4, or alternatively an mRNA species transcribed from such a gene which is subsequently translatable into a polypeptide sequence which comprises, or is substantially homologous to, an amino acid sequence such as the one found in SEQ ID NO:2 or SEQ ID NO:4. These nucleic acid segments are represented by those that include an agouti nucleic acid sequence essentially as set forth by a contiguous sequence from SEQ ID NO:1 or SEQ ID NO:3.

Regarding the novel agouti-encoding nucleic acid segments, the present invention encompasses nucleic acid segments, that can be isolated from virtually any source, that are free from total genomic DNA and that encode one or more proteins having agouti or agouti-like activity as described herein. In particular, RNA and DNA segments encoding one or more agouti or agouti-related polypeptide species may also encode proteins, polypeptides, subunits, functional domains, and the like.

As used herein, the term "DNA segment" refers to a DNA molecule that has been isolated free of total genomic DNA of a particular species. Therefore, a DNA segment encoding an agouti protein refers to a DNA segment that contains one or more agouti coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a nucleic acid segment comprising an isolated or purified agouti gene refers to a nucleic acid segment including agouti coding sequences and, in certain aspects, regulatory sequences, isolated substantially away from other naturally occurring genes or protein encoding sequences. Preferably the sequence encodes an agouti protein, and more preferably, comprises an agouti gene, in particular, an agouti protein or an agouti gene from a human cell line or a murine cell line. In this respect, the term "gene" is used for simplicity to refer to a functional protein, polypeptide or peptide encoding unit. As will be understood by those in the art, this functional term includes both genomic sequences, extra-genomic and plasmid-encoded sequences and smaller engineered gene segments that express, or may be adapted to express, proteins, polypeptides or peptides. Such segments may be naturally isolated, or modified synthetically by the hand of man.

"Isolated substantially away from other coding sequences" means that the gene of interest, in this case, a gene encoding an agouti protein, forms the significant part of the coding region of the DNA segment, and that the DNA segment does not contain large portions of naturally-occurring coding DNA, such as large chromosomal fragments or other functional genes or polypeptide coding regions. Of course, this refers to the DNA segment as originally isolated, and does not exclude genes or coding regions later added to the segment by the hand of man.

In particular embodiments, the invention concerns isolated nucleic acid segments and recombinant vectors incorporating nucleic acid sequences that encode an agouti protein or peptide species that comprises a contiguous amino acid sequence from SEQ ID NO:2 or SEQ ID NO:4, or biologically-functional equivalents thereof. In other particular embodiments, the invention concerns isolated DNA segments and recombinant vectors incorporating DNA sequences that comprises a sequence essentially as set forth in SEQ ID NO:1 or SEQ ID NO:3, or a biologically-functionalvariant thereof.

The term "a sequence essentially as set forth in SEQ ID NO:1 or SEQ ID NO:3" means that the sequence substantially corresponds to a portion of the DNA sequence listed in SEQ ID NO:1 or SEQ ID NO:3, and has relatively few nucleotides that are not identical to, or a biologically functional equivalent of, the nucleic acid sequence of SEQ ID NO:1 or SEQ ID NO:3. Such nucleotide sequences are also considered to be essentially as those disclosed herein when they encode essentially the same amino acid sequences as disclosed, or that they encode biologically functional equivalent amino acids tot hose as disclosed herein. In particular, preferred nucleotide sequences are those which encode the amino acid sequence of SEQ ID NO:2 or SEQ ID NO:4, or biologically functional equivalents, and substantially homologous sequences thereof.

The term "biologically functional equivalent" is well understood in the art and is further defined in detail herein (e.g., see Illustrative Embodiments). Accordingly, sequences that have between about 70% and about 80%; or more preferably, between about 81% and about 90%; or even more preferably, between about 91% and about 99%; of amino acids that are identical or functionally equivalent to the amino acids disclosed herein, will be sequences that are "essentially as set forth in SEQ ID NO:2 or SEQ ID NO:4".

In certain other embodiments, the invention concerns isolated DNA segments and recombinant vectors that include within their sequence a nucleic acid sequence essentially as set forth in SEQ ID NO:1 or SEQ ID NO:3. The term "essentially as set forth in SEQ ID NO:1 or SEQ ID NO:3" is used in the same sense as described above and means that the nucleic acid sequence substantially corresponds to a portion of SEQ ID NO:1 or SEQ ID NO:3, and has relatively few nucleotides residues that are not identical, or functionally equivalent, to the nucleotide residues of SEQ ID NO:1 or SEQ ID NO:3. Again, DNA segments that encode proteins exhibiting an agouti protein-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of the polypeptide's biological agouti activity where protein expression is concerned. The addition of terminal sequences particularly applies to nucleic acid sequences that may, for example, include various non-coding sequences flanking either of the 5' or 3' portions of the coding region or may include various upstream or downstream regulatory or structural genes.

Naturally, the present invention also encompasses DNA segments that are complementary, or essentially complementary, to the sequence set forth in SEQ ID NO:1 or SEQ ID NO:3. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3, under relatively stringent conditions such as those described herein.

The nucleic acid segments of the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1 or SEQ ID NO:3, such as about 14 nucleotides, and that are up to about 10,000 or about 5,000 base pairs in length, with segments of about 3,000 being preferred in certain cases. DNA segments with total lengths of about 2,000, about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid sequence disclosed in SEQ ID NO:1 or SEQ ID NO:3 or to the amino acid sequence disclosed in SEQ ID NO:2 or SEQ ID NO:4. Recombinant vectors and isolated DNA segments may therefore variously include the agouti coding regions themselves, coding regions bearing selected alterations or modifications in the basic coding region, or they may encode larger polypeptides that nevertheless include an agouti protein coding region or may encode biologically functional equivalent proteins or peptides that have variant amino acids sequences.

The DNA segments of the present invention encompass biologically functional equivalent agouti proteins and agouti-derived peptides, in particular those agouti proteins isolated from mammals, and particularly humans and from mice. DNA segments isolated from mammalian species which are homologous to agouti-encoding nucleic acid sequences are particularly preferred for use in the methods disclosed herein. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the agouti coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter or an enhancer. The promoter (or enhancer) may be in the form of the promoter or enhancer that is naturally associated with an agouti protein gene, as may be obtained by isolating the 5' non-coding sequences located upstream of the coding segment, for example, using recombinant cloning and/or PCR™ technology, in connection with the compositions disclosed herein. The enhancer may be obtained by isolating the 5' non-coding sequence located upstream of the coding sequence; by isolating the 3' non-coding sequence located downstream of the coding sequences; or by isolating one or more intronic sequences located within the gene that contain one or more enhancer regions, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an agouti protein gene in its natural environment. Such promoters may include agouti promoters themselves, or promoters normally associated with other genes, and in particular other transcription factor genes, or promoters isolated from any bacterial, viral, eukaryotic, or mammalian cell. Naturally, it will be important to employ a promoter that effectively directs the expression of the agouti-encoding DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides.

Prokaryotic expression of nucleic acid segments of the present invention may be performed using methods known to those of skill in the art, and will likely comprise expression vectors and promotor sequences such as those provided by tac, ara, trp, lac, lacUV5 or T7.

When expression of an agouti polypeptide is desired in eukaryotic cells, a number of expression systems are available and known to those of skill in the art. An exemplary eukaryotic promoter system contemplated for use in high-level expression is the Pichia expression vector system available from Pharmacia LKB Biotechnology.

In connection with expression embodiments to prepare one or more recombinant agouti proteins or agouti-derived peptides, it is contemplated that longer DNA segments will most often be used, with DNA segments encoding the entire agouti protein or one or more functional domains, epitopes, ligand binding domains, subunits, etc. therefore being most preferred. However, it will be appreciated that the use of shorter DNA segments to direct the expression of an agouti protein or an agouti-derived peptide or epitopic core region, such as may be used to generate anti-agouti antibodies, also falls within the scope of the invention. DNA segments that encode peptide antigens from about 15 to about 100 amino acids in length, or more preferably, from about 15 to about 50 amino acids in length are contemplated to be particularly useful.

The agouti gene and DNA segments derived therefrom may also be used in connection with somatic expression in an animal or in the creation of a transgenic animal, and in particular a transgenic mammal such as a mouse. Again, in such embodiments, the use of a recombinant vector that directs the expression of the full-length or active agouti polypeptide is particularly contemplated. Expression of agouti transgenes in animals is particularly contemplated to be useful in the production of anti-agouti antibodies and the regulation or modulation of agouti expression or activity in vivo.

Probes and Primers for Agouti Gene Segments

In addition to their use in directing the expression of an agouti protein, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:1 or SEQ ID NO:3 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to agouti-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15, 16, 17, 18, 19, 20 or even 25, 30, 35, 40, 45, or 50, or even of 100–200 nucleotides or so, identical or complementary to SEQ ID NO:1 or SEQ ID NO:3 are particularly contemplated as hybridization probes for use in, e.g., Southern and Northern blotting. This would allow an agouti polypeptide or regulatory gene product to be analyzed, both in diverse tissues, cell types and also in various cell lines, etc. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 16 or 17 or so and up to and including about 80, 90, or 100 or nucleotides, but larger contiguous complementarily stretches may be used, according to the length complementary sequences one wishes to detect.

The use of a hybridization probe of about 17 to about 25 or 30 or so nucleotides in length allows the formation of a duplex molecule that is both stable and selective. Molecules having contiguous complementary sequences over stretches greater than about 17 or 18 or 19 or so bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 35 or so contiguous nucleotides, or even longer where desired.

Hybridization probes may be selected from any portion of any of the sequences disclosed herein. All that is required is to review the sequence set forth in SEQ ID NO:1 or SEQ ID NO:3, or to any continuous portion of the sequence, from about 17 to about 25 or 30 or so nucleotides in length up to and including the full length sequence, that one wishes to utilize as a probe or primer. The choice of probe and primer sequences may be governed by various factors, such as, by way of example only, one may wish to employ primers from towards the termini of the total sequence.

The process of selecting and preparing a nucleic acid segment that includes a contiguous sequence from within SEQ ID NO:1 or SEQ ID NO:3, may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of the entire agouti gene or gene fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating related agouti-encoding genes.

Of course, for some applications, for example, where one desires to prepare mutants employing a mutant primer strand hybridized to an underlying template or where one seeks to isolate one or more agouti-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

The present invention provides methods capable of detecting nucleic acid sequences associated with a gene in which expression of the gene product correlates with the development of diabetes, hyperamylinemia, neoplasms and obesity in animals, which comprises a) providing a test sample comprising nucleic acids isolated from a test animal specimen, b) providing at least one pair of single stranded oligonucleotide primers selected so that the oligonucleotides of the pair are complementary to the 5' and 3' ends of one of double stranded cDNA nucleic acid sequences associated with the mRNA from the gene, c) combining the primer pair with the test sample under conditions such that the primer pair will hybridize sufficiently specifically to its nucleic acid sequence, d) treating the hybridized primers under conditions such that primer extension products are simultaneously synthesized for all sequences to which a primer is hybridized, e) repeating steps c) and d) until the nucleic acid sequences present are sufficiently amplified to be detected, and f) detecting the amplified nucleic acid sequences.

Recombinant Vectors Expressing Agouti-Derived Epitopes

A particular aspect of this invention provides novel ways in which to utilize recombinant agouti-derived peptides, nucleic acid segments encoding these peptides, recombinant vectors and transformed host cells comprising agouti-derived DNA segments. As is well known to those of skill in the art, many such vectors and host cells are readily available, one particular detailed example of a suitable vector for expression in mammalian cells is that described in U.S. Pat. No. 5,168,050, incorporated herein by reference. Other vectors suitable for expression in mammalian cells include, pAcMP3 (Pharmingen, San Diego), pVL1393 (Pharmingen, San Diego), and pSKII+ (Ross et al., 1990). However, there is no requirement that a highly purified vector be used, so long as the coding segment employed encodes a protein or peptide of interest (e.g., an agouti-derived epitopic sequence) and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various regulatory sequences.

After identifying an appropriate epitope-encoding nucleic acid molecule, it may be inserted into any one of the many vectors currently known in the art, so that it will direct the expression and production of the protein or peptide epitope of interest when incorporated into a host cell. In a recombinant expression vector, the coding portion of the DNA segment is positioned under the control of a promoter. The promoter may be in the form of the promoter which is naturally associated with an agouti-encoding nucleic acid segment, as may be obtained by isolating the 5' non-coding sequences located upstream of the coding segment, for example, using recombinant cloning and/or PCR™ technology, in connection with the compositions disclosed herein. Direct amplification of nucleic acids using the PCR™ technology of U.S. Pat. Nos. 4,683,195 and 4,683,202 (each specifically incorporated herein by reference) are particularly contemplated to be useful in such methodologies.

In certain embodiments, it is contemplated that particular advantages will be gained by positioning the agouti-encoding DNA segment under the control of a recombinant, or heterologous, promoter. As used herein, a recombinant or heterologous promoter is intended to refer to a promoter that is not normally associated with an agouti gene segment in its natural environment. Such promoters may include those normally associated with other genes, and/or promoters isolated from any other bacterial, viral, eukaryotic, or mammalian cell. Naturally, it will be important to employ a promoter that effectively directs the expression of the DNA segment in the particular cell containing the vector comprising an agouti epitope-encoding nucleic acid segment.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. For eukaryotic expression, the currently preferred promoters are those such as CMV, RSV LTR, the SV40 promoter alone, and the SV40 promoter in combination with the SV40 enhancer. Prokaryotic expression of agouti nucleic acid segments may be performed using methods known to those of skill in the art, and will likely comprise expression vectors and promotor sequences such as those provided by tac, ara, trp, lac, lacUV5 or T7.

Pharmaceutical Compositions

Another aspect of the present invention includes novel compositions comprising isolated and purified agouti-derived peptides, synthetic modifications of these epitopic peptides, peptides derived from site-specifically-mutagenized nucleic acid segments encoding such peptides, and antibodies derived from such peptides. It will, of course, be understood that one or more than one agouti-encoding nucleic acid segment may be used in the methods and compositions of the invention. The nucleic acid delivery methods may thus entail the administration of one, two, three, or more, agouti nucleic acid segments encoding one or more transcription factors. The maximum number of nucleic acid segments that may be applied is limited only by practical considerations, such as the effort involved in simultaneously preparing a large number of nucleic acid segment constructs or even the possibility of eliciting an adverse cytotoxic effect.

The particular combination of nucleic acid segments may be two or more distinct nucleic acid segments; or it may be such that a nucleic acid segment from one gene encoding agouti is combined with another nucleic acid segment and/or another peptide or protein such as a cytoskeletal protein, cofactor targeting protein, chaperone, or other biomolecule such as a vitamin, hormone or growth factor gene. Such a composition may even further comprise one or more nucleic acid segments or genes encoding portions or all of one or more cell-surface receptors or agouti-specific targeting proteins capable of interacting with the agouti polypeptide.

In using multiple nucleic acid segments, they may be combined on a single genetic construct under control of one or more promoters, or they may be prepared as separate constructs of the same or different types. Thus, an almost endless combination of different nucleic acid segments and genetic constructs may be employed. Certain combinations of nucleic acid segments may be designed to, or their use may otherwise result in, achieving synergistic effects on agouti activity and/or stimulation of an immune response against peptides derived from translation of such agouti nucleic acid segments. Any and all such combinations are intended to fall within the scope of the present invention. Indeed, many synergistic effects have been described in the scientific literature, so that one of ordinary skill in the art would readily be able to identify likely synergistic combinations of nucleic acid segments, or even nucleic acid segment-peptide combinations.

It will also be understood that, if desired, the nucleic acid segment or gene encoding a particular agouti-derived peptide may be administered in combination with further agents, such as, e.g., proteins or polypeptides or various pharmaceutically-active agents. So long as the composition comprises a nucleic acid segment encoding all or portions of an agouti polypeptide, there is virtually no limit to other components which may also be included, given that the additional agents do not cause a significant adverse effect upon contact with the target cells or host tissues. The nucleic acids may thus be delivered along with various other agents as required in the particular instance. The formulation of pharmaceutically-acceptable excipients and carrier solutions are well-known to those of skill in the art, as is the development of suitable dosing and treatment regimens for using the particular compositions herein described in oral, parenteral, and/or intravenous administration and formulation.

Methods of Using Agouti Pharmaceutical Compositions

The agouti pharmaceutical compositions disclosed herein may be delivered in a variety of methods depending upon the particular application. For oral administration, the compositions may be formulated with an inert diluent or with an assimilable edible carrier, or they may be enclosed in hard- or soft-shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate, dispersed in dentifrices, including: gels, pastes, powders and slurries, or added in a therapeutically effective amount to a paste dentifrice that may include water, binders, abrasives, flavoring agents, foaming agents, and humectants.

Alternatively, the agouti pharmaceutical compositions disclosed herein may be administered parenterally, intravenously, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Therapeutic, Diagnostic, and Immunological Kits

The invention also encompasses agouti-derived peptide antigen compositions together with pharmaceutically-acceptable excipients, carriers, diluents, adjuvants, and other components, such as additional peptides, antigens, cell membrane preparations, or even attenuated whole-cell compositions as may be employed in the formulation of particular vaccines.

The polypeptides, antibodies and polynucleotides of the present invention may be supplied in the form of a kit, alone, or in the form of a pharmaceutical composition as described herein.

The administration of the antibodies, polynucleotides, or polypeptides of the present invention may be for therapeutic purpose. The administration of the protein or peptides serves to prevent or attenuate any subsequent disease development associated with the overexpression of the agouti gene product in a mammal. When provided therapeutically, the protein or peptide is provided at (or shortly after) any symptom of disease caused by expression of the agouti gene product or substantially homologous gene product. The therapeutic administration of the immunogen serves to attenuate the disease. It is expected that small peptides homologous to a portion of the agouti gene product may inhibit the function of the fill length gene product.

Using the peptide antigens described herein, the present invention also provides methods of generating an immune response, which methods generally comprise administering to an animal, a pharmaceutically-acceptable composition comprising an immunologically effective amount of an agouti-derived peptide composition. Preferred animals include mammals, and particularly humans. Other preferred animals include murines, bovines, equines, porcines, canines, and felines. The composition may include partially or significantly purified agouti-derived peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 30 and about 100 amino acids in length will often be preferred. The antigenic proteins or peptides may also be combined with other agents, such as other peptides or nucleic acid compositions, if desired.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various therapeutic embodiments.

Further means contemplated by the inventors for generating an immune response in an animal includes administering to the animal, or human subject, a pharmaceutically-acceptable composition comprising an immunologically effective amount of a nucleic acid composition encoding a peptide epitope, or an immunologically effective amount of an attenuated live organism that includes and expresses such a nucleic acid composition. The "immunologically effective amounts" are those amounts capable of stimulating a B cell and/or T cell response.

Immunoformulations of this invention, whether intended for vaccination, treatment, or for the generation of antibodies specific to agouti and related proteins. Antigenic functional equivalents of these proteins and peptides also fall within the scope of the present invention. An "antigenically functional equivalent" protein or peptide is one that incorporates an epitope that is immunologically cross-reactive with one or more epitopes derived from the agouti proteins disclosed. Antigenically functional equivalents, or epitopic sequences, may be first designed or predicted and then tested, or may simply be directly tested for cross-reactivity.

The identification or design of suitable agouti epitopes, and/or their functional equivalents, suitable for use in immunoformulations, vaccines, or simply as antigens (e.g., for use in detection protocols), is a relatively straightforward matter. For example, one may employ the methods of Hopp (as disclosed in U.S. Pat. No. 4,554,101, which is specifically incorporated herein by reference) in the identification and preparation of epitopes from amino acid sequences on the basis of hydrophilicity. These methods, described in several other papers, and software programs based thereon, can also be used to identify epitopic core sequences. For example, Chou and Fasman (1974a,b; 1978a,b; 1979); Jameson and Wolf (1988); Wolf et al. (1988); and Kyte and Doolittle (1982) all address this subject in several scientific publications. The amino acid sequence of these "epitopic core sequences" may then be readily incorporated into peptides, either through the application of peptide synthesis or recombinant technology.

It is proposed that the use of shorter antigenic peptides, e.g., about 25 to about 50, or even about 15 to 25 amino acids in length, that incorporate modified epitopes of an agouti protein will provide advantages in certain circumstances, for example, in the preparation of vaccines or in immunologic detection assays. Exemplary advantages include the ease of preparation and purification, the relatively low cost and improved reproducibility of production, and advantageous biodistribution.

In still further embodiments, the present invention concerns immunodetection methods and associated kits. It is contemplated that the proteins or peptides of the invention may be employed to detect antibodies having reactivity therewith, or, alternatively, antibodies prepared in accordance with the present invention, may be employed to detect agouti proteins or peptides. Either type of kit may be used in the immunodetection of agouti compositions. The kits may also be used in antigen or antibody purification, as appropriate.

In general, the preferred immunodetection methods will include first obtaining a sample suspected of containing an agouti-reactive antibody, such as a biological sample from a patient, and contacting the sample with a first agouti protein or peptide under conditions effective to allow the formation of an immunocomplex (primary immune complex). One then detects the presence of any primary immunocomplexes that are formed.

Contacting the chosen sample with the agouti-derived protein or peptide under conditions effective to allow the formation of (primary) immune complexes is generally a matter of simply adding the protein or peptide composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies and the remaining bound label is then detected.

For diagnostic purposes, it is proposed that virtually any sample suspected of containing either the antibodies of interest may be employed. Exemplary samples include clinical samples obtained from a patient such as blood or serum samples, bronchoalveolar fluid, ear swabs, sputum samples, middle ear fluid or even perhaps urine samples may be employed. This allows for the diagnosis of meningitis, otitis media, pneumonia, bacteremia and postpartum sepsis. Furthermore, it is contemplated that such embodiments may have application to non-clinical samples, such as in the titering of antibody samples, in the selection of hybridomas, and the like. Alternatively, the clinical samples may be from veterinary sources and may include such domestic animals as cattle, sheep, and goats. Samples from feline, canine, and equine sources may also be used in accordance with the methods described herein.

In related embodiments, the present invention contemplates the preparation of kits that may be employed to detect the presence of agouti-derived epitope-specific antibodies in a sample. Generally speaking, kits in accordance with the present invention will include a suitable protein or peptide together with an immunodetection reagent, and a means for containing the protein or peptide and reagent.

The immunodetection reagent will typically comprise a label associated with an agouti protein or peptide, or associated with a secondary binding ligand. Exemplary ligands might include a secondary antibody directed against the first agouti protein or peptide or antibody, or a biotin or avidin (or streptavidin) ligand having an associated label. Detectable labels linked to antibodies that have binding affinity for a human antibody are also contemplated, e.g., for protocols where the first reagent is an agouti peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

Recombinant Host Cells and Vectors

Particular aspects of the invention concern the use of plasmid vectors for the cloning and expression of recombinant peptides, and particular peptides incorporating either native, or site-specifically mutated agouti epitopes. The generation of recombinant vectors, transformation of host cells, and expression of recombinant proteins is well-known to those of skill in the art. Prokaryotic hosts are preferred for expression of the peptide compositions of the present invention. Some examples of prokaryotic hosts are *E. coli* strains JM101, XL1-Blue™, RR1, LE392, B, $\chi^{1776}$ (ATCC 31537), and W3110 (F⁻, λ⁻, prototrophic, ATCC 273325). Enterobacteriaceae species such as *Salmonella typhimurium* and

*Serratia marcescens,* and other Gram-negative hosts such as various Pseudomonas species may also find utility in the recombinant expression of genetic constructs disclosed herein.

Alternatively, Gram-positive cocci such as *S. epidermidis, S. zooepidemicus, S. xylosus,* and *S. hominus,* and bacilli such as *Bacillus subtilis* may also be used for the expression of these constructs and the isolation of native or recombinant peptides therefrom.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be typically transformed using vectors such as pBR322, or any of its derivatives (Bolivar et al., 1977). pBR322 contains genes for ampicillin and tetracycline resistance and thus provides easy means for identifying transformed cells. pBR322, its derivatives, or other microbial plasmids or bacteriophage may also contain, or be modified to contain, promoters which can be used by the microbial organism for expression of endogenous proteins. Other vectors include pGEM4 (Promega), EMBL3 (Stratagene), pBluescript II (Stratagene), and pCRII (Invitrogen).

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). The use of recombinant and native microbial promoters is well-known to those of skill in the art, and details concerning their nucleotide sequences and specific methodologies are in the public domain, enabling a skilled worker to construct particular recombinant vectors and expression systems for the purpose of producing compositions of the present invention.

In addition to the preferred embodiment expression in prokaryotes, eukaryotic microbes, such as yeast cultures may also be used in conjunction with the methods disclosed herein. *Saccharomyces cerevisiae,* or common baker's yeast is the most commonly used among eukaryotic microorganisms, although a number of other species may also be employed for such eukaryotic expression systems. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3N of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Agouti Antibody Composition

The present invention also relates to antibodies, antigen-binding fragments of the antibodies, chimeric antibodies and their functional equivalents that react with a protein or fragment that is encoded by a gene in which expression of the gene product is associated with the development of the following diseases: insulin-independent diabetes, obesity, hyperamylinemia and neoplasms. The antibodies or their functional equivalents may be used as therapeutic agents in preventing or treating such diseases in animals. The antibodies or their functional equivalents may be used in immunoassays. Such assays are useful for monitoring the disease progression and are useful for monitoring the efficacy us of therapeutic agents during the course of treatment of insulin-independent diabetes, obesity, hyperamylinemia and neoplasms.

Reference to antibodies throughout the specification includes whole polyclonal and monoclonal antibodies, and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. An antibody can be a polyclonal or a monoclonal antibody. In a preferred embodiment, an antibody is a polyclonal antibody. Means for preparing and characterizing antibodies are well known in the art (See, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for agouti and agouti-derived peptides and/or epitopes may be prepared using conventional immunization techniques, as will be generally known to those of skill in the art. A composition containing antigenic agouti epitopes can be used to immunize one or more experimental animals, such as a rabbit or mouse, which will then proceed to produce specific antibodies against epitope-containing agouti peptides. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i.e., B-cells of different lineage. Monoclonal antibodies, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

To obtain monoclonal antibodies, one would also initially immunize an experimental animal, often preferably a mouse, with an agouti protein or agouti-derived peptide or epitope-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting monoclonal antibodies against agouti-derived epitopes. Hybridomas which produce monoclonal antibodies to the selected antigens are identified using standard techniques, such as ELISA and Western blot methods. Hybridoma clones can then be cultured in liquid media and the culture supernatants purified to provide the agouti and agouti-derived epitope-specific monoclonal antibodies.

It is proposed that the monoclonal antibodies of the present invention will find useful application in standard immunochemical procedures, such as ELISA and Western blot methods, as well as other procedures which may utilize antibody specific to the agouti or agouti-derived epitopes.

Additionally, it is proposed that monoclonal antibodies specific to the particular agouti-derived peptide may be utilized in other useful applications. For example, their use in immunoabsorbent protocols may be useful in purifying native or recombinant peptide species or synthetic or natural variants thereof.

In general, both poly- and monoclonal antibodies against these peptides may be used in a variety of embodiments. For example, they may be employed in antibody cloning protocols to obtain cDNAs or genes encoding the peptides disclosed herein or related proteins. They may also be used in inhibition studies to analyze the effects of agouti-derived peptides in cells or animals. Anti-agouti epitope antibodies will also be useful in immunolocalization studies to analyze the distribution of agouti proteins in various cellular events, for example, to determine the cellular or tissue-specific distribution of the agouti peptide under different physiological conditions. A particularly useful application of such antibodies is in purifying native or recombinant agouti or agouti-derived peptides, for example, using an antibody affinity column. The operation of all such immunological techniques will be known to those of skill in the art in light of the present disclosure.

In addition to use as a therapeutic agent, the compositions can be used to prepare antibodies to agouti protein. The antibodies also can be used directly as therapeutic agents. The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/ human hybridomas. Humanized antibodies (i.e. nonimmunogenic in a human) may be produced, for example, by replacing an immunogenic portion of an antibody with a corresponding, but nonimmunogenic portion (i.e. chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Eur. Pat. Appl. Publ. No EP 184187; U.S. Pat. No. 4,935,496; Eur. Pat. Appl. Publ. No. EP 171496; Eur. Pat. Appl. Publ. No. EP 173494; Intl Pat. Appl. Publ. No. WO 86/01533; Cabilly et al., 1987; Nishimura et al., 1987; Wood et al., 1985; Shaw et al., 1988, all incorporated herein by reference). General reviews of "humanized" chimeric antibodies are provided by Morrison, 1985 and by Oi et al., 1986.

Suitable "humanized" antibodies can be alternatively produced by CDR or CEA substitution (Jones et al., 1986; Verhoeyan et al., 1988; Biedler et al., 1988, all incorporated herein by reference).

The antibodies or antigen binding fragments may also be produced by genetic engineering. The technology for expression of both heavy and light cain genes in *E. coli* is the subject of Intl. Pat. Appl. Publ. No. WO 90/1443, Intl. Pat. Appl. Publ. No. WO 90/1443, and Intl. Pat. Appl. Publ. No. WO 90/14424, as well as in Huse et al. (1989).

It may be preferable to use monoclonal antibodies. Monoclonal anti-agouti antibodies or anti-idiotype antibodies can be produced as follows. The spleen or lymphocytes from an immunized animal are removed and immortalized or used to prepare hybridomas by methods known to those skilled in the art. (Goding, 1983). To produce a human-human hybridoma, a human lymphocyte donor is selected. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. Cells producing antibodies of the desired specificity are selected. Such antibodies are useful in immunoassays for diagnosing or prognosing of diseases associated with expression of the agouti gene product.

Expression of Recombinant Proteins

Recombinant clones expressing the agouti-encoding nucleic acid segments may be used to prepare purified peptide antigens as well as mutant or variant protein species in significant quantities. The selected antigens, and variants thereof, are proposed to have significant utility in regulating, modulating, altering, changing, increasing, and/or decreasing agouti activity. For example, it is proposed that these antigens, or peptide variants, or antibodies against such antigens may be used in immunoassays to detect agouti antibodies or as vaccines or immunotherapeutics.

Since antibodies, including monoclonal antibodies, to the agouti epitopes of the present invention are described herein, the use of immunoabsorbent techniques to purify these peptides, or their immunologically cross-reactive variants, is also contemplated. It is proposed that useful antibodies for this purpose may be prepared generally by the techniques disclosed hereinbelow, or as is generally known in the art for the preparation of monoclonals (see, e.g., U. S. Pat. Nos. 4,514,498 and 4,740,467), and those reactive with the desired protein or peptides selected.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence.

Antibidy Compositions and Formulations Thereof

Means for preparing and characterizing antibodies are well known in the art (see, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well knovn in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polycloral antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No.

4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol./vol.) PEG, by Gefter et al. (1977). The use of electrically induced fusion methods is also appropriate (Goding, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azasenne. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzynme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines may also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinty chromatography.

Epitopic Core Sequences

The present invention is also directed to agouti protein or peptide compositions, free from total cells and other peptides, which comprise a purified agouti protein or peptide which incorporates an epitope that is immunologically cross-reactive with one or more of the agouti-specific antibodies of the present invention.

As used herein, the term "incorporating an epitope(s) that is immunologically cross-reactive with one or more anti-agouti antibodies" is intended to refer to a peptide or protein antigen which includes a primary, secondary or tertiary structure similar to an epitope located within an agouti polypeptide. The level of similarity will generally be to such a degree that monoclonal or polyclonal antibodies directed against the agouti polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of agouti epitopes and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of from about 5 to about 25 amino acids in length, and more preferably of from about 8 to about 20 amino acids in length. It is proposed that shorter antigeric peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/inmmunogenic core sequences which result in a "universal" epitopic peptide directed to agouti-related sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on an agouti-specific antibody. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 or 6 amino acids in length, with sequences on the order of about 8 up to and including about 25 or so amino acids being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity.

Moreover, numerous computer programs are available for use in predicting antigenic portions of proteins (see e.g., Jameson and Wolf, 1988; Wolf et al., 1988). Computerized peptide sequence analysis programs (e.g., DNAStar™ software, DNAStar, Inc., Madison, Wis.) may also be usefull in designing synthetic epitopes and epitope analogs in accordance with the present disclosure.

The agouti peptides provided by this invention are ideal targets for use as vaccines or immunoreagents. In this regard, particular advantages may be realized through the preparation of synthetic agouti peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as an agouti or agouti-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between an agouti protein and any test antigen, one would first label the agouti protein with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to a known antibody. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label.

The reactivity of the labeled antigen, e.g., an agouti-derived peptide, in the absence of any test antigen would be the control high value. The control low value would be obtained by incubating the labeled antigen with an excess of unlabeled antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available pepltide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefintely, e.g., in metered aliquots that may be rehydrated with a predetermined amount of water (preferably distilled) or buffer prior to use.

Methods of Using Agouti Nucleic Acid Sequences

The present invention also encompasses novel oligonucleotide probes useful in methods to amplify nucleic acid sequences, cloning of a gene or portions thereof and detecting the gene in which the expression of the gene product correlates with the development of diabetes hyperamylinemia, neoplasms and obesity in animals. Such probes are also useful in methods of diagnosing or prognosing such diseases. Of interest are probes which are capable of hybridizing to the agouti gene or substantially homologous sequences or portions thereof; or a homologous or counterpart gene in animals, preferably mammals and of particular interest, the human counterpart gene to agouti. The invention further relates to a method for detection of the agouti gene or counterpart genes in animals in biological samples based on selective amplification of gene fragments utilizing primers derived from the agouti genomic or cDNA or substantially homologous sequences.

The invention also relates to the use of single-stranded anti-sense poly- or oligonucleotides derived form the agouti genomic cDNA or substantially homologous sequences to inhibit the expression of the agouti gene or counterpart genes in animals as a means of inhibiting of modulating the diseases; obesity, diabetes, hypernsulinemia and tumors.

The DNA sequence information disclosed herein allows for the preparation of relatively short DNA (or RNA) sequences having the ability to specifically hybridize to nucleic acid sequences encoding portions of the agouti gene. In these aspects, nucleic acid probes of an appropriate length are prepared based on a consideration of the natural sequence and the size of the particular nucleic acid segment used. Such nucleic acid segments may be those of native agouti or agouti-derived, or alternatively, may be DNA sequences which have undergone site-specific mutations to generate any of the novel peptides disclosed herein. The ability of such nucleic acid probes to specifically hybridize to the corresponding agouti nucleic acid sequences lend them particular utility in a variety of embodiments. However, other uses are envisioned, including the expression of protein products, the use of the sequence information for the preparation of mutant species primers, or primers for use in preparing other genetic constructions. Such primers may also be used as diagnostic compositions for the isolation and identification of epitope-encoding nucleic acid segments from proteins related to agouti, and to agouti polypeptides from a variety of species, cell lines, or organisms.

To provide certain of the advantages in accordance with the present invention, the preferred agouti nucleic acid sequences employed for hybridization studies or assays would include sequences that have, or are complementary to, at least an about 14 or 15 to about 20 or so contiguous nucleotide stretch of the sequence as described in SEQ ID NO:1, although sequences of about 30 to about 50 or so nucleotides are also envisioned to be useful. A size of at least about 14 or 15 or even 20 or so nucleotides in length helps to ensure that the fragment will be of sufficient length to form a duplex molecule that is both stable and selective. Molecules having complementary sequences over stretches greater than about 14–15 or 20 bases in length are generally preferred, though, in order to increase stability and selectivity of the hybrid, and thereby improve the quality and degree of specific hybrid molecules obtained. Thus, one will generally prefer to design nucleic acid molecules having agouti-gene-complementary stretches of about 15 to 25 or so nucleotides, or even longer, such as about 30, or about 50, or about 100, or even about 200 or 300 or so nucleotides, where desired. Such fragments may be readily prepared by, for example, directly synthesizing the fragment by chemical means, by application of nucleic acid reproduction technology, such as the PCR™ technology of U.S. Pat. Nos. 4,683,195 and 4,683,202 (each specifically incorporated herein by reference), or by introducing selected sequences into recombinant vectors for recombinant production.

The inventors further contemplate that such nucleic acid segments will have utility in the overexpression of agouti-derived polypeptide epitopes described herein, and the preparation of recombinant vectors containing native and site-specific-mutageninzed DNA segments comprising particular epitope regions from the agouti gene.

The invention will find particular utility as the basis for diagnostic hybridization assays for detecting agouti-specific RNAs or DNAs in clinical samples. Exemplary clinical samples that can be assayed for the presence of agouti or agouti-encoding nucleic acids include middle ear fluid, sputum, bronchoalveolar fluid and the like. Such samples may be of human, murine, equine, bovine, feline, porcine, or canine origins. A variety of hybridization techniques and systems are known that can be used in connection with the hybridization aspects of the invention, including diagnostic assays such as those described in U.S. Pat. No. 4,358,535, incorporated herein by reference. Samples derived from non-human mammalian sources, including animals of economic significance such as domestic farm animals, may also provide the basis for clinical specimens.

Accordingly, the nucleotide sequences of the invention are important for their ability to selectively form duplex molecules with complementary stretches of the nucleic acid segments encoding agouti-derived epitopes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by about 0.02 M to about 0.15 M NaCl at temperatures of about 50° C. to about 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as about 0.15 M to about 0.9 M salt, at temperatures ranging from about 20° C. to about 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated agouti-encoding clones. In particular embodiments, mutant clone colonies growing on solid media that contain variants of the agouti gene could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of these genes may be utilized to identify those clones growing on solid media that contain sequence variants of the entire genes. These clones can then be grown to obtain desired quantities of the variant nucleic acid sequences or the corresponding antigens.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, that are capable of giving a detectable signal. In preferred diagnostic embodiments, one will likely desire to employ an enzyme tag such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., middle ear effusion, bronchoalveolar lavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

Other objects, features and advantages of the present invention will become apparent from the following detailed description. It should be understood, however, that the detailed description and the specific examples, while indicating preferred embodiments of the invention, are given by way of illustrationonly, since various changes and modifications within the spirit and scope of the invention will become apparent to those skilled in the art from this detailed description.

Methods of Producing Transgenic Animals

There are several means by which transgenic animals can be made. One method involves the use of a transfecting retrovirus containing the transgene. Another method involves directly injecting the transgene into the embryo. Yet another method employs the embryonic stem cell methodology known to workers in this field.

Preferably, transcription of the gene is under the control of a promoter sequence different from the promoter sequence controlling transcription of the endogenous coding sequence. Transcription of the gene can also be under the control of a synthetic promoter sequence. The promoter sequence controlling transcription of the gene may be active (i.e. can promote gene expression) in all tissues for example β-actin promoter or may be a tissue specific promoter such as the insulin promoter, which would direct expression to the β-cells within the pancreas. The promoter that controls transcription of the recombinant gene may be of viral origin; example are promoters sometimes derived from mouse mammary tumor virus (MMTV) and cytomegalovirus (CMV).

Introduction of the gene at the fertilized oocyte stage ensures that the gene sequence will be present in the germ cells and somatic cells of the transgenic "founder" animal. (As used herein, founder (abbreviated "F") means the animal into which the gene was originally introduced at the one cell mouse embryo stage.) The presence of the gene sequence in the germ cells of the transgenic founder animal in turn means that some of the founder animal's descendants will carry the gene sequence in germ cells and somatic cells. Introduction of the gene sequence at a later embryonic stage might result in the gene's absence from some somatic cells or germ cells of the founder animal, but the descendants of such an animal that inherit the gene will carry the gene in all of their germ cells and somatic cells.

The transgenic animals of the invention can be used as models to test for agents potentially useful in the treatment of non-insulin-dependent diabetes, obesity, hyperamylinemia and various cancers including neoplasms. The agent to be tested can be administered to an animal of the invention and the disease state monitored. The transgenic animals of the invention can also be used to test a material suspected of promoting non-insulin-dependent diabetes, obesity, hyperamylinemia and neoplasms. The transgenic animals of the present invention are useful for screening potentially diagnostic reagents for the diagnosis or prognosis of diabetes, obesity and cancer in mammals such as humans, or diagnostic reagents which may be predictive of the development of such diseases in an animal.

The transgenic animals of the present invention are also useful in determining the therapeutically effective dose of such therapeutic agents for use in treatment of animals afflicted with diabetes, obesity and cancers, in particular humans so afflicted. Until now, there have been no satisfactory animal models in which these diseases can be made to occur in a reliable and predictable fashion in a substantial proportion of animals in which these agents could be tested, and from which the gene at the mutant locus has been cloned.

The animals of the invention can also be used as a source of cells for cell culture. Cells from the animals may advantageously exhibit desirable properties as cultured cells. Where the promoter sequence controlling transcription of the gene sequence is inducible, cell growth rate and other culture characteristics can be controlled by adding or eliminating the inducing factor.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Shown is the identification of an exon near the distal inversion breakpoint of IslGso. Restriction map of a region of DNA that maps to the agouti locus and is associated with structural alterations in the extreme agouti mutations, IslGso and $a^{5MNU}$. The positions of two DNA probes that lie in close proximity to the distal inversion breakpoint in IslGso and the 2.8-kb deletion in $a^{5MNU}$ are indicated. R, EcoRI; B, BamHI; X, XbaI.

FIG. 1B. Shown is the identification of an exon near the distal inversion breakpoint of IslGso. Identification of a segment of DNA near the distal inversion breakpoint of IslGso that is conserved in genomic DNA from several mammalian species. Probe A in (A) was $^{32}P$ labeled and hybridized to EcoRI(R)- or PstI(P)- digested DNA from hamster, cat, and dog. The extensive smearing in hamster DNA is due to the presence of a rodent-specific repetitive element in probe A. The λ HindIII molecular size standard is shown on the left in kilobases.

FIG. 1C. Shown is the identification of an exon near the distal inversion breakpoint of IslGso. Identification of coding sequence near the distal inversion breakpoint of IslGso by Northern blot analysis. Probe B in (A) was $^{32}P$ labeled and hybridized to poly(A)$^+$ RNA from wild-type skin of a day 4 neonate. The positions of the 28S and 18SrRNA subunits are indicated on the left. Higher molecular size smearing was due to the presence of moderately repetitive sequences in the probe.

FIG. 2. Shown is the nucleotide and predicted amino acid sequence of the cDNA. The putative signal peptide sequence is underscored with a double line and the polyadenylation signal with a single line. The boxed region represents a highly basic domain that has the potential to be phosphorylated at a number of sites designated by PO$_4$. The asterisk denotes a potential N-linked glycosylation site, and cysteine residues are indicated by closed circles. Arrows delimit the boundaries of the four individual exons.

FIG. 3C. Shown is the intro-exon structure of the wild-type locus and two extreme nonagouti mutations. Nucleotide sequence of the distal inversion breakpoint of IslGso and the 5' and 3' deletion breakpoints of $a^{5MNU}$ compared with the wild type. The vertical bars indicate the positions of the DNA breakpoints. The lowercase nucleotides in IslGso represent sequence of the Id gene, and the horizontal lines in $a^{5MNU}$ represent deleted nucleotides.

FIG. 9B. Shown is the molecular analysis of the size-altered $A^y$ transcript. Nucleotide sequence comparison of the wild-type and $A^y$ cDNA clones, and comparison of the 5' end of the $A^y$ cDNA with its corresponding genomic region. The sequence divergence point is positioned with a vertical line and corresponds to the junction between the first and second exons of the wild-type cDNA. Also, at this same junction point, the genomic sequence diverges from the $A^y$ cDNA and is followed by a canonical 5' splice donor (Mount, 1982).

FIG. 10B. Nucleotide sequence comparison of mouse and human exons of the agouti gene; the mouse sequence is shown above, and the human sequence is shown below. Identical nucleotides are represented as dots, different nucleotides are indicated, and an absence of nucleotides is noted as a dash. Actual exon sequences and the sequences of the 5' splice donors and 3' splice acceptors are separated by a space and vertical lines. The proposed translational initiation codons and stop codons are underscored by single lines, and the potential polyadenylylation signals are underscored by double lines.

FIG. 11. Comparison of the amino acid sequence of the mouse agouti gene with that deducted from the homologous regions of human clone h20B1. Shown above is the reported mouse sequence (Bultman et al., 1992); shown below is the human sequence as predicted from the ORF created by the juxtaposition of the regions from FIG. 10A and FIG. 10B that are homologous to the individual agout exons. Identities are represented by dots, and differences are indicated; absences of amino acids are noted as dashes.

FIG. 12A. Assignment of clone h20B1 to human chromosome 20q11.2. Two partial metaphases (Upper, Lower) showing specific double signals by FISH at 20q11.2 (arrows) after hybridization with h20B1 DNA (Left) and the corresponding DAPI-fluorescence pattern of the same metaphases (Right).

FIG. 19A. The 5.2-kb fragment of DNA inserted in the agouti gene in the new dominant yellow mutation ($A^{iapy}$) is an IAP. Genomic restriction map of the IAP inserted in $A^{iapy}$ and the wild-type agouti sequence surrounding the site of integration. The LAP is shown as a rectangle, with the hatched regions representing the two LTRs and the open portion depicting the remainder of the proviral genome. The IAP inserted in aan antisense orientation, 51-bp upstream of the first coding exon, and the insertion resulted in a 6-bp duplication of agouti sequence (underlined) at the site of integration. The estimated total size (5.2-kb) and the diagnostic internal 4-kb HindIII fragment suggest that this IAP is a ($\Delta$) element (Kuff and Lueders, 1988). (B) BamHI; (E) EcoRI; (H) HindIII.

FIG. 19B. The 5.2-kb fragment of DNA inserted in the agouti gene in the new dominant yellow mutation ($A^{iapy}$) is an IAP. Complete nucleotide sequence of the 5' LTR of the IAP inserted in $A^{iapy}$. The boundaries of the U3, repeat (R), and U5 regions are indicated above the sequence. In the U3 region, three enhancers are each underscored with a horizontal line, and the caat box sequence and tata box replacement sequence (gttgt) are shown in bold. Four CpG sites (three HhaI restriction enzyme recognition sites [gcgc] and one HpaII site [ccgg]) are bracketed above and below the sequence.

FIG. 19C. The 5.2-kb fragment of DNA inserted in the agouti gene in the new dominant yellow mutation ($A^{iapy}$) is an IAP. Complete nucleotide sequence of the 3' LTR of the IAP inserted in $A^{iapy}$. The boundaries of the U3, repeat (R), and U5 regions are indicated above the sequence. Shown are the sense strands of both LTRs.

FIG. 26. Expression of the murine agouti peptide. Ten micrograms of medium protein from T. ni cells 48 h after infection of either a wild-type baculovirus or the agouti expression baculovirus was loaded onto a 4–20% SDS/PAGE gel (NOVEX, San Diego, Calif.) and silver-stained. A duplicate gel was transferred to nitrocellulose and probed with either an agouti anti-peptide antibody or preimmune antibody. (Left) Silver-stained gel of the conditioned medium. The agouti polypeptide is not readily apparent. (Right) Western blot of a duplicate gel. The anti-agouti peptide antibody detects a protein of 21-kDa.

FIG. 27A. β-actin promoter-agouti (BAPa) and phosphoglycerate kinase promoter-agouti (PGKPa) transgene expression constructs. The components of the 5.3-kb BAPa construct are indicated. All of the components are from the human β-actin gene except the agouti cDNA and the simian virus 40 polyadenylylation signals. The first /3-actin exon (78-bp) is untranslated, and the 18-actin intron contains the endogenous enhancer and splice acceptor and donor sites.

FIG. 27B. The 1.7-kb PGKPa construct consists of the agouti cDNA under the tranceptional control of the promoter/enhancer region of the mouse Pgk-1 gene from base pair −437 to +65 (McBurney et al., 1991). The polyadenylylation signals are provided by the Pgk-1 3' flanking region. For both constructs, "promoter" refers to the upstream region of the gene that contains the promoter and additional 5' flanking DNA. The mRNAs expected to be expressed from these constructs are indicated below them. Arrows indicate sites of transcription initiation. C, ClaI; H, HindIII; E, EcoRI; B, BamHI; P, PstI.

DESCRIPTION OF ILLUSTRATIVE EMBODIMENTS

Some Advantages of the Invention

Figure 3A:
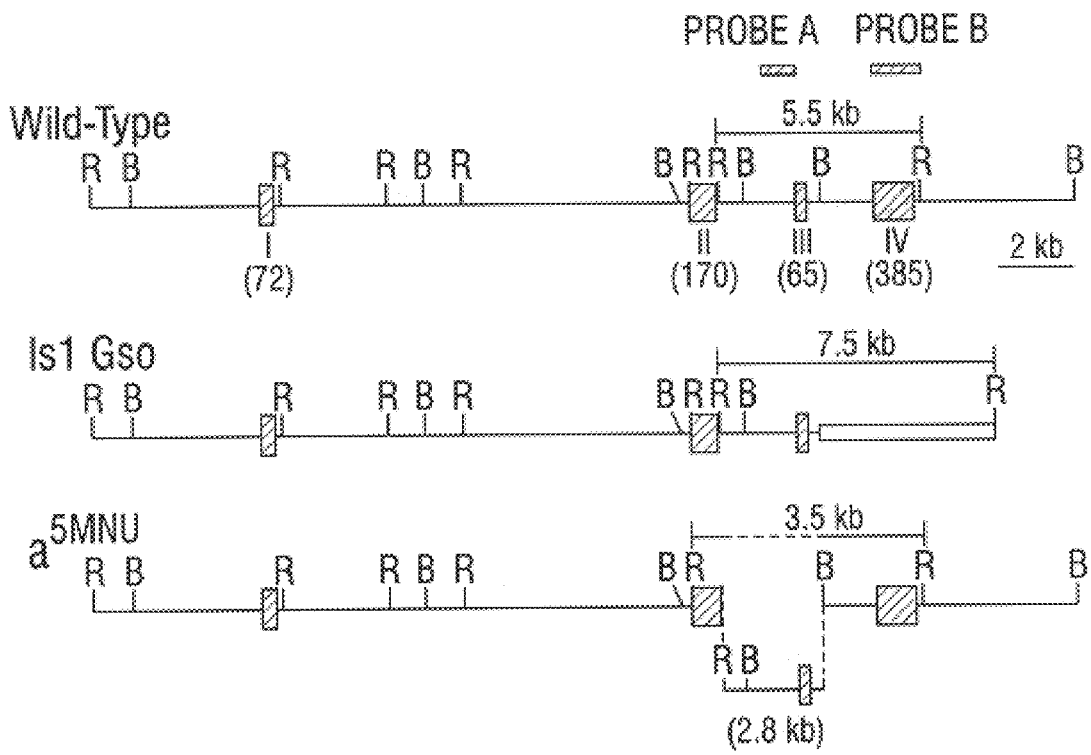
FIG. 3A. Shown is the intro-exon structure of the wild-type locus and two extreme nonagouti mutations. Schematic representation of the genomic structure of the agouti gene in DNA from wild-type, IslGso, and $a^{5MNU}$ mice. The four exons are depicted as closed rectangles, and the introns and flanking sequences are shown as a solid line. The first exon, which is 72-bp long in the cDNA clone, is 8–10-bp longer at its 5' end based on RNAase protection studies. The 3' junction of the last exon corresponds to the 3' end of the cDNA clone, immediately upstream of the poly(A) tract. The precise location of each intron-exon junction was ascertained by identifying where genomic DNA sequences diverged from the cDNA sequence. At each splice junction, the genomic DNA sequence matched the canonical sequence for 5' splice donor and 3' splice acceptor sites (Mount, 1982). The open rectangle in the IslGso schematic represents genomic DNA from the Id gene in the opposite transcriptional orientation relative to agouti. The 2.8-kb intragenic deletion in the $a^{5MNU}$ mutation is depicted by a horizontal dashed line above the mutant locus, with the deleted region shown below the mutant locus. The positions of two probes (A and B) and the sizes of the EcoRI fragments they identify are shown. R, EcoRI; B, BamHI.

The particular uses and advantages of the invention include, but are not limited to: detection and cloning of the gene in which expression of the gene product correlates with the development of diabetes, hyperamylinemia, neoplasms and obesity in animals; detection of the agouti gene and substantially homologous DNA sequences; detection of mutations in the gene; early detection of animals at risk of developing diabetes, obesity, neoplasms, and hyperamylinemia; and early treatment of afflicted animals.

The present invention is useful as a screening method for the detection of the gene in which expression of the gene product correlates with the development of diabetes, hyperamylinemia, neoplasms and obesity in animals, preferably the agouti gene or substantially homologous genes in animals, preferably mammals. The inventive method utilizes amplification of nucleic acid sequences specifically associated with the gene, oligonucleotides or primer pairs, each specific for a nucleic acid sequence of the gene, provide the basis for amplification of the desired nucleic acid sequence. The inventive methods can be used to 1) identify the presence of the gene or 2) to screen for the presence of mutations in the gene.

Agouti Mice

The coat color of the wild-type mouse (and many other mammalian species) results from the formation of a subterminal yellow band in an otherwise black or brown hair shaft, a process that is regulated by the agouti locus in chromosome 2. Unlike many other regions of the mouse genome that regulate coat pigmentation, the agouti locus does not function in a melanocyte-specific manner, but rather elicits its response from within the follicular environment. Specifically, it appears that the agouti locus normally regulates the differential production of black and yellow pigments, by the melanocyte, through some direct or indirect form of intercellular communication.

Many spontaneous and induced mutations have been characterized at the agouti locus, and two of these in particular, $A^y$ (lethal yellow) and $A^{vy}$ (viable yellow), are dominant and have relevance to human health. Both of these mutations exhibit a complex phenotype which includes hyperphagia, increased efficiency of food utilization, obesity, increased muscle mass and body size, hyperinsulinemia, insulin resistance, hyperamylinemia, impaired glucose tolerance, potentiation of responses to tumorigenic stimuli, and enhanced promotion and progression of transformed cells by factors associated with the obesity (reviewed in Wolff et al., 1986; see also Wolff et al., 1987; Gill and Yen, 1991).

The present invention encompasses the cloning and identification of the agouti gene. This gene is approximately 18 kb in length, contains four exons, and gives rise to a 0.8-kb mRNA that has the potential to encode a 131-amino acid secreted protein (Woychik et al., 1990a; Bultman et al., 1991; Bultman et al., 1992). The present invention includes a polypeptide of approximately 131 amino acids in length and approximately 15,000 daltons in molecular size (FIG. 2) and functionally equivalent peptides or fragments thereof. This protein is secreted, since it contains a putative signal peptide at its N-terminus (FIG. 2). In addition, the molecule has several potential phosphorylation sites, a highly basic domain in the middle of the protein, and a cysteine-rich region near its C-terminus. Normally, as expected, the agouti mRNA is only produced within neonatal skin. However, the present invention has shown that the wild-type agouti gene product is ectopically overexpressed in mutants carrying the $A^y$ or $A^{vy}$ alleles (Bultman et al., 1992). It has been shown by the present invention that the ubiquitous expression of the normal agouti gene product correlates with the development of hyperamylinemia, neoplasms, insulin-independent diabetes and obesity and may be directly responsible for the dominant pleiotropic effects associated with $A^y$ and $A^{vy}$ and equivalent mutations in other animals, preferably mammals.

The cloning of the gene of the present invention, is the first and presently the only gene that has been cloned that is directly associated with an obesity/diabetes phenotype in an animal model. Other rodent models for obesity, including the ob/ob and db/db mouse mutants, along with the obese F(a/Fa) Zucker rat, have been studied extensively, and many investigators have been unsuccessful in cloning the genes associated with these mutants. The present methods and probes are useful in isolating and cloning analogous, or counterpart genes in other animals, especially mammals. Probes which hybridize to the mouse agouti gene have been shown to hybridize to a unique human sequence with substantial homology to a portion of the mouse agouti gene. Such probes are useful for the isolation and cloning of the human counterpart agouti gene.

Based on studies of the $A^y$ and $A^{vy}$ mutants, ectopic expression of the agouti gene in muscle, liver and/or adipose tissue, the major targets insulin action, causes the insulin resistance, hyperinsulinemia, decreased glucose tolerance, and also the obesity. Transgenic mouse of the present invention are useful for evaluating the relationship of obesity to the development of insulin resistance associated with type II diabetes. To test whether expression of the agouti exclusively within adipose tissue in associated with just the obesity, and whether the expression within the liver and/or muscle exclusively caused the insulin-resistance, lines of transgenic mice that express the agouti gene specifically either in adipose tissue, or in the liver and/or muscle are used. This is done by placing the agouti gene under the control of muscle and/or liver, and fat-specific promoters/enhancers. Transgenic mice carrying each of the different tissue-specific expression constructs are analyzed for expression compared to their non transgienic (littermates and $A^y$/– mice as controls).

The polymerase chain reaction ("PCR™") has been a significant development in genetic analysis, allowing amplification of minute amounts of a specified gene sequence (U.S. Pat. Nos. 4,683,195; 4,683,202; 4,800,159; Eisenstein, 1990 Schochetman et al., 1988), all incorporated herein by reference. In this method, a pair of single-stranded oligonucleotide primers, each complementary to sequences on opposite strands of the target DNA, are selected to encompass the target sequence to be amplified and define the two ends of the amplified stretch of DNA. After separating double stranded DNA and annealing the primers to the 3' end of the target sequence on each strand, two complementary second strands are synthesized by extension of the annealed primers using a DNA polymerase, i.e. a new single strand of DNA is synthesized for each annealed primer. These newly synthesized DNAs, as well as the original DNA sequence, can then be used for a second cycle of primer annealing and DNA synthesis. Accordingly, the desired target DNA sequence is amplified geometrically with each repetition of the cycle. Typically, within a few hours a target DNA sequence can be amplified 100,000 fold, particularly when automated methods are used to perform the cyclic reactions.

The polymerase chain reaction can also be used to specifically amplify only those target sequences which are expressed, i.e. those which are transcribed. To do so, mRNA is isolated and cDNA is made from the RNA using reverse transcriptase. The cDNA, which represents the expressed genes, is then used as target DNA in the PCR™ amplification reaction.

Because of its high sensitivity and specificity, PCR™ has been successfully used as a means for identifying microorganisms and viruses in the diagnosis of infections disease (Eisenstein, 1990; Shih et al., 1990; Lifson et al., 1990; Anceschi et al., 1990). PCR™ amplification has been used to detect changes in expression of the dTMP synthase gene (i.e. changes in the level of mRNA) associated with drug resistance in human tumors (Scanlon, 1989; Kashani-Sabet et al., 1988). PCR™ has also been used to analyze point mutations in HIV-1 reverse transcriptase which confer resistance to AZT (Larder et al., 1989) and point mutations in the dihydrofolate reductase-thymidylate synthase gene associated with pyrimeth ie resistance in *Plasmodium falciparum* (Cowman et al., 1988; Zolg et al., 1989; Tanaka et al., 1990; Zolg et al., 1990).

The present invention provides methods capable of detecting nucleic acid sequences associated with a gene in which expression of the gene product correlates with the development of diabetes, hyperamylinemia, neoplasms and obesity in animals which comprise a) providing a test sample comprising nucleic acid isolated from a specimen from a test animal, b) providing pairs of single stranded oligonucleotide primers seleited so that the oligonucleotides of each pair are complementary to the 3' ends of one double stranded DNA target sequences associated with the gene, c) combining the primer pairs with the test sample under conditions such that each primer pair will hybridize sufficiently specifically to its target sequence, d) treating the hybridized primers under conditions such that primer extension products are simultaneously synthesized for all sequences to which a primer is hybridized, e) repeating steps c) and d) until the target sequences present are sufficiently amplified to be detected, and f) detecting the amplified target sequences.

Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of antibodies from solution wherein the matrix contains agouti peptide epitopes such as those derived from mammalian agouti proteins, covalently-coupled to a Sepharose CL6B or CL4B. This matrix binds the antibodies of the present invention directly and allows their separation by elution with an appropriate gradient such as salt, GuHCl, pH, or urea.

Ribozymes

In certain embodiments, it may be important to provide agouti compositions which comprise one or more ribozymes, or to perform methods using one or more agouti compositions in combination with ribozyme technology. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93123569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramoleicular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g, Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No.92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Int. Pat. Appl. Publ. No. WO 94/02595 describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an IL-5 related condition. Such RNA is detected by determining the presence of a cleavage product after treatment with a ribozyme using standard methodology.

Liposomes and Nanocapsules

In certain embodiments, the inventor contemplates the use of liposomes and/or nanocapsules for the introduction of agouti compositions into host cells. Such formulations may be preferred for the introduction of pharmaceutically-acceptable formulations of the polypeptides, pharmaceuticals, and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). More recently, liposomes were developed with improved serum stability and circulation half-times (Gabizon and Papahadjopoulos, 1988; Allen and Choun, 1987).

In one instance, the disclosed composition may be entrapped in a liposome. Liposomes are vesicular structures characterized by a phospholipid bilayer membrane and an inner aqueous medium. Multilamellar liposomes have multiple lipid layers separated by aqueous medium. The term "liposome" is intended to mean a composition arising spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyano-acrylate nanoparticles that meet these requirements are contemplated for use in the present invention, and such particles may be are easily made, as described (Couvreur et al., 1977; 1988). Methods of preparing polyalkyl-cyano-acrylate nanoparticles containing biologically active substances and their use are described in U.S. Pat. Nos. 4,329,332, 4,489,055, and 4,913,908.

Pharmaceutical compositions containing nanocapsules for the oral delivery of active agents are described in U.S. Pat. Nos. 5,500,224 and 5,620,708. U.S. Pat. No. 5,500,224 describes a pharmaceutical composition in the form of a colloidal suspension of nanocapsules comprising an oily phase consisting essentially of an oil containing dissolved therein a surfactant and suspended therein a plurality of nanocapsules having a diameter of less than 500 nanometers. U.S. Pat. No. 5,620,708 describes compositions and methods for the oral administration of drugs and other active agents. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitive drugs, such as polypeptides, in the intestines can be avoided while absorption of proteins and polypeptides form the intestinal tract is increased.

U.S. Pat. Nos. 5,641,515 and 5,698,515 describe the use of nanocapsules for the oral administration of a polypetide, specifically, insulin and are incorporated herein by reference. U.S. Pat. No. 5,698,515 described insulin containing nanocapsules intended for oral administration of insulin which comprises a hydrophilic polymer modified with an inhibitor of proteolytic enzyme, insulin and water, wherein the inhibitor of proteolytic enzymes is ovomucoid isolated from duck or turkey egg whites. U.S. Pat. No. 5,556,617 describes the use of nanoparticles as pharmaceutical treatment of the upper epidermal layers by topical application on the skin.

Poly(alkyl cyanoacrylate) nanocapsules have been used as biodegradable polymeric drug carriers for subcutaneous and peroral delivery of octreotide, a long-acting somatostatin analogue. The nanocapsules, prepared by interfacial emulsion polymerization of isobutyl cyanoacrylate, were 216 nm in diameter and incorporated 60% of octreotide. Nanocapsules were administered subcutaneously and the octreotide-loaded nanocapsules (20 mg/kg) suppressed the insulinaemia peak induced by intravenous glucose overload and depressed insulin secretion over 48 h. When administered perorally to oestrogen-treated rats, octreotide loaded nanocapsules (200 and 100 mg/kg) significantly improved the reduction of prolactin secretion and slightly increased plasma octreotide levels (Damge et al., 1997).

The negative surface charge of nanocapsules makes them particularly susceptible to lysozyme (LZM), a positively-charged enzyme that is highly concentrated in mucosas. This interaction causes destabilization of the nanocapsule by LZM; however, it was observed that the destabilizing effects caused by the adsorption of LZM onto the nanocapsules can be prevented by previous adsorption of the cationic poly (amino acid) poly-L-lysine (Calvo et al., 1997).

Calvo et al., 1996 describe the use of poly-epsilon-caprolactone (PECL) microparticles for the ocular bioavailability of drugs. Their study showed that PECL nanoparticles and nanocapsules as well as submicron emulsions are shown to be novel corneal drug carriers, and represent a useful approach for increasing the ocular bioavailability of drugs.

An excellent review of nanoparticles and nanocapsular carriers is provided by Arshady 1996. Arshady notes that one of the major obstacles to the targeted delivery of colloidal carriers, or nanocapsules, is the body's own defense mechanism in capturing foreign particles by the reticuloendothelial system (RES). This means that following intravenous administration, practically all nanometer size particles are captured by the RES (mainly the liver). The review describes recent initiatives on the design of macromolecular homing devices which seem to disguise nanoparticles from the RES and, hence, are of potential interest to the targeted delivery of nanocapsular carriers. The idea is based on a graft copolymer model embodying a link site for attachment to the carrier, a floating pad for maintaining the particles afloat in the blood stream, an affinity ligand for site-specific delivery and a structural tune for balancing the overall structure of the homing device.

Yu and Chang, 1996 describe the use of nanocapsules containing hemoglobin as potential blood substitutes. They use different polymers including polylactic acid and polyisobutyl-cyanoacrylate and modify the surface of the nanocapsules with polyethylene glycol (PEG) or with PEG 2000 PE. The surface modified nanocapsules containing hemoglobin survive longer in the circulation.

U.S. Pat. No. 5,451,410 describes the use of modified amino acid for the encapsulation of active agents. Modified amino acids and methods for the preparation and used as oral delivery systems for pharmaceutical agents are described. The modified amino acids are preparable by reacting single amino acids or mixtures of two or more kinds of amino acids with an amino modifying agent such as benzene sulfonyl chloride, benzoyl chloride, and hippuryl chloride. The modified amino acids form encapsulating microspheres in the presence of the active agent under sphere-forming conditions. Alternatively, the modified amino acids may be used as a carrier by simply mixing the amino acids with the active agent. The modified amino acids are particularly useful in delivering peptides, e.g., insulin or calmodulin, or other agents which are sensitive to the denaturing conditions of the gastrointestinal tract.

Vectors for Cloning, Gene Transfer and Expression

Within certain embodiments expression vectors are employed to express the agouti polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided. That the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988a, 1988b). IRES elements from two members of the picornavirus family (polio and encephalomyocarditis) have been described (Pelletier and Sonenberg, 1988), as well an IRES from a mammalian message (Macejak and Sarnow, 1991, 1992). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Delivery of Expression Vectors

There are a number of ways in which expression vectors may introduced into cells. In certain embodiments of the invention, the expression construct comprises a virus or engineered construct derived from a viral genome which is used to deliver an agouti composition to a target cell. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Generation and propagation of adenovirus vectors, which are replication deficient, depend on a unique helper cell line, designated 293, which was transfonmed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Rich et al. 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Methods for culturing 293 cells and propagating adenovirus have been described. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld el al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows, the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975). A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation, via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In one embodiment, such expression constructs may be entrapped in a liposome, lipid complex, nanocapsule, or other formulation using one or more of the methods disclosed in Section 4.8. Also contemplated are lipofectamine-DNA complexes. For example, liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP 0360257, specifically incorporated herein by reference).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e. a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

Expression of Agouti-Derived Epitopes

For the expression of agouti-derived epitopes, once a suitable clone or clones have been obtained, whether they be native sequences or genetically-modified, one may proceed to prepare an expression system for the recombinant preparation of agouti-derived epitopes. The engineering of DNA segment(s) for expression in a prokaryotic or eukaryotic system may be performed by techniques generally known to those of skill in recombinant expression. It is believed that virtually any expression system may be employed in the expression of agouti-derived epitopes.

Agouti-derived epitopes may be successfully expressed in eukaryotic expression systems, however, it is also envisioned that bacterial expression systems may be preferred for the preparation of agouti-derived epitopes for all purposes. The DNA sequences encoding the full-length, truncated, site-specifically modified, mutagenized, or derivitized agouti peptide may be separately expressed in bacterial systems, with the encoded proteins being expressed as fusions with β-galactosidase, ubiquitin, *Schistosoma japonicum* glutathione S-transferase, *S. aureus* Protein A, maltose binding protein, and the like. It is believed that prokaryotic expression systems, and particularly bacterial expression systems will ultimately have advantages over eukaryotic expression in terms of ease of use and quantity of materials obtained thereby.

It is proposed that transformation of host cells with DNA segments encoding such epitopes will provide a convenient means for obtaining agouti-derived epitope peptides. Genomic or extra-chromosomal sequences are suitable for eukaryotic expression when present in appropriate expression vectors, and under suitable conditions to permit expression of the encoded protein, as the host cell will, of course, process the nucleic acid transcripts to yield functional mRNA for subsequent translation into protein.

It is similarly believed that almost any eukaryotic expression system may be utilized for the expression of agouti-derived epitopes, e.g., baculovirus-based, glutamine synthase-based or dihydrofolate reductase-based systems may be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes agouti-derived epitope-encoding DNA sequences, an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

It is contemplated that virtually any of the commonly employed host cells can be used in connection with the expression of agouti-derived epitopes in accordance herewith. Examples include cell lines typically employed for eukaryotic expression such as 293, AtT-20, HepG2, VERO, HeLa, CHO, WI 38, BHK, COS-7, RIN, L6, 3T3-L1, and MDCK cell lines. Examples of tissues that may be employed to express agouti-derived polypeptides include insect cells such as T. ni cells or mammalian tissue such as skin, skeletal muscle, small intestine, liver, white adipose tissue, brown adipose tissue, kidney, brain, testis, salivary gland, spleen, lung, stomach, or colon.

It is contemplated that agouti-derived epitopic peptides may be "overexpressed", i.e., expressed in increased levels relative to its natural expression in human cells, or even relative to the expression of other proteins in a recombinant host cell containing agouti-derived epitope-encoding DNA segments. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometer scanning of the resultant gel or blot. A specific increase in the level of the recombinant protein or peptide in comparison to the level in natural agouti-derived peptide-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding an agouti-derived epitope peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventors have noticed that the level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

Detection of Peptide and Antibody Compositions

Immunoassays of the present invention may be a radioimmunoassay, Western blot assay, immunofluorescent assay, enzyme immunoassay, chemiluminescent assay, immunohistochemical assay and the like. Standard techniques known in the art for ELISA have been described (Rose and Bigazzi, 1980; Campbell et al., 1964, both of which are incorporated herein by reference). Such assays may be a direct, indirect, competitive, or noncompetitive immunoassay as described in the art (Oellerich, 1984). Biological samples appropriate for such detection assays include, but are not limited to, tissue biopsy extracts, cerebrospinal fluid, pleural fluid, urine and the like.

In one embodiment, test sample is reacted with a solid phase reagent having surface-bound anti-agouti antibodies. The solid surface reagent can be prepared by known techniques for attaching protein to solid support material. These attachment methods include non-specific adsorption of the antibody to the support or covalent attachment of the antibody to a reactive group on the support. After reaction of the test sample with anti-agouti antibody, unbound sample components are removed by washing and the antigen-antibody complex is reacted with a labelled secondary antibody. The label may be an enzyme which is detected by incubating the solid support in the presence of a suitable fluorimetric or calorimetric reagent. Other detectable labels may also be used, such as radiolabels or colloidal gold, and the like.

It will be further understood that certain of the polypeptides may be present in quantities below the detection limits of typical staining procedures such as Coomassie brilliant blue or silver staining, which are usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently-, or colloidal gold-tagged. Means for the labeling and detection of such two-step secondary antibody techniques are well-known to those of skill in the art.

Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of the disclosed proteins and peptides is not limited to such assays, and that other useful embodiments include RIAs and other non-enzyme linked antibody binding assays and procedures.

In preferred ELISA assays, proteins or peptides incorporating the novel protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween™. These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween™, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween™).

After incubation with the second labeled or enzyme-tagged antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Immunoprecipitation

The antibodies of the present invention are particularly useful for the isolation of agouti protein antigens by immunoprecipitation. Immunoprecipitation involves the separation of the target antigen component from a complex mixture, and is used to discriminate or isolate minute amounts of protein. In an alternative embodiment the antibodies of the present invention are useful for the close juxtaposition of two antigens, This is particularly useful for increasing the localized concentration of antigens, e.g., enzyme-substrate pairs.

In a related embodiment, antibodies of the present invention are useful for regulating the activity of agouti proteins. Detection of the binding between the antibodies and antigenic compositions may be accomplished by using radioactively labeled antibodies or alternatively, radioactively-labeled agouti protein or peptides derived therefrom. Alternatively, assays employing biotin-labeled antibodies are also well-known in the art as described (Bayer and Wilchek, 1980).

Western Blots

The compositions of the present invention will find great use in immunoblot or western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods for use in conjunction with Western blotting include enzymatically-, radiolabel-, or fluorescently-tagged secondary antibodies against the toxin moiety are considered to be of particular use in this regard.

Screening Assays

Host cells that have been transformed may be used in the screening of natural and artificially derived compounds or mixtures to select those that are capable of complexing with the agouti proteins or peptides of the present invention. This could be useful in the search for compounds that inhibit or otherwise disrupt, or even enhance the activity of agouti. It is contemplated that effective pharmaceutical agents may be developed by identifying compounds that complex with the particular agouti epitopes, including, for example, compounds isolated from natural sources, such as plant, animal and marine sources, and various synthetic compounds. Natural or man-made compounds that may be tested in this manner may also include various minerals and proteins, peptides or antibodies.

Diagnosing Neoplams and Other Cancers Involving Agouti

In certain embodiments, the inventors have determined that agouti expression is associated with the development of neoplasm and other malignancies. Therefore, in certain circumstances, agouti and the corresponding gene which encodes it may be employed as a diagnostic or prognostic indicator of cancer. More specifically, point mutations, deletions, insertions or regulatory perturbations relating to agouti may cause cancer or promote cancer development, cause or promoter tumor progression at a primary site, and/or cause or promote metastasis. Other phenomena associated with malignancy that may be affected by agouti expression include angiogenesis and tissue invasion.

One embodiment of the instant invention comprises a method for detecting variation in the expression of agouti. This may comprises determining that level of agouti or determining specific alterations in the expressed product. Obviously, this sort of assay has importance in the diagnosis of related cancers. Such cancer may involve cancers of the breast or ovaries, or alternatively, cancers involving the lung, liver, spleen, brain kidney, pancreas, small intestine, blood cells, lymph node, colon, endometrium, stomach, prostate, testicle, skin, head and neck, esophagus, bone marrow, blood or other tissue. In particular, the present invention relates to the diagnosis of breast and ovarian cancers.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals.

Following detection, one may compare the results seen in a given patient with a statistically significant reference group of normal patients and patients that have agouti-related pathologies. In this way, it is possible to correlate the amount or kind of agouti detected with various clinical states.

Various types of defects are to be identified. Thus, "alterations" should be read as including deletions, insertions, point mutations and duplications. Point mutations result in stop codons, frameshift mutations or amino acid substitutions. Somatic mutations are those occurring in nongermline tissues. Germ-line tissue can occur in any tissue and are inherited. Mutations in and outside the coding region also may affect the amount of agouti produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

Primers and Probes

The term primer, as defined herein, is meant to encompass any nucleic acid that is capable of priming the synthesis of a nascent nucleic acid in a template-dependent process. Typically, primers are oligonucleotides from about ten to about fifteen base pairs in length or even longer sequences such as those from about twenty to about 30 base pairs or more in length, with even longer sequences be employed for certain applications. Primers may be provided in doublestanded or single-stranded form, although the singlestranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemiluminescent (luciferase).

Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure (RT-PCR™) may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/U.S. Ser. No. 87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2,202,328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an, excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Int. Pat. Appl. Publ. No. WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Eur. Pat. Appl. Publ. No. EP 329,822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of $E.$ $coli$ DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu and Wang, (1989), incorporated herein by reference in its entirety.

Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989. Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder et al., 1968a, Freifelder et al., 1968b; Freifelder, 1982).

Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols (see Sambrook et al., 1989). For example, chromophore or radiolabel probes or primers identify the target during or following amplification. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the agouti gene that may then be analyzed by direct sequencing.

Kit Components

All the essential materials and reagents required for detecting and sequencing agouti and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR™ products and the relative mRNA abundance is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundance of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundance of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundance made for many different RNA samples, such as is the case when examining RNA samples for differential expression, become distorted in such a way as to make differences in relative abundance of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

Chip Technologies

Specifically contemplated by the present inventors are chip-based DNA technologies such as those described by Hacia et al. (1996; 1998) and Shoemaker et al. (1996). Briefly, these techniques involve quantitative methods for analyzing large numbers of genes rapidly and accurately. Shoemaker et al. (1996) describe the use chip-based DNA technologies to identify yeast deletion mutants containing a unique oligonucleotide tag.

Hacia et al. (1996) use high-density arrays consisting of over 96,600 oligonucleotides 20-nucleotides in length to screen for a wide range of hetrozygous mutations in a specific exon of BRCA1. Reference and test samples were co-hybridized with the arrrays and differences in the hybridization patterns were compared. The authors found that DNA chip-based detection of genetic alterations was both accurate and sensitive enough to detect a single nucleotide alteration in a 3.45 kb DNA fragment.

Hacia et al. also have used DNA chip technology to compare sequence information from homologous genes in closely related species (1998). This study provided guidelines for identifying highly accurate, hybridization-based sequence calls. Furthermore, the study describes a method of generating sequence information from less conserved sequences.

Affymetrix has pioneered the use of high density peptide and oligonucleotide chips and have developed a number of applications using such chips (Fodor et al., 1993). These applications include DNA sequence analysis (Pease et al., 1994), analysis of drug-resistant mutations of viral genomes (Lipshutz et al., 1995), and analysis of DNA and RNA sequences for polymorphisms (Chee et al., 1996).

Methods for Screening Active Compounds

The present invention also contemplates the use of agouti and active fragments, and agouti nucleic acids, in the screening of compounds for activity in either stimulating agouti activity, overcoming the lack of agouti or blocking the effect of a mutant agouti molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, phosphatase activity, anti-phosphatase activity, phosphorylation of agouti, dephosphorylation of agouti, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

In Vitro Assays

In one embodiment, the invention is to be applied for the screening of compounds that bind to the agouti molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of agouti to a natural or artificial substrate or binding partner. Competitive binding assays can be performed in which one of the agents (agouti, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with agouti and washed. Bound polypeptide is detected by various methods.

Purified agouti can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the agouti active region to a solid phase.

Various cell lines containing wild-type or natural or engineered mutations in agouti can be used to study various functional attributes of agouti and how a candidate compound affects these attributes. Methods for engineering mutations are described elsewhere in this document, as are naturally-occurring mutations in agouti that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of agouti, or related pathways, may be explored. This may involve assays such as those for protein expression, enzyme function, substrate utilization, phosphorylation states of various molecules including agouti, cAMP levels, mRNA expression (including differential display of whole cell or polyA RNA) and others.

In Vivo Assays

The present invention also encompasses the use of various animal models. Here, the identity seen between human and mouse agouti provides an excellent opportunity to examine the function of agouti in a whole animal system where it is normally expressed. By developing or isolating mutant cells lines that fail to express normal agouti, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type agouti may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for agouti or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a agouti-specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved agouti activity or which act as stimulators, inhibitors, agonists, antagonists or agouti or molecules affected by agouti function. By virtue of the availability of cloned 1p31 sequences described herein, sufficient amounts of agouti can be produced to perform crystallographic studies. In addition, knowledge of the polypeptide sequences permits computer employed predictions of structure-function relationships.

Transgenic Animals

In one embodiment of the invention, transgenic animals are produced which contain a functional transgene encoding a functional agouti polypeptide or variants thereof. Transgenic animals expressing agouti transgenes, recombinant cell lines derived from such animals and transgenic embryos may be useful in methods for screening for and identifying agents that induce or repress function of agouti. Transgenic animals of the present invention also can be used as models for studying indications such as cancers.

In one embodiment of the invention, a agouti transgene is introduced into a non-human host to produce a transgenic animal expressing a human, rat, monkey, hamster or murine agouti gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous agouti by homologous recombination between the transgene and the endogenous gene; or the endogenous gene may be eliminated by deletion as in the preparation of "knock-out" animals. Typically, a agouti gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress agouti or express a mutant form of the polypeptide. Alternatively, the absence of agouti in "knock-out" mice permits the study of the effects that loss of agouti protein has on a cell in vivo. Knock-out mice also provide a model for the development of agouti-related cancers, and particularly ovarian and breast cancers.

As noted above, transgenic animals and cell lines derived from such animals may find use in certain testing experiments. In this regard, transgenic animals and cell lines capable of expressing wild-type or mutant agouti may be exposed to test substances. These test substances can be screened for the ability to enhance wild-type agouti expression and or function or impair the expression or function of mutant agouti.

Methods For Treating Agouti Related Malignancies

The present invention also involves, in another embodiment, the treatment of cancers, and in particularly neoplasms affected by agouti expresison in a cell. The types of cancer that may be treated, according to the present invention, is limited only by the involvement of agouti. By involvement, it is not even a requirement that agouti be mutated or abnormal—the overexpression of this tumor suppressor may actually overcome other lesions within the cell. Thus, it is contemplated that a wide variety of tumors may be treated using agouti therapy, particularly those of the breast and ovaries, but also cancers of the lung, liver, spleen, brain kidney, lymph node, pancreas, small intestine, blood cells, colon, stomach, endometrium, prostate, testicle, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

Gene Therapy

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing agouti to that cell. Because agouti transcripts have been identified not only in humans, but also in rat, mouse, monkey, and hamster, any of these nucleic acids could be used in human or animal therapy, as could any of the gene sequence variants discussed above which would encode the same, or a biologically equivalent polypeptide. The development and use of such genes for treatment of cancers using a "gene therapy" approach are well known to those of skill in the art. Particularly preferred expression vectors are viral vectors such as adenovirus, adeno-associated virus, herpesvirus, vaccinia virus and retrovirus. Also preferred is an expression vector that is contained within, or formulating using encapsulation within a lipid vesicle, lipid particle, liposome, or liposome-derived composition.

Those of skill in the art are well aware of how to apply gene delivery to in vivo and ex vivo situations. For viral vectors, one generally will prepare a viral vector stock. Depending on the kind of virus and the titer attainable, one may deliver anywhere on the order of from about $1 \times 10^4$ to about $1 \times 10^6$ infectious particles to the patient. Alternatively, one may deliver higher concentrations of infectious particles to the patient, on the order of from about $1 \times 10^9$ to about $1 \times 10^{12}$ or higher, depending upon the particular formulation, application, or cancer to be treated. Similar figures may be extrapolated for liposomal or other non-viral formulations by comparing relative uptake efficiencies. Formulation as a pharmaceutically acceptable composition is known in the art, as discussed supra.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way agouti may be utilized according to the present invention.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that agouti could serve as a target for an immune effector given that (a) it is unlikely to be expressed on the surface of the cell and (b) that the presence, not absence, of agouti is associated with the normal state. However, it is possible tat particular mutant forms of agouti may be targeted by immunotherapy, either using antibodies, antibody conjugates or immune effector cells.

A more likely scenario is that immunotherapy could be used as part of a combined therapy, in conjunction with agouti-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Protein Therapy

Another therapy approach is the provision, to a subject, of agouti polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

Combined Therapy with Immunotherapy, Chemotherapy or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that agouti replacement therapy could be used similarly in conjunction with chemo- or radiotherapeutic intervention. It also may prove effective to combine agouti gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a agouti expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agouti or the other agent will be desired. Various combinations may be employed, where agouti is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a agouti expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a agouti expression construct, as described above.

Agents that directly cross-link nucleic acids, specifically DNA, are envisaged to facilitate DNA damage leading to a synergistic, antineoplastic combination with agouti. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil(5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of agouti expression constructs to patients with agouti-linked cancers will be a very efficient method for delivering a therapeutically effective gene to counteract the clinical disease, and particularly to cancers such as ovarian and breast cancer. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining agouti-targeted therapies with chemo- and radiotherapies, it also is contemplated that combination with other gene therapies will be advantageous. For example, targeting of agouti and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

It also should be pointed out that any of the foregoing therapies may prove useful by themselves in treating a agouti-related cancer. In this regard, reference to chemotherapeutics and non-agouti gene therapy in combination should also be read as a contemplation that these approaches may be employed separately.

Site-Specific Mutagenesis

In certain embodiments, the invention provides mutant agouti polynucleotides and/or polypeptides. When it is desirable to prepare such a mutant, one may introduce one or more mutations into either the protein or, alternatively, into the DNA sequence encoding the protein for the purpose of producing a mutated protein with altered biochemical and/or biophysical properties.

To that end, the present invention encompasses both site-specific mutagenesis methods and random mutagenesis of a nucleic acid segment encoding an agouti protein in the manner described herein.

The means for mutagenizing a DNA segment encoding an agouti polypeptide are well-known to those of skill in the art. Modifications may be made by random, or site-specific mutagenesis procedures. The nucleic acid may be modified by altering its structure through the addition or deletion of one or more nucleotides from the sequence.

Mutagenesis may be performed in accordance with any of the techniques known in the art such as and not limited to synthesizing an oligonucleotide having one or more mutations within the sequence of a particular agouti polypeptide. A "suitable host" is any host which will express an agouti polypeptide, such as and not limited to mammalian, fungal, or bacterial host cells.

In particular, site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both side of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159 (each of which is specifically incorporated herein by reference in its entirety). Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, specifically incorporated herein by reference in its entirety, describes an alternative method of amplification similar to LCR for binding probe pairs to a target sequence.

Qbeta Replicase™, described in Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having 3' and 5' end sequences of non-Cry-specific DNA and an internal sequence of a Cry-specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a cry-specific expressed nucleic acid.

Still other amplification methods described in Great Britain Pat. Appl. No. 2 202 328, and in Intl. Pat. Appl. Publ. No. PCT/U.S. Ser. No. 89/01025, each of which is incorporated herein by reference in its entirety, may be used in accordance with the present invention. In the former application, "modified" primers are used in PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has agouti polypeptide-specific sequences. Following polymerization, DNA/RNA hybrids are digested with RNase H while double stranded DNA molecules are heat denatured again. In either case the single stranded DNA is made fully double stranded by addition of second agouti polypeptide-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate agouti polypeptide-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e., new templates are not produced from the resultant RNA transcripts. Other amplification methods include "RACE" (Frohman, 1990), and "one-sided PCR™" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional Equivalents

Modification and changes may be made in the structure of the agouti and agouti-related proteins and peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0"1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0);

methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
Cloning of the Murine Agouti Gene
Materials and Methods
Animals

All mice were maintained at the Oak Ridge National Laboratory, including the SB B+T stock, derived from a mutation that arose spontaneously at the Oak Ridge National Laboratory in an SEC/E×C57BL/E mating.

DNS Isolation and Southern Blot Analysis

Genomic DNA (μg) was digested with restriction enzymes, electrophoresed through agarose gels, and blotted to GeneScreen (DuPont, Wilmington, Del.) utilizing standard procedures (Ausubel et al., 1988; Sambrook et al., 1989). Radiolabeled hybridization probes were prepared with the random hexamer labeling technique (Feinberg and Vogelstein, 1984). Prior to hybridization, probe 1.5 was reassociated with sheared, genomic mouse DNA to prevent the hybridization of repetitive sequence (Sealey et al., 1985). Posthybridization filter washing was conducted under high stringency (0.2×SSC, 0.1% SDS at −68° C.) or reduced stringency (0.2×SSC, 0.1% SDS at 50° C.) conditions for membranes containing DNA from mice or other mammalian species, respectively.

RNA Preparation and Northern Blot Analysis

Total RNA was prepared using the guanidine isothiocyanate procedure (Ausubel et al., 1988), enriched for poly (A)+ RNA using an oligo (dT)-cellulose column (Aviv and Leder, 1972), electrophoresed through formaldehyde gels, and blotted to GeneScreen (DuPont) utilizing standard procedures known in the art. The membrane was hybridized and washed under high stringency conditions as described above for Southern blot analysis.

Isolation of cDNA

Poly (A)+ RNA was prepared from day 5 neonatal skin (C3H strain) or adult $A^y$ IslGso kidney or testis as described above, and double-stranded cDNA was subsequently prepared with reverse transcriptase using standard procedures (Ausubel et al., 1988; Sambrook et al., 1989. After the addition of EcoRI linkers, the cDNA was ligated into the λgt10 vector (Stratagene, La Jolla, Calif.), packaged in vitro, and screened with probe B (FIG. 1A) (for the neonatal skin cDNA library) or the wild-type cDNA clone (for the $A^y$/IslGso cDNA libraries) using standard procedures (Ausubel et al., 1988; Sambrook et al., 1989). Positive clones were purified using conventional methods and subcloned into pGEM (Promega, Madison, Wis.) or pBluescript (Stratagene) for further analysis.

Isolation of Genomic Clones

Genomic spleen DNA from the strain 129/RI was partially digested with Sau3A and size fractionated on a 10%–40% sucrose gradient (Sambrook et al, 1989). Fractions containing 35–45-kb fragments were ligated into the cosmid vector c2RB (Bates and Swift, 1983), packaged in vitro, and screened using standard procedures (Ausubel et al., 1988; Sambrook et al., 1989). Utilizing the cDNA clone as a probe, cosmid subfragments were isolated and subcloned into pGEM (Promega) or pBluescript (Stratagene) by standard procedures.

DNA Sequencing

Genomic and cDNA clones were sequenced by the Sanger dideoxynucleotide method (Sanger et al., 1977) using T7 DNA polymerase (United States Biochemical, Cleveland, Ohio) (Tabor and Richardson, 1987). Analysis of the DNA sequence was performed using the University of Wisconsin Genetics Computing Group sequence analysis programs (Devereux et al., 1984).

Results

Isolation of a cDNA Clone and Genomic Structure of the A Locus

Having established from previous work that the distal inversion breakpoint of IslGso likely lies within the agouti locus (Bultman et al., 1991), the inventors initiated a search to find an locus exon. Interspecific hybridizations identified a region of DNA near the distal inversion breakpoint of IslGso (FIG. 1A) that is conserved in a number of mammalian species (FIG. 1B). This evolutionarily conserved region was subsequently shown to be expressed based on its ability to hybridize to a 0.8-kb transcript in RNA prepared from neonatal skin of wild-type animals (FIG. 1C). Neonatal skin cDNA libraries were subsequently prepared and screened with probe B (FIG. 1A), resulting in the identification of several clones, one of which contained the entire coding region and is nearly full length. The total size of this cDNA clone is 800-bp, which is comparable with the size of the RNA seen on Northern blots. The complete nucleotide sequence is 692-bp, excluding the poly(A) tract (FIG. 2). The cDNA contains an open reading frame extending from nucleotide 83 through 478, beginning with an ATG codon flanked by sequence that is in agreement with consensus sequence for translation initiation (Kozak, 1987). The hexanucleotide AATAAT is present within the 3' untranslated sequence immediately preceding the poly(a) tract and probably represents the polyadenylation signal of the gene (Sheets et al., 1990; Durkop et al., 1992).

The translation product deduced from the open reading frame is 131 amino acids in length with a molecular size estimated to be 15,000 daltons (FIG. 2). Searches of the NBRF and SWISSPROT data bases using the algorithm FASTA (Pearson and Lipman, 1988) failed to identify any proteins with significant sequence homology. The N-terminus may comprise a signal peptide, since it is hydrophobic (Kyte and Doolite, 1982) and includes a possible cleavage site after residue 22 (von Heijne, 1986). A highly basic domain containing 16 lysine or arginine residues in a stretch of 29 amino acids is present in the center of the predicted protein and is followed by a polyproline stretch. At the carboxyl terminus, 10 of the final 40 amino acids are cysteines, and in four instances, cysteine residues are spaced 6 amino acids apart. In addition, one putative N-linked glycosylation site and nine potential serine/threonine kinase phosphorylation sites are present within the predicted protein, five of which lie within the highly basic domain.

To educate the intron-exon composition of the gene corresponding to the cDNA clone presented in FIG. 2, overlapping genomic clones were isolated and characterized utilizing the cDNA clone as a probe. Comparison of the structure of the genomic and cDNA clones revealed that the gene contains four exons (FIG. 3A). The first exon of the cDNA is 72-bp in length and is composed entirely of 5' untranslated sequence. The first intron is approximately 11.5-kb in length and is followed by the second (170-bp), third (65-bp), and fourth (385-bp) exons, which are separated by introns of 2.5-kb and 2.8-kb, respectively (FIG. 3A). The gene spans an overall distance of 18-kb.

Wild-Type Pattern of Expression

Figure 4:
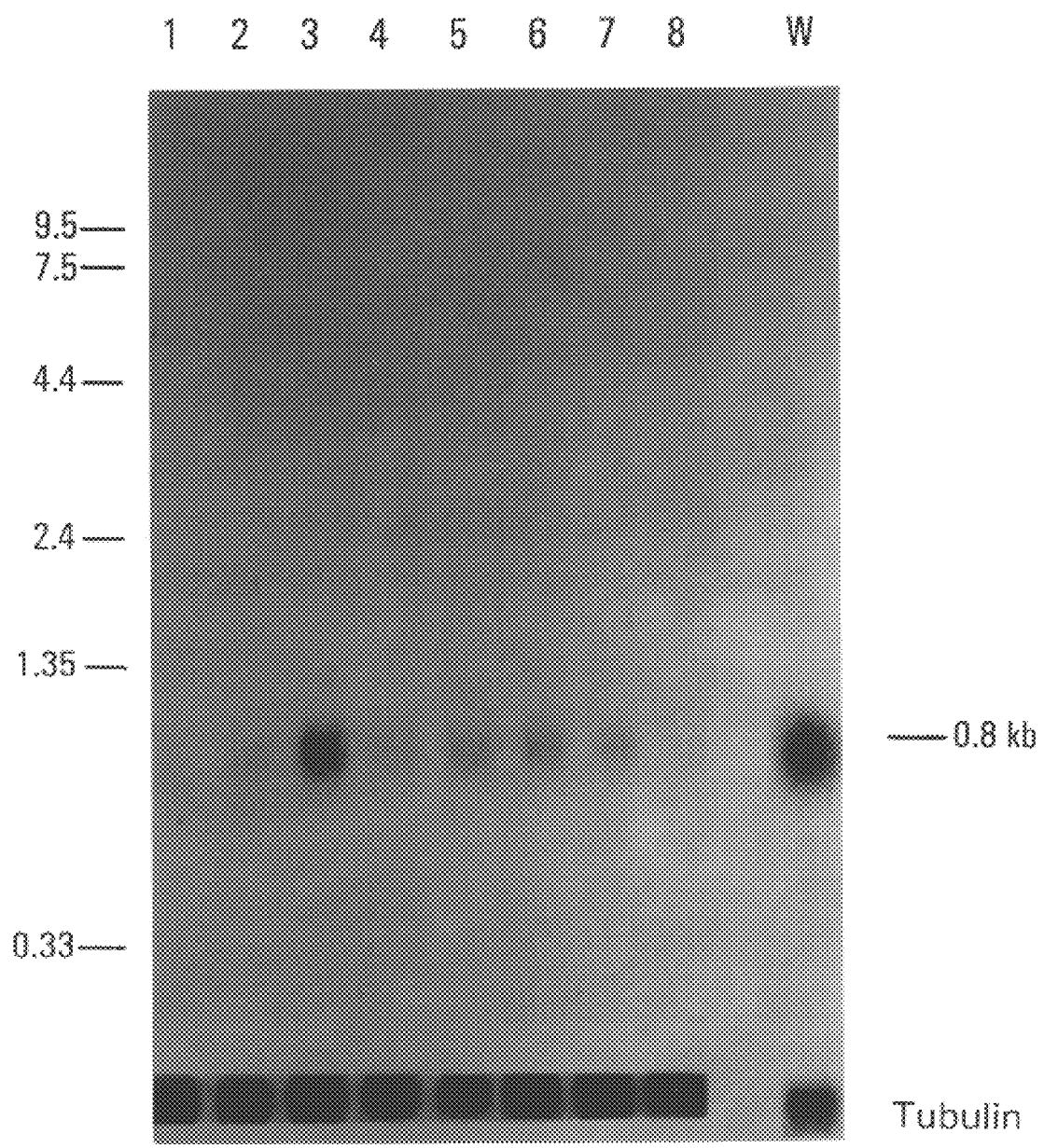
FIG. 4. Shown is a northern blot analysis of wild-type (A/A) neonatal skin. The full-length cDNA clone (FIG. 2) was $^{32}P$ labelled and hybridized to poly(A)$^+$ RNA (2.5 μg per lane) from skin of day 1–8 wild-type neonates (1–8) and day 6 W/W$^v$ neonates (W). RNA molecular size standards are shown on the left in kilobases. The filter was subsequently hybridized with a tubulin probe as a control to analyze the quantity and quality of the RNA in each lane.

Utilizing the cDNA clone as a probe, poly(a)$^+$ RNA from the skin of newborn wild-type mice was examined at daily intervals and was shown to express the 0.8-kb transcript throughout early postnatal development; the level of expression appeared to be greatest, however, during days 2–7 (FIG. 4). To determine whether the 0.8-kb transcript is expressed exclusively by melanocytes within the hair follicle, W/W$^v$ mice were examined because they lack hair bulb melanocytes owing to a defect in the c-kit gene (Geissler et al., 1988). The 0.8-kb transcript was shown to be present in neonatal skin from W/W$^v$ mice (FIG. 4), indicating that it is expressed by the follicular environment.

Figure 5:
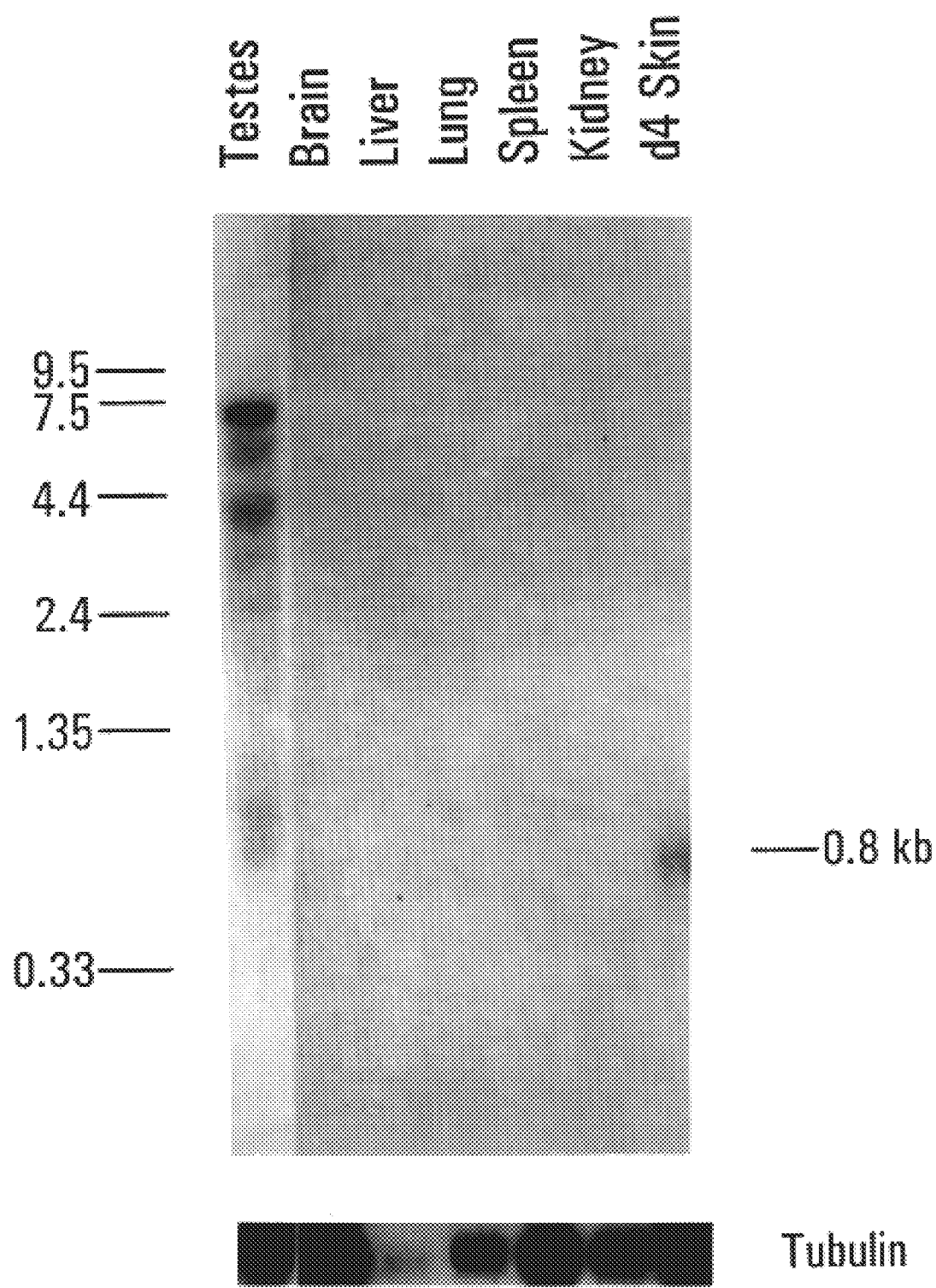
FIG. 5. Shown is a northern blot analysis of adult tissues from wild-type (A/A) mice. The fill-length cDNA clone was $^{32}P$ labeled and hybridized to a variety of poly(A)$^+$ RNAs (2.5 μg per lane). RNA molecular size standards are shown on the left in kilobases. The filter was subsequently hybridized with a tubulin probe as a control to analyze the quantity and quality of the RNA in each lane.

Poly(A)$^+$ RNA was also analyzed from a variety of wild-type adult issues (FIG. 5). Based on Northern blot analysis and RNAase protection assays, it was determined that none of the testis-specific transcripts were expressed in neonatal skin. Thus, it is unlikely that the testis-specific transcripts are playing any role in a locus function.

Changes in Genes Structure and Expression in A-Locus Mutations

Figure 3B:
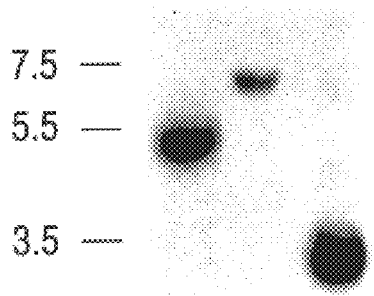
FIG. 3B. Shown is the intro-exon structure of the wild-type locus and two extreme nonagouti mutations. Identification of RFLVs specifically associated with the IslGso and $a^{5MNU}$ mutations. Wild-type (lane 1, C3H strain), IslGso homozygous (lane 2), and $a^{5MNU}$ homozygous (lane 3) genomic DNA was digested with EccoRI, blotted, and hybridized with a $^{32}P$-labelled fragment of DNA corresponding to probe A (lanes 1 and 2) or probe B (lane 3) in (A). The sizes of the DNA fragments detected by probes A and B are shown on the left in kilobases.

In an attempt to provide evidence that the gene that has been characterized is in fact the agouti gene, the inventors tested whether it is structurally altered in agent-induced or spontaneous a locus mutations. First of all, utilizing two probes from with the 5.5-kb wild-type EcoRI fragment at the 3' end of the gene, mutant locus-specific restriction fragment length variants (RFLVs) of 7.5-kb and 3.5-kb were detected for the agent-induced extreme nonagouti mutations Isl-Gso and $a^{5MNU}$ (FIG. 3B), respectively. Additional studies revealed that the 7.5-kb RFLV arises from a DNA structural alteration at the distal inversion breakpoint of IslGso, which causes the 5' half of the gene to be juxtaposed with a portion of the Id gene (Maas et al., 1990; Woychik et al., 1990b) in the opposite transcriptional orientation (FIG. 3A and FIG. 3B). For $a^{5MNU}$, the 3.5-kb RFLV is due to an intragenic deletion encompassing 2.8-kb of genomic DNA, which includes the third exon (FIG. 3A and FIG. 3B). The distal inversion breakpoint of IslGso and the deletion breakpoint of $a^{5MNU}$ have also been characterized by nucleotide sequence analysis (FIG. 3C).

Figure 6A:
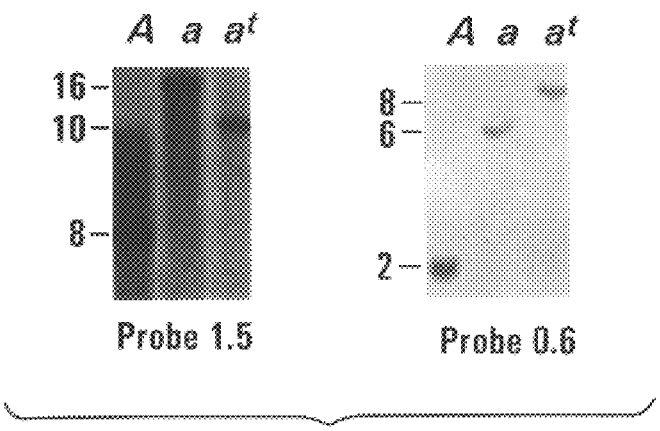
FIG. 6A. Shown is the identification of dna structural alterations associated with the a and a$^t$ alleles. Wild-type (A, C3H strain), nonagouti (a, C57BL/E strain), and black-and-tan (a$^t$, SB B+T stock) genomic DNA was digested with BamHI or BglII, blotted, and hybridized with a $^{32}P$-labeled fragment of DNA corresponding to probe 1.5 (BamHI digest) or probe 0.6 (BglII digest), shown as thick horizontal lines in the illustration of the wild-type allele in (FIG. 6B). The size of the DNA fragments detected by the two probes are shown in the left margin in kilobases. The SB B+T mutation arose in a cross between the strains SEC/E and C57BL/E, both of which are nonagouti (a/a) homozygotes and display a 16.0-kb BamHI fragment with probe 1.5 and a 6.0-kb BglII fragment with probe 0.6, although only the C57BL/E result is shown. The parental strain from which the original nonagouti a mutation rose is not known; however, two wild-type inbred strains, FVB/N and 101, were analyzed in addition to C3H, and all displayed the wild-type pattern illustrated for C3H.
Figure 6B:
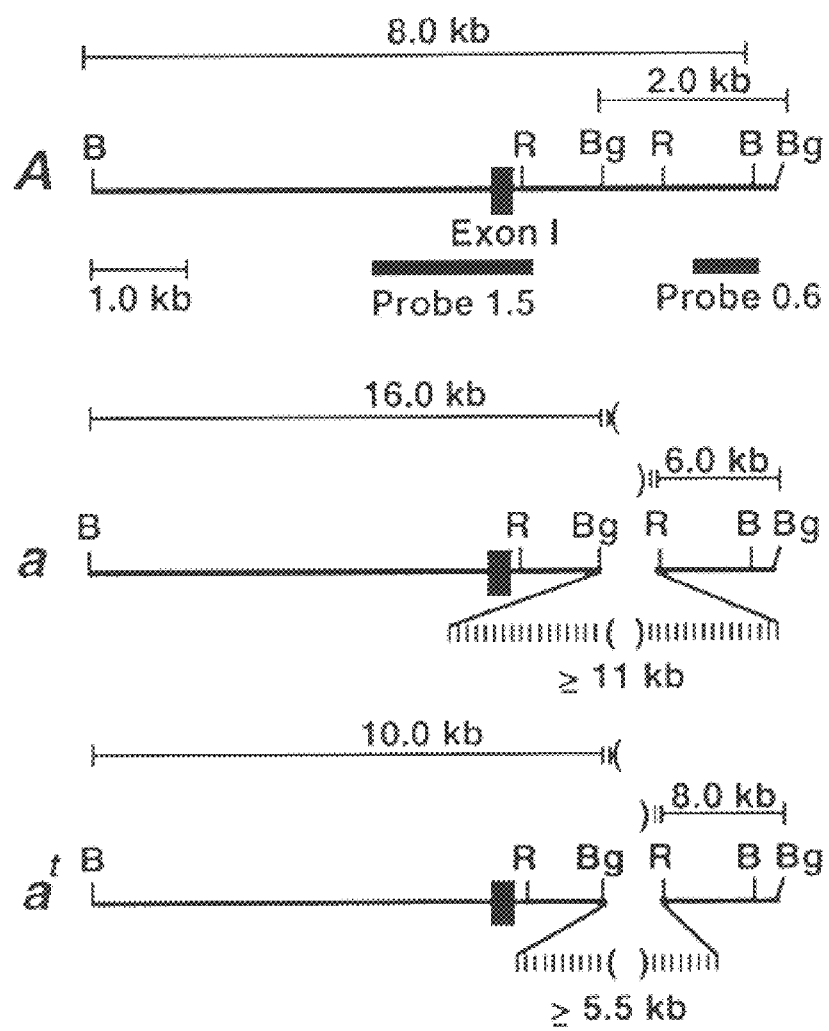
FIG. 6B. Shown is the identification of DNA structural alterations associated with the a and $a^t$ alleles. Schematic representation of 5' end of the gene shown in FIG. 3 from wild-type (A), nonagouti (a), and SB B+T mutant ($a^t$) mice. The first exon is shown as a closed rectangle, and the bold horizontal line represents the 5' flanking sequence and portion of the first intron. Probe 1.5 detects a 8.0-kb fragment in wild type, and RFLV fragments of 16.0-kb and 10.0-kb in the a and $a^t$ mutant alleles, respectively. Probe 0.6 detects a 2.0-kb wild-type fragment and RFLV muLtant allele-specific fragments of 6.0-kb in a and 8.0-kb in $a^t$. These RFLVs are due to the presence of at least 11-kb (a) or 5.5-kb ($a^t$) of additional sequence in the mutant alleles within a highly localized 700-bp region on the wild-type DNA between BglII and EcoRI sites. The insertions for each allele have not yet been cloned and mapped, and therefore are depicted by vertical bars with open parentheses at the end. B, BamHI; R, EcoRI; Bg, BglII.

In additional studies, the inventors also analyzed the molecular structure of the original nonagouti mutation (a) and a black-and-tan (a$^t$) allele called SB B+T that arose spontaneously in a cross of the SEC/E and C57BL/E inbred lines at the Oak Ridge National Laboratory. For these studies, probes containing either the first exon (probe 1.5) or a portion of the first intron (probe 0.6) each detected a distinct mutant locus-specific FLV associated with the a and a$^t$ mutations (FIG. 6A and FIG. 6B). Based on this analysis, it appears that each of these mutant alleles contains a structural alteration caused by the presence of extra DNA (at least 11-kb or 5-kb for the a or a$^t$ mutations, respectively) within a region corresponding to a 700-bp BglII-EcoRI fragment within the first intron of the wild-type gene (FIG. 6B).

Figure 7:
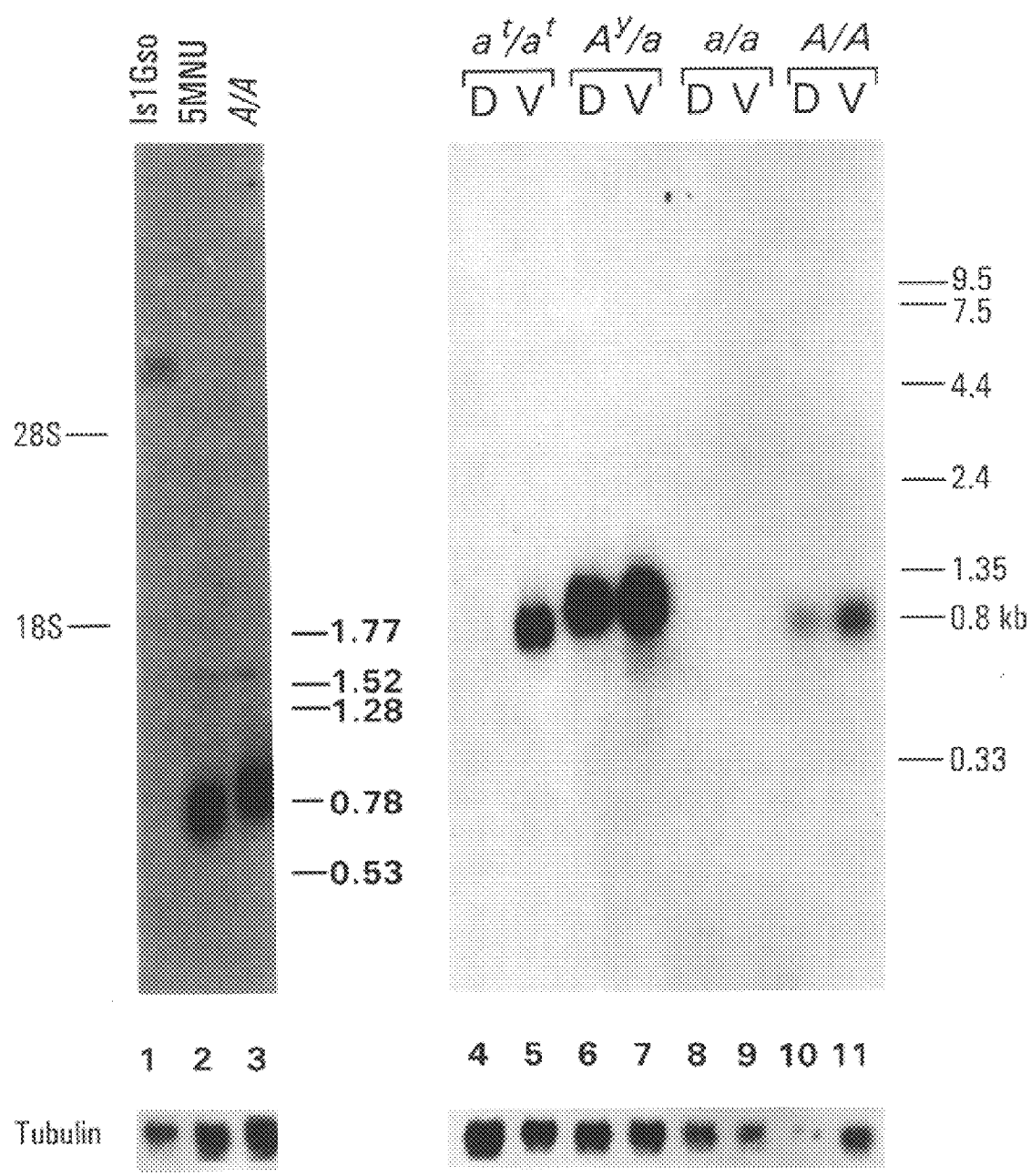
FIG. 7. Shown is a northern blot analysis of neonatal skin from several agouti locus mutants. The full-length cDNA clone (FIG. 2) was $^{32}$P labelled and hybridized to poly(A)$^+$ RNA (2.5 μg per lane) from neonatal skin of spontaneous or agent-induced a locus mutations. RNA molecular size standards (in kilobases) and the positions of the 28S and 18S rRNA subunits are shown. The filter was subsequently hybridized with a tubulin probe as a control to analyze the quantity and quality of the RNA in each lane. D, skin derived from the dorsal surface of neonates; V, skin derived from the ventral surface of neonates; IslGso, day 4 IslGso homozygote; 5MNU, day 5 $a^{5MNU}$ homozygote; A/A, day 5 wild type; $a^t/a^t$, day 5 black-and-tan; $A^y$/a, day 6 lethal yellow heterozygote; a/a, day 6 nonagouti (C57BL/10).

As expected, the DNA structural alterations in IslGso, $a^{5MNU}$, a, and a$^t$ cause detectable changes in the expression of the gene. Production of the 0.8-kb transcript is absent in neonatal skin from IslGso homozygotes and is replaced by a low abundance 8.0-kb transcript that likely arises from cryptic elements on the rearranged gene segments (FIG. 7, lane 1). In neonatal skin from $a^{5MNU}$ homozygotes, a transcript is present at wild-type levels, but is decreased in size to an extent that is consistent with a deletion of the third exon of the gene (FIG. 7, compare lanes 2 and 3). Deletion of the third exon results in the removal of 21 codons and the introduction of a frame shift within the last exxon (FIG. 3A). The original nonagouti mutation in C57BL mice does not express the 0.8-kb transcript (FIG. 7, lane 8 and 9). In black-and-tan neonates, the 0.8-kb transcript is absent in skin derived from the black, dorsal surface, but is overexpressed in skin derived from the yellow, ventral surface (FIG. 7, lanes 4 and 5). Control samples from wild-type (A/A) mice showed similar levels of expression of the 0.8-kb transcript in the dorsal and ventral surfaces (FIG. 7, lanes 10 and 11). Notably, A$^y$ is associated with a marked increase in expression of a larger than normal transcript (FIG. 7, lanes 6 and 7).

Deregulated Expression in Lethal Yellow Heterozygotes

Figure 8:
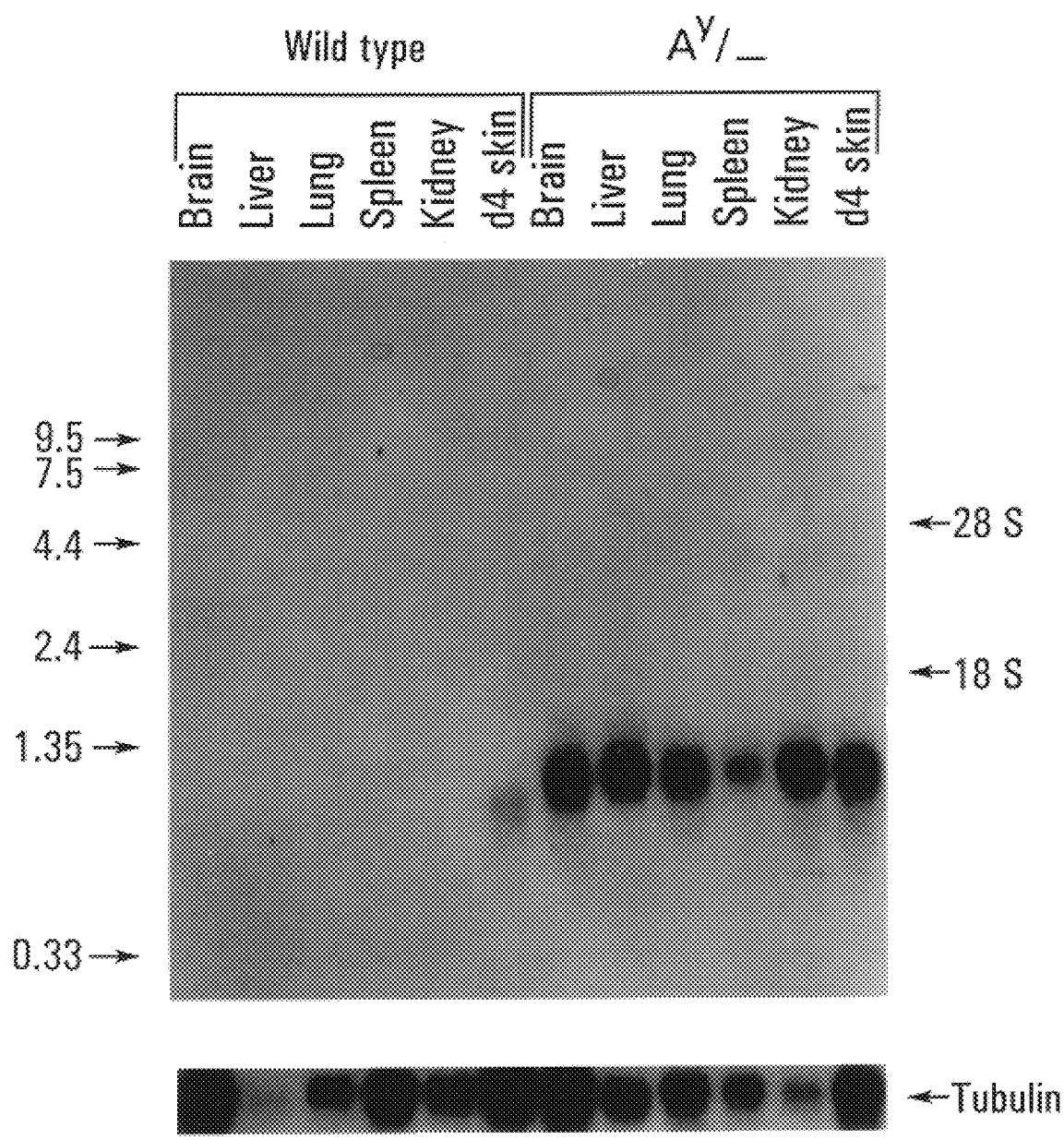
FIG. 8. Shown is a northern blot analysis of adult tissues from wild-type and lethal yellow heterozygotes. The full-length cDNA clone (FIG. 2) was $^{32}$P-labelled and hybridized to poly(A)$^{30}$ RNA (2.5 μg per lane) from adult tissues or neonatal skin of wild-type or $A^y$/– mutant animals. RNA molecular size standards are shown on the left in kilobases, the positions of the 28S and 18S rRNA subunits are indicated on the right. The filter was subsequently hybridized with a tubulin probe as a control to analyze the quantity and quality of the RNA in each lane. $A^y$/–, $A^y$ heterozygotes with genotypes of $A^y$/a and $A^y$/a were used in this analysis; d4 skin, day 4 postnatal skin; d6 skin, day 6 postnatal skin.
Figure 9A:
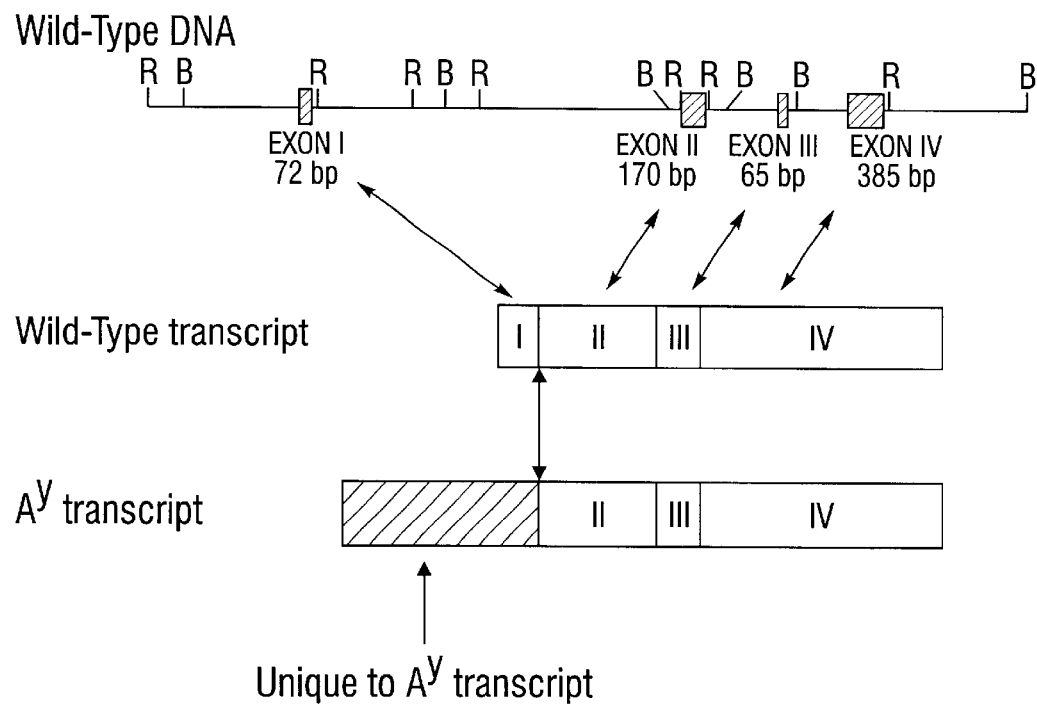
FIG. 9A. Shown is the molecular analysis of the size-altered $A^y$ transcript. Schematic representation of the wild-type and lethal yellow ($A^y$) transcripts produced by the agouti locus. Based on the analysis of cDNA clones, the $A^y$ transcript is identical to the wild-type transcript for the sequence derived from the second, third, and fourth exons. However, the 5' end of the second exon and the $A^y$ transcript is flanked by a sequence that is different from the region corresponding to the first exon on the wild-type transcript. Moreover, preliminary evidence suggests that this sequence unique to $A^y$ corresponds to the first noncoding exon (approximately 300 nt in length) of another gene. The genomic organization of the wild-type gene is shown above, with the four exons depicted as closed rectangles and the introns and flanking sequences shown as a solid line. B, BamHI; R, EcoRI.

Lethal yellow (A$^y$) heterozygotes display a number of pleiotropic effects, including pronounced obesity, a diabetes like condition, and a propensity to develop a variety of spontaneous and induced neoplasms in the adult. To examine the molecular defect associated with A$^y$ allele more precisely, a number of adult tissues from lethal yellow heterozygotes were analyzed for expression of the gene that has been characterized. In striking contrast with wild-type mice, where expression is restricted to testis and neonatal skin, A$^y$ animals overexpressed a size-altered transcript in every tissue examined (FIG. 8). To characterize the nature of the increased size of the A$^y$ transcript, an adult kidney and testis cDNA library was prepared from lethal yellow heterozygotes and screened using the wild-type cDNA clone as a probe. Analysis of several A$^y$ cDNA clones indicated that the first exon of the agouti gene has been replaced by novel sequence on the A$^y$ transcript, whereas the second, third, and fourth agouti exons, which contain the entire coding region, remain intact (FIG. 9A). Moreover, characterization of the genomic region flanking the novel sequence revealed a potential intron-exon consensus sequence precisely at the point of divergence with cDNA clone (FIG. 9B). This result strongly suggests that the altered size A$^y$ transcript arises through a mechanism that involves splicing of the region of novel sequence to the second exon of the gene.

Characterization of the Agouti Locus Gene

This example describes the cloning and characterization of a gene contained within a region of DNA that is approximately 18-kb in length. This gene is structurally altered in several different a locus mutations. For example, the distal inversion breakpoint associated with the recessive mutation, Is1Gso, breaks this gene within its third intron, and the 2.8-kb genomic deletion associated with a$^{5MNU}$ is an intragenic mutation that specifically deletes the third exon and causes a frame shift in the last exon of this gene (FIG. 3). DNA structural alterations of this gene have also been identified that are associated with the a and a$^r$ alleles (FIG. 6). Additionally, the mRNA expressed from the A$^y$ allele is longer than normal, and arises from a replacement of the first exon with a region of novel sequence added to the 5' end of the transcript (FIG. 9). Further evidence that this gene is associated with the agouti locus is based on the inventors' finding that the original recessive nonagouti allele associated with the C57BL strain fails to express the normal 0.8-kb transcript in neonatal skin (FIG. 7, lanes 8 and 9). The transcripts produced from the a$^r$ and A$^y$ alleles are also expressed in a deregulated manner (FIG. 7, lanes 4–7), with A$^y$ being ectopically expressed in many adult tissues (FIG. 8). The fact that this gene is directly associated with these mutations strongly suggests that it is, in fact, the one gene associated with a locus function.

The normal pattern of expression of this gene is also consistent with its being responsible for the functions associated with the agouti locus. The production and deposition of phaeomelanin in the growing agouti hair shaft occurs during days 3–7 of neonatal development, coincident with the appearance of the subapical yellow band (Sakurai et al., 1975). The observation that expression of this gene is maximal during days 2–7 correlates with phaeomelanin production. Expression of this gene also correlates with the production of phaeomelanin in the a$^t$, A$^y$, and a mutants, particularly in a$^t$, where expression is present at high levels in the yellow-colored hair of the ventrum, but absent in the black-colored hair of the dorsum (FIG. 7, lanes 4–9). Most significantly, the inventors found that this gene is expressed in neonatal skin from W/W$^v$ animals (which lack hair bulb melanocytes), consistent with early skin grafting studies indicating that the agouti gene is expressed in the follicular environment and not within the melanocytes (Silvers and Russell, 1955; Silvers, 1958a, 1958b, 1961, 1979). However, in situ hybridization analysis of neonatal skin will be necessary to identify the cell type(s) expressing the agouti gene.

Expression from this region of DNA in wild-type, adult tissues is limited to testis (FIG. 5). The functional significance of the testis-specific expression is presently unclear, particularly since it appears that the unique-sized RNA transcripts produced in testis are not expressed in neonatal skin, elsewhere during development, or in other adult tissues (FIG. 5). Other characterized developmental genes that do not have any obvious function in testis, such as Id (Woychik et al., 1990b), also express testis-specific transcripts. It may turn out that either there is no functional significance of the expression of these genes in the testis whatsoever or there is a presently unknown, testis-specific function associated with this expression.

Based on the fact that the structure and expression of this gene is directly affected by the most dominant agouti locus mutation (A$^y$), mutations in the middle of the dominance hierarchy (a$^t$, a), and the most recessive member of the agouti allelic series (a$^x$), and the fact that the pattern of expression of this gene is compatible with normal a locus function, this gene is, in fact, the agouti gene.

Hypothetical Interaction with the Extension Locus

Analysis of the sequence of the cDNA clone predicts a small polypeptide 131 amino acids in length and approximately 15,000 daltons in molecular size (FIG. 2). This protein is secreted, due to the signal peptide at its N-terminus (FIG. 2). In addition, the molecule has several potential phosphorylation sites, a highly basic domain in the middle of the protein, and a cysteine-rich region near its C-terminus. However, neither of these domains resembles any characterized motif or can yet be ascribed a particular function.

Since the a locus, like steel (McCulloch et al., 1965; Mayer and Green, 1989; Dexter and Moore, 1977), does not act in a cell-autonomous manner, it is attractive to speculate that the agouti gene product. like the steel factor, functions as a ligand for some as yet undetermined receptor on the melanocyte. Interestingly, the extension locus (e) in chromosome 8 of the mouse acts in a cell-autonomous manner and produces pigmentation phenotypes similar to a (Silvers, 1979). However, dominant e locus mutations cause an all-black phenotype similar to that observed in recessive a locus mutations, and recessive e locus mutations cause an all-yellow phenotype similar to that observed in dominant a locus mutations. Making the assumption that dominant mutations at these two loci are associated with gain of function and recessive mutations are associated with loss of function, a straightforward model (like that for the steel and dominant-white spotting loci) in which the e locus encodes a melanocyte-specific receptor that is directly activated by a ligand produced by the agouti locus is unlikely.

Alternatively, Takeuchi et al. (1989) described a model for a potential interaction between the a and e loci based on their studies with skin explants from A$^y$/a or e/e mice. They proposed that α-melanocyte-stimulating hormone (α-MSH) binds to its receptor on the surface of the melanocyte, triggering a cascade of biochemical events culminating in the elevation of cyclic AMP levels, which act as a second messenger to produce eumelanin. The e locus hypothetically encodes a protein that modulates the production of cyclic AMP via interaction with adenylate cyclase in the membrane of melanocytes. In this model, the agouti protein could function as a ligand to compete with α-MSH for binding of its receptor, preventing an in-crease of cyclic AMP in the melanocyte and resulting in the production of phaeomelanin. As discussed above, the finding that the product of the agouti locus may be a small secreted protein is compatible with this model.

Deregulated Expression in Lethal Yellow Heterozygotes

Lethal yellow (A$^y$) is an allele of particular interest because it is a recessive lethal and is associated with a number of dominant pleiotropic effects in the heterozygous condition. In 1905, A$^y$ was the first lethal mutation to be documented in a mammal (Cuenot, 1905; Castle and Little, 1910). Lethal yellow homozygotes display characteristic abnormalities at the morula and blastula stages of development (Calarco and Pedersen, 1976) and die before implantation is complete (Robertson, 1942). The cause of death is presumably due to a delay in giant cell differentiation, thereby preventing attachment of the embryo to the endometrial cells lining the uterus (Eaton and Green, 1989). In addition, lethal yellow heterozygotes exhibit a systemic stimulation in body growth, reduced fertility in females (Granholm et al., 1986), a diabetes-like syndrome (Hellerström and Hellman, 1963), pronounced obesity (Dickerson and Gowen, 1947; Fenton and Chase, 1951; Carpenter and Mayer, 1958; Plocher and Powley, 1976; Friedman and Leibel, 1992), and a propensity to develop a variety of spontaneous and induced neoplasms (Heston, 1942; Heston and Deringer, 1947; Heston and Vlahakis, 1961, 1962, 1963; Deringer, 1970).

In an attempt to characterize the nature of the molecular defect associated with the A$^y$ allele, mRNA was prepared from a variety of adult tissues from $A^y$ heterozygotes (FIG. 8). Whereas the agouti gene is normally expressed only in testis and neonatal skin, the $A^y$ allele is associated with overproduction of agouti RNA transcripts in both neo-natal skin and in every adult tissue that the inventors have analyzed to date (FIG. 8). Based on these findings, it appears that deregulated overexpression of the a locus gene is directly responsible for the yellow coat color and, most importantly, for the dominant pleiotropic effects observed in $A^y$ heterozygotes. It is unlikely that the dominant pleiotropic effects associated with $A^y$ are due to the production of an altered agouti gene product, because the coding exons of the gene are unaltered, with the larger than normal transcript resulting from a 5' extension of the 0.8-kb mRNA (FIG. 9). Also, analysis of a new allele with a phenotype identical to viable yellow ($A^{vy}$) (for a review of $A^{vy}$, see Wolff et al., 1986) revealed that the agouti gene is overexpressed in the same deregulated manner but produces a normal-sized mRNA.

Agouti is a Single Gene Locus

Genetic studies involving several thousand offspring of a locus mutants revealed three unequivocal and two probable recombination events between $A^y$ and $a^x$ (Russell et al., 1963), as well as one and two possible recombinations between $A^y$ and $a^t$, and $A^y$ and a, respectively (Siracusa et al., 1987a). In each case, the recombination frequency was on the order of 0.1%, and flanking markers in the crosses showed $A^y$ to lie proximal to $a^x$ (Russell et al., 1963). Based on this result, it was hypothesized that either the agouti gene was very large or $A^y$ was associated with a separate gene that is pseudoallelic with agouti. The inventors' results help to resolve this issue and point to a single gene hypothesis. In each case, with the $A^y$, $a^t$, and a alleles unique alterations in the structure and expression of the single 18-kb gene are observed. If $A^y$ were associated with a different gene, one would not have expected to see structural and expression changes in the same gene for all three mutations. The large number of alleles and the wide range of pheno-types associated with the agouti locus have been used as evidence by some investigators to propose that the agouti locus is comprised of multiple "mini-loci" and not a single gene (reviewed in Silvers, 1979). According to this hypothesis, each gene of the mini-locus plays a role in regulating pigmentation in different parts of the body, particularly over the dorsal and ventral surfaces, and around the pinnae, nipples, and perineum. Support for this assertion stems from the finding that changes from yellow to black pigmentation proceed from the dorsal to the ventral regions as one progresses from the most dominant to the most recessive mutation of the agouti allelic series. For example, phaeomelanin progressively disappears from the mid-dorsum with $A^i$/a ($A^i$, intermediate yellow), from the lateral dorsum with $a^t/a^t$, from the ventral surface with a/a, and from the pinnae, nipples, and perineum with $a^e/a^e$ (Silvers, 1979). With the mini-locus hypothesis, different genes should be affected by mutations associated with the individual alleles in the hierarchy. The finding that the structure and expression of the same gene is affected by mutations at the top ($A^y$), middle ($a^t$ and a), and bottom ($a^e$) of the allelic series demonstrates that the mini-locus hypothesis is not correct. On the other hand, a single gene hypothesis, which has also been proposed for the agouti locus (Silvers, 1979), is supported by these data and by many genetic observations, the most compelling of which is the fact that the mini-locus hypothesis would be expected to produce some phenotypes with darker hair on the ventrum than on the dorsum, or with solid black or yellow hair of the dorsum and agouti hair on the ventral surface, aft these phenotypes have never been observed (Silvers, 1979). These data clearly support the single gene hypothesis for the agouti locus.

Example 3

Methods for Tissue-Specific Agouti Gene Expression in Muscle

Several promoter/enhancers that drive tissue-specific gene expression in muscle, adipose tissue, and liver have been identified. The following promoter/enhancers, have been extensively characterized, shown to drive optimal levels of tissue specification transcription in transgenic mice, and are available as published plasmid expression cassettes. An expression cassette contains the regulatory elements necessary for expression of an inserted gene. These include a promotor and polyadenylation site and if necessary an enhancer element. For muscle specific expression, the rat myosin light chain is used. (MLC1/3) gene promoter/enhancer from clone pMLC1CAT920, which has been used previously to drive high level expression of a chloramphenicol acetyltransferase (CAT) transgene exclusively in skeletal muscle of transgenic mice (Rosenthal et al., 1989). In this pUC9-based clone, a 1.5-kb HindIII fragment containing the MLC1 promoter, cap site, and 105-bp of 5' untranslated sequence is fused to a 1.6-kb HindIII-BamHI fragment containing the CAT gene with the small intron and polyadenylation site of the SV40 t antigen, which is followed (3') by a 920-bp BamHI fragment containing a strong, muscle specific enhancer element that is normally located >24-kb downstream of the MLC1 transcription start site. The CAT gene is excised exercised from this clone by HindIII-BamHI digestion and the full-length cDNA a depicted in FIG. 2 (cDNA16), substantially homologous sequences, analogs or functionally equivalent sequences is inserted into this site. This MLC1 promoter-agouti-MLC1 enhancer clone is linearized and microinjected into the pronuclei fertilized eggs, and transgenic lines are produced.

Example 3

Methods for Tissue-Specific Agouti Gene Expression in Adipose Tissue

To express the agouti gene exclusively in adipose tissue, the murine adipocyte P2 (aP2) gene promoter/enhancer contained in clone 5.4aP2CAT is used, which has been shown to direct very high level CAT expression specifically to adipose tissue in transgenic mice (Ross et al., 1990). This clone consists of an upstream fragment (−5.4-kb to +21-bp relative to the transcription start site) of the aP2 gene, that contains the promoter and a strong adipocyte-specific enhancer (located in the −5.4-kb to −4.9-kb DNA segment), linked to the CAT gene with the small intron and polyadenylation site of the SV 40 t minigene. The CAT gene is replaced by the agouti minigene paP2Pe-agouti-SVpA to generate the expression construct. Specifically, a 1.1-kb HindIII-ClaI fragment containing the agouti cDNA and SV40 polyA signal from the pBAP-a-SVpA plasmid is cloned into the NotI site of the p-5.4aP2 plasmid using NotI linkers (clone paP2PE-a-SVpA). A 6.6-kb KpnI-SacII fragment containing the aP2 promoter-agouti expression cassette isolated from the vector sequences in paP2Pe-agouti-SVpA and is used for microinjection. In this case, an ~1-kb) agouti transcript is produced from this expression cassette, which is several hundred nucleotides larger than the endogenous agouti transcript.

Example 4
Methods for Tissue-Specific Agouti Gene Expression in Liver

To achieve liver-specific expression of the agouti gene, the mouse albumin gene promoter/enhancer from the clone Nb.3alb-HGH is used, which has been used successfully to achieve liver-specific expression of the human growth hormone (hGH) gene in transgenic mice at levels near that of endogenous albumin gene expression (Pinkert et al., 1987). This clone contains an upstream (−10.4 to −8.5-kb) albumin enhancer-containing fragment, linked to the liver-specific albumin promoter, which is fused to the hGH structural gene. The hGH gene is replaced with the agouti minigene and transgenic mice are generated as described above. Specifically, a 1.1-kb SalI fragment containing the agouti cDNA and SV40 polyadenylation signal is cloned into the SalI site of the NB-0.3alb plasmid just 3' to the albumin enhancer/promoter. After CsC1 purification of the plasmid, a 3.5-kb SacI-KpnI fragment containing the expression cassette is isolated away from the vector sequences and used for microinjection. Expression of the agouti cDNA from this cassette produces an ~1-kb transcript, which is several hundred nucleotides longer than the endogenous agouti transcript.

Transgenic mice that express agouti either in liver, muscle, or fat, establishes whether expression in the liver/muscle is sufficient for the insulin resistance without obesity, and whether expression exclusively in adipose tissue is sufficient to cause obesity without the diabetes. In the event that expression in both the liver/muscle and adipose tissue are both necessary for either the insulin resistance and/or obesity, the different individual transgenic lines are intercrossed to generate mice expressing agouti in difference combinations of two tissues (i.e. liver and muscle, muscle and fat, and liver and fat). These mice in turn, are mated to mice expressing agouti solely in the third remaining tissue to generate transgenic mice that express agouti in all three tissues. This establishes the contribution of each tissue necessary for the obesity and insulin resistance traits. Additionally, the transgenic lines that express the agouti gene in the liver should yield information regarding the role of the agouti gene product in the development of liver tumors.

EXAMPLE 5
Methods for Tissue-Specific Agouti Gene Expression in Pancreas

For expression in the pancreas the islet cell specific promoter from the rat insulin gene is utilized. Obesity/diabetes effects associated with the ectopic expression of the agouti gene in the β-cells of the pancreas are analyzed. The resulting transgenic animals are used to study the expression of agouti in the pancreas to determine if this causes an increased secretion of amylin, and that the resulting hyperamylinemia, which in turn, causes the insulin resistance.

Example 6
Methods for Preparing an Agouti-Transgenic Mouse

Clones may be linearized and microinjected into the pronuclei of fertilized eggs as described in U.S. Pat. Nos. 5,175,384; 5,175,383; 5,175,385; 4,870,009; 5,174,986, incorporated herein by reference.

Briefly, the DNA fragment used for injection are released from the vector with the appropriate restriction endonucleases and purified by agarose gel electrophoresis and glass-powder purification. The final DNA concentration is adjusted to an appropriate concentration. Fertilized mouse eggs are recovered from females. The DNA fragments in a solution at 3–5 μg/ml are injected into the pronucleus of each fertilized egg essentially as described (Hogan et al., 1986). The eggs are transplanted into pseudopregnant female mice for gestation to term. At 3 to 4 wk of age, tissue from the tail of the mice is removed. The DNA is analyzed for the presence of the integrated promoter-agouti cDNA-enhancer sequences within the mouse chromosomal DNA, as shown by hybridization to radioactively labeled agouti cDNA probe DNA. Both "Southern blot" and "Northern blot" hybridizations are performed (Sambrook, 1989). For the hybridization, the chromosomal DNA is digested into fragments using restriction endonuclease which cut the agouti cDNA into known lengths to indicate the authenticity of the added gene. Northern blotting analysis may be used to determine the size of the mRNA expressed from the transgene. Two transgenic agouti mice may then be mated and then offspring produced to establish a transgenic line.

Example 7
Cloning the Agouti Gene Homolog from Humans

Several genes that map close to the agouti locus on mouse chromosome 2 also map to the same relative positions on human chromosome 20. Based on the syntenic relationship between the distal section of mouse chromosome 2 and human chromosome 20, it can be predicted that any human homologue of the agouti gene would also map to human chromosome 20. This is quite significant since a gene associated with mature onset diabetes has also been mapped to human chromosome 20.

Utilizing the full-length mouse agouti cDNA as a probe, the human genome was searched for cross-hybridizing fragments, and a unique-copy cross-hybridizing fragment on human genome blots was identified. This result strongly suggests that there is a unique-copy gene in humans that is homologous to the mouse agouti gene. The cross-hybridizing human fragment is cloned and characterized the structure of the corresponding gene and to map it on the human genome. For this purpose a human genomic library is screened with the mouse cDNA clone. The positive clones are purified, and the specific restriction fragments which cross-hybridize with the mouse cDNA subcloned and sequenced. The gene is mapped using FISH (Fluorescence In Situ Hybridization) map the gene on metaphase human chromosomes utilizing the human genomic clone as a probe using the method as described by Lawrence et al. (1990), or by both genomic mapping procedures (Lichter et al., 1990a, 1990b, and Jauch et al., 1990).

Example 8
Diagnosis of Agouti-Associated Defects in Mammals

The agouti gene or analogous genes and mutations in human or other animals may be detected by Southern or Northern blot analyses using radiolabled nucleotide probes. Also, this type of analysis can be accomplished with PCR™ or RT-PCR™ technique which have been described above. The probes are based on the cDNA sequence of the agouti gene as depicted in FIG. 2 or from substantially homologous sequences or portions thereof.

DNA or RNA samples from test animals are prepared for analysis by techniques known in the art, and a Southern or Northern blot analysis is conducted using the nucleotide probes. The banding pattern of the test sample is compared to a known standard sample pattern.

Differences in the test pattern are indicative of mutations in the gene and are predictive of the development of diabetes, obesity, neoplasms and amylinemia in the test animal.

Example 9
Isolation and Characterization of Agouti Polypeptides

The agouti gene encodes a 131-amino acid polypeptide. The agouti protein is secreted since it contains a hydrophobic leader region terming in a consensus signal peptide cleavage site. The 131 amino acid protein (minus its signal peptide) may be the active form of protein or it may require further processing to form a biologically active molecule. Various full-length and truncated forms of the protein will be made recombinantly to determine the portions necessary for activity. Comparison of eukaryotic and prokaryoticly expressed proteins will indicate if glycosylation is required for activity. Natural or recombinant protein may be purified by methods known in the art such as affinity chromatography, immunoaffinity chromatography, HPLC and the like.

Example 10
Production and Use of Antibodies Specific for the Agouti Gene Products Recombinant agouti protein is used for the production of antibodies against the agouti protein. The antibody are useful for establishing the location of the agouti gene product within tissues of the animal. Specifically, polyclonal and monoclonal antibodies are prepared utilizing standard procedures, and the titer of the polyclonal antibodies will be determined by standard ELISA. For the RI-agouti transgenics, serum levels of the agouti protein will be established with a standard ELISA analysis. Monoclonal antibodies are produced as previously described above.

Immunohistochemistry is performed on formalin fixed, paraffin embedded tissues using supersensitive biotinylated anti-rabbit antibodies followed by HRP-labeled strepavidin. (Prior to use in histochemistry, the serum is absorbed with mouse liver powder.) DAB (DAB=Diaminobenzidine) may be used as a chromogen color reagent and slides is counterstained with Mayers hematoxylin. Specificity of the staining is controlled by including tissues stained with preimmune rabbit serum treated as above. In addition, anti-agouti serum is passed over an affinity column made of agouti protein coupled to appropriate gel matrix (Reacti-gel™, Sepharose, etc.) as well as gels coupled with unrelated proteins. The gel coupled to agouti protein removes all histochemical activity for agouti from the flow through, and the eluted antibody restores the same specific activity.

Example 11
Identification of the Receptor/Ligand for the Agouti Gene Product Since the a locus, like steel, does not act in a cell-autonomous manner, the agouti gene product, like the steel factor, many function as a ligand for receptor on the melanocyte. Interestingly, the extension locus (e) in a chromosome 8 of the mouse acts in a cell-autonomous manner and produces pigmentation phenotypes similar to a. However, dominant e-locus mutations cause an all-black phenotype similar to that observed in recessive a-locus mutations, and recessive e-locus mutations cause an all-yellow phenotype similar to that observed in dominant a-locus mutations. Making the assumption that dominant mutations at these two loci are associated with gain of function and recessive mutations are associated with loss of function, a straightforward model (like that for the steel and dominant-white spotting loci) in which the e locus encodes a melanocyte-specific receptor that is directly activated by a ligand produced by the agouti locus is unlikely.

Alternatively, Takeuchi et al. (1989) described a model for a potential interaction between the a and e loci based on their studies with skin explants from $A^y/a$ or e/e mice. They proposed that α-melanocyte-stimulating hormone (α-MSH) binds to its receptor on the surface of the melanocyte, triggering a cascade of biochemical events culminating in the elevation of cyclic AMP levels, which act as a second messenger to produce eumelanin. The e locus hypothetically encodes a protein that modulates the production of cyclic AMP via interaction with adenylate cyclase in the membrane of melanocytes. In this model, the agouti protein may function as a ligand to compete with α-MSH for binding of its receptor, preventing an increase of cyclic AMP in the melanocyte and resulting in the production of phaeomelanin. The finding that the product of the agouti locus may be a small secreted protein is compatible with this model, although the agouti gene product shares no sequence homology with α-MSH.

Using the isolated or recombinant agouti gene product or fragments and analogs thereof, methods will be devised to determine the receptor for the agouti gene product and role of receptor in the development of diabetes, obesity, amylinemia and tumors.

Example 12
Screening of Drugs for Treatment of Diabetes, Obesity, Amylinemia or Tumors Transgenic animals may be used to study the effects of potentially therapeutic drugs. In an illustrative embodiment a group of 24 transgenic mice may be subdivided into 4 groups. Three groups are fed repelletized Purina 5008 chow and one group of mice are fed the same chow containing the test drug for two wk. All mice are fed Purina 5008 chow without drug during the third wk. Body weight and food consumption are monitored and blood samples are collected before the study is initiated (day 0) and after 7 (day 7) and 14 days (day 14) of treatment. Blood samples are collected from tail veins between 0800 and 1000, with the mice being bled in the same order each time. Blood samples are analyzed directly for serum amylin.

To test insulin sensitivity after drug treatment, mice are fasted overnight (17 h) from day 14 to day 15. Blood glucose is measured in the morning of day 15 immediately before injections at 0 time. At that time, each mouse receives one i.p., injection of 1 g/kg glucose and one i.p. injection of porcine insulin or saline. The two injections are given consecutively on different sides of the abdomen. The 3 control groups are given saline, 0.25 units insulin/kg or 0.5 units insulin/kg, respectively. The drug-treated mice are given 0.25 units insulin/kg. Blood glucose concentrations are then measured at 30, 60 and 120 min after the injections.

Radioimmunoassays kits for insulin are purchased from Diagnostic Products Corporation (San Diego, Calif.). Rat insulin is used as a standard and porcine insulin for injections are obtained at Eli Lilly & Co. (Indianapolis, Ind.). Radioimmunoassay kits for rat amylin are purchased from Peninsula (Belmont, Calif.). The lowest level of detection in the amylin assay is less than 3 pg/assay tube using unextracted plasma (Gill and Yen, 1991). Blood glucose is measured by the glucose oxidase method with a model 300 Alpkem Rapid Flow Analyzer (Clackamaus, Oreg.). Incubating 100 μg drug per ml of blood or plasma are tested to make sure that the drug does not interfere with the assays for blood glucose, plasma insulin, and amylin.

Animals are also monitored for the development of tumors in tissues and size of tumors. Data are reported as mean±s.e.m. and analyzed by Student's test or by the two sample t-test at each point. Percent changes of day 0 were calculated individually and reported as mean ± of N—6 or 18 mice. The insulin/amylin ratios are calculated on molar basis.

Example 13
Molecular Structure and Chromosomal Mapping of Human Agouti

Although the agouti banded pigmentation pattern is conserved in many mammalian species (Searle, 1968), there is no reported evidence that humans ever develop agouti pigmented hair. For this reason, it was initially unclear whether humans had an agouti gene. On the other hand, the similarities between the phenotype in dominant agouti mutants and non-insulin-dependent diabetes in humans raised the question of whether a human agouti gene, if it exists, could be involved in certain forms of diabetes and/or obesity in humans. Additionally, the association between the ectopic expression of agouti and the development of tumors in mice led to the question of whether the occurrence of any human tumors might be associated with the deregulated expression of a human agouti gene. For these reasons, the inventors set out to determine whether humans contain an agouti gene and to clone and characterize the structure of such a gene, if it exists.

This example describes the claims and characterization of the human agouti gene, which is highly homologous to murine agouti. The gene maps to a region of chromosome 20 that exhibits synteny conservation with the corresponding region of mouse chromosome 2 (Siracusa and Abbott, 1993; Löffler et al., 1993). This portion of human chromosome 20 is closely linked to several traits, including a deletion complex involved in the development of myeloid leukemia (Roulston et al., 1993) and a region associated with a locus (MODY) which has been implicated in the development of non-insulin-dependent diabetes mellitus (Rothschild et al., 1993).

Materials and Methods
Southern Blotting

Ten micrograms of genomic DNA was digested with restriction enzymes, electrophoresed through agarose gels, and blotted to Gene-Screen (DuPont) using standard procedures (Ausubel et al., 1988; Sambrook et al., 1989). Radiolabeled hybridization probes were prepared with the random hexamer-labeling technique (Feinberg and Vogelstein, 1984). Repetitive sequences were reassociated with sheared genomic DNA before hybridization. Posthybridization filter washes were conducted under a reduced stringency condition (e.g., 0.2×standard saline/citrate/0.1% SDS at 46° C.) or under a high-stringency condition (e.g., 0.2×standard saline/citrate/0.1% SSC/0.1% SDS at 68° C.).

Isolation of a Human Genomic Clone

A Sau3A partially digested human genomic lambda library in EMBL3 was prepared and screened with a $^{32}$P-labeled mouse agouti full-length cDNA probe that had been reassociated with human sheared genomic DNA. One positive clone was purified, and several restriction fragments were subcloned into the pGEM4 vector (Promega) for sequencing. Specifically, a 1.2-kb PstI fragment, which hybridized to the mouse cDNA probe, but not total mouse DNA, the inventors subcloned to generate the sequence homologous to the first coding exon.

A 4.5-kb EcoRI fragment, which hybridized to two overlapping labeled 42-base oligonucleotides (5'-CACTGAACAAGAAATCCAA-GAAGATCAGCAGAAAAGAAGCCG-3' (SEQ ID NO:5) and 5'-TTGGAAGA-CCTCTTCCGCTTCT CGGCTTCTTTTCTGCTGATC-3' (SEQ ID NO:6) complimentary to the 5' or 3' ends of mouse exon III, respectively, with 25-bp overlapping in the middle, was subcloned and used to generate the sequence homologous to the second coding exon. A 6.2-kb EcoRI fragment, which hybridized to a probe containing mouse exon IV, was subcloned and used to generate the sequence of the region homologous to the last agouti exon.

DNA Sequencing

Genomic subclones were sequence by; the Sanger dideoxynucleotide chain-termination method (Sanger et al., 1977) using T7 DNA polymerase (United States Biochemical) (Tabor and Richardson, 1987). DNA sequence was analyzed by using the University of Wisconsin Genetics Computing Group sequence-analysis programs (Devereux et al., 1984).

Chromosomal Assignment

For chromosomal assignment of the human agouti gene, PCR™ with 24 DNA samples from the NIGMS Cell Repository human-rodent somatic-cell-hybrid mapping panel 2 (Drwinga et al., 1993) and 3 samples from the human (NA1MR91), mouse (NA05862), and Chinese hamster (NA106588) parental cell lines, respectively, were done. An oligonucleotide (5'-CCTCTTACCATTACCCCTGA-3') (SEQ ID NO:7), corresponding to flanking intron sequence 35-bp upstream of exon II and an oligonucleotide (5'-CTAGGTGACTTACCCACAAT-3') (SEQ ID NO:8), corresponding to the 3' splice junction of exon II, were used as primers A and B, respectively. PCR™ was done in 50-µl volumes containing 100 ng of template DNA, 15 pM of primer A and B, 50 mM KCl, 10 mM Tris Cl, 15 mM MgCl$_2$, 0.01% (wt/vol) gelatin, 250 mM of each dNTP, and 1.4 units of Taq polymerase. Initial denaturation was at 95° C. for 4 min, followed by 32 cycles, each consisting of 1 min at 94° C., 1 min at 55° C., and 2 min at 72° C. Ethidium bromide-stained PCR™ fragments were visualized after separation on a nondenaturing polyacrylamide gel.

Mapping by Fluorescence in Situ Hybridization (FISH)

Prometephase chromosomes for FISH analysis were obtained from cultured human lymphocytes following a slightly modified version of the method described by Rybak et al. (1982). For regional mapping of the human agouti gene, the 17-kb genomic probe h20B1 was labeled with biotin-16-dUTP (Boehringer Mannheim) by nick translation. Labeling, hybridization, and signal detection was done as described (Lichter et al., 1988; Rao et al., 1992). The signal was amplified twice using biotinylated goat anti-avidin immunoglobulins (Vector). Slides were counterstained in ethidium bromide or 4', 6-diamidino-2-phenylindole dihydrochloride (DAPI) for band identification and were mounted in anti-fade solution containing 90% (vol./vol.) glycerol/10% phosphate-buffered saline/phenylene diamine at 1 µg/ml. A Zeiss axiophot fluorescence microscope (×63, filter LP420 and LP520) was used for analysis, and representative metaphases were photographed on Scotch T640 film. The map position of the agouti locus was determined by the assignment of FISH signals to G-bands and also by length measurements and its expression in terms of fractional length (FL) from the p terminus (pter) values (FL-pter) according to Lichter et al. (1990).

RNA Isolation and Reverse Transcriptase-PCR™

Poly(A)+ RNA from normal human female subcutaneous adipose tissue was isolated using the FastTrack mRNA isolation kit with guanidinium-based lysis buffer (Invitrogen). Poly(A)+ RNA from the remaining tissues was purchased from Clontech. Two hundred nanograms of poly (A)+ RNA was reverse-transcribed to first-strand cDNA using random-hexamer primers and avian myeloblastosis virus reverse transcriptase (Invitrogen). One-twentieth of the reaction mixture was then subjected to specific PCR™ amplification as follows. PCR™ was done for 1 cycle (94° C., 5 min), 35 cycles (94° C., 30 sec; 65° C., 1 min; 72° C., 1 min), and 1 cycle (72° C., 5 min) in 5% (vol./vol.) glycerol with Taq I polymerase and 0.5 µM 5' primer:

(5'-ATGGATGTCACCCGCTTAC-TCCTGGCC-3') (SEQ ID NO:9)

and 3' primer: (5'-GCGCTCAGCAGTTGA-GGCTGAGCACGC-3' (SEQ ID NO:10)

which corresponds to the 5' or 3' ends of the putative open reading from (ORF) of the juxtaposed exons on h20B1, respectively. The glyceraldehyde-3-phosphate dehydrogenase (GAPDH) primers (Clontech) were added to separate PCR™ reactions as a control for the same reverse transcriptase product. Amplified PCR™ products were subjected to electrophoresis on 1% agarose gel.

Results

Isolation of Human Agouti Clone

To determine whether the agouti gene has been conserved in the human genome, the mouse cDNA clone was hybridized to Southern blots containing human genomic DNA. Reduced stringency hybridization conditions allowed for detection of cross-hybridizing DNA fragments with a variety of restriction enzymes. Based on this result, the same mouse agouti cDNA probe was used to screen a human genomic library. This led to the isolation of a human genomic lambda clone called h20B1. Restriction mapping of this clone revealed that it contains an insert of ≈7-kb.

Figure 10A:
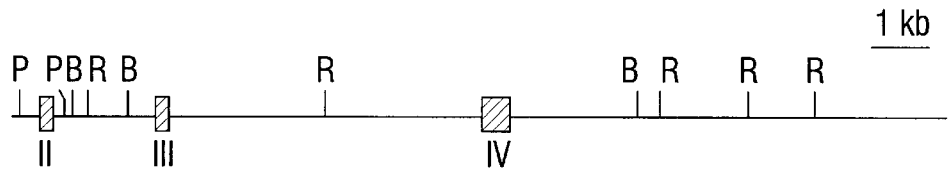
FIG. 10A. Genomic structure of human clone h20B1. Regions homologous to the three coding exons of the mouse gene are represented by black boxes and Roman numerals. P, Pst I; R, EcoRI; B, BamHI.

Characterization of clone h20B 1 revealed the presence of three distinct segments that each cross-hybridize with one of the three coding exons of the mouse agouti gene (FIG. 10A and FIG. 10B). These cross-hybridizing regions were subcloned and subjected to nucleotide sequence analysis using primers derived form the sequences of the individual mouse exons. This analysis revealed that each cross-hybridizing region of h20B1 contains sequence that is homologous with one of the three coding exons of the mouse agouti gene. Additionally, each conserved region is flanked by consensus splice donor and acceptor sites, except for the last region which, as expected, is flanked only by a splice acceptor at its 5' end. A polypyrimidine tract and putative branch point signals 10–50-bp upstream of each conserved 3' splice acceptor site were also identified.

Most notably, the ORF defined by the mouse agouti gene is retained within the individual blocks of conserved sequences in clone h20B1 (FIG. 10A and FIG. 10B). In fact, juxtaposition of these conserved regions through the putative splice donor and acceptor sequences gives rise to an ORF of 396-bp (SEQ ID NO:3). This ORF has the potential to encode a protein of 132 amino acids (SEQ ID NO:4), which is very similar to the 131-amino acid murine protein (SEQ ID NO:2). The ORF begins with a translation initiation codon (ATG) and ends with a stop codon (TGA) at positions nearly identical to that of the mouse (FIG. 10A and FIG. 10B). In the region corresponding to exon IV, a single polyadenylylation signal (AATATA) is located at a similar position to the AATAAAT found in the mouse.

Comparison of the mouse and human regions indicates that the ORF sequences are 85% identical at the nucleotide sequence level (FIG. 10A and FIG. 10B). In contrast, the human regions corresponding to the 5' and 3' untranslated portions of the mouse mRNA have diverged considerably (FIG. 10A and FIG. 10B). The human sequence has a 3-bp deletion within the region corresponding to exon III and a 6-bp deletion within the region corresponding to exon IV. Both of the sequence differences are in increments of 3-bp, which preserve the evolutionarily conserved ORF. Overall, comparison of the deduced amino acid sequences shows that the predicted human protein is 80% identical to that in the mouse (85% homology with conservative changes) (FIG. 11). Like the mouse protein, the amino terminus of the putative human protein contains all of the features of a signal peptide, including a consensus cleavage site. The highly basic domain and the cysteine-rich domain near the carboxyl terminus are also conserved between the predicted mouse and human proteins.

Chromosomal Mapping

Several genes linked to agouti in mouse chromosome 2 map to the long arm of human chromosome 20 (Siracusa and Abbott, 1993; Löffler et al., 1993). In an attempt to determine whether clone h20B1 also maps to human chromosome 20, PCR™ was performed on 24 DNA samples from the NIGMS Cell Repository human-rodent somatic cell hybrid panel 2 (Drwinga et al., 1993). Primers for this study overlapped the region homologous to mouse exon II, and, as expected, gave rise to a 238-bp amplified fragment using human genomic DNA or DNA from the parental human cell line NAIMR91 as a template. Analysis of the somatic-cell-hybrid panel 2 revealed that the agouti-specific 238-bp fragment was detected only in cell line NA10478, which is known to carry only human chromosome 20 in 84% and only chromosome 4 in another 8% of its cells (Drwinga el al., 1993). No specific products were amplified from the parental mouse line (NA05862), from the Chinese hamster cell line (NA10658), or from any of the other cell hybrids—particularly hybrid NA10115, which carries only human chromosome 4. These data unequivocally map clone h20B1 to human chromosome 20.

Figure 12B:
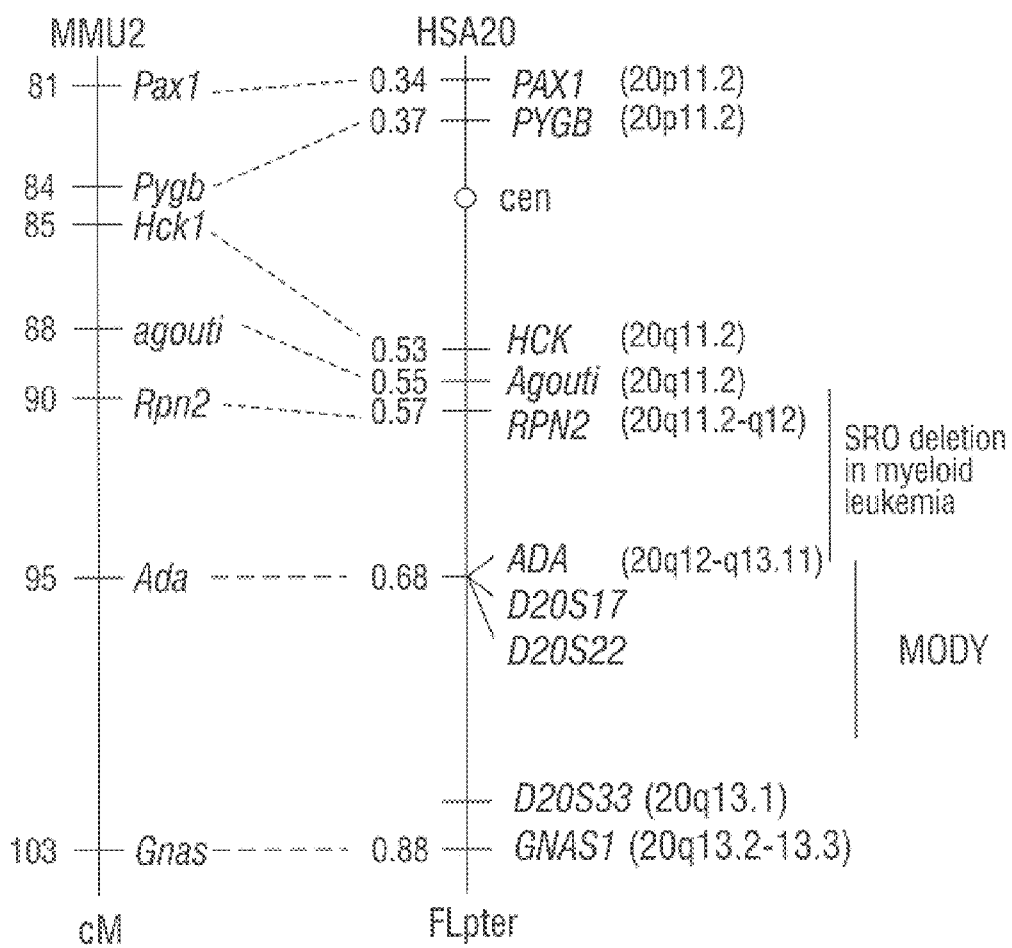
FIG. 12B. Localization of the agouti gene within the physical FISH map of human chromosome 20 (HSA20) based on mean FL-pter values (Löffler et al., 1993) demonstrating conservation of synteny within the respective segment on the composite linkage map of mouse chromosome 2 (MMU2) (Siracusa and Abbott, 1993). Numbers to the left of MMU2 indicate genetic distances in centimorgans (cM) of the loci from the centromere. Numbers to the left of HSA20 indicate physical map positions of the loci as measured by FISH and expressed as FL-pter. The cytogenetic bands in which the human loci are located are indicated in parentheses at right of the chromosome. To the far right are indicated the locations on the cytogenetic map within which the MODY locus may lie based on genetic linkage data (Rothschild et al., 1993) and the regions of the chromosome commonly deleted in patients with myeloid leukemia (Roulston et al., 1993).

For regional localization studies, FISH was done by using clone h20B1 as a probe. Hybridization was seen in the majority of metaphases in the proximal long arm of chromosome 20 (FIG. 12A and FIG. 12B). Specific FISH signals were not seen on any of the other chromosomes. According to the banding pattern of 4',6-diamidino-2-phenylindole (DAPI)-stained metaphase chromosomes, the FISH signals for the agouti gene could be assigned to band 20q11.2. A few individual signals were detected on chromatids at other chromosomal sites in some metaphases, although their pattern was inconsistent; therefore, these signals were attributed to nonspecific background hybridization.

The position of h20B1 DNA on the physical FISH map of chromosome 20 (FIG. 12A and FIG. 12B) was determined by length measurements from 13 selected chromosomes 20, and the result from this analysis were expressed in terms of FL-pter. The mean FL-pter value was determined to be 0.55±0.05, which corroborates the localization to band 20q11.2 (FIG. 12A). This assignment was also recently confirmed by FISH mapping of a 450-kb yeast artificial chromosome carrying the sequences hybridizing to h20B1. For this purpose, length measurements of 11 selected chromosomes 20 hybridized with this yeast artificial chromosome probe revealed an FL-pter value of 0.55±0.04, which is essentially identical to that obtained with the h20B1 clone.

Expression in Human Tissues

Figure 13:
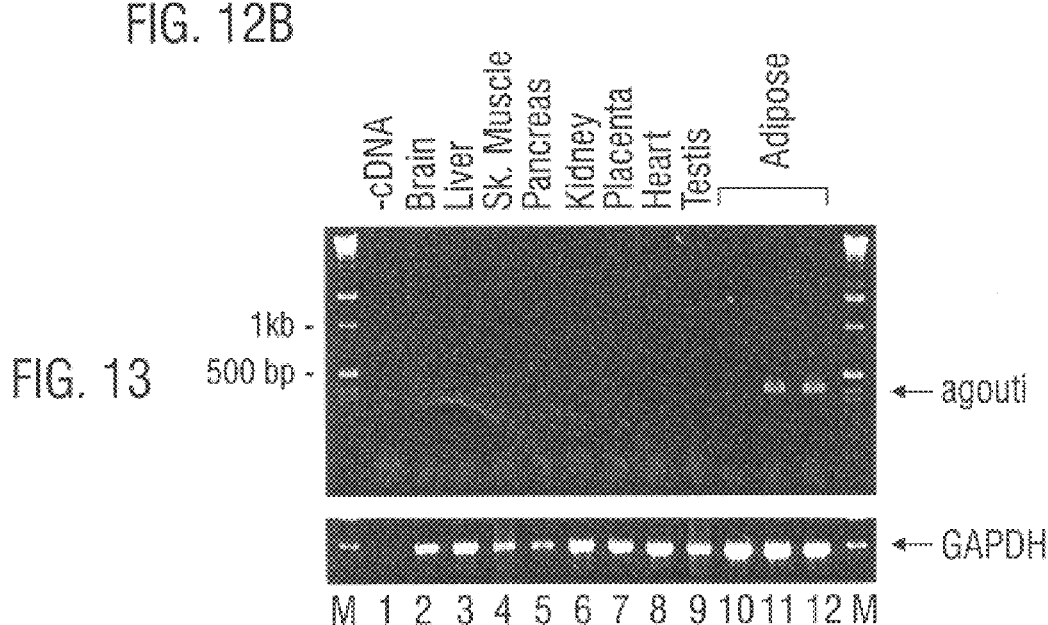
FIG. 13. Tissue distribution of human transcripts. (Upper) Amplified PCR™ products using agouti-specific primers and cDNA template reverse-transcribed from poly(A)$^+$ RNA of various tissues. Lanes: 1, no cDNA template in PCR™ reaction; 2–9, RNA from brain, liver, skeletal muscle, pancreas, kidney, placenta, heart, and testis, respectively; 10–12, RNA from adipose tissue of three different normal individuals. (Lower) Amplified PCR™ products using human glyceraldehyde-3-phosphate dehydrogenase (GAPDH)-specific primers as a control.

In an initial attempt to evaluate whether the homologous sequences on clone h20B1 are expressed, the inventors used reverse transcriptase-PCR™ to assay for the presence of transcripts in a variety of adult human tissues, including three tissues that have been implicated in non-insulindependent diabetes mellitus (muscle, liver and fat). As shown in FIG. 13, the expected 403-bp agouti-specific fragment was detected only in adipose tissue and testis. To confirm that this 403-bp fragment actually arose form the corresponding human mRNA, the PCR™ fragment was purified, subjected to nuclectide sequence analysis, and found to contain the sequences within the mouse-human homologous regions in the h20B1 clone. This result indicated that the homologous sequences in the h20B1 clone actually correspond to exons of functional gene that is expressed in selected human tissues.

Discussion

Using a cross-species hybridization approach, the inventors have isolated a human genomic clone that contains three evolutionarily conserved blocks of sequence, each of which correspond to one of the three exons that compose the entire coding region of the mouse agouti gene. The fact that the human clone contains a conserved ORF that is expressed in an RNA transcript and is predicted to encode a protein that is highly homologous and nearly identical in size to that of the mouse gene suggests that the conserved sequences from clone h20B1 actually correspond to the coding exons of a functional gene. Based on these findings, coupled with the mapping data, the inventors propose that the evolutionarily conserved sequences in h20B1 actually correspond to the coding exons of the human homolog of the agouti gene.

FISH mapping studies described here indicate that human agouti is closely linked to the MODY locus (FIG. 12A and FIG. 12B). MODY is a form of non-insulin-dependent diabetes mellitis that has an early age of onset and an autosomal dominant mode of inheritance (Fajans et al., 1992). Based on the fact that the dominant yellow agouti mutations in the mouse exhibit a non-insulin-dependent diabetic-like condition similar to that observed in MODY patients, the inventors evaluated whether agouti was a candidate gene for MODY based on the close linkage between the two. Analysis of the inventors' comprehensive FISH data revealed that agouti maps to band 20q11.2, which is the region where the loci HCK and RPN2 have been mapped (FIG. 12A and FIG. 12B) (Löffler et al., 1993). All three of these loci, HCK-agouti-RPN2, are located slightly more proximal to the 13-centimorgan sex-averaged interval encompassing ADA, D20S17, PPGB, D20S16, and D20S75, which is the region where MODY has been mapped (Rothschild et al., 1993). Therefore, taking into account only the genetic linkage data of MODY and the physical assignment of agouti to a slightly more proximal 20q segment (FIG. 12B), it appears that agouti is unrelated to MODY However, because the MODY locus mapping to chromosome 20 is based solely on a single family called RW (Rothschild et al., 1993), it is possible that a specific chromosomal structural alteration, such as an inversion, occurred in this family and that this feature of the mutation affects genetic recombination in a manner that would interfere with its accurate placement on a physical map of the region. This being the case, it is still possible that human agouti is associated with MODY in the RW family.

With respect to whether the human agouti gene is involved in tumor formation in humans, Roulston et al. (1993) recently reported that a region of human chromosome 20q is commonly deleted in patients with myeloid leukemia. By cytogenetic and FISH analysis, a commonly deleted interstitial segment (SRO) mapping to 20q11.2-q12 was identified that contains the ADA and SRC loci and is flanked proximally by the ribophorin 2 gene locus (RPN2) and distally by D20S17 (Roulston et al., 1993). FISH results place the agouti gene close to the proximal boundary of this commonly deleted segment (Roulston et al., 1993).

Although the agouti pattern of pigmentation is evolutionarily conserved throughout many mammalian species, there has never been a published report describing human hair with the banded agouti-like pigmentation pattern. Therefore, the question arises as to what role, if any, the human agouti gene may have in pigmentation. The very strong sequence conservation within the coding exons of the gene would argue that the agouti gene has some functional role in humans. One possibility is that agouti has an identical function in humans and mice and that this includes signaling the melanocyte to produce phaeomelanosomes. In this case, the lack of banded agouti pigmentation in humans could be related to the fact that humans have a continuous hair-growth cycle, which is different from the discontinuous molting hair growth cycles exhibited by various mammalian species that display agouti pigmentation. Alternatively, it is possible that the human and murine agouti genes have evolved different regulatory mechanisms for expression.

Example 14

Agouti is an Antagonist of the Melanocyte-Stimulating-Hormone Receptor

This example demonstrates that agouti is a high-affinity antagonist of the MSH receptor and blocks α-MSH stimulation of adenylyl cyclase, the effector through which α-MSH induces eumelanin synthesis. Agouti was also found to be an antagonist of the melanocortin-4 receptor (Gantz et al., 1993; Mountjoy et al., 1994), a related MSH-binding receptor. Consequently, the obesity caused by ectopic expression of agouti in the lethal yellow ($A^y$) mouse (Dickerson and Gowen, 1947) may be due to the inhibition of melanocortin receptor(s) outside the hair follicle.

Materials and Methods

Preparation of Transfected Insect Cells

T. ni cells were infected at an MOI of 2 with pAcMP3-M agouti virus or control virus and media were collected 48 h post-infection. This medium was directly loaded onto a Poros-20 HS cation-exchange column (PerSeptive Biosystems, MA) and bound protein eluted with NaCl concentrations from 0.2–1.0 M. The 0.8 M fraction was dialyzed into 50 mM NaCl, 20 mM PIPE, pH 6.5, and then diluted for assay. Agouti concentrations were estimated form gel electrophoresis and amino-acid analysis of purified protein. Media controls consisted of unrelated baculovirus supernatants collected 48 h post-infection and purified by NaCl elution of a Poros-20 HS column as for agouti.

Preparation of Agouti Protein

Figure 14:
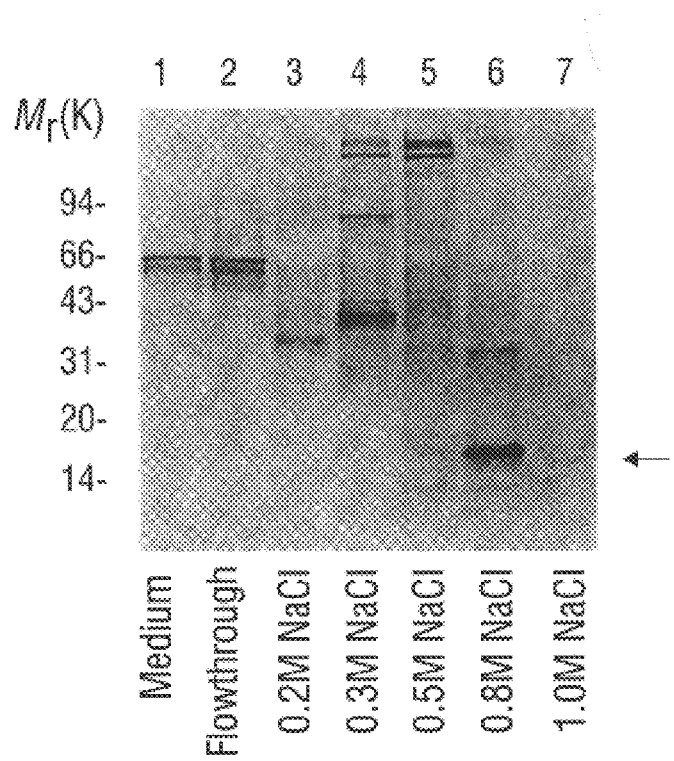
FIG. 14. Production and purification of recombinant agouti polypeptide. A 614-bp XbaI/PstI fragment of the full-length mouse agouti cDNA was subcloned into a XbaI/PstI-digested baculovirus expression vector pAcMP3 (PharMingen, San Diego, Calif.). Virus was produced using standard methods (Summers and Smith, 1987). 1 $\mu$g of each sample was electrophoresed on a 4–20% Tris-glycine gel (Novex, San Diego, Calif.) and visualized by ProBlue (Integrated Separation Systems, MA) staining. The agouti protein eluted with the 0.8 M-NaCl wash. The 18.5-K agouti species (arrow) was not observed in media infected with wild-type virus, and was demonstrated, after eluision from the gel, to contain agouti by N-terminal sequencing. Lanes: 1, 48 h post-infection medium from pAcMP3-M agouti-infected cells; 2, flow-through from Poros-20 HS column; 3–7, NaCl elutions from Poros-20 HS column. Arrow indicates authentic agouti protein.

Agouti protein was prepared as FIG. 14. Two independent preparations of agouti yielded similar results. 293 cells ($5 \times 10^5$) and 293 cells expressing human TSH-R were preloaded with 5 $\mu$Ci $^3$H-adenine for 1.5 h at 37° C. in a 5% $CO_2$ incubator. Cells were stimulated with varying concentrations of α-MSH (FIG. 15A) or bovine TSH (FIG. 15B) in the presence or absence of 0.7 nM agouti for 40 min in cyclase assay incubation medium (Dulbecco's modified Eagle's medium containing 0.1 mg ml bovine serum albumin and 0.1 mM isobutylmethylxanthine).

Medium was aspirated and 2.5% perchloric acid containing 0.1 mM cAMP was used to stop the incubation. Adenylyl cyclase activity was calculated by determining the percent conversion of $^3$H-adenine to $^3$H-cAMP as described (Salomon, 1991; Johnson and Salomon, 1991). Correlation of cAMP accumulation measured in this assay with actual adenylyl cyclase activity is made under the assumption that isobutymethylxanthine effectively blocks cAMP degradation. Data represent means and standard deviations from triplicate data points.

Adenylyl Cyclase Activity Assays (FIGS. 16A, 16B, 16C) was measured as for FIG. 15. $EC_{50}$ values were calculated using GraphPad InPlot version 4.0.

Competition binding with radiolabelled ACTH (FIG. 16D and FIG. 16E) has been described (Rainey et al., 1989): $1 \times 10^6$ cells were washed twice with binding medium containing $9 \times 10^{-11}$ M $^{125}$I-labelled $ACTH_{1-39}$ (200,000 c.p.m.; Amersham) and different concentrations of agouti, control protein or cold ACTH for 2 h at 22° C. Cells were then washed, lysed and counted as before (Rainey et al., 1989) and data were analyzed using the Kaleidagraph software package. Nonspecific binding, determined as the amount of radioactivity bound at $10^{-5}$ M cold ACTH, was 10% of the total counts bound.

Transfection of Cell Lines

The effect of agouti on α-MSH stimulation of adenylyl cyclase activity was examined in 293 cells transfected with the rMC3-R, hMC4-R or mMC5-R. Methods are described in FIG. 15 legend. Data represent means from triplicate data points and bars indicate standard deviation.

Two models have been proposed for the mechanism by which agouti protein inhibits stimulation of melanogenesis by α-MSH: (1) agouti is a negative regulator of the cyclic AMP signalling pathway acting trough a unique agouti receptor (Conklin and Bourne, 1993), or (2) agouti is a competitive antagonist of α-MSH (Jackson, 1993). The inventors produced recombinant agouti protein using the baculovirus expression system in order to test these hypotheses. The band indicated by the arrow in FIG. 14 was absent from Trichiplusia cells not infected with the agouti/baculovirus vector by N-terminal sequencing. Agouti pooled from the 0.8 M NaCl elution shown in this preparation was estimated to be 75% pure, resulting in an effective agouti concentration of ~0.14 mg ml$^{-1}$.

Figure 15A:
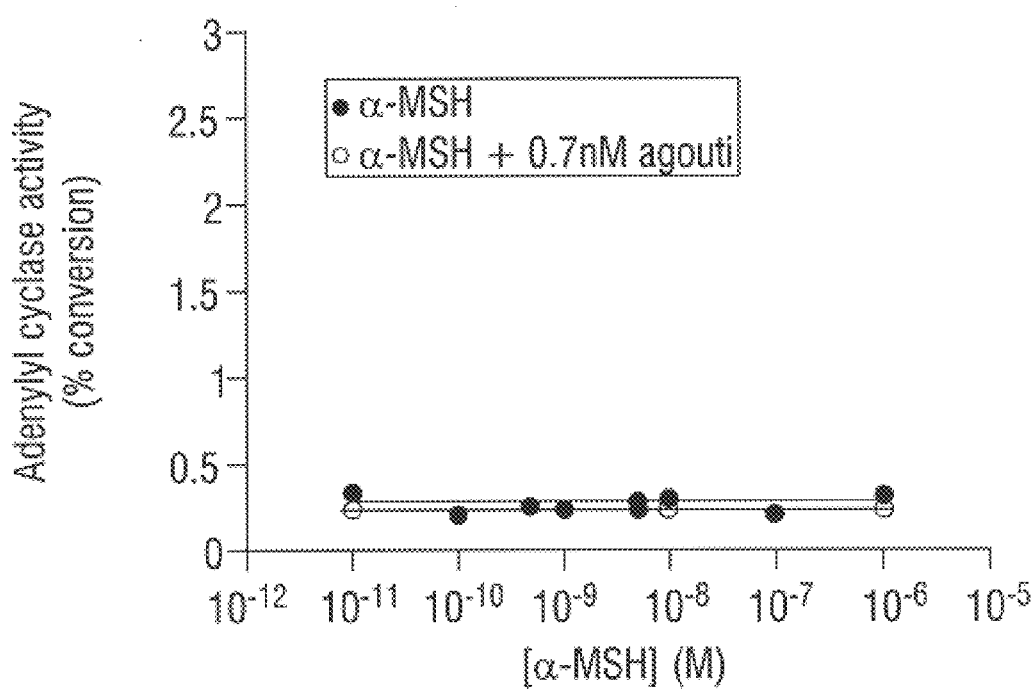
FIG. 15A. Agouti does not affect basal or TSH-R-stimulated adenylyl cyclase activity. Adenylyl cyclase assay showing no effect of agouti on basal levels of this enzyme in untransfected 293 cells. $\alpha$-MSH treatment also elicits no response, demonstrating the absence of endogenous melanocortin receptors in this cell line.
Figure 15B:
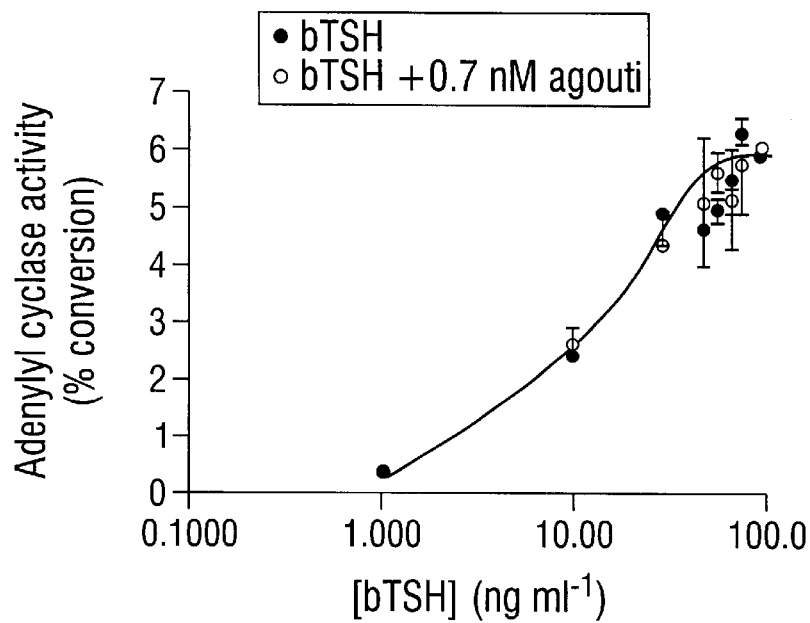
FIG. 15B. Adenylyl cyclase assay showing no effect of agouti protein on the cAMP signaling pathway following activation by bovine thyroid-stimulating hormone (TSH) of adenylyl cyclase in 293 cells transfected with human TSH-receptor.

Agouti action was examined initially on the B16F10 murine melanoma cell line (Siegrist et al., 1988). Agouti (0.7 nM) shifted the half-maximal effective concentration ($EC_{50}$) for stimulation of adenylyl cyclase by α-MSH in these cells from 1.7±0.24 nM to 13.4±3.3 nM. To characterize agouti action further, the effects of agouti on the MSH receptor (MSH-R) and other G-protein-coupled receptors stably transfected into the human embryonic kidney 292 cell were examined (Mountjoy et al., 1994; Frazier et al., 1990; Roselli-Rehfuss et al., 1993). α-MSH had no effect on the cAMP pathway in untransfected 293 cells, demonstrating the absence of endogenous melanocortin receptors in this cell line (FIG. 15A). Furthermore, addition of agouti (0.7 nM) had no effect on the basal adenylyl cyclase levels. Agouti also had no effect on the ability of thyroid-stimulating hormone (TSH) to bind to its receptor and stimulate adenylyl cyclase in TSH-R-transfected 293 cells (FIG. 15B). As the TSH-R couples to the same G protein as do the melanocortin receptors, $G_s$, this study shows that agouti acts upstream of $G_s$ in the cAMP signalling pathway.

Figure 16A:
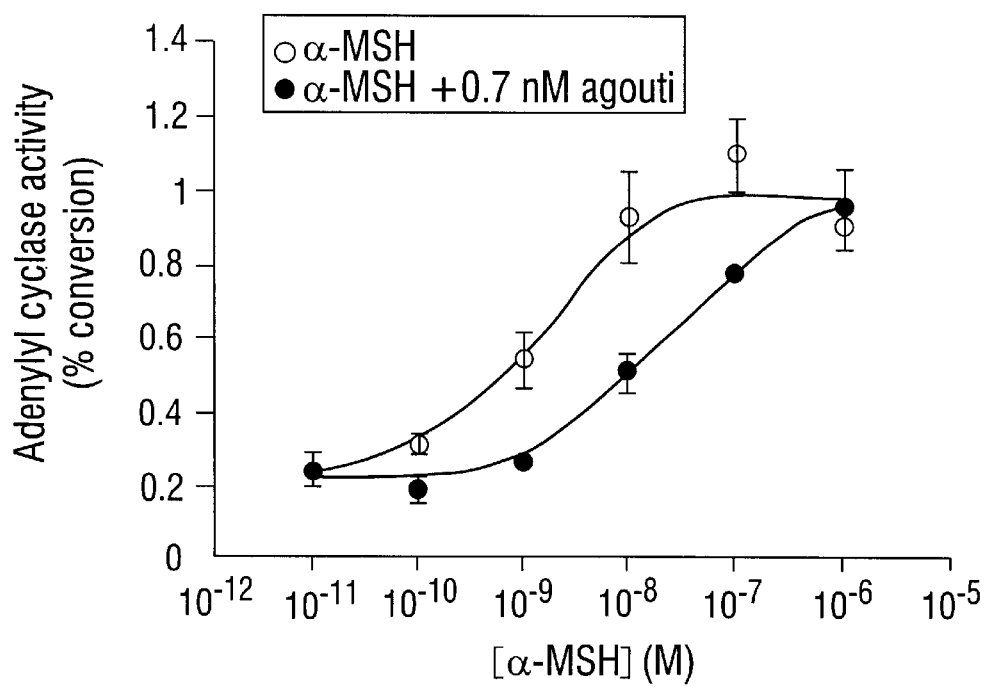
FIG. 16A. Agouti is an antagonist of $\alpha$-MSH at the murine MSH receptor. Agouti inhibits activation of the mMSH-R by $\alpha$-MSH in stably transfected 293 cells, as monitored by stimulation of adenylyl cyclase.
Figure 16B:
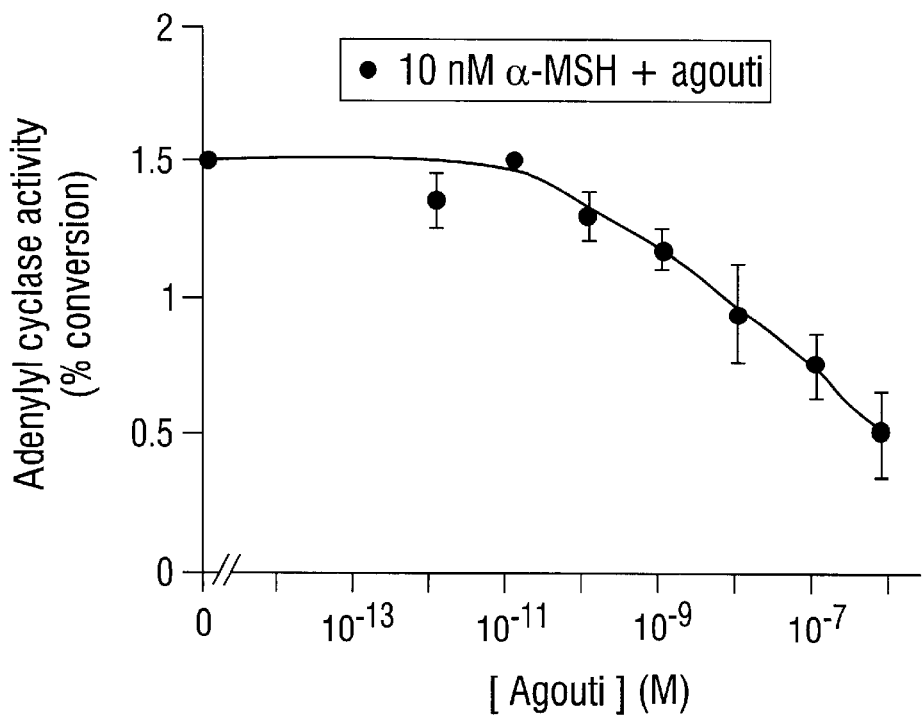
FIG. 16B. Agouti inhibition of murine MSH-R activation is dose-responsive. mMSH-R expressing 293 cells were stimulated with 10 nM $\alpha$-MSH in the presence of agouti ($10^{-12}$–$7\times10^{-7}$ M).
Figure 16C:
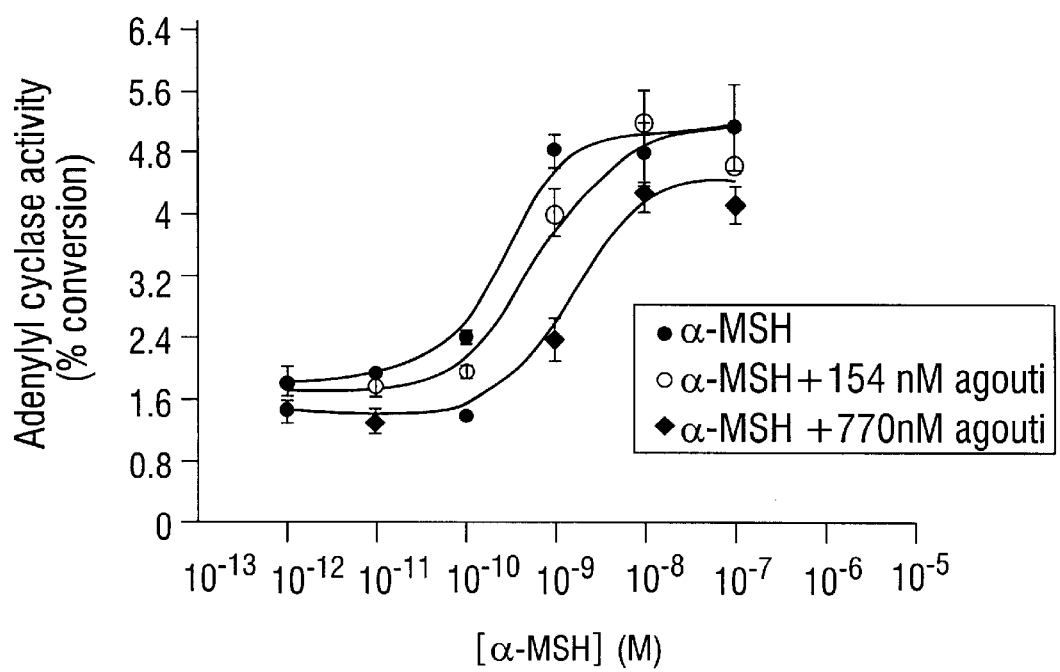
FIG. 16C. Agouti inhibits activation of human MSH-R at high protein concentrations. No inhibition of MSH-R activation by 0.7 nM agouti was obseried. $EC_{50}$ values were $2.3\pm0.8\times10^{-10}$M (no agouti), $8.8\pm2.1\times10^{-10}$ M (154 nM agouti), and $1.1\pm1.5\times^{-9}$ M (770 nM agouti).

In contrast, the same concentration of agouti protein produced a significant shift in the adenylyl cyclase/functional coupling curve of the murine MSH-R expressed in 293 cells (FIG. 16A). Control supernatants from baculovirus-infected cells at the same total protein concentration had no effect. Agouti protein (0.7 nM) increased the $EC_{50}$ for activation of adenylyl cyclase from $1.5 \pm 1.1 \times 10^{-9}$ to $2.2 \pm 1.2 \times 10^{-8}$ M, but did not alter the maximally induced activity of the receptor. The apparent $K_i$ value calculated from four independent studies was $3.2 \pm 2.6 \times 10^{-10}$ M. A dose-response curve demonstrated increasing inhibition of the murine MSH-R by agouti at concentrations from below $10^{-9}$ M up to $10^{-6}$ M (FIG. 16B). The human MSH receptor was also inhibited by agouti but only at much higher protein concentrations (FIG. 16C). It is conceivable that, unlike its murine counterpart, human agouti is a high-affinity antagonist of the human MSH-R. But as the wild-type agouti pigmentation phenotype is not commonly observed in man, it is possible that agouti no longer antagonizes MSH-R function in the human hair follicle.

Figure 16D:
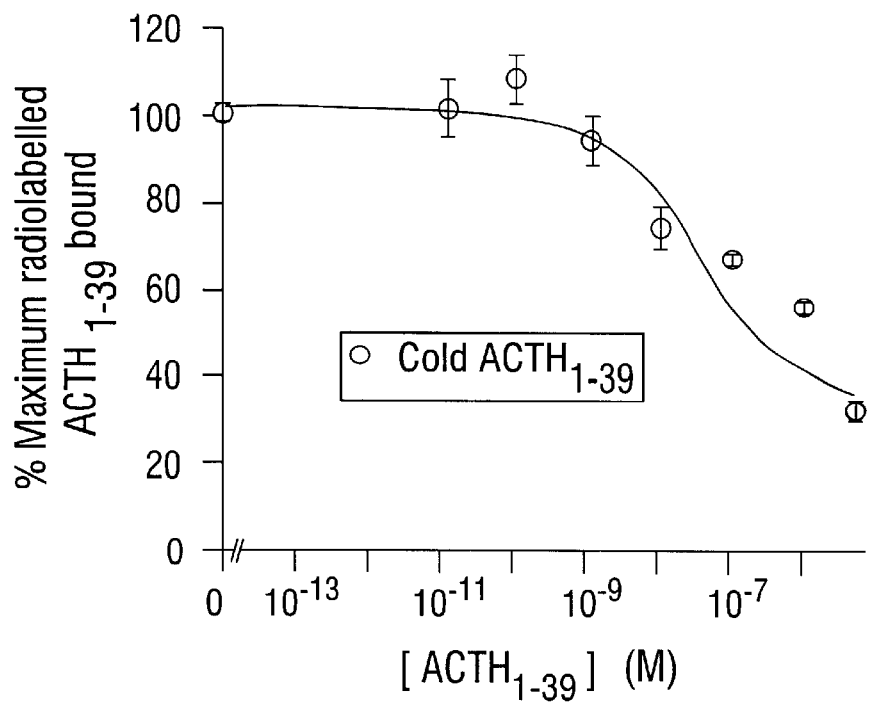
FIG. 16D. Competition binding demonstrates murine MSH-R expression in the Cloudman M-3 melanoma cell line.
Figure 16E:
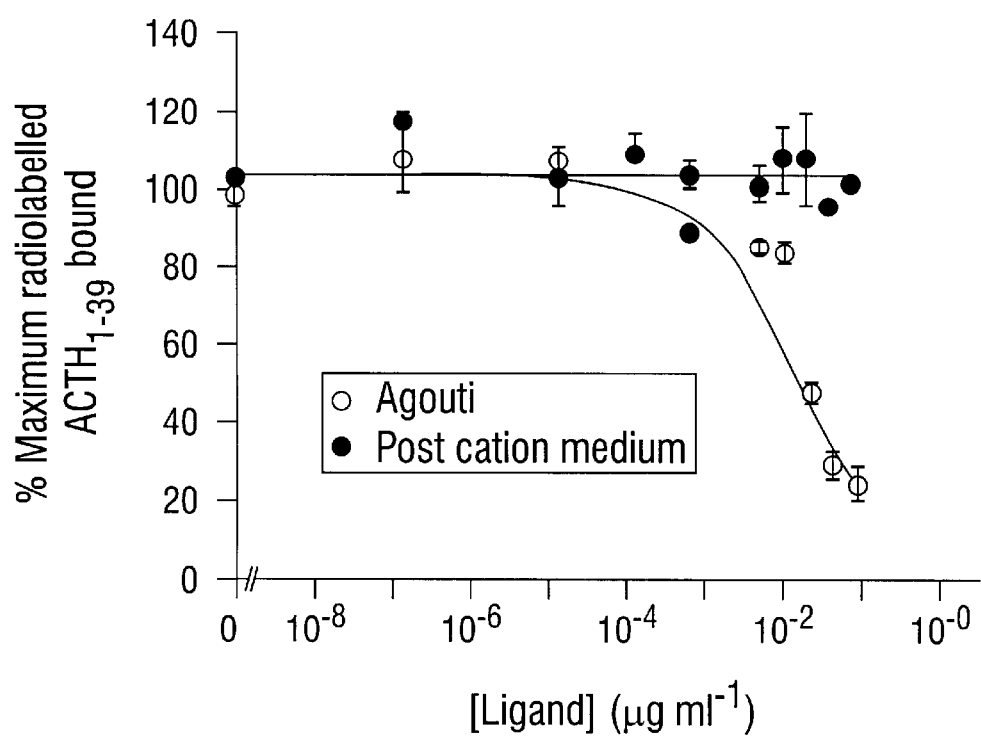
FIG. 16E. Competition binding demonstrates agouti protein blocks $^{125}$I-labelled $ACTH_{1-39}$ binding to mouse MSH-R. Baculovirus supernatants from SF9 cells infected with a virus containing an unrelated gene insert were purified in parallel with agouti protein and did not block $^{125}$I-labelled $ACTH_{1-39}$ binding to MSH-R up to 0.01 $\mu$g ml$^{-1}$. Values are shown as protein concentrations to compare agouti with control protein.

The ability of agouti to shift the MSH-R functional coupling curve without affecting maximal receptor activation suggested that agouti was acting as a competitive antagonist. To investigate this further, the ability of the protein to compete with another melanocortin peptide for binding to the mouse MSH-R was examined. Adrenocorticotropic hormone (ACTH), which contains the α-MSH peptide in its first 13 amino acids, can be radiolabelled at Tyr23 without loss of potency and binds to the same site on the melanocortin receptors as does α-MSH (Gantz et al., 1993; Roselli-Rehfuss et al., 1993; Ganz et al., 1993). Competition binding studies were performed with $^{125}$I-labelled $ACTH_{1-39}$ and the M-3 subclone of the Cloudman murine melanoma cell line. This cell line was used because of the high density of MSH receptors expressed on the plasma membrane (10,000–50,000), in contrast to the MSH-R-transfected 293 cells, which were estimated to express under 1,000 MSH receptors per cell. ACTH bound the MSH-R with a $K_d$ of $6.3 \pm 13.3 \times 10^{-8}$ M, within the range of previously reported values (Siegrist et al., 1988) (FIG. 16D). Using a single-site model, agouti protein blocked 50% of specific ACTH binding to the MSH receptor at a concentration of 1.2±0.7 ng m$^{-1}$ ($K_i$=$IC_{50}$ (half-maximal inhibitory concentration)=$6.6 \pm 3.8 \times 10^{-10}$ M) (FIG. 16E). Similar results were obtained when a synthetic radiolabelled α-MSH analog ($Nle_4$, D-$Phe_7$-α-MSH) was used as the radiolabelled ligand. As a control, baculovirus supernatant from T. ni cells infected with a baculovirus construct containing an unrelated gene insert was purified as described for agouti. This protein had no activity in this assay (FIG. 16E) or on α-MSH stimulation of adenylyl cyclase in MSH-R-transfected 293 cells.

Figure 17A:
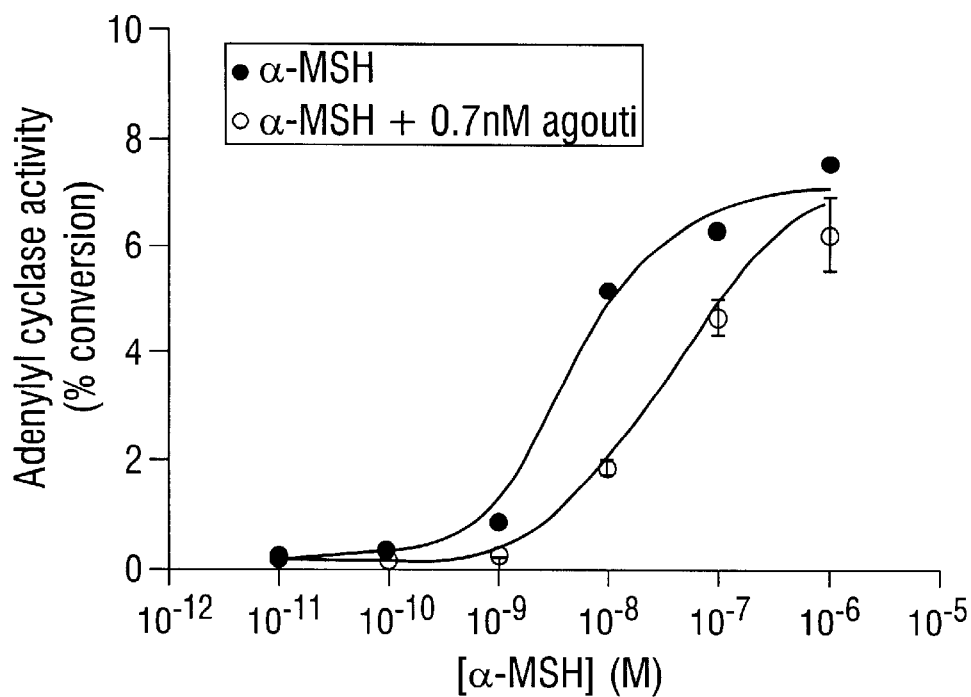
FIG. 17A. Agouti is an antagonist of the human MC4-R. Agouti antagonizes $\alpha$-MSH activation of human MC4-R.
Figure 17B:
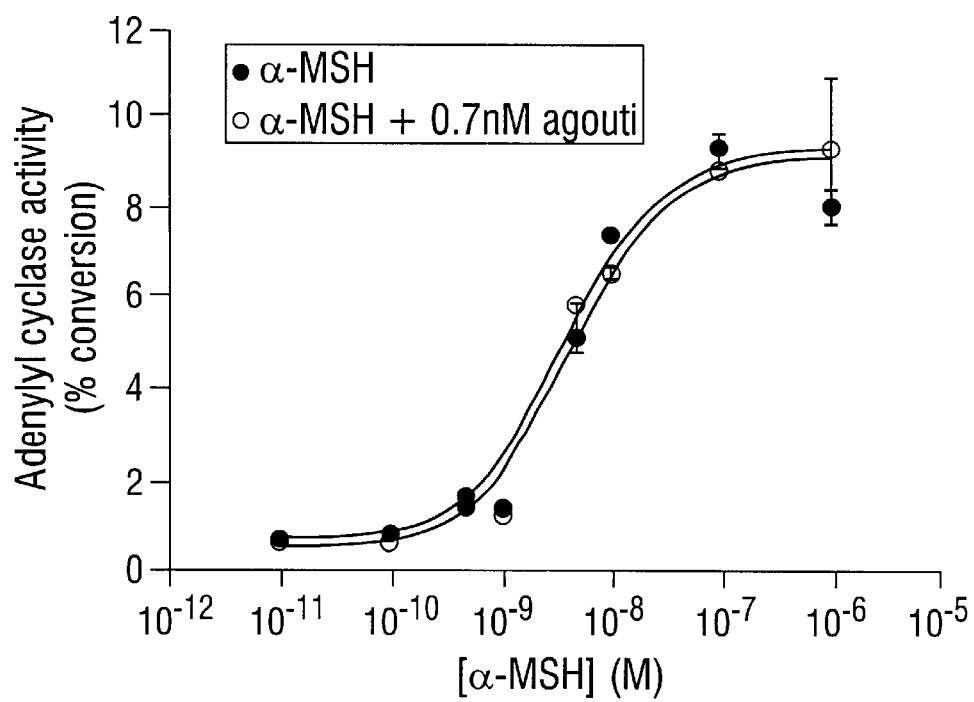
FIG. 17B. Agouti protein does not affect $\alpha$-MSH activation of rat MC3-R.
Figure 17C:
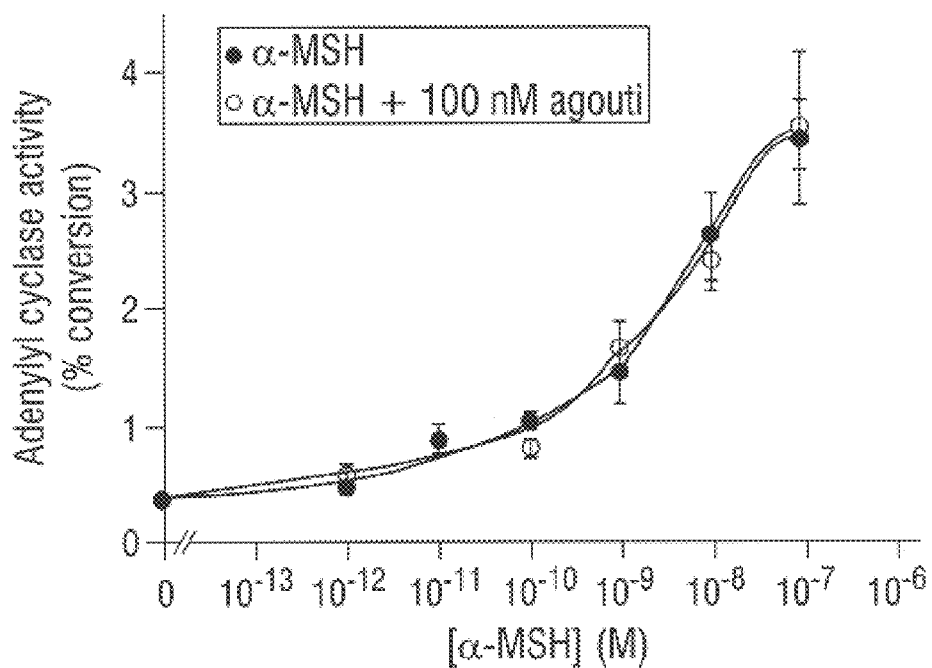
FIG. 17C. Agouti protein does not affect $\alpha$-MSH activation of mouse MC5-R. $EC_{50}$ values for adenylyl cyclase activation by rat MC3-R or human MC4-R stimulated with $\alpha$-MSH, or $\alpha$-MSH plus 0.7 nM agouti, respectively, were: rMC3-R, $4.2\pm0.8\times10^{-9}$ M; $4.1\pm0.9\times10^{-9}$ M; hMC4-R, $4.9\pm2.4\times10^{-9}$ M; $3.3\pm0.5\times10^{-8}$ M.

So far there are five members of the melanocortin receptor family, MC1-R (MSH-R) (Mountjoy et al., 1992; Chhajlani and Wikberg, 1992), MC2-R (ACTH-R) (Mountjoy et al., 1992), MC3-R (Roselli-Rehfuss et al., 1993; Ganz et al., 1993), MC4-R (Gantz et al., 1993; Mountjoy et al., 1994) and MC5-R (Chhajlani et al., 1993; Desarnaud et al., 1994). No functions have yet been described for the latter three members of the family, but the MC3-R and MC4-R are expressed primarily in the central nervous system in brain nuclei involved in neuroendocrine and autonomic control. Surprisingly, agouti was also found to be a potent antagonist of α-MSH activation of the MC4-R (FIG. 17A). Once again, the protein appeared to act like a competitive antagonist, not significantly interfering with maximal activation of the receptor. The same concentration of agouti (0.7 nM) did not antagonize activation of the MC3 or MC5 receptors, and the MC5-R was unaffected even at 100 nM agouti concentrations (FIG. 17B and FIG. 17C).

Results show that agouti is a high-affinity antagonist of the MSH-R, and of at least one of the other melanocortin receptors. Agouti appears to function as a competitive antagonist, inhibiting agonist binding to the MSH-R. This unique bifunctional regulation of the MSH-R by α-MSH and agouti allows for fine spatial and temporal regulation of eumelanin and phaeomelanin synthesis. These findings also provide a context for understanding the complex interactions of agouti and extension (MSH-R) responsible for many mammalian coat color variants, such as the variable black and tan markings I the German shepherd, resulting from combinations of two extension ($E^m$, E) and three agouti ($A^s$, $a^y$, $a^t$) alleles (Little, 1957).

Example 15
Differential Expression of Agouti Allele ($A^{IAPY}$) is Correlated with Methylation State and is Influenced by Parental Lineage The agouti gene normally confers the wild-type coat color of mice. Dominant mutations at the agouti locus result in a pleiotropic syndrome that is characterized by excessive amounts of yellow pigment in the coat, obesity, a non-insulin-dependent diabetic-like condition, and the propensity to form a variety of tumors. This example describes a dominant mutation at the agouti locus in which an intracisternal A-particle (IAP) has integrated in an antisense orientation immediately 5' of the first coding exon of the gene. This mutation, was named $A^{iapy}$, results in the ectopic expression of the agouti gene through the utilization of a cryptic promoter within the IAP 5' long terminal repeat (LTR). The coat color of $A^{iapy}/-$ mice ranges from solid yellow to a pigment pattern that is similar to wild type (pseudoagouti), and the expressivity of this mutant phenotype varies with parental inheritance. Those offspring with a yellow coat ectopically express agouti mRNA at high levels and exhibit marked obesity, whereas pseudoagouti mice express agouti mRNA at a very low level and their weights do not differ from wild-type littermates. Data are presented to show that the differential expressivity of the $A^{iapy}$ allele is correlated with the methylation status of the inserted IAP 5' LTR. These data further support the hypothesis that in dominant yellow mutations at the agouti locus, it is the ubiquitous expression of the wild-type agouti coding sequence that is responsible for the yellow coat color, obesity, diabetes, and tumorigenesis.

The pelage of wild-type mice has a pigmentation pattern called agouti, in which individual hairs have a black tip, a subapical band of yellow, and a black base. The agouti locus in chromosome 2 regulates this alternating production of black (eumelanin) and yellow (phaeomelanin) pigment granules that are deposited in growing hairs. No fewer than 19 alleles have been identified at the agouti locus that result in varying amounts of phaeomelanin and eumelanin being distributed across the dorsal and ventral surfaces of the body. These agouti alleles form a complex dominance hierarchy in which alleles that lead to the production of phaeomelanin in one region of the body, for example the dorsum, are dominant to those alleles that produce eumelanin in the same body region (for review, see Silvers, 1979).

Mice carrying agouti-locus alleles that are at the top of the dominance hierachy can be readily identified by their predominantly yellow pelage. These alleles also confer a number of dominant pleiotropic effects which, in addition to the excessive production of phaeomelanin in the coat, include obesity, an insulin-resistant diabetic condition, and the formation of a variety of tumors. Lethal yellow ($A^y$), the most dominant of the agouti-locus alleles, is characterized by mice with a solid yellow coat and a marked prevalence of the remaining pleiotropic effects. Homozygosity for $A^y$ leads to preimplantation embryonic lethality, which may be attributable to the disruption of a second gene called Raly (hn-RNP associated with lethal yellow) that is tightly linked to agouti (Michaud et al., 1993; 1994a;b;c). The second most dominant allele in the agouti hierarchy is called viable yellow ($A^{vy}$) animals carrying this mutation may also have a solid yellow pelage and all of the other dominant pleiotropic effects of $A^y$, but, as the name implies, homozygotes are viable.

The $A^{vy}$ allele is of special interest because the expressivity of the phenotype can vary considerably from one individual carrying this mutation to another, even among siblings of a single litter. For example, $A^{vy}/-$ mice exhibit a broad spectrum of coat colors that range from solid yellow, to yellow with varying amounts of agouti mottling, all the way to a coat color that has been referred to as pseudoagouti, which is similar to wild-type agouti pigmentation. Interestingly, an increased amount of phaeomelanin in the coats of mice carrying the $A^{vy}$ allele (i.e. the yellow and mottled phenotypes) is correlated with the expression of the other traits associated with this mutation, namely, obesity, diabetes, and tumorigenesis. Consistent with these observations, pseudoagouti mice remain lean and are not as likely to develop tumors as are their yellow siblings (for review, see Wolff et al., 1986; Wolff, 1987). Additionally, the expressivity of the $A^{vy}$ allele varies with parental inheritance. Female $A^{vy}/a$ mice mated with nonagouti (a/a) males produce <1% of the wild-type-like pseudoagouti class of offspring, whereas $A^{vy}/a$ males mated with a/a females produce anywhere from 10% to 34% pseudo-agouti progeny, depending on the strain of the a/a female (Wolff, 1971, 1978).

The agouti gene consists of three coding exons that are coupled with different 5'-noncoding exons to give rise to what is referred to as form I or form II transcripts (Bultman et al., 1994). Both the form I and form II agouti transcripts are ~0.8-kb in size and are expressed in the skin during hair growth. The expression of the form I transcript appears to be associated with the banded agouti pigmentation on both the dorsum and the ventrum, whereas form II transcripts are produced mainly in ventral skin throughout the hair growth process, which correlates with the predominance of phaeomelanin on the ventral surface of mice carrying the white-bellied agouti ($A^w$) and black-and-tan ($a^t$) alleles (Bultman et al., 1994).

The $A^y$ allele was characterized at the molecular level and shown to result from a 170-kb deletion in sequences upstream of the agouti gene, including the entire coding region of an unrelated gene called Raly (Michaud et al., 1993; 1994a;b;c). The net effect of this deletion is that the Raly promoter now directs the ubiquitous expression of agouti mRNA and protein in $A^y$ heterozygotes. The deletion of Raly from the $A^y$ allele causes the recessive embryonic lethality and that the ectopic overexpression of agouti in heterozygous $A^y$ mice is responsible for the dominant pleiotropic effects associated with this allele (Bultman et al., 1992; Michaud et al., 1993; 1994a;b;c).

This example describes a dominant mutation at the agouti locus, intracisternal A-particle yellow ($A^{iapy}$), in which an IAP has inserted in an antisense orientation, 51-bp upstream of the first coding exon of agouti. Transcription of the $A^{iapy}$ allele initiates from within the IAP, resulting in the ubiquitous ectopic overexpression of the wild-type agouti-coding sequence. The phenotype produced by $A^{iapy}$ is remarkably similar to $A^{vy}$ in that homozygotes are viable, and the coat color ranges from solid yellow, to varying amounts of yellow and pseudoagouti mottling, to pseudoagouti. Furthermore, yellow $A^{iapy}/-$ mice be-come severely obese, whereas their pseudoagouti siblings have normal weights. Importantly, there is a positive correlation between increasing amounts of phaeomelanin in the coats of $A^{iapy}/-$ mice and increasing levels of the ectopically expressed agouti mRNA. Interestingly, the increased agouti expression is associated with decreased levels of methylation of the IAP 5' long terminal repeat (LTR).

Materials and Methods
Mice

The $A^{iapy}$ allele arose from a spontaneous mutation of the A allele that occurred in a mating of a C3H (A/A) male to a C57BL/6J (a/a) female at The Jackson Laboratory (Bar Harbor, Me.). The subsequent breeding and maintenance of this line was done at the Oak Ridge National Laboratory, Oak Ridge, Tenn.). The $A^{iapy}$ line is currently being maintained on a C57BL/6N background.

RNA Analysis

Total cellular RNA from all tissues was extracted using the guanidine isothiocyanate procedure (Ausubel et al., 1988), enriched for poly(A)$^+$ RNA using an oligo(dT)-cellulose column (Aviv and Leder, 1972), electrophoresed through formaldehyde gels, and blotted to GeneScreen (DuPont) using standard procedures (Ausubel et al., 1988). Radiolabeled hybridization probes were prepared with the random hexamer labeling technique (Feinberg and Vogelstein, 1984). Posthybridization filter washes were conducted at high stringency (0.2×SSC, 0.1% SDS, 68° C.).

For RT-PCR™ analyses, 10 µg of total RNA was reverse transcribed (Kawasaki, 1990), ethanol precipitated and resuspended in 20 µl of H$_2$O and PCR™ analysis was performed with 2 µl of the sample as described previously (Pieretti et al., 1991). The sequences of the oligonucleotide primers used for the RT-PCR™ analysis in FIG. 22 are as follows:

I, 5'-GAACTGGCATCAAAGTACCA-3' (SEQ ID NO:11);

II, 5'-CAATGCTCCTGCCTCTGCCA-3' (SEQ ID NO:12);

III, 5'-CCTGGCTCATGCGCAGATT-3' (SEQ ID NO:13); and

IV, 5'-TTCCGCTTCTCGGCTTCTTT-3' (SEQ ID NO:14).

Southern Blot Analysis

Genomic DNA (10 µg) was digested with restriction enzymes, electrophoresed through agarose gels, and blotted to GeneScreen (DuPont) using standard procedures (Ausubel et al., 1988; Sambrook et al., 1989). Probe preparation and posthybridization filter washes were performed as described above.

Isolation of Genomic Clones

Genomic spleen and kidney DNA from an $A^{vy}$ homozygote was partially digested with Sau3A and size fractionated on a 10–40% sucrose gradient (Sambrook et al., 1989). Fractions containing 18- to 23-kb fragments were ligated into the λ vector, EMBL3 (Stratagene), packaged in vitro, and screened with $^{32}$P-labeled probe A (FIG. 18B) using standard procedures (Sambrook et al., 1989). Positive clones were purified, and portions were subcloned into pBluescript II (Stratagene).

DNA Sequencing

Genomic clones were sequenced by the Sanger dideoxynucleotide method (Sanger et al., 1977) using T7 DNA polymerase (United States Biochemical Corp.) (Tabor and Richardson, 1987). Analysis of DNA sequence was performed by use of the University of Wisconsin Genetics Computing Group sequence analysis programs (Devereux et al., 1984), and GenBank data base searches were conducted using the BLAST algorithm (Altschul et al., 1990).

Results

Genetic Characterization of a Spontaneous, Dominant Mutation at the Agouti Locus The original spontaneous mutant was a female with a mottled yellow and pseudoagouti coat and was born from the mating of a C3H (A/A) male to a C57BL/6J (a/a) female. The mutant founder female was backcrossed to her C3H father, resulting in four agouti offspring and five mutant offspring with coat colors ranging from solid yellow to yellow with moderate amounts of pseudoagouti mottling. Two of the agouti offspring from this backcross mating were sib mated, resulting in a litter of 10, 3 of which had nonagouti (a/a) black coats, indicating that one of the A alleles from the C3H father mutated to a new dominant allele (A*). Therefore, the genotype of the original spontaneous mutant is A*/a, which was subsequently verified by breeding this female to an a/a (C57BL/6N) male. Taken together, these and other breeding data suggest that A* is an allele at the agouti locus that exhibits Mendelian inheritance and is dominant to both the A and a alleles.

The phenotype produced by A* is essentially identical to $A^{vy}$ in that homozygotes are viable and the coat color ranges from solid yellow, through varying degrees of yellow and pseudoagouti mottling, to pseudoagouti. Moreover, like $A^{vy}$, where the expressivity of the mutant phenotype is dependent on whether the allele is passed through the male or the female germ line, the A* allele is also expressed in a differential manner depending on parental lineage. For example, the mating of A*/A* or A*/a (A*/–) females to a/a males produced 2 of 81 A*/a progeny (2.5%) that were pseudoagouti. The mating of A*/– males to a/a females produced 43 of 106 A*/a progeny (40.6%) that were pseudoagouti. Whereas the percentage of pseudoagouti offspring that arise from mutant male or female parents differs between A* and $A^{vy}$, in all other respects the phenotypes of these two alleles appear to be identical. These data suggest that A* may represent a new allele at the agouti locus that produces a phenotype like $A^{vy}$.

Figure 18A:
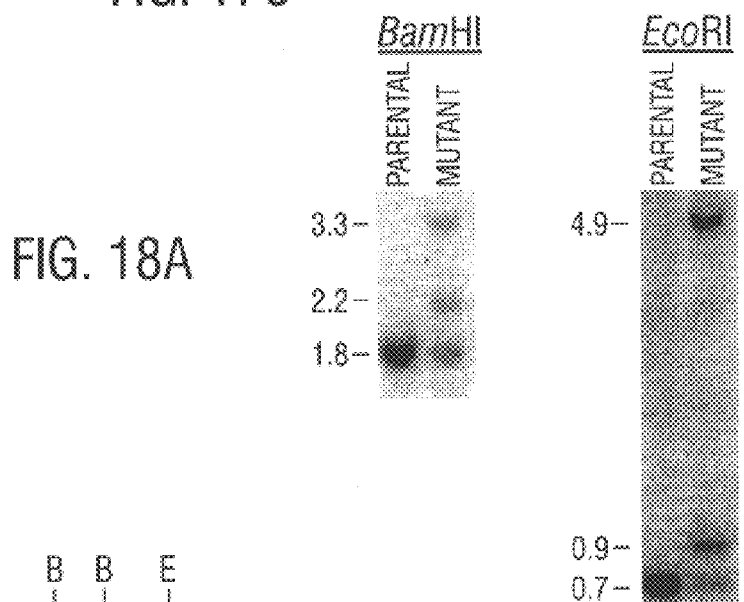
FIG. 18A. Southern blot analysis reveals that the new dorninant yellow mutation at the agouti locus contains a 5.2-kb insertion immediately upstream of the first coding exon of the gene. Genomic DNAs from the original spontaneous mutant (A*/a) and her parents [C3H (A/A) male and C57BL/6J (a/a) female] were digested with BamHI or EcoRI, blotted, and hybridized with a $^{32}$P-labeled fragment of DNA corresponding to the wild-type agouti 0.7-kb EcoRI fragment that contains the first coding exon (probe A in FIG. 18B). Because the founder (A*/a) arose from the mating of a single A/A male to two a/a females, and it was not known which of the two a/a females gave birth to the founder, DNAs from the male and both females were included in the analysis. Probe A detects the same sized parental DNA fragments for both the A and a alleles (Bultman et al., 1992), so only a single parental DNA sample (a/a female) is shown. Probe A detects a 1.8-kb BamHI fragment in parental DNA, and two RFLPs of 3.3 and 2.2-kb in the mutant DNA because the probe extends to both sides of the insertion. In EcoRI-digested DNA, probe A detects a 0.7-kb parental fragment and two RFLPs of 4.9 and 0.9-kb that are associated with the mutant allele. Sizes of DNA fragments detected are shown at left in kilobases.
Figure 18B:
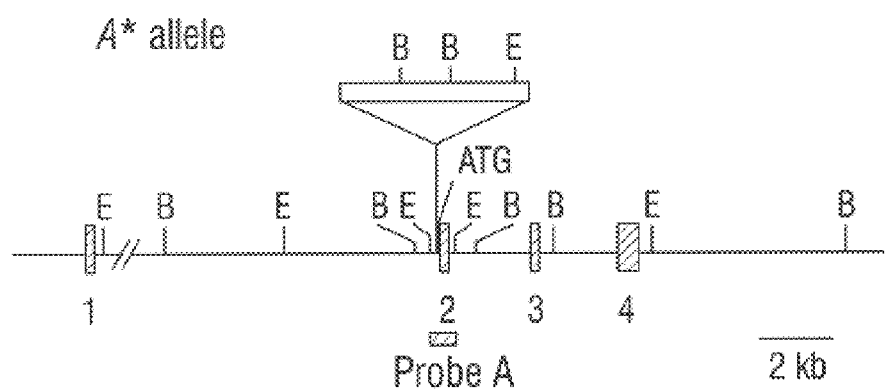
FIG. 18B. Southern blot analysis reveals that the new dominant yellow mutation at the agouti locus contains a 5.2-kb insertion immediately upstream of the first coding exon of the gene. Genomic restriction map of the new mutant agouti locus allele (A*). The horizontal line represents wild-type agouti sequence. The solid boxes depict the four agouti exons associated with form I agouti mRNA (Bultman et al. 1994) and are numbered sequentially. In the mutant allele, a 5.2-kb fragment of DNA (open rectangle) has inserted immediately upstream of the first coding exon of the agouti gene (indicated by the ATG start codon in exon 2) in the paternal A allele. Probe A is indicated by a horizontal bar. The restriction map is drawn to scale, except for the exons that are enlarged for clarity. (B) BamHI; (E) EcoRI.

To determine the molecular nature of the A* mutation, genomic DNAs from the mutant founder and her parents were digested with a variety of enzymes, blotted, and hybridized with a $^{32}$P-labeled, wild-type agouti cDNA probe. The cDNA probe detected restriction fragment length polymorphisms (RFLPs) only in the region near the first coding exon of the agouti gene in the A* allele. Subsequently, DNAs of the mutant founder and her parents were digested with BamHI or EcoRI, blotted, and hybridized with a $^{32}$P-labeled, 0.7-kb EcoRI fragment derived from wild-type DNA (probe A in FIG. 18B) that contains the first coding exon. Probe A detects the expected sized parental fragments, along with two RFLPs each in BamHI- and EcoRI-digested DNAs that are specific to the mutant locus (FIG. 18A). These data, together with additional restriction mapping of the mutant locus, indicate that a 5.2-kb fragment of DNA has inserted within the 0.7-kb EcoRI region that was used as a probe for these studies (FIG. 18B). Additionally, it was determined by Southern blot analysis that this region of the agouti gene is not rearranged in the $A^{vy}$ allele, demonstrating that A* does represent a new mutation of A.

To characterize the 5.2-kb fragment of DNA inserted into the mutant allele, probe A (FIG. 18B) was used to isolate a clone from an A*/A* genomic λ library. Characterization and DNA sequence analysis of portions of the cloned region revealed that the inserted sequence in the mutant allele is an intact IAP of the IΔI type (FIGS. 19A, 19B, 19C). Complete sequence analysis of the IAP 5' LTR revealed that it contains all of the structural features associated with a functional LTR (FIG. 19B). Additionally, sequence analysis of the DNA flanking the inserted IAP revealed the presence of a 6-bp duplication of host genomic DNA precisely at the site of integration, suggesting that the IAP integrated through a mechanism common to retroviral-like elements in the mammalian genome (Heidmann and Heidmann, 1991).

Additional mapping demonstrated that the LAP inserted in an antisense orientation relative to the agouti gene, 51-bp upstream of the 5' end of the first coding exon of agouti (FIGS. 19A, FIG. 19B, FIG. 19C). Because the LAP insertion is not present in either parent and is the only rearrangement detected in A*, new agouti locus allele has been named $A^{iapy}$. That the IAP insertion is responsible for the phenotype is apparent from the expression analyses presented below.

$A^{IAPY}$ Expression

Figure 20:
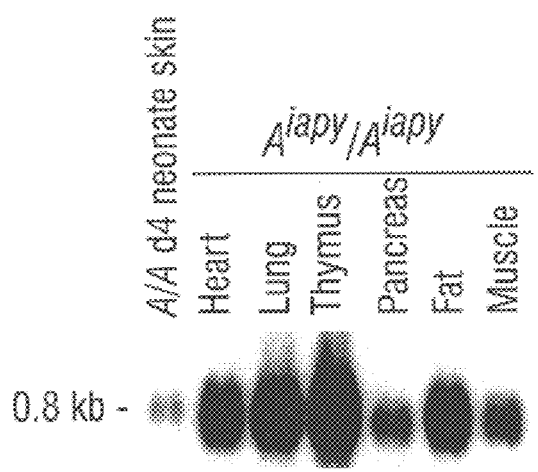
FIG. 20. Northern blot analysis demonstrates that $A^{iapy}$ mRNA is ectopically overexpressed in a variety of adult tissues. A wild-type agouti cDNA clone was $^{32}$P-labeled and hybridized to poly(A)$^+$ RNA (~2.5 µg/lane, except for pancreas and muscle, which are underloaded) from several adult $A^{iapy}/A^{iapy}$ tissues and from 4-day-old A/A neonate skin, which served as a positive control.

Previously, as an initial step in analyzing the molecular nature of the $A^{iapy}$ mutation, it was demonstrated that adult heterozygotes ($A^{iapy}$/A) with solid yellow coat colors ectopically overexpress wild-type-sized agouti mRNA in brain, testes, spleen, small intestine, kidney, and liver (Michaud et al., 1993). Additionally, RNA was analyzed from the adult heart, lung, thymus, pancreas, fat, and muscle from $A^{iapy}/A^{iapy}$ mice with solid yellow coats (FIG. 20). Collectively, these results demonstrate that the expression of the agouti gene from the $A^{iapy}$ allele is deregulated in a manner that results in the ectopic overexpression of a normal-sized agouti mRNA in a ubiquitous manner.

Figure 21:
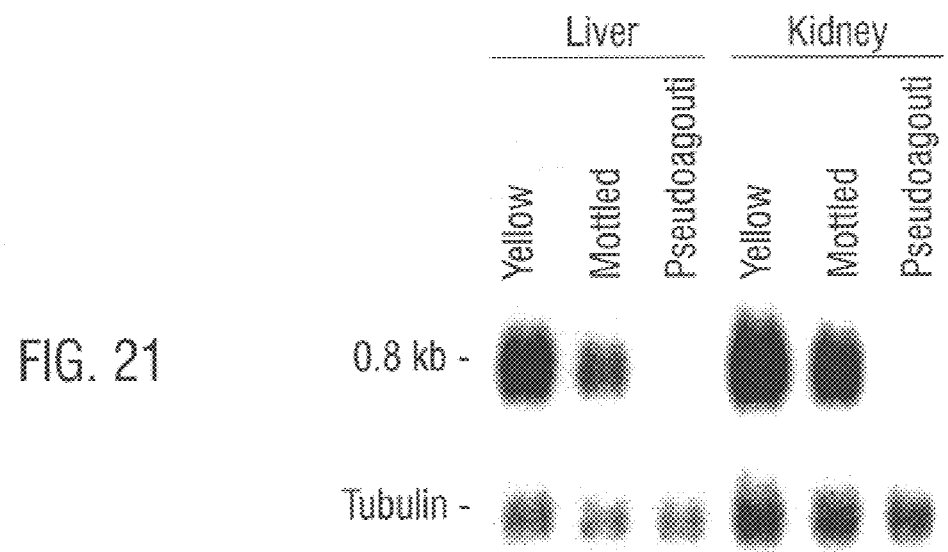
FIG. 21. Northern blot analysis of agouti locus expression in adult liver and kidney from $A^{iapy}/a$ mice with either a solid yellow, moderately mottled (yellow plus pseudoagouti mix), or completely pseudoagouti coat color. The same wild-type agouti cDNA clone that was used in FIG. 20 was $^{32}$P-labeled and hybridized to poly(A)$^+$ RNA (~2.5 µg/lane) from the kidney and liver of $A^{iapy}$ mice exhibiting the two extremes (yellow and pseudo-agouti) and an intermediate (mottled) in the full spectrum of coat color phenotypes. The filter was also hybridized with a chicken tubulin probe to control for the quantity and quality of RNA in each lane. With a longer exposure of this filter, a low level of agouti expression was detected in pseudoagouti liver but not in pseudoagouti kidney.

To determine whether the mount of yellow pigmentation in the coats of mice carrying the $A^{iapy}$ allele correlates with the level of ectopic agouti mRNA expression, RNA from the liver and kidney of solid yellow, mottled, and pseudoagouti mice was evaluated by Northern blot analysis (FIG. 21). The data demonstrate that the level of ectopic agouti expression in the liver and kidney of $A^{iapy}$/a mice is directly correlated with the amount of phaeomelanin in the coat; solid yellow mice express agouti ectopically at very high levels, pseudoagouti mice express agouti ectopically at barely detectable levels, and mottled mice express agouti at intermediate levels (FIG. 21). These results are consistent with the observation that yellow and mottled $A^{iapy}$/– mice become markedly obese (up to 75 grams), whereas their pseudoagouti siblings have normal weights (~30 grams).

Transcription of the $A^{IAPY}$ mRNA Initiates within the IAP

Figure 22A:
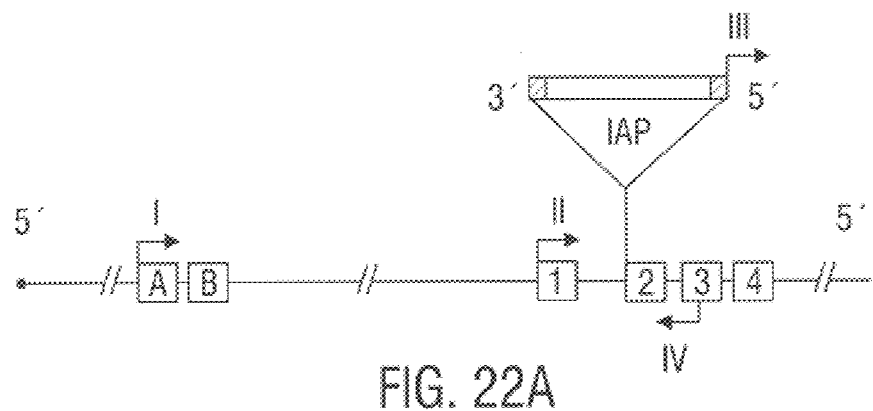
FIG. 22A. RT-PCR™ analysis reveals that transcription of agouti from the $A^{iapy}$ allele initiates from the inserted IAP genome. RT-PCR™ strategy used to determine the location of initiation of agouti transcription from the $A^{iapy}$ allele. Shown is the structure of the wild-type agouti gene as it was originally described (exons 1–4; Bullman et al., 1992) and the recently identified (Michaud et al., 1993; Bultman el al., 1994), additional 5'-non-coding exons A and B (the single box A actually represents two agouti exons (Michaud et al., 1994a;b;c). Also shown is the IAP, its location of insertion into the agouti gene, and the 5'→3' tranccriptional orientation of agouti and the IAP. The wild-type agouti gene produces several different transcripts that each contain the three coding exons (2–4) of the gene but differ in their 5'-noncoding exons (form I transcripts contain exon 1, and form II transcripts contain exon A only or exons A and B [Bultman et al., 1994]). Primers I or II were each used in conjunction with primer IV to detect the normal form II or form I agouti transcripts, respectively. Primer III was used in conjunction with primer IV to detect any transcripts initiating from the IAP 5' LTR.

When IAPs transpose in the murine genome, they can up- or down-regulate the expression of other genes, depending on the orientation of the LAP and its position of integration relative to the target gene. These retroviral-like elements can act to enhance transcription from the endogenous promoter of a gene or can initiate transcription from within its LTRs (for review, see Kuff and Lueders, 1988). To determine whether the ectopic transcription of agouti from the $A^{iapy}$ allele initiates from the normal agouti promoters or from within the inserted IAP genome in an adult tissue that does not normally express the 0.8-kb agouti mRNA, the inventors utilized a reverse transcriptase-polymerase chain reaction (RT-PCR™ strategy (FIG. 22A). Total RNA was prepared from the thymus of an adult $A^{iapy}/A^{iapy}$ mouse and was compared with RNA from 4-day-old dorsal skin of an A/A mouse, which produces only the normal form I agouti mRNA, and-RNA from a sample of 5-day-old ventral skin of an $A^{w}$/A animal, which expresses both the normal form I and II agouti transcripts. These RNA samples were reverse transcribed and subjected to PCR™ with primers that would uniquely amplify the normal form I and form II transcripts, or transcripts that would arise from the antisense strand of the LAP 5' LTR (FIG. 22A). The PCR™ products were blotted and hybridized with a probe corresponding to the coding region of the agouti gene (FIG. 22B).

Figure 22B:
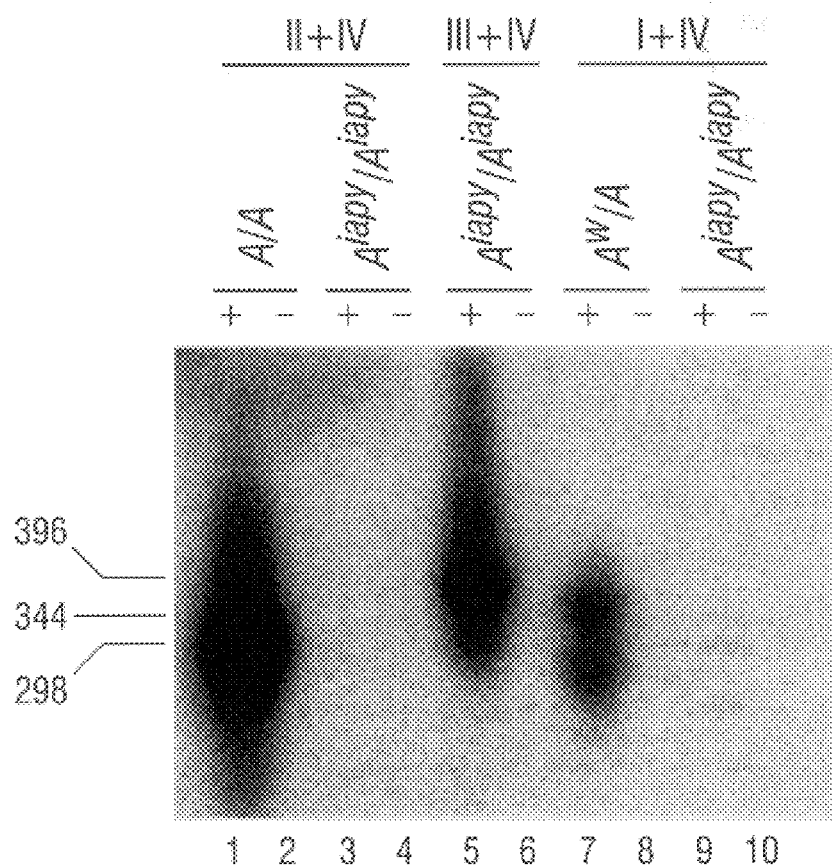
FIG. 22B. RT-PCR™ analysis reveals that transcription of agouti from the $A^{iapy}$ allele initiates from the inserted IAP genome. RT-PCR™ assay for determining the location of initiation of agouti transcription from the $A^{iapy}$ allele. Total RNA (10 µg) from adult $A^{iapy}/A^{iapy}$ thymus, 4-day-old A/A dorsal neonate skin (control for form I transcript), and 5-day-old $A^w/A$ ventral neonate skin (control for form II transcripts) was reverse transcribed and subjected to PCR™ with different combinations of primers as indicated. The PCR™ products were electrophoresed through a 3% agarose gel, blotted, and hybridized with a $^{32}$P-labeled agouti cDNA probe, which consists primarily of the three coding exons (2–4). Each lane is numbered below, and above is shown whether reverse transcriptase was (+) or was not (−) included in the RT reaction (control for contaminating genomic DNA), the genotype of the RNA sample, and the primers used in the PCR™ reaction. Oligonucleotide primers from the mouse β-actin gene were used as an internal control for each PCR™ reaction. A β-actin fragment of the expected size was observed in all five RT+ reactions (lanes 1, 3, 5, 7, 9) by ethidium bromide staining of the DNA in the agarose gel prior to transfer. Primer combinations II and IV (lane 1), and I and IV (lane 7) amplified the expected sized fragments from form I and form II agouti transcripts, respectively. Two fragments are expected in lane 7 because exon B is alternately processed in ventral-specific transcripts of $A^w$ mice (Bultman et al., 1994). Only primers III and IV amplified the expected sized fragment from the $A^{iapy}$ RT temnplate (lane 5). DNA molecular size standards are shown at left in base pairs.

The cDNA probe detected PCR™ products of the expected size that were amplified from the form I and form II agouti transcripts in the skin RNAs from both the A/A and $A^{vy}$/A controls (FIG. 22B). On the other hand, the primer combinations (II+IV and I+IV) that amplified these expected sized wild-type fragments failed to amplify any fragments in total RNA from the $A^{iapy}/A^{iapy}$ mouse, clearly indicating that the ectopic expression in the mutant animals is not attributable to the activation of expression from the wild-type agouti promoters. However, the primer pair (III+IV) designed specifically to amplify transcripts arising from the IAP 5' LTR did amplify the expected size $A^{iapy}$ fragment (FIG. 22B). These data indicate that ectopic transcription of agouti from the $A^{iapy}$ allele in adult mice does not initiate from either of the agouti promoters that normally give rise to form I and form II transcripts in skin but, instead, initiates from within the inserted IAP 5' LTR.

The Methylation State of the IAP 5' LTR is Correlated with the Level of $A^{IAPY}$ Expression It has been reported that IAP gene expression in mouse cells is regulated by CpG methylation of HhaI and HpaII restriction enzyme sites located in the 5' LTR and that increasing levels of methylation are correlated with decreasing levels of LAP expression (Morgan and Hunrig, 1984; Feenstra et al., 1986; Falzon and Kuff, 1991; Lamb et al., 1991). On the basis of this knowledge and the fact that transcription of agouti from the $A^{iapy}$ allele is initiated from within the inserted IAP LTR, the inventors considered the possibility that the range of coat color phenotypes and associated pleiotropic effects exhibited by $A^{iapy}$/– mice may be a direct reflection of the differential methylation status of the individual IAP LTRs within these mice.

Figure 23A:
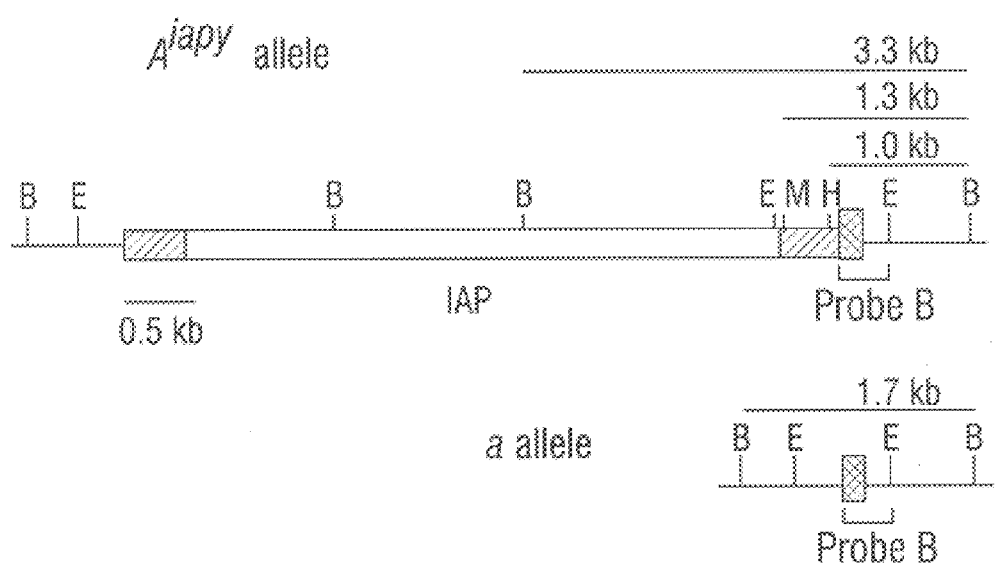
FIG. 23A. Southern blot analysis reveals that the differential expression of agouti from the $A^{iapy}$ allele is associated with the methylation state of the 5' LTR in the inserted IAP. Genomic restriction maps of a portion of the $A^{iapy}$ and a agouti alleles. The horizontal lines in each map correspond to agouti genomic sequence flanking exon 2, which is indicated by the solid box. The IAP proviral element present in the $A^{iapy}$ allele is shown as a rectangle, with the hatched regions indicating the two LTRs and the open region depicting the remainder of the IAP genome. The IAP inserted in an antisense orientation relative to the transcriptional orientation of agouti, so that the 5' LTR is the one located closest to agouti exon 2 (see FIG. 22A). Shown above each map is the size (in kb) and position (extent of horizontal line) of the restriction fragments observed in the Southern blot in FIG. 23B. The bracketed region below exon 2 corresponds to probe B used in FIG. 23B. (B) BamHI; (E) EcoRI; (H) HhaI: (M) MspI-HpaII. There are three HhaI sites and MspI-HpaII site present in the IAP 5' LTR (FIG. 19B), but only one of the HhaI sites is shown because of space considerations.
Figure 23B:
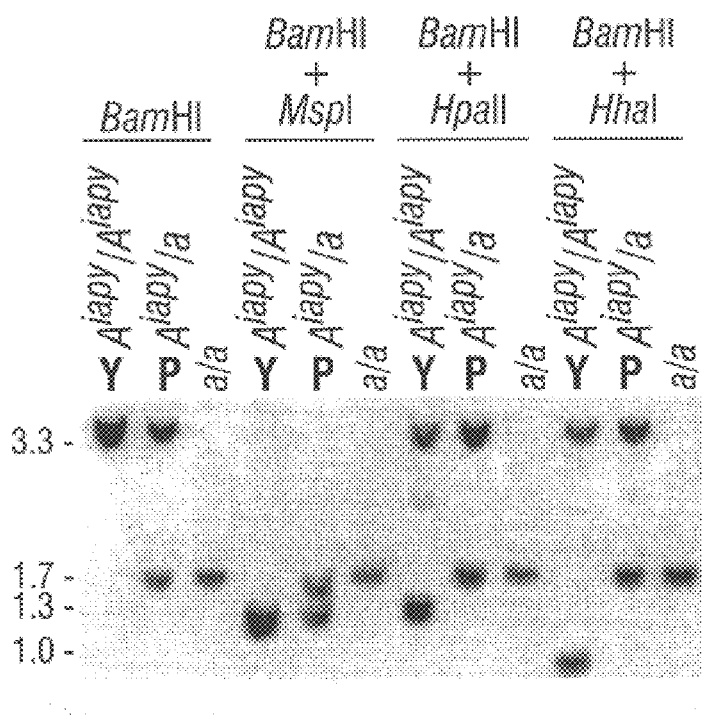
FIG. 23B. Southern blot analysis reveals that the differential expression of agouti from the $A^{iapy}$ allele is associated with the methylation state of the 5' LTR in the inserted IAp. Southern blot analysis of the methylation state of the IAP 5' LTR in $A^{iapy}$ mice with solid yellow vs. completely pseudoagouti coat colors. Genomic DNAs from mice with a solid yellow (Y, $A^{iapy}/A^{iapy}$), pseudoagouti (P, $A^{iapy}/a$), or nonagouti black (a/a) coat color with digested with BamHI, BamHI and MspI, BamHI and HpaII, or BamHI and HhaI, blotted, and hybridized with $^{32}$P-labeled probe B. (The faintly detected 2.5-kb fragments seen only in BamHI/HpaII- and BamHI/HhaI-digested DNAs of the mouse with the solid yellow coat probably result from the occasional cutting at additional HpaII or HhaI sites located in the 3.3-kb fragment between the BamHI and EcoRI sites in the IAP in cells where the HpaII or HhaI sites located in the IAP 5' LTR are methylated and not cut). Sizes of DNA fragments detected are shown at left in kilobases.

To test whether or not the methylation state of the integrated IAP 5' LTR correlates with agouti expression in $A^{iapy}$/– mice, a study was designed to analyze directly the level of CpG methylation at the HpaII and HhaI restriction enzyme sites within this 5' LTR. For this purpose, genomic DNAs from solid yellow ($A^{iapy}/A^{iapy}$), pseudoagouti ($A^{iapy}$/a), and nonagouti control (a/a) mice were digested with BamHI; BamHI+MspI; BamHI+HpaII; and BamHI+HhaI. These samples were blotted and hybridized with probe B, which lies immediately 3' of the inserted LAP element (FIG. 23A). The methylation-sensitive HpaII and HhaI sites occur at defined positions within the 5' LTR (FIG. 19B). In BamHI-digested DNAs, probe B detects a 1.7-kb fragment indicative of the balancer a allele used in these studies, whereas a 3.3-kb fragment is detected for the $A^{iapy}$ allele as a result of the insertion of the LAP immediately 5' of the second exon (FIG. 23B). For the BamHI/MspI-digested samples, as expected, probe B detects a 1.3-kb fragment for the $A^{iapy}$ allele from both yellow and pseudoagouti mice because MspI (a methylation insensitive isoschizomer of HpaII) cuts the 3.3-kb BamHI fragment to completion (FIG. 23B). When $A^{iapy}$ DNA is digested with BamHI and HpaII, probe B detects only the 3.3-kb fragment in the pseudoagouti mouse, which indicates that the $A^{iapy}$ allele is fully methylated at the HpaII site within the LAP 5' LTR. However, in the DNA from the yellow $A^{iapy}$ mouse, a substantial quantity of the 3.3-kb fragment is digested by HpaII, which is indicated by the detection of both the 3.3- and 1.3-kb fragments. A similar result is seen with the BamHI/HhaI-digested $A^{iapy}$ DNAs (FIG. 23B). Taken together, these data demonstrate that several methylation-sensitive HpaII and HhaI restriction enzyme sites in the regulatory region of the LAP 5' LTR in the $A^{iapy}$ allele are almost completely methylated in pseudoagouti mice, but are hypomethylated in solid yellow mice.

Discussion

Dominant mutations at the agouti locus are each characterized by a number of pleiotropic effects that include the development of a yellow pelage, marked obesity, noninsulin-dependent diabetes, and a variety of spontaneous and induced tumors (for review, see Wolff et al., 1986; Wolff, 1987). Analysis of the $A^y$ mutation suggests that the development of these dominant pleiotropic effects is caused by the ubiquitous expression of agouti. In $A^y$, it was determined that a 170-kb deletion that includes all of the coding exons of an upstream gene called Raly leads to the production of chimeric Raly/agouti transcripts. These chimeric transcripts retain the coding potential of the wild-type agouti gene and are ubiquitously expressed under the influence of the Raly promoter.

A new dominant yellow agouti mutation overexpresses agouti mRNA with a broad tissue distribution that resembles that observed for $A^y$. This new mutation, called $A^{iapy}$, arose from the insertion of an IAP proviral element 51-bp upstream of the first coding exon of the agouti gene. An RT-PCR™ analysis of the transcript expressed from this allele revealed that a cryptic promoter from within the IAP 5' LTR activates transcription of the downstream agouti coding exons and leads to the production of a wild-type-sized 0.8-kb mRNA. Although the transcript has a normal size, it contains a structural alteration at its 5' end that involves the replacement of the normal agouti noncoding sequences with a section of the IAP 5' LTR and the 50-bp of agouti intron sequence that occurs between the inserted IAP and the first coding exon of the agouti gene (determined on the basis of the size of the PCR™ product in a 3% agarose gel; FIG. 22A and FIG. 22B). This structurally altered agouti mRNA nevertheless appears to retain the capacity to encode a wild-type agouti protein. Therefore, mice carrying either the $A^{iapy}$ or $A^y$ alleles each develop the dominant pleiotropic effects as a consequence of the ectopic overexpression of the agouti gene.

IAPs are defective retroviruses encoded by a large family of endogenous proviral elements that occur at ~1000 copies per haploid genome in Mus musculus (Lueders and Kuff, 1980; Ono et al., 1980). Functionally, LAPs can transpose to novel places in the mouse genome and result in insertional mutations by activating or inactivating target gene expression (for review, see Kuff and Lueders, 1988; Kuff et al., 1986; Kongsuwan et al., 1989; Brigle et al., 1992; Algate and McCubrey, 1993). A number of studies have evaluated the expression of IAPs in a developing and neoplasmic tissues (Dupressior and Heidmann, 1996, 1997; Peuch et al., 1997; de Bergeyck et al., 1994; Carter et al., 1988). Particularly relevant to this study is the observation that some IAP LTRs are capable of acting in a bidirectional manner to activate target gene expression (Horowitz et al., 1984; Christy and Huang, 1988). Therefore, the finding that an IAP element has transposed into the agouti gene in the $A^{iapy}$ allele and that $A^{iapy}/-$ mice express agouti mRNA under the influence of a cryptic promoter within the IAP LTR is consistent with these previous findings.

$A^{iapy}$ has a number of features in common with the $A^{vy}$ mutation. Homozygetes of both of these mutations are viable, which distinguishes them from the $A^y$ mutation, and both develop the traits characteristic of dominant agouti alleles. Most notably, like $A^{vy}$, the $A^{iapy}$ allele shows a variable expressivity of its associated dominant traits. Specifically, the pelage of individual mice carrying the $A^{iapy}$ or $A^{vy}$ mutation can range from entirely yellow, to varying amounts of yellow and pseudoagouti mottling, all the way to an entirely pseudoagouti pigmentation pattern, which is difficult to distinguish from the wild-type agouti coat color. Whereas $A^{iapy}$ is phenotypically most similar to $A^{vy}$, it is clear that it is a new allele of agouti and not a repeat mutation of $A^{vy}$ primarily because the $A^{vy}$ allele does not contain an IAP insertion at the same site as in $A^{iapy}$.

However, on the basis of the overall similarity between $A^{iapy}$ and $A^{vy}$ in their genetic and phenotypic characteristics, the inventors propose that the agouti gene may be deregulated in a similar manner in both of these mutant alleles. It is possible that $A^{vy}$ may also be associated with the insertion of an IAP or perhaps another retroviral-like element. If $A^{vy}$ is the result of an IAP insertion, then the minor differences between the expressivity of the $A^{iapy}$ and $A^{vy}$ mutations may result from different features of the regulatory regions of each IAP element and/or their different positions of integration into the agouti gene. Alternatively, the minor differences between the expression of these two mutations may simply be a consequence of their different genetic backgrounds.

The variability in the expression of $A^{vy}$ was previously attributed to metabolic characteristics of the maternal oviductal and uterine enviromnent (Wolff, 1978). For the $A^{iapy}$ mutation, increasing amounts of phaeomelanin in the coats of these mice correlates well with increasing levels of ectopic agouti gene expression in the kidney and liver, which do not normally express agouti. This finding is particularly noteworthy because it suggests that the epigenetic factors resulting in variegated expression of agouti in the coat may also act on other, and possibly all, tissues to an equal extent within a given individual. Moreover, this predicted role of methylation in the expression of the $A^{iapy}$ allele is in agreement with the observation that the expression of IAP proviral elements is inversely correlated with the methylation state of their 5' LTRs; increased levels of methylation are associated with decreased levels of expression (Feenstra et al., 1986. Recent evidence has also shown that transcription factors bind to domains in IAP LTRs that encompass CpG sites, and methylation of cytosine residues at these CpG sites can inhibit transcription factor binding and gene expression (Falzon and Kuff, 1989; 1991; Lamb et al., 1991; Satyamoorthy et al., 1993). Given that the transcription of agouti from the $A^{iapy}$ allele appears to initiate from the 5' LTR of the inserted IAP, it seems quite likely that the wide range of agouti gene expression exhibited by $A^{iapy}/-$ mice may be attributable to the methylation state of the IAP regulatory region.

On the basis of the fact that $A^{iapy}/-$ mice with mottled coats have regions of completely yellow hair adjacent to patches of fur that exhibit pseudoagouti-banded pigmentation, the inventors predict that the methylation of the IAP regulatory region in each individual cell is an all or none phenomenon. This would suggest that in mice with mottled coats, the intermediate level of agouti expression detected by Northern analysis (FIG. 21) is attributable to mosaicism within the animal with respect to cells that do and do not ectopically express agouti. According to this proposal, those animals expressing the pseudoagouti phenotype would contain a fully methylated 5' LTR in virtually all of their cells and, hence, would express the agouti gene ectopically at extremely low levels. Moreover, the fact that the mice with the pseudoagouti phenotype develop a pigmentation pattern that is similar to the banded wild-type agouti coloration, as opposed to a solid black pelage, which is indicative of the inactivation of the agouti gene, suggests that the fully methylated LTR makes the IAP virtually invisible to the gene. Consequently, the inventors predict that the form I agouti transcript will be expressed in a normal manner in the skin of pseudoagouti mice, which is consistent with the observation that some hairs of pseudoagouti mice appear identical to wild-type agouti hairs (Galbraith and Wolff, 1974). However, because many aberrant banding pigmentation patterns are also present in the hairs of pseudoagouti mice (Galbraith and Wolff, 1974), it is possible that very low levels of ectopic agouti expression can trigger a slightly altered pigmentation pattern, but not the obesity, diabetes, or tumors, which may require higher levels of constitute agouti expression.

Interestingly, the variable level of expression of the dominant traits in mice carrying the $A^{iapy}$ and $A^{vy}$ alleles is influenced by parental inheritance. The expressivity of both alleles is higher when passed through the female germ line. This is particularly true for $A^{vy}$, where females produce <1% of the wild-type-like pseudoagouti class of offspring. In the $A^{iapy}$ allele, there is also a marked effect of parental inheritance, but the expressivity of the mutant phenotype is lower than in $A^{vy}$, regardless of whether the mutation was passed through the female or the male germ line. This is evidenced by the fact that $A^{iapy}/-$ females produce 2.5% pseudoagouti offspring compared with <1% for $A^{iapy}/a$ females, and $A^{iapy}/-$ males have 40.6% pseudoagouti offspring compared with 10–34% for $A^{vy}/a$ males. The fact that IAPs are hypermethylated during spermatogenesis but are hypomethylated in the developing octet (Sanford et al., 1987) leads the inventors to speculate that the differential expression of the $A^{iapy}$ phenotype (and possibly $A^{vy}$) associated with parental inheritance may result, in part, from differences in DNA methylation of IAPs during oogenesis and spermatogenesis that persist after the time of extensive de novo methylation in the embryo (Sanford et al., 1987).

Example 16
Agouti Regulation of Intracellular Calcium: Role in the Insulin Resistance of Viable Yellow Mice Because the yellow obese mutants are hyperinsulinemic and insulin resistant and because type I muscle fibers (e.g., soleus muscle) are a primary target for insulin action, the inventors considered the possibility that the muscle is responsive to the action of the agouti protein in yellow obese mutants. There are multiple potential cellular sites of insulin resistance; one such site is dysfunctional regulation of $[Ca^{2+}]_i$. Evaluations in $[Ca^{2+}]_i$ have been shown to result in insulin resistance in several systems (Draznin et al., 1987; Kelly et al., 1989; Byyny et al., 1992; Zemel et al., 1991; Reusch et al., 1993; Begum et al., 1992; Begum et al., 1991), although the relationship between $[Ca^{2+}]_i$ and insulin signal transduction is complex and poorly understood. Accordingly, a series of studies were performed to measure intracellular $Ca^{2+}$ levels and transport in insulin-sensitive tissue (skeletal muscle) of mice carrying the $A^{vy}$ allele of agouti and to determine the role of the agouti protein in regulating $[Ca^{2+}]_i$. This example shows that adult $A^{vy}/a$ mice (where a refers to nonagouti) exhibit increases in soleus $Ca^{2+}$ influx and $[Ca^{2+}]_i$ that correlate well with the degree of obesity in the animals. Conditioned medium containing recombinant agouti protein stimulates significant increases in $[Ca^{2+}]_i$ in both freshly isolated and cultured skeletal muscle myocytes.

Materials and Methods
Animals

C57BL/6J-$A^{vy}$ mice were purchased from The Jackson Laboratory and maintained at the Oak Ridge National Laboratory (Oak Ridge, Tenn.) by mating $A^{vy}/a$ mice to a/a nonagouti black siblings. Studies were conducted on 3- to 5-month-old male and female viable yellow ($A^{vy}/a$) mice exhibiting either pseudoagouti, mottled, or yellow coat colors (see Results) and were compared with age-matched nonagouti black (a/a) mice.

Preparation of Isolated Skeletal Myocytes

Isolated soleus and gastrocnemius myocytes were prepared essentially as described by Beam and Knudson (1988). Briefly, tissue was isolated from animals following an overnight fast and gently teased apart along the longitudinal axis. The tissue was then incubated at 37° C. for 40 min in a HEPES-buffered salt solution (HBSS; 138 mM NaCl/ 1.8 mM $CaCl_2$/0.8 mM $MgSO_4$/0.9 mM $NaH_2PO_4$/4 mM $NaHCO_3$/25 mM glucose/6 mM glutanine/20 mM Hepes/ 0.5% bovine serum albumin) containing type I collagenase at 2 mg/ml. After filtration and centrifugation, the cell pellets were resuspended in HBSS for measurement of $[Ca^{2+}]_i$.

Preparation of Cultured L6 Myocytes

L6 skeletal muscle myocytes were purchased from American Type Culture Collection (Rockville, Md.) in passage 4. Cells ($1.8 \times 10^6$) were plated in a 150-$cm^2$ flask containing Dulbecco's modified Eagle's medium (DMEM) supplemented with 5% fetal calf serum, 5% fetal bovine serum, 50 units of penicillin per ml, 5 µg of streptomycin per ml, and 10% glucose and were maintained in an atmosphere containing 5% $CO_2$ and 100% humidity. For sequential passage, nonconfluent cells were rinsed with a $Ca^{2+}/Mg^{2+}$-free Hanks' balanced salt solution (Sigma, St. Louis, Mo.) and treated with trypsin at 0.5 mg/ml for 2 min. Released cells were recovered by centrifugation. For $[Ca^{2+}]_i$ determination, cells were trypsinized and resuspended in HBSS at a density of ≈$10^6$ cells per ml.

Expression of Murine Agouti cDNA

A 707-bp EcoRV/PstI fragment of the full-length agouti cDNA was subcloned into a SmaI/PstI site in the baculoviral expression vector pVL1393 (PharMingen), TORand the construct was verified by sequencing. This construct was then packaged and titered by standard methods (Summers and Smith, 1987). T. ni cells were then infected at a multiplicity of infection of 2, and the medium was collected 48 h after infection. This medium was then filtered with a 5-kDa cutoff Sartorius filter and used directly ("agouti-conditioned" medium). Controls consisted of medium alone and medium collected 48 h after infection from T. ni cells infected with the wild-type baculovirus ("control medium").

Rabbit anti-peptide antibodies were generated against a fragment of murine agouti comprising the predicted amino acid residues from position 25 to position 40 (Bultman et al., 1992). Samples of control and conditioned medium were electrophoresed on a 4–20% SDS/PAGE gel and blotted to nitrocellulose. Immunoblots (Western blots) were performed with the agouti anti-peptide antibody in 50 mM Tris, pH 7.5/150 mM NaCl/3% bovine serum albumin (fraction 5, Sigma) at a 1:500 dilution. The second antibody was goat anti-rabbit IgG conjugated to alkaline phosphatase at 1:3000.

Northern Blot Analysis

Total cellular RNA from all tissues was extracted by the guanidine thiocyanate procedure (Ausubel et al., 1988), enriched for poly(A)$^+$ RNA by using an oligo(dT)-cellulose column (Aviv and Leder, 1972), electrophoresed through formaldehyde gels, and blotted to GeneScreen (DuPont) by standard procedures (Ausubel et al., 1988). The radiolabeled agouti probe was prepared with the random hexamer labeling technique (Feinberg and Vogelstein, 1984). Posthybridization filter washes were conducted at high stringency (in 0.03 M NaCl/0.0003 M sodium citrate/0.1% SDS at 68° C.).

$[Ca^{2+}]_i$ Determination $[Ca^{2+}]_i$ values in freshly isolated soleus and gastroncnemius myocytes and in suspensions of L6 myocytes were determined spectrofluorometrically in fura-2-loaded cells as described (Kim and Zemel, 1993; Abel and Zemel, 1993). Briefly, cell suspensions were loaded with fura-2 acetoxymethyl ester and incubated in the dark for 20 min at 37° C. with shaking, washed with HBSS, and resuspended immediately prior to $[Ca^{2+}]_i$ determination. $[Ca^{2+}]_i$ was measured by using dual excitation (340 and 380 nm) and single emission (510 nm) fluorometry. Digitonin (25 µM) and Tris/EGTA (both 100 mM, pH 8.7) were used to determine maximal and minimal fluorescent ratios, respectively, and $[Ca^{2+}]_i$ was then calculated from fluorescent ratios by the equation of (Grynkiewicz et al., 1985). To evaluate the effects of the agouti-conditioned media, cells were preincubated in a 1:9 (vol./vol.) mixture of conditioned or control medium and HBSS for 40 min, washed, resuspended, and loaded with fura-2 as above.

$^{45}Ca^{2+}$ Efflux and Influx

Soleus $^{45}Ca^{2+}$ efflux and influx were determined by using slight modifications of methods previously described (Reddy et al., 1990). For efflux, the soleus muscle was loaded with $^{45}Ca^{2+}$ by incubation in a physiological salt solution (PSS) containing 1 µCi (37 kBq) of $^{45}Ca^{2+}$/ml while being gassed with 95% $CO_2$/5% $O_2$ at 37° C. The washout of radioactivity into unlabeled medium was then followed for 90 min. $^{45}Ca^{2+}$ efflux was expressed as a percentage of the original $^{45}Ca^{2+}$ load remaining in the tissue at each point (Reddy et al., 1990), and the $Ca^{2+}$ efflux rate constant was then calculated from the $^{45}Ca^{2+}$ efflux curve. To determine $Ca^{2+}$ influx, soleus segments were equilibrated in PSS for 10 min at 37° C. while being gassed with 95% $CO_2$/5%. They were then transferred to PSS containing 1 µCi of $^{45}Ca^{2+}$/ml for 2–10 min to measure the rate of $Ca^{2+}$ influx.

Statistical Anaylsis

Comparisons between $A^{vy}/a$ and a/a mice or between agouti-conditioned and control medium were evaluated via Student's t-test. Comparisons among black, pseudoagouti, mottled, and yellow animals were evaluated via one-way analysis of variance. The effects of agouti-conditioned versus control medium on $[Ca^{2+}]_i$ in the presence or absence of extracellular $Ca^{2+}$ were assessed by two-way (incubation medium×buffer) analysis of variance. The relationship between $[Ca^{2+}]_i$ and body weight was determined via linear regression analysis.

Results

Figure 24:
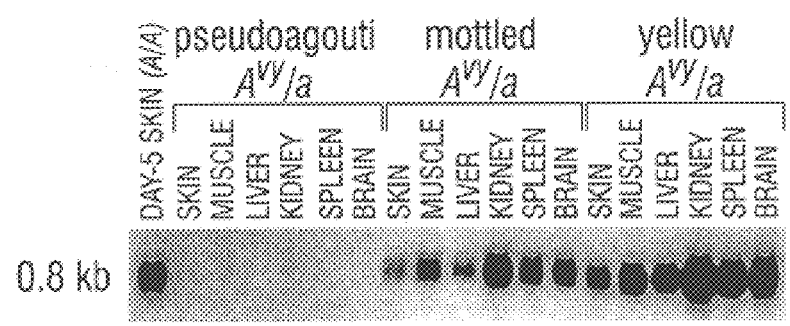
FIG. 24. Northern blot analysis of agouti locus expression in various tissues from adult viable yellow ($A^{vy}/a$) mice exhibiting either a completely pseudoagouti, moderately mottled (pseudoagouti plus yellow mix), or solid yellow coat color. Neonate skin from a day 5 wild-type agouti (A/A) mouse was included as a positive control. A wild-type agouti cDNA clone was $^{32}$P-labeled and hybridized to these poly (A)* RNAs (2.5 µg per lane, except for the following: mottled skin, 1.4 µg; mottled muscle, 2.0 µg; and yellow skin, 2.0 µg).

To evaluate the effect of the ectopic expression of the agouti gene on $[Ca^{2+}]_i$, the inventors chose to use mice carrying the $A^{vy}$ mutant allele as their model animals. $A^{vy}/a$ mice are especially well suited for these studies because the agouti gene is ectopically expressed at various levels in individual animals that carry the mutant sequences, and the level of agouti expression correlates with the degree to which the animals express the mutant phenotype (FIG. 24). For example, $A^{vy}/-$ mice with high or moderate levels of ectopic agouti expression have completely yellow fur or are mottled with patches of agouti-like hair mixed with totally yellow hair, respectively; these animals have a high propensity to develop the obesity and hyperinsulinemia traits. On the other hand, mice that ectopically express agouti at very low levels have a coat color that is similar to the wild-type agouti color and are referred to as pseudoagouti. Pseudoagouti mice have normal body weights and are not hyperinsulinemic. Although there is a direct correlation between the amount of yellow pigment in the coats of $A^{vy}/-$ mice and the level of agouti expression in many tissues of the body (FIG. 24), mice with even small amounts of yellow pigment in their coats may become obese and hyperinsulinemic, suggesting that there may be a threshold level at which agouti exerts these effects. Therefore, the effect of agouti protein on $[Ca^{2+}]_i$ and insulin resistance can be studied in sibling $A^{vy}/-$ mice that differ only in their level of agouti expression, and their coat colors provide a general indication of the level of ectopic agouti expression and their propensity to become obese and hyperinsulinemic.

Figure 25:
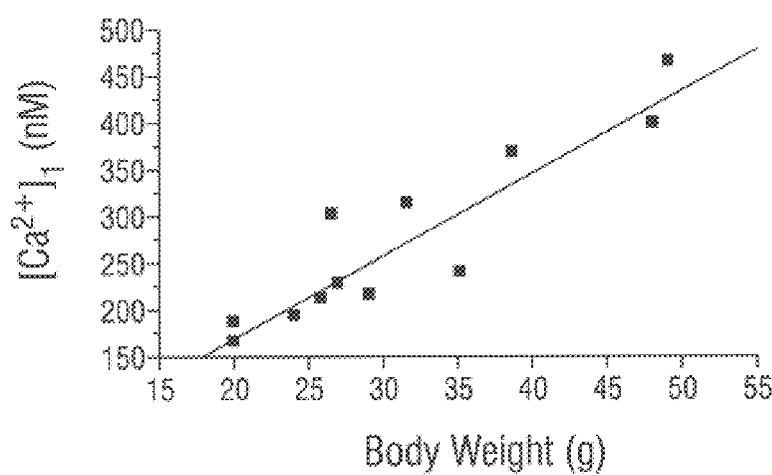
FIG. 25. Relationship between body weight and $[Ca^{2+}]_i$ in freshly isolated soleus myocytes from viable yellow mice with either a pseudoagouti, mottled or yellow coat color. There is a significant correlation (r=0.91, P<0.01; n:=18) between $[Ca^{2+}]_i$ and body weight.

This study was conducted in a muscle consisting primarily of insulin-sensitive type I muscle fibers (soleus) and in a muscle containing primarily less insulin-sensitive type II fibers (white gastrocnemius). Collectively, $A^{vy}/a$ of both genders exhibited 37% greater soleus muscle $[Ca^{2+}]_i$ compared with nonagouti black controls (P<0.01). However, this difference was dependent upon the degree of phenotypic expression of the $A^{vy}$ genotype; soleus $[Ca^{2+}]_i$ in the pseudoagouti animals was not significantly different from that in a/a mice, whereas a 2-fold increase was found in the yellow mice (Table 2). The mottled $A^{vy}/a$ animals exhibited levels only slightly lower than those of the yellow mice. These variations in $[Ca^{2+}]_i$ closely tracked the heterogeneity in body weight, and there was a high degree of correlation between the two (r=0.91, P<0.01; FIG. 25). These data are also consistent with the previous observations that pseudoagouti mice do not become obese, whereas both mottled and yellow mice have the propensity to become severely obese.

TABLE 2

[CA2+]₁ AND CA²⁺ FLUX IN NONAGOUTI BLACK (A/A) AND VIABLE YELLOW ($A^{VY}$/A) MICE WITH VARIOUS LEVELS OF ECTOPIC AGOUTI EXPRESSION

| Measurement | Nonagouti black mice | Viable yellow mice | | |
|---|---|---|---|---|
| | | Pseudoagouti | Mottled | Yellow |
| [Ca2+]i, nM | | | | |
| Soleus | 174 ± 6 | 177 ± 8 | 308 ± 35* | 330 ± 39* |
| Gastrocnemius | 293 ± 28 | 283 ± 29 | 476 ± 36* | 350 ± 40 |
| $^{45}Ca^{2+}$ flux | | | | |
| Efflux rate† | 11.9 ± 3.2 | ND | ND | 10.1 ± 1.8 |
| Influx rate† | 115 ± 28 | ND | ND | 166 ± 32* |

*Significantly different from nonagouti black (P<0.01).
†Units for the efflux and influx rates are as follows: efflux, min–1; influx, cpm/ng of protein/min.

In gastrocnemius, $[Ca^{2+}]_i$ was increased only in male mottled and yellow mice compared with the nonagouti control mice (Table 3), and there was no significant relationship between body weight and $[Ca^{2+}]_i$ in this muscle type.

To evaluate the cause of the increased $[Ca^{2+}]_i$, $Ca^{2+}$ efflux and influx studies were conducted in soleus muscle. Basal $Ca^{2+}$ efflux was not significantly different between $A^{vy}/a$ and a/a mice (Table 3), although insulin-stimulated efflux was diminished, consistent with a diminution in $Ca^{2+}$-ATPase activity in insulin resistance (Abel and Zemel, 1993; Reddy et al., 1990; Shehin et al., 1989. In contrast, the basal $Ca^{2+}$ influx rate was significantly increased in $A^{vy}/a$ mice (Table 3).

TABLE 3

EFFECTS OF AGOUTI-CONDITIONED MEDIUM ON $[Ca^{2+}]_i$ IN LG CULTURED SKELETAL MYOCYTES IN THE PRESENCE OR ABSENCE OF EXTRACELLULAR $Ca^{2+}$

| Treatment* | Medium | |
|---|---|---|
| | Control | Agouti conditioned |
| $Ca^{2+}$-containing | 84.8 ± 3.3 | 123.2 ± 4.8† |
| $Ca^{2+}$-free | 88.7 ± 4.0 | 95.7 ± 2.7 |

*n = 8 per group
†P<0.01.

To directly evaluate the role of the agouti gene product in regulating skeletal muscle $[Ca^{2+}]_i$, the inventors prepared conditioned medium containing recombinant agouti protein. For this purpose, the wild-type agouti cDNA was subcloned into a baculovirus expression vector, and T. ni cells were infected with either the agouti expression baculovirus or a wild-type baculovirus control. The medium from cells infected with the agouti expression virus produced a polypeptide that reacted against an agouti anti-peptide antibody (FIG. 26). The controls, including medium from mock-infected cells and medium from cells infected with a wild-type virus, showed no such immunoreactive species. In the agouti-conditioned medium, the antibody was competitively blocked by incubating with the peptide antigen, and the premium serum did not react with the agouti-containing medium. Additionally, the medium had agouti biological activity, since it was used to antagonize the ability of α-MSH to stimulate cAMP production in B16f10 melanoma cells (Lu et al., 1994).

Because the medium is highly fluorescent, acute effects of agouti-conditioned medium on $[Ca^{2+}]_i$ were not studied. Instead, cells were incubated in agouti-conditioned or control medium for 40 min and washed, and then $[Ca^{2+}]_i$ was measured. This 40 min incubation period prior to $[Ca^{2+}]_i$ measurement was comparable to the time required to isolate and study mouse soleus and gastrocnemius myocytes. The agouti-conditioned medium caused a significant increase in $[Ca^{2+}]_i$ in L6 cultured myocytes (Table 3) and in soleus myocytes isolated from nonagouti black mice. However, myocytes isolated from $A^{vy}/a$ mice, in which $[Ca^{2+}]_i$ was already elevated, exhibited no further increase after incubation in agouti-conditioned medium. Agouti-mediated increases in $[Ca^{2+}]_i$ were dependent upon extracellular $Ca^{2+}$, as no such increase was found in $Ca^{2+}$-free medium (Table 3).

Discussion

Although the genetic defect in yellow obese mice involves the ectopic expression of the agouti gene, it previously was unclear which tissues were responding specifically to the agouti gene product in a manner that causes the obesity and hyperinsulinemia/insulin resistance. It also was unknown how the agouti protein was effecting a response at the cellular level. This example shows that adult $A^{vy}/a$ mice exhibit significant increases in soleus $Ca^{2+}$ influx and $[Ca^{2+}]_i$ and that these increases correspond with ectopic agouti expression and obesity. Moreover, conditioned medium containing recombinant agouti protein stimulated significant increases in $[Ca^{2+}]_i$ in both freshly isolated and cultured skeletal muscle myocytes. These data provide compelling evidence to support a direct role of agouti in modulating soleus responses to insulin. Accordingly, the action of agouti on type I muscle fibers in the yellow obese mutants may contribute to their insulin resistance.

Although the $A^{vy}/a$ mice exhibited a decrease in insulin-stimulated soleus $Ca^{2+}$ efflux, there was no decrease in basal efflux. This is consistent with the inventors' previous observations in rat aortic smooth muscle, in which impaired $Ca^{2+}$-ATPase-mediated $Ca^{2+}$ efflux was a result rather than a cause of insulin resistance (Aviv and Leder, 1972; Levy et al., 1989; Zemel et al., 1993; Sowers et al., 1991). In contrast, the $A^{vy}/a$ mice did exhibit an increase in $Ca^{2+}$ influx. Therefore, increased $[Ca^{2+}]_i$ in mice carrying the $A^{vy}$ allele of agouti appears to result from an increase in $Ca^{2+}$ influx rather than from either an impairment in $Ca^{2+}$ efflux or an increase in $Ca^{2+}$ release from sarco/endoplasmic reticulum stores. This suggestion is further supported by the observation that the increase in $[Ca^{2+}]_i$ in L6 skeletal myocytes in response to incubation in agouti-conditioned medium was dependent upon extracellular $Ca^{2+}$ and did not occur in a $Ca^{2+}$-free medium. However, it is also possible that agouti-mediated effects on receptor interactions may be dependent upon the presence of extracellular $Ca^{2+}$.

Several lines of evidence support a role for $Ca^{2+}$ in modulating tissue insulin sensitivity. Draznin et al., 1987, demonstrated an optimal range of $[Ca^{2+}]_i$ for maximizing insulin-stimulated glucose transport, with elevations beyond this range causing marked decreases in adipocyte insulin sensitivity. Similarly, data from a number of studies indicate that increasing $[Ca^{2+}]_i$ in isolated adipocytes results in significant inhibition of insulin-stimulated glucose transport (Reusch et al., 1993; Begum et al., 1992; Begum et al., 1991) and oxidation (Kelly et al., 1989). In addition, $Ca^{2+}$ entry blockage in obese elderly humans resulted in significant increases in peripheral insulin sensitivity (Byyny et al., 1992; Zemel et al., 1991). Finally, Resnick et al. (1991) reported that obese patients exhibited a 41% increase in $[Ca^{2+}]_i$ compared with their lean counterparts. Moreover, there was a significant positive correlation between erythrocyte $[Ca^{2+}]_i$ and body mass index in lean and obese subjects, similar to the correlation between soleus muscle $[Ca^{2+}]_i$ and body weight observed in the present study (FIG. 25).

It appears that elevations in $[Ca^{2+}]_i$ may, in part, result in insulin resistance by affecting the phosphorylation of glucose transporter type 4 (Glut4) and other insulin-sensitive substrates within the cell (Reusch et al., 1993; Begum et al., 1992; Begum et al., 1991). Glut4 is the primary insulin-responsive glucose transporter in the cell, and its activity is regulated by serine phosphorylation (Lawrence et al., 1990). Normally, insulin activates phosphoserine phosphatase 1, which dephosphorylates and, hence, activates Glut4 (Lawrence et al., 1990). Recently, Reusch et al. (1993) reported that $K^+$ depolarization or parathyroid hormone treatments increased $[Ca2+]_i$ in isolated adipocytes and that this appeared to result in an increased phosphorylation of Glut4. This effect was likely due directly to changes in $[Ca^{2+}]_i$ because treatment with nitrenlipine, which blocks entry of $Ca^{2+}$ into the cell, maintained normal Glut4 levels of phosphorylation. These effects of increased $[Ca^{2+}]_i$ on phosphorylation of Glut4 appeared to be mediated by $Ca^{2+}$—induced phosphorylation and activation of inhibitor 1, which functions to inhibit phosphoserine phosphatase 1 activity (Begum et, 1992). Overall, based on these findings, the inventors predict that the hyperinsulinemia/insulin resistance in the yellow obese mutants causes increased $[Ca^{2+}]_i$ in soleus muscle, which induces increased activity of inhibitor 1. This effect leads to an increase in phosphorylation of PP1, which, in turn, results in an increased phosphorylation and inactivation of the insulin-responsive substrates within the cell, including Glut4.

Example 17
Ectopic Expression of the Agouti Gene in Transgenic Mice Causes Obesity, Features of Type II Diabetes and Yellow Fur Several dominant mutations at the agouti (a) locus confer a phenotype of obesity and yellow fir in mice (Silvers, 1979). The most extensively analyzed dominant mutations, lethal yellow ($A^{vy}$) and viable yellow ($A^y$), also cause a form of type II diabetes that is characterized by insulin resistance (Frigeri et al., 1983; Salem and Wolff, 1989a; Salem and Wolff, 1989b; Salem et al., 1989a; Salem et al., 1989b), pancreatic islet hypertrophy and hypexplasia (Hellerstrom and Hellman, 1963; Warbritton et al., 1994), hyperinsulinemia (Friegeri et al., 1983; Salem and Wolff, 1989a; Salem and Wolff, 1989b; Salem et al., 1989a; Salem et al., 1989b; Gill and Yen, 1990; Wolff, 1971; Wolff et al., 1990), and impaired glucose tolerance (Friegeri et al., 1983; Salem and Wolff, 1989a; Salem and Wolff, 1989b; Salem et al., 1989a; Salem et al., 1989b; Friegeri, 1988). Moderate nonfasted hyperglycemia has also been observed in males, but seldom in females (Friegeri et al, 1983; Salem et al, 1989a; Salem et al, 1989b; Hellerstrom and Hellman, 1963; Wolff et al, 1990; Carpenter and Mayer, 1958). In addition to obesity and diabetes, $A^y/-$ and $A^{vy}/-$ mice have greater-than-normal muscular and skeletal growth and an increased risk of developing hyperplasia or neoplasia in a variety of tissues. Mice that carry these dominant a-locus mutations and exhibit the pleiotropic effects are referred to as obese yellow mutants.

In adult wild-type mice (A/A and $A^w$/A), agouti gene expression has been detected thus far in the skin during the hair growth cycle and not in liver, muscle, fat, or nunerous other tissues (Bultman et al., 1992; Miller et al., 1993). In contrast, in each of the dominant obese yellow mutants analyzed, agouti gene expression has been altered in a manner that results in the expression of agouti mRNAs in numerous, if not all, tissues (Bultman et al., 1992; Michaud et al., 1993; Michaud et al., 1994a, Michaud et al., 1994b; Duhl et al., 1994). Each of these different mRNA forms has the potential to encode a normal agouti protein (Bultman et al., 1992; Michaud et al., 1993; Michaud et al., 1994a, Michaud et al., 1994b; Duhl et al., 1994). These observations suggested that the action of an ectopic agouti protein is responsible for the obesity, diabetes, and other dominant pleiotropic effects in these mutant mice (Bultman et al., 1992; Michaud et al., 1993; Michaud et al., 1994a, Michaud et al., 1994b). However, since each of the dominant mutant alleles analyzed contains structural changes in or near the agouti locus, including a 170-kb deletion of 5' flanking DNA (Michaud et al., 1994a; Michaud et al., 1994b) and the insertion of retrotransposable elements within the locus (Michaud et al., 1994a; Michaud et al., 1994b; Duhl et al., 1994), it was unclear whether the widespread expression of agouti per se causes the pleiotropic effects or whether effects of these mutations on an additional gene located in the vicinity of the agouti locus contribute to the complex phenotype. This example demonstrates that transgenic mice that ectopically express a wild-type agouti cDNA in numerous tissues develop the obesity, hyperinsulinemia, hyperglycemia, and yellow fur commonly observed in the spontaneous obese yellow mutants.

Materials and Methods
Mice

All mice were maintained at the Oak Ridge National Laboratory. The FVB/N (A/A) mice were obtained from the inventors' partially inbred stock, and C57BL/6J (a/a; nonagouti black) mice were purchased from The Jackson Laboratory. The $A^y$/A mice are Ft-hybrids resulting from a cross between mice of the inventors' $A^y$/a stock (originally on the C57BL/6 background) with FVB/N mice. All mice were provided with a high-fat diet (Mouse Diet 5015, PMI Feeds, ≧11% fat) and water ad libitum, except those used in FVB/N line maintenance, which were fed a normal diet (Lab Diet, PMI Feeds, 4.5% fat).

Agouti Expression Constructs

The portion of the agouti cDNA included in the expression constructs extends from nucleotide 8 to nucleotide 662 in the previously reported agouti cDNA sequence (Bultman et al., 1992). It was generated by PCR™ amplification (Bultman et al., 1994) from the agouti cDNA clone (Bultman et al., 1992) by using the oligonucleotide primers 5'-ACAGGAAAGACATTCTGGC-CTGGC-3' (forward) (SEQ ID NO:15) and 5'-TTTAGCTTCCACTAGGTT-TCC-3' (reverse) (SEQ ID NO:16). The amplified product was cloned directly into the pCRII vector (Invitrogen) and subcloned into pBluescript II (Stratagene) as a 676-bp EcoRl fragment (clone pa-E.68). To generate the initial expression construct, designated BAPa (FIG. 27A), the cDNA segment was isolated from pa-E.68 as a HindIII-BamHI fragment and cloned into the corresponding sites of pBAP.2 (Ray et al., 1991). To make the second construct, designated PGKPa (FIG. 27B), the neomycin-resistance gene of the PGK-neo expression vector (McBurney et al., 1991) was removed by Pst I digestion and replaced with the 676-bp EcoRI agouti cDNA fragment after filling in the EcoRI ends with the Klenow fragment and introducing Pst I ends by linker ligation (Sambrook et al., 1989). The nucleotide sequences of the agouti cDNA and immediate flanking regions were determined (Sambrook et al., 1989) to verify the integrity of the expression constructs.

Transgenic Mice

One-cell FVB/N embryos were microinjected with either the BAPa (5.3-kb Cla I fragment) or PGKPa (1.7-kb EcoRI-HindIII fragment) construct (3 µg/ml in 10 mM Tris-HCl, pH 7.5/0.1 mM EDTA), and transgenic mice were derived as described (Hogan et al., 1986).

DNA (Southern) and RNA (Northern) Blot Analysis

Southern- and Northern-blot hybridization analyses were performed as described (Bultman et al., 1992; Sambrook et al., 1989). The Raly cDNA probe has been de-scribed (Michaud et al., 1993); the agouti cDNA probe was the 676-bp EcoRI cDNA fragment in clone pa-E.68.

Weight Gain and Blood Analysis

From 4 to 24 wk of age, body weights of mice were measured every 2 wk (±3 days), after which weights were taken every 4 wk. Blood was obtained by retroorbital sinus puncture from nonfasted mice of various ages. Plasma insulin levels were measured by RIA (ICN) with porcine insulin as a standard, and glucose levels were determined by glucose oxidase (Trinder reagent; Sigma Chemical Co.) or hexokinase/glucose-6-phosphate dehydrogenase (Abbott) assays. All data are reported as the mean±SEM for four categories of mice: transgenic females, control females, transgenic males, and control males. Statistical comparison between transgenic mice and controls was performed by using an unpaired two-group t-test (STATVIEW II; Abacus Concepts, Berkeley, Calif.).

Results
Analysis of Transgene-Directed Agouti Gene Expression

The objective of this work was to generate and study transgenic mice that ectopically express wild-type agouti transgenes in as many tissues as possible. To accomplish this, the wild-type agouti cDNA was placed under the transcriptional control of either the human β-actin or mouse Pgk-1 gene promoter and enhancer (expression constructs BAPa and PGKPa, respectively; FIG. 27). β-actin and Pgk-1 promoters have been reported to direct widespread gene expression in transgenic mice (Ray et al., 1991; Balling et al., 1989; Pravtcheva et al., 1991). Several BAPa and PGKPa transgenic founder mice were generated by pronuclear microinjection of the expression constructs. Transgenic lines were established from two BAPa founder mice and one PGKPa founder (lines TgN(BAPa)20Rpw, TgN (BAPa)52Rpw and TgN(PGKPa)8Rpw, abbreviated here BAPa20, BAPa52, and PGKPa8, respectively) and maintained in the FVB/N (albino) strain.

Figure 28:
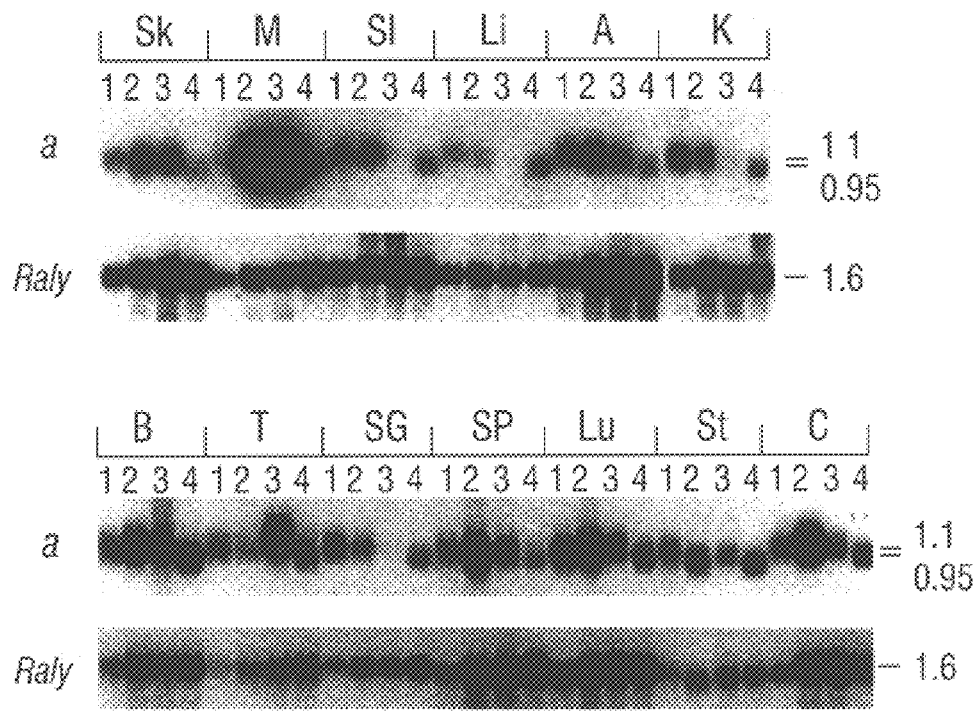
FIG. 28. Expression of agouti transgene-derived mRNAs in several tissues of adult transgenic (Tg/−) mice. Northern blots containing poly(A)$^+$ RNA ($\approx$2.5 µg per lane) from tissues of Tg/− and A$^y$/A mice were hybridized with a radiolabeled agouti cDNA probe and subsequently with a cDNA probe for the Raly gene, which was used as a loading control because it is expressed at comparable levels in numerous tissues of mice (Michaud et al., 1993). Lanes 1–4 refer to A$^y$/A, BAPa20/−, BAPa52/−, and PGKPa8/− mice, respectively. Sk, skin; M, skeletal muscle; SI, small intestine; Li, liver, A, white adipose tissue; K, kidney; B, brain; T, testis; SG, salivary gland; Sp, spleen; Lu, lung; St, stomach; C, colon. Numbers refer to average sizes (kb) of the mRNAs. An of the mRNAs detected in Tg/− mice with the agouti probe were derived from transgene expression, since agouti is not expressed in any adult tissues or wild-type mice (Bultman et al., 1992).

Adult mice that were hemizygous for the transgene (Tg/−) were examined for the levels of ectopic agouti gene expression. The levels of transgene-derived agouti mRNA in numerous tissues of Tg/− mice from lines BAPa20, BAPa52, and PGKP-a8 are shown in FIG. 28. Agouti mRNA levels in A$^y$/A mice are also shown for comparison. Tg/– mice from lines BAPa20 and PGKPa8 (i.e. BAPa20/– and PGKPa8/– mice) express the agouti transgenes at high levels in all of the 14 tissues examined and produce mRNAs of the expected sizes (1.1-kb and 0.95-kb in BAPa20/– and PGKPa8/–, respectively). In contrast, BAPa52/– mice express very low or undetectable levels of agouti mRNA in liver, pancreas, small intestine, kidneys, and salivary gland, and high levels in the remaining tissues. Unexpectedly, BAPa20/– and BAPa52/– animals express agouti at extremely high levels in skeletal muscle. BAPa20/– mice express agouti at higher levels than A$^y$/A mice in every tissue examined except liver, pancreas, kidney, testis, and salivary gland. In contrast, the levels of agouti mRNA in PGKPa8/– mice are less than those in A$^y$/A mice in most tissues, whereas the levels are roughly comparable in skin, muscle, stomach, and brain. In the livers of PGKPa8/– mice, the level of agouti expression is considerably greater than in A$^y$/A mice.

Transgenic Mice Ectopically Expressing Agouti Develop Yellow Fur, Obesity, Hyperinsulinemia, and Hyperglycemia Since the BAPa20/– and PGKPa8/– mice expressed the agouti transgenes in all of the tissues examined, these mice were analyzed for several of the phenotypic traits of the obese yellow mutants. In view of the fact that BAPa52/– mice did not express agouti in all of their tissues, they were not analyzed further in this study. Because several previous studies reported that A$^y$/– mice become much more obese on Ft hybrid backgrounds than on inbred backgrounds (reviewed in Wolff and Pitot, 1973; Fenton and Chase, 1951), Tg/– mice on the wild-type FVB/N genetic background (A/A) were mated with non-agouti-black C57BL/6J (a/a) mice, and the (C57BL/6J×FVB/N)F$_1$ [i.e. (B×F)F$_1$] Tg/– progeny were analyzed for several of the dominant pleiotropic effects. In addition, many of the A$^y$/– and A$^{vy}$/– mice studied previously carried the a allele or had genetic backgrounds that included contributions from the C57BL or C57BL/6 strains (Gill and Yen, 1990; Wolff et al., 1986; Wolff and Pitot, 1973).

Although FVB/N mice have the agouti (A/A) genotype, it was not possible to observe the effects of ectopic agouti gene expression on coat color in Tg/– mice on the FVB/N genetic background because FVB/N mice are albino (c/c). Therefore, the availability of the (B×F)Ft Tg/– offspring (Tg/–; A/a; C/c), which are pigmented, allowed the inventors to evaluate these effects. The (B×F)Ft BAPa20/– and PGKPa8/– progeny have solid yellow or mottled yellow fur, respectively, as opposed to the agouti coat of the nontransgenic littermates (+/+; A/a; C/c). This was the first available evidence indicating that the agouti transgenes are capable of giving rise to functional protein that can alter the phenotype of the animals.

Figure 29A:
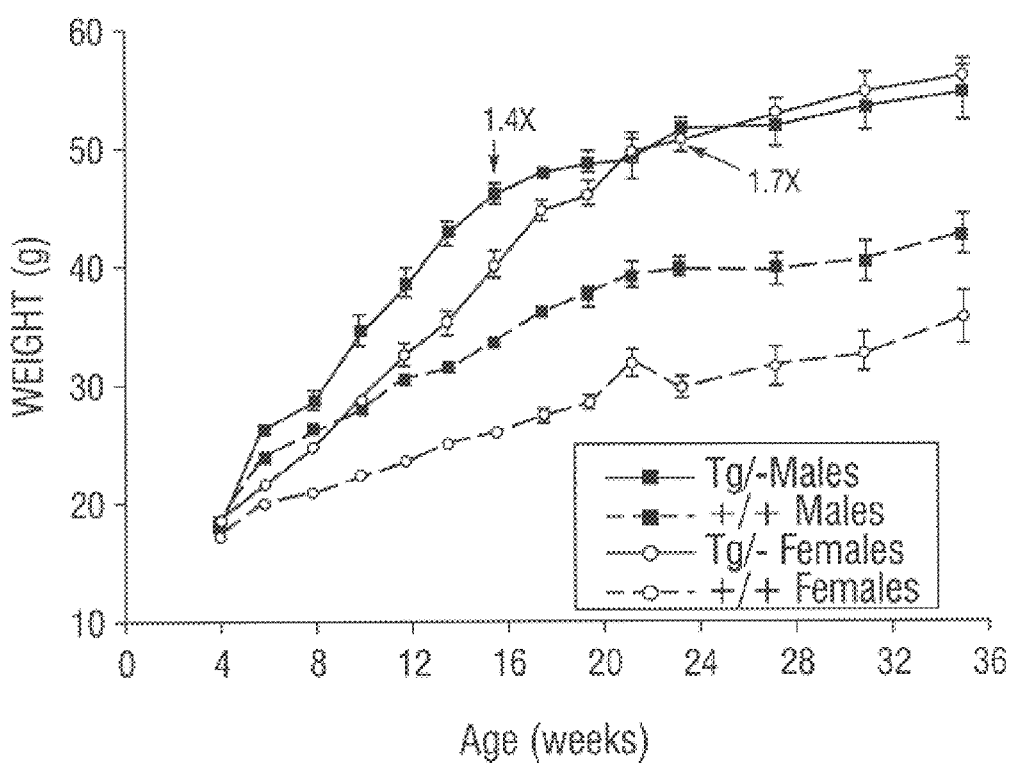
FIG. 29. Weight gain of transgenic (Tg/−) and normal control nontransgenic (−/+) mice from lines BAPa20 (Upper) and PGKPa8 (Lower). Average weights in grams are plotted with respect to age in wk. Separate curves are shown for each genotype and sex. Bars represent 1 SE from the mean. The mean weights of Tg/− mice were significantly greater than those of nontransgenic +/+ littermates (P<0.01) at every age point except at 4 wk for male BAPa20/− mice. 4 and 6 wk for female PGKPa8/− mice, and 4, 8, and 12 wk for male PGKPa8/− mice. Arrows indicate time points at which weights of Tg/− mice reach their greatest difference from controls (indicated as fold increase of Tg/− mice over +/+ controls).
Figure 29B:
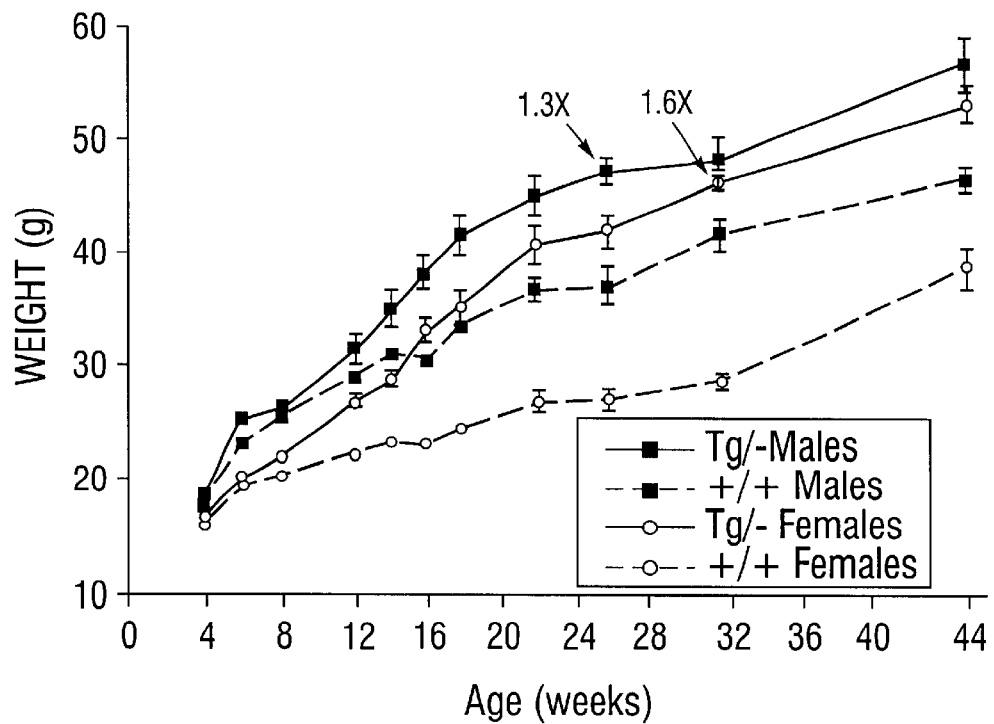

The weights of yellow Tg/– mice and nontransgenic litter-mate controls were analyzed as they matured, beginning at 4 wk of age. In view of reports that the weight gain of A$^y$/– and A$^{vy}$/– mice is accelerated relative to control littermates when fed high-fat diets (Frigeri et al., 1988; Carpenter and Mayer, 1958; Fenton and Chase, 1951), the Tg/– and control mice were fed a high-fat diet ($\geq 11\%$ fat) during their entire lifespan to accentuate any effect that the agouti transgene expression may have on weight gain. The weight gain analyses revealed that yellow BAPa20/– and PGKPa8/– mice of both sexes develop a marked obesity relative to their control littermates (FIG. 29). The average weights of BAPa20/– mice first became significantly greater (P<0.01) than control weights by about 4 and 6 wk of age in females and males, respectively (FIG. 29 Upper). PGKPa8/– females and males first became consistently heavier (P<0.01) than controls by 8 and 14 wk of age, respectively (FIG. 29 Lower). Tg/– females ultimately developed a greater obesity relative to controls (1.7-fold increase in line BAPa20 at 24 wk of age and 1.6-fold increase in line PGKPa8 at 32 wk of age) than did Tg/– males (1.4-fold increase in line BAPa20 at 16 wk of age and 1.3-fold increase in line PGKPa8 at 26 wk of age) (FIG. 29). At similar ages, BAPa20/– mice were heavier than PGKPa8/– mice (e.g., BAPa20/– mice are 1.2-fold heavier than PGKPa8/– mice at 16 wk of age; FIG. 29).

Figure 30A:
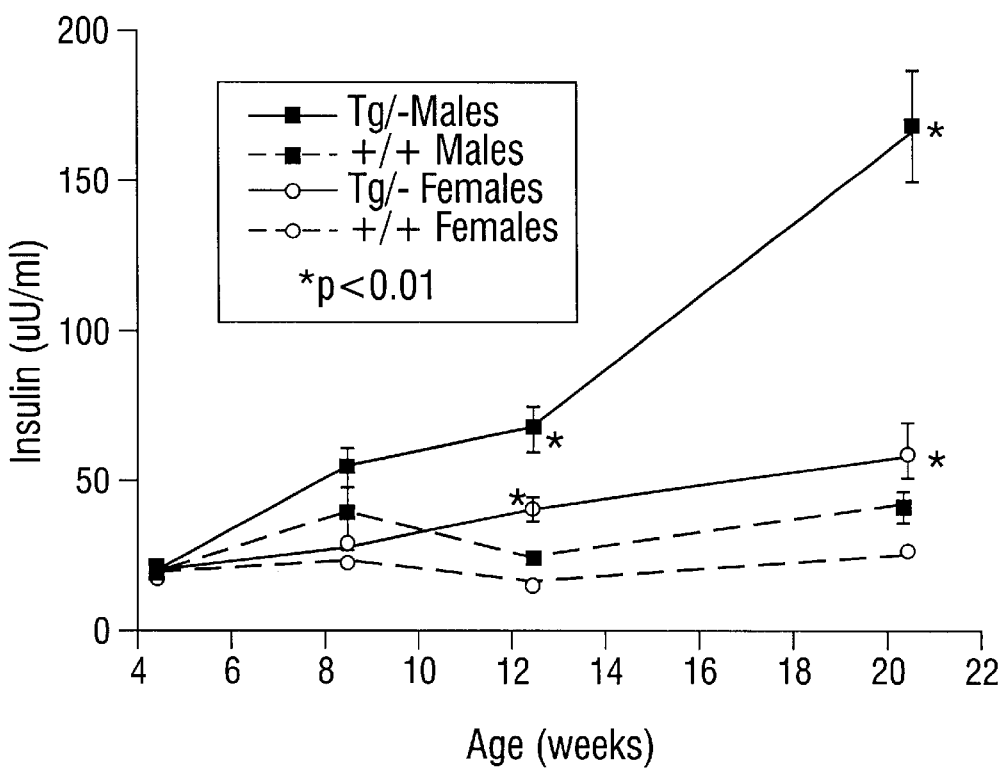
FIG. 30. Mean plasma insulin levels in microunits (µU) of insulin per ml plotted as a fimction of age in wk for transgenic lines BAPa20 (Upper) and PGKPa8 (Lower). Separate curves are shown for each genotype and sex. Bars represent I SE from the mean. The mean insulin levels of Tg/− mice that are significantly greater (P<0.01) than those of nontransgenic +/+ controls are marked with an asterisk.
Figure 30B:
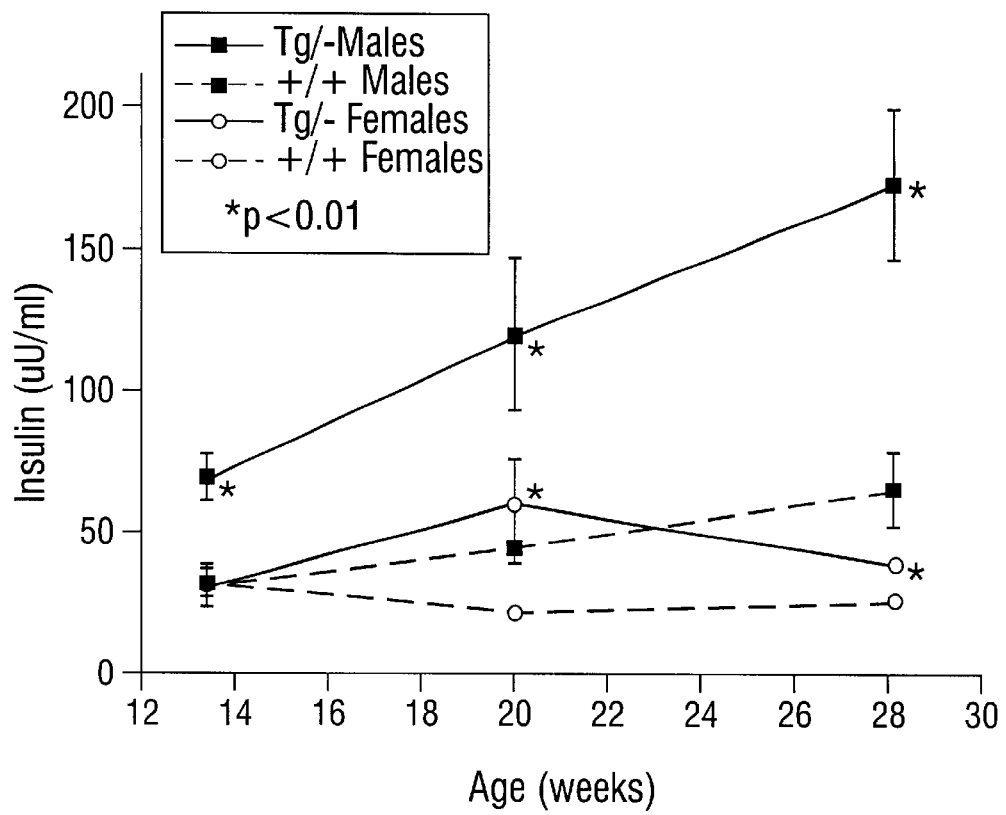

The plasma insulin and glucose levels of the Tg/– mice and littermate controls were also analyzed as they aged. By 20 wk of age, yellow BAPa20/– and PGKPa8/– mice of both sexes had developed significantly higher (P<0.01) levels of insulin in their blood than control littermates, but the hyperinsulinemia was more severe in males than in females (FIG. 30).

Figure 31A:
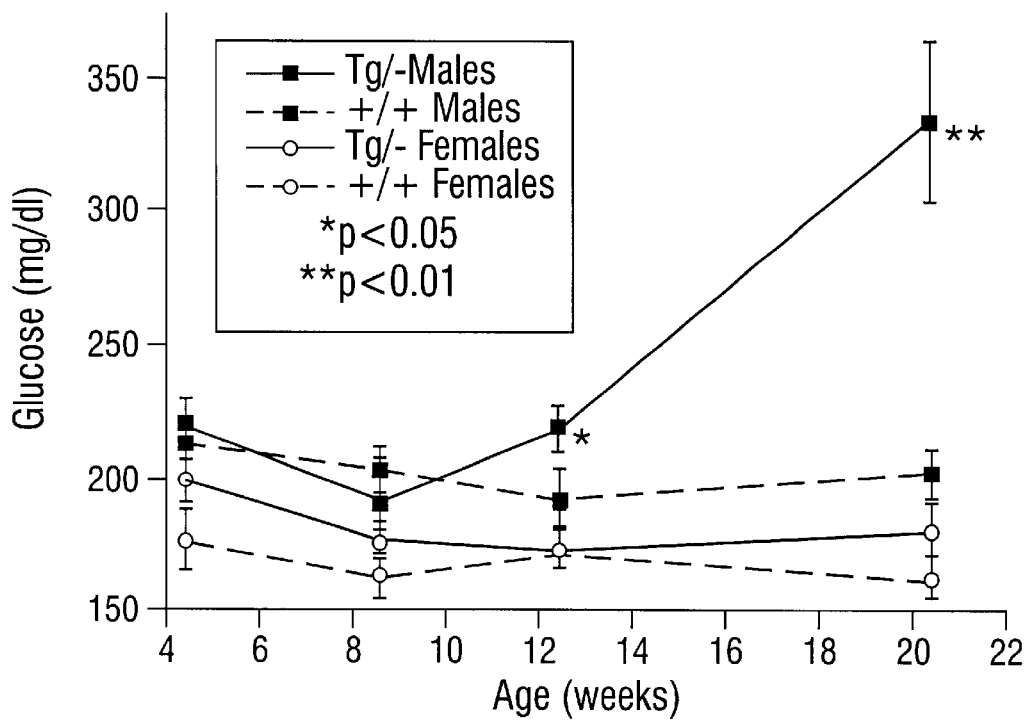
FIG. 31. Mean plasma glucose levels in mg of glucose per dl plotted as a function of age in wk for transgenic lines BAPa20 (Upper) and PGKPa8 (Lower). Separate curves are shown for each genotype and sex. Bars represent 1 SE from the mean. The mean glucose levels of Tg/− mice that are significantly greater than those of nontransgenic +/+ controls are marked with one or two asterisks as indicated.
Figure 31B:
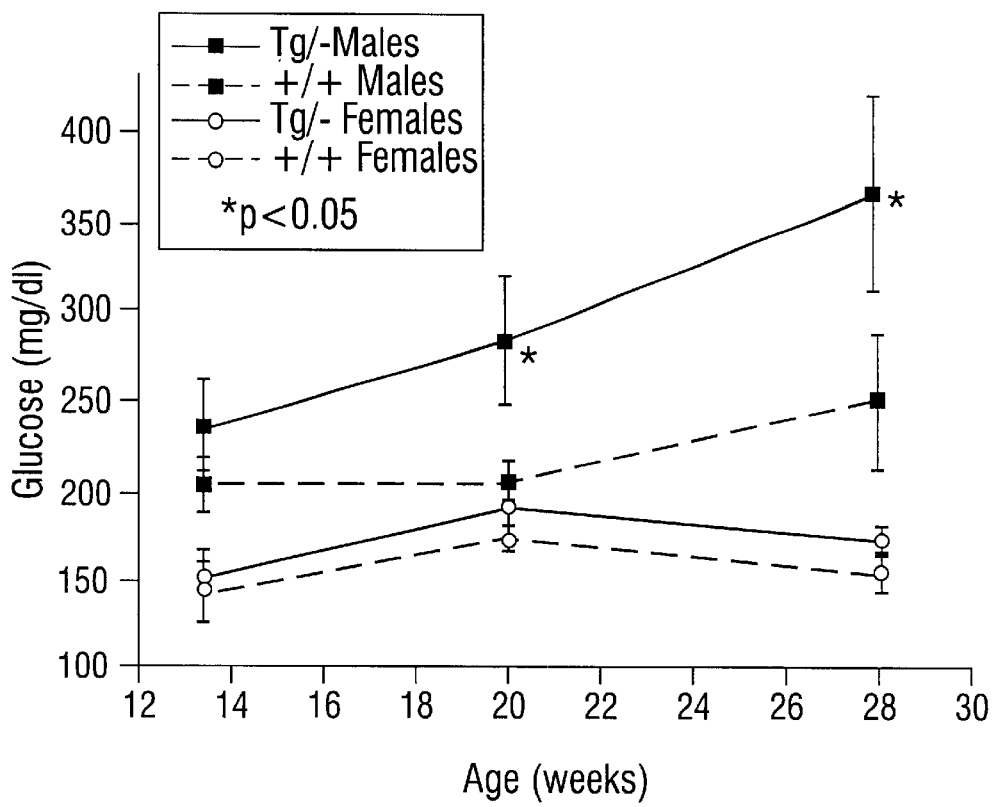
Figure 32:
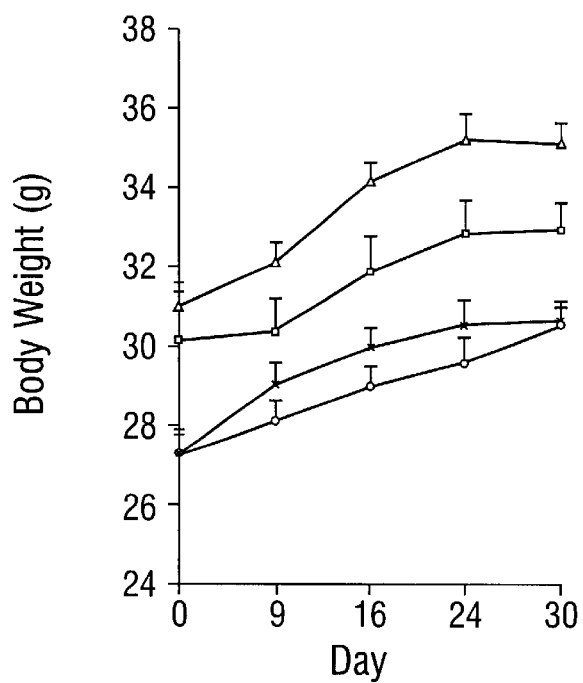
FIG. 32. Weight gain of transgenic (Tg/−) and control (+/+) mice in either control or nifedipine diet. Average weights in grams are plotted over the 30 days of the study. O: Control mice on control diet (n=5); x: control mice on nifedipine diet (n=5): □: Transgenic mice on control diet (n=6); Δ: transgenic mice on nifedipine diet (n=6). Data are reported as mean±SE.

Not only did the ectopic expression of agouti lead to hyperinsulinemia in these Tg/– mice, but it also caused male Tg/– mice from both lines to become hyperglycemic (FIG. 31). By about 20 wk of age, the plasma glucose levels off male BAPa20/– mice increased to levels that were $\approx 70\%$ greater than those of controls (FIG. 31 Upper), while male PGKPa8/– mice developed glucose levels 40% greater than those of controls (FIG. 31 Lower). In contrast to males, female Tg/– mice did not exhibit significant elevations in their plasma glucose levels at any of the individual ages examined (FIG. 31), even though they were hyperinsulinemic (FIG. 30) and obese (FIG. 29). As was found for the extent of obesity, the BAPa20/– mice were more hyperinsulinemic and hyperglycemic than PGKPa8/– mice at similar ages.

Discussion

To test the hypothesis that the ectopic expression of the agouti gene is the only primary molecular abnormality responsible for the obesity and the form of type II diabetes exhibited by the spontaneous obese yellow mice, the inventors generated transgenic mice that express the wild-type agouti cDNA in all 14 tissues analyzed. Tg/– mice of both sexes developed yellow fur, obesity, and hyperinsulinemia. Tg/– males also became hyperglycemic by 12–20 wk of age; in contrast, Tg/– females did not develop hyperglycemia despite becoming considerably hyperinsulinemic. This effect is consistent with previous observations of hyperglycemia in male but not female obese yellow mice (Frigeri et al., 1983; Salem et al., 1989a; Salem et al., 1989b; Hellerstrom and Hellman, 1963; Wolff et al., 1990; Carpenter and Mayer, 1958) and with the reported antihyperglycemic effects of estrogens in genetically obese-diabetic (db/db) mice (Leiter et al., 1987). These results demonstrate unequivocally that ectopic expression of a normal agouti protein alone is sufficient to cause yellow fur, obesity, and a form of type II diabetes in mice. In view of the close association between obesity and the increased susceptibility to cancer in the A$^y$/– and A$^{vy}$/– mice (Wolff et al., 1986), the inventors predict that the Tg/– mice will also be more tumor-prone than their +/+ litter-mates.

Close examination of the data in FIGS. 28, FIG. 29, FIG. 30, and FIG. 31 reveals that the level of ectopic agouti gene expression may influence the time of onset and severity of the obesity, hyperinsulinemia, and hyperglycemia. The level of agouti expression in most tissues of PGKPa8/– mice is less than the level observed in the same tissues of A$^y$/A mice, while the level of agouti mRNA is greater in most tissues of BAPa20/– mice than in A$^y$/A mice (FIG. 28). These differences in agouti expression between the different transgenic lines correlate with the findings that solid yellow BAPa20/− mice are more severely obese, hyperinsulinemic, and hyperglycemic than mottled yellow PGKPa8/− animals at similar ages (FIG. 28, FIG. 29, FIG. 30, and FIG. 31). Therefore, it may be that increasing the average overall level of ectopic agouti gene expression may actually increase the rate of progression of these disorders. Additionally, the fact that PGKPa8/− mice do eventually develop the obese yellow traits whereas "pseudoagouti" $A^{iapy}/a$ and $A^{vy}/a$ mice do not (Wolff, 1971; Michaud et al., 1994a; Michaud et al., 1994b; Wolff, 1965a;b), despite having very low levels of ectopic agouti gene expression (Michaud et al., 1994a; Michaud et al., 1994b; Duhl et al., 1994; Zemel et al., 1994), suggests that a threshold level of expression, between the levels found in the pseudoagouti and PGKPa8/− mice, is required for the development of yellow fur, obesity, and diabetes.

The finding that solid yellow BAPa20/− mice develop obesity and diabetes faster than mottled yellow PGKPa8/− mice is in contrast to the previously reported observation that solid yellow and mottled yellow, $A^{vy}/a$ mice, which do show differences in the level of agouti expression (Zemel et al., 1994), do not show any consistent difference in the development of obesity (Wolff, 1965a;b). One possibility for the unexpected finding is that the difference between the levels of agouti expression in BAPa20/− and PGKPa8/− mice may be greater than that between the levels of expression in solid yellow and mottled yellow, $A^{vy}/a$ mice.

It has been demonstrated that although the agouti protein is secreted, it appears to function in a localized manner (Silvers, 1979) and is probably not present at high levels in the general circulation (Wolff, 1963). Widespread ectopic expression of the normal agouti protein induces the obesity and diabetes of the obese yellow mutants. However, the ectopic expression of the agouti protein in a specific tissue(s) is directly responsible for the development of the dominant phenotypic effects in these animals. For example, it may be that the ectopic expression of the protein in muscle is solely responsible for the insulin resistance, obesity, and eventual diabetes and that its expression elsewhere in the animal does not alter the phenotype. $A^{vy}/a$ mice have elevated levels of intracellular free calcium ($[Ca^{2+}]_i$) in their soleus muscle and recombinant agouti protein induces elevated $[Ca^{2+}]_i$ levels in skeletal muscle myocytes in vitro. Skeletal muscle is the primary site of peripheral glucose disposal (Moller, 1993), and increased $[Ca^{2+}]_i$ can lead to insulin resistance and hyperinsulinemia (Draznin et al., 1987; Zemel et al., 1991). In fact, the finding that hyperinsulinemia is known to lead to obesity by stimulating lipogenesis and decreasing lipolysis (Moller, 1993) suggests that the obesity of dominant yellow agouti-locus mutants may be a secondary effect of the insulin resistance and hyperinsulinemia.

Example 18
The Effects of Calcium Channel Blockade on Agouti-Induced Obesity

Transgenic mice designed to express the agouti coding portion in a ubiquitous manner also develop a syndrome of obesity, hyperinsulinemia, hyperglycemia, and yellow coat color similar to the Avy mutation, demonstrating that ectopic overexpression of the agouti gene is directly responsible for pleiotropic effects associated with dominant agouti mutations (Klebig et al., 1995; Perry et al., 1995). However, the mechanism linking this pigmentation gene to obesity has not yet been identified.

Several lines of evidence have indicated that intracellular $Ca^{2+}$ ($[Ca^{2+}]_i$) appears to be involved in metabolic derangements, including obesity and insulin resistance (Draznin et al., 1988; Draznin et al., 1987; Byyny et al., 1992). Obese patients exhibit increased basal $[Ca^{2+}]_i$ in adipocytes (Draznin et al., 1988), whereas increasing $[Ca^{2+}]_i$ in rat adipocytes reduces insulin stimulated glucose transport (Draznin et al., 1987). Further, $Ca^{2+}$ channel blockade enhances insulin sensitivity in obese and glucose-intolerant subjects (Byyny et al., 1992).

This example demonstrates that $Ca^{2+}$ channel blockade reduces FAS expression and activity and decreases adipose tissue mass in transgenic mice that ubiquitously overexpress agouti.

Materials and Methods

Animals and Diets

Transgenic mice were generated as previously described (Klebig et al., 1995). Mice were made transgenic by pronuclear microinjection of a β-actin promoter agouti transgene into FVB/N single cell embryos and maintained on the FVB/N background. Before being placed on the experimental diets, 7-week-old male transgenic and control mice were acclimatized on a powdered high-fat diet (mouse diet 5015, PMI Feeds, ≧11% fat) for 1 w. They were then randomly assigned to either a control or nifedipine (Sigma, St. Louis, Mo.) (1 g/kg diet) diet and fed ad libitum for 30 days. Food intakes were measured every other day. On day 27, food was held overnight for 12 h fasting and blood was collected from the tail vein for glucose determination, followed by refeeding. On day 30, animals were anesthetized with sodium pentobarbital (50 mg/kg body weight) (Abbott Laboratories, North Chicago, Ill.) and blood was obtained by cardiac puncture for blood glucose and plasma triglyceride and insulin determination. Fat pads (epididymal, perirenal, retroperitonaeal, inguinal, and sub-scapular fats) and skeletal muscles (gastrocnemius muscles) were dissected, immediately weighed, frozen in liquid nitrogen, and stored at −80° C. FAS activity and mRNA levels were measured in adipose tissues as described below.

Core Temperature

Core temperature was used as an indirect metabolic index to determine whether 1) thermogenesis is decreased in transgenic mice overexpressing agouti, and 2) nifedipine treatment increases core temperature. Temperature was measured weekly via a thermocouple (Columbus Instruments, Columbus, Ohio). The probe was inserted a constant distance (1.8 cm) into the rectum of each animal. After stabilization (10 sec), the temperature was recorded every 5 sec for 30 sec. All temperature measurements were made between 9:00 and 10:30 AM.

Blood Glucose and Plasma Insulin and Triglyceride Analysis

Blood glucose was measured using a blood glucose monitoring system (Milpitas, Calif.). Plasma triglyceride levels were measured spectrophotometrically using an enzyme-based assay kit (Sigma) and plasma insulin levels were measured by a radioimmunoassay kit (INCSTAR, Stillwater, Minn.).

Fatty Acid Synthase Activity

Fatty acid synthase activity was measured by a modification of the spectrophotometric method (Lowry et al., 1951). Subcutaneous adipose tissue were sonicated (1:3 wt/vol) in 250 mM sucrose buffer containing 1 mM EDTA (GIBCO, Gaithersburg, Md.), 1 mM dithiothreitol, and 100 μM phenylmethylsulfonyl fluoride (Sigma) (pH 7.4). Homogenates were centrifuged at 14,000×g for 15 min (at 4° C.) and the supernatants were used for enzyme assays. Assays were started by the addition of malonyl CoA; enzyme activities were expressed as nmol NADPH oxidized $min^{-1}$ $mg^{-1}$ of protein. Protein was determined by the modified method of Lowry et al. (1951) using bovine serum albumin as a standard.

Dot Blot Analysis

Total cellular RNA was extracted by cesium chloride density gradient method (Jones et al., 1996). cDNA probes for FAS (pFAS7, cloned by Dr. J. W. Porter's group and obtained from Dr. A. G. Goodridge) were radiolabeled by the random primer method. Dot blot analysis using 1, 3, and 5 μg RNA was performed by a modification of the method of Meyuhas et al. (1987). Total RNA was placed in an Eppendorf tube, brought to 50 μl with ice-cold water. 30 μl 20×SSC and 20 μl 37% formaldehyde were added, and the solution was incubated at 65° C. for 10 min. Samples were spotted into nylon membranes (New England Nuclear, Wilmington, Del.) in a vacuum dot blot apparatus, rinsed with 4×SSC, and air dried. The membranes were hybridized with radiolabeled FAS probe as described previously (Moustaid and Sui, 1991). After visualization and quantitation, the membranes were stripped and reprobed with β-actin as a loading control, and data are expressed as FAS:actin ratio. Visualization and quantitation were conducted using the Ambis 4000 direct β-counting and imaging system.

Statistical Analysis

All data were presented as mean±SE for four groups of mice: control mice on control diet, control mice on nifedipine diet, transgenic mice on control diet, and transgenic mice on nifedipine diet. Data were analyzed via two-way (diet×animal) analysis of variance or, in cases where only two groups were being compared, by Student's t-test.

Results

Figure 33A:
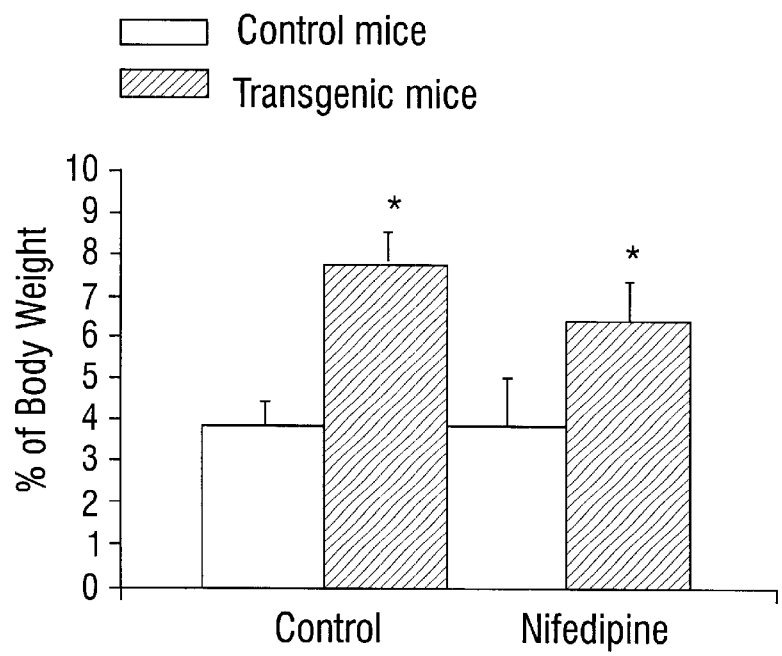
FIG. 33A. The effect of nifedipine treatment on fat pad weights and gastrocnemius skeletal muscle weight in transgenic (Tg/−) (n=5 in control diet, n=6 in nifedipine diet) and control mice (+/+) (n=4 in both diets). Average of the total amount of visceral (epididymal, perirenal, and retroperitonaeal) fat and subcutaneous (inguinal and subscapular) fat is expressed as % of body weight. Data are reported as mean ±SE. *P<0.007.
Figure 33B:
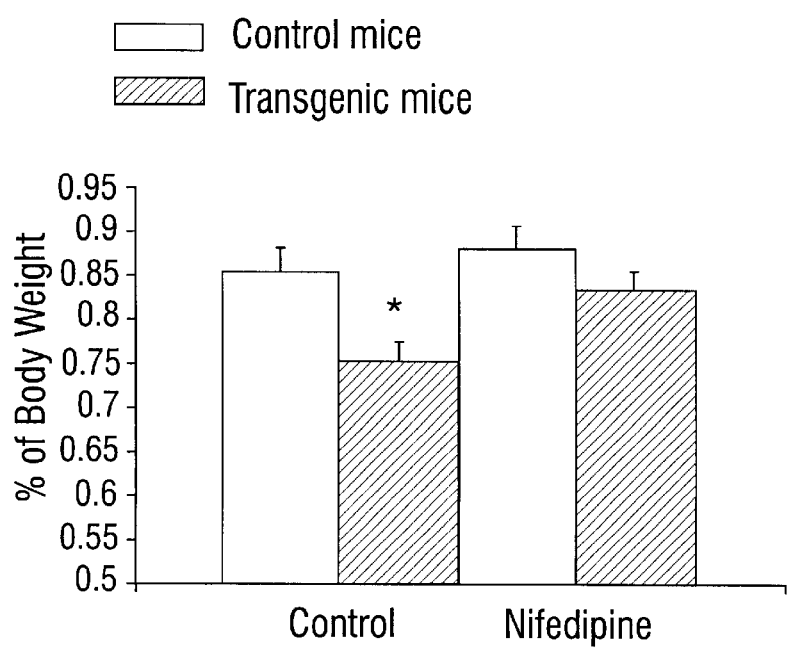
FIG. 33B. Average weight of gastrocnemius skeletal muscle are expressed as % of body weight. Data are reported as mean±SE. *P<0.02.

At study initiation (8 wk of age), the transgenic mice (n=12) exhibited significantly higher body weight than the control mice (n=10) (30.54±0.66 vs. 27.26±0.28 g; P<0.001). The increased body weight of the transgenic mice was maintained over the 30 days on diet, and nifedipine was without effect in both groups (FIG. 31). The transgenic mice also exhibited an approximately twofold increase in fat pad mass (both visceral and subcutaneous) compared to the control mice (2.62±0.27 vs. 1.21±0.19 g; P=0.002). However, nifedipine treatment resulted in a significant reduction in fat pad weight compared to control diet (1.81±0.14 vs. 1.58±0.23 g, P<0.001 in visceral [epidydimal, perirenal and retroperitoneal] fat; 0.81±0.14 vs. 0.62±0.1, P=0.02 in subcutaneous [inguinal and subscapular] fat) in the transgenic mice, but was without effect in the control mice. The total weight of the five fat pads measured was decreased by 18% in the nifedipine-treated transgenic animals (P<0.007). Fat pad weight expressed as percent of body weight is shown in FIG. 33A. Gastrocnemius muscle weight was not different between control and transgenic mice; however, nifedipine treatment significantly increased gastrocnemius muscle weight by 12% compared to the control diet (0.284±0.005 vs. 0.253±0.005 g; P=0.0009) in the transgenic mice and was without effect in the control mice. When expressed as percent of body weight, gastrocnemius muscle weight follows similar trends, as shown in FIG. 33B. This combination of reduced fat pad mass and increased muscle mass may explain the lack of nifedipine effect on body weight in the transgenic mice.

Figure 34:
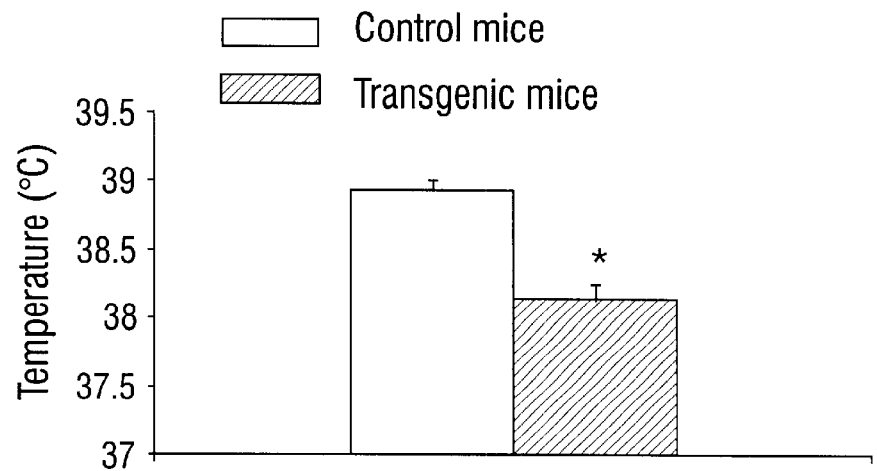
FIG. 34. The basal (day 0) core temperature in transgenic (Tg/−) (n=12) and control (+/+) (n=10) mice at 8 wk of age. Data are reported as mean±SE. *P<0.0005.

At 8 wk of age, the transgenic mice had a 0.81° C. decrease in core temperature compared to the control mice (FIG. 34), indicating decreased thermogenesis in these animals. Nifedipine treatment selectively increased core temperature in the transgenic mice by 0.62° C. (P=0.02) after 14 days of treatment, but this effect did not persist until the end of the study.

Figure 35A:
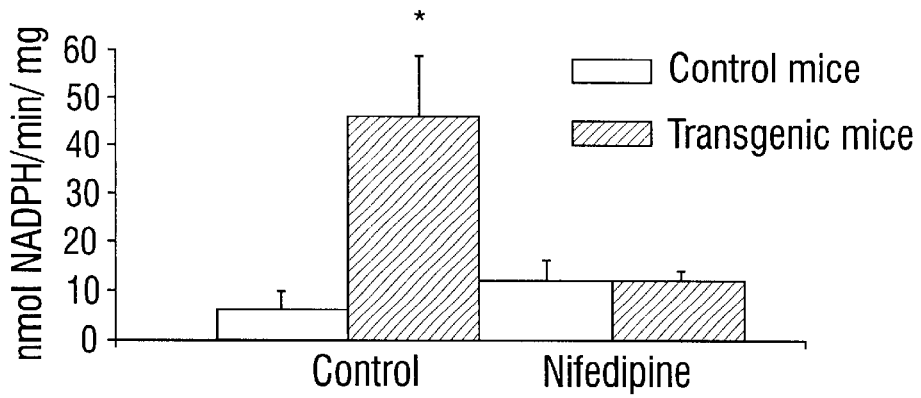
FIG. 35A. The effect of nifedipine treatment on fatty acid synthase activity in subcutaneous (inguinal and subscapular) adipocytes and fatty acid synthase mRNA levels in visceral (epididymal, perirenal, and retroperitoneal) adipocyte of transgenic (Tg/−) (n=5 in control diet, n=6 in nifedipine diet) and control mice (+/+) (n=4 in both diets). Enzyme activity is expressed in nmol NADPH oxidized min$^{-1}$ mg$^{-1}$ of protein. Data are reported as mean±SE. *P=0.009.
Figure 35B:
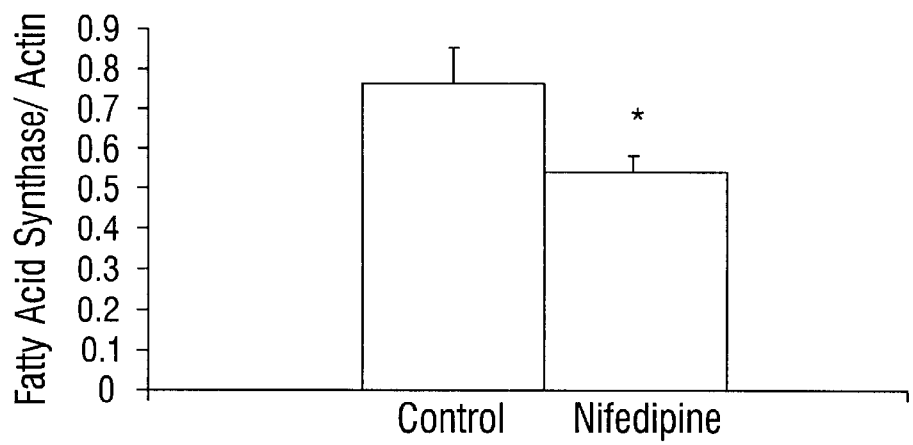
FIG. 35B. Total RNA was extracted from visceral adipose tissue of transgenic mice in either control or nifedipine diet and analyzed by dot blot, as described. Data were not available from the control mice due to the limiting quantities of adipose tissue available from those lean animals. Data obtained from the direct β-counting imaging system are normalized to RNA levels for β-actin. Data are reported as mean±SE. *P=0.04 Values are the mean±SE.

To test the role of de novo fatty acid synthesis in agouti-associated obesity, the inventors measured the activity of FAS in adipose tissue. The transgenic mice exhibited a 7.2-fold increased in FAS activity in subcutaneous adipose tissue compared tot he control mice, whereas nifedipine treatment completely prevented this stimulation of FAS activity (FIG. 35A). Similarly, there was a modest decrease in FAS mRNA levels in visceral adipose tissue of the transgenic mice treated with nifedipine compared to that of the transgenic mice on the control diet (FIG. 35B).

The transgenic mice had approximately twofold higher fed plasma insulin levels than the control mice (P<0.05) (Table 4). Nifedipine treatment completely blocked the hyperinsulinemia in the transgenic mice, but was without effect on the control mice (Table 4). Nifedipine treatment also improved insulin sensitivity, as manifested by the fall in plasma insulin to glucose ratio in the transgenic mice (P<0.05) (Table 4). Nifedipine treatment was without effect on blood glucose levels in either fasted or fed mice. There was also no effect of nifedipine on fasted plasma triglyceride contents (Table 4).

TABLE 4

BLOOD GLUCOSE AND PLASMA INSULIN AND TRIGLYCERIDE LEVELS

| | Control | | Transgenic | |
|---|---|---|---|---|
| | Control | Nifedipine | Control | Nifedipine |
| Glucose, mg/dl | | | | |
| Fasted | 121.3 ± 6.5 | 125.3 ± 7.8 | 115.5 ± 8.9 | 100.4 ± 15.2 |
| Fed | 243.0 ± 7.6 | 213.8 ± 18.6 | 230.6 ± 21.6 | 235.8 ± 9.7 |
| Insulin, ng/ml (fed) | 14.96 ± 5.3 | 16.74 ± 8.69 | 32.39 ± 4.9* | 13.40 ± 1.96 |
| Insulin/glucose (fed) | 0.06 ± 0.02 | 0.084 ± 0.05 | 0.140 ± 0.02* | 0.057 ± 0.001 |
| Triglyceride, mg/dl (fasted) | 107 ± 14.2 | 83.4 ± 20.1 | 76.5 ± 11.6 | 62.8 ± 5.6 |

Discussion $Ca^{2+}$ channel antagonism with nifedipine resulted in a reduction of fat pad mass in the transgenic mice accompanied by an increase in skeletal muscle mass. This suggests that $[Ca^{2+}]_i$ may modulate the flow of energy between storage in adipose tissue and its use for muscle accretion. This concept is supported by the observation that the reduction in core temperature in the transgenic mice was partially corrected with nifedipine treatment, although this correction was not sustained beyond 2 wk. The reason for the treatment return of this elevation on core temperature is not clear, although it may be developmentally related, as the nifedipine intervention was initiated well after a stable decrease in core temperature was apparent in the transgenic animals.

FAS is a multifunctional enzyme that carries all of the seven reactions involved in the synthesis of long-chain saturated fatty acid (palmitate) from acetyl CoA and malonyl CoA (Smith, 1994). FAS protein concentration closely parallels its enzyme activity and is highly sensitive to nutritional and hormonal states (Wakil et al., 1983; Volpe and Vagelow, 1976; Volpe and Vagelow, 1974; Girard et al., 1994). Fasting or a high-fat diet causes a dramatic suppression of FAS synthesis, whereas refeeding or high carbohydrate diet, especially glucose, markedly increases FAS synthesis (Blake and Clarke, 1990; Clarke et al., 1990; Chakrabarty and Leveille, 1969). Several hormones, including insulin, stimulate FAS expression and activity, whereas glucagon and cAMP suppress them (Lakshmanan et al., 1972). An insulin response element has been found in the FAS promoter region (Moustaid et al., 1994; Wolf et al., 1994), and chronic hyperinsulinemia induces an increase in FAS mRNA level and activity in both rat liver and white adipose tissue (Chakrabarty and Leveille, 1969). Moreover, obese Zucker rats have been reported to overexpress FAS mRNA in adipose tissue (Guichard et al., 1992).

Nifedipine treatment normalized both FAS mRNA levels and activities and plasma insulin levels in the transgenic mice. The mechanism of the insulin-lowering effect of nifedipine is not clear. However, because an increase in $Ca^{2+}$ is a signal for β-cell insulin secretion (Malaisse and Sener, 1981) and several $Ca^{2+}$ antagonists (such as verapamil, nifedipine, nitrendipine, and other dihydropyridines) have been found in vitro to induce a dose-related reversible inhibition of insulin release (Malaisse, 1973), it is possible that agouti-induced $Ca^{2+}$ influx may stimulate β-cell insulin release and that this effect is blocked by nifedipine. Alternatively, reduction in circulating insulin with nifedipine may be simply due to an improvement in insulin sensitivity in these mice, as manifested by the fall in the plasma insulin to glucose ratio (Table 4). Similarly, clinical studies have demonstrated that $Ca^{2+}$ channel blockers, including nitrendipine and diltiazem, induce a reduction in fasting serum insulin levels without changing fasting serum glucose and improve insulin sensitivity in obese hypertensive men and women (Beer et al., 1994; Beer et al., 1993). Furthermore, an anti-obesity effect of $Ca^{2+}$ channel antagonists has been reported in rodents (Yoshida et al., 1994; Radin et al., 1993), even though the mechanism is not clear. Therefore, it is difficult to distinguish the nifedipine effect on the primary genetic lesion from secondary phenotypic abnormalities, such as hyperinsulinemia in the transgenic mice.

It has been demonstrated that the agouti protein stimulates FAS activity in a $[Ca^{2+}]_i$-dependent fashion. Accordingly, it may be inferred that the inventors' observations of reduced FAS mRNA and activity and reduced adiposity in the transgenic mice on nifedipine diet result from inhibition of agouti stimulation of FAS expression. However, since the nifedipine treatment also normalized the hyperinsulinemia found in the transgenic mice, the reduction in circulating insulin is likely to have also contributed to the decrease in FAS activity and body fat. Indeed, it is likely that this anti-obesity effect of nifedipine may have resulted both from inhibition of agouti-induced $Ca^{2+}$ influx in adipocytes and from the hypoinsulinemic effect, because the inventors have found agouti and insulin to exhibit synergistic effects in stimulating FAS gene transcription.

Nifedipine completely prevented the sevenfold increase in FAS activity stimulated by agouti in subcutaneous adipose tissue, but only modestly reduced FAS mRNA levels in visceral adipose tissue. It is not clear whether this discrepancy is due to the difference in source of adipose tissue or whether agouti and/or $Ca^{2+}$ have effects on FAS activity independent of transcriptional regulation. However, data indicate that agouti regulation of FAS activity is transcriptionally mediated (Jones et al., 1996), suggesting that the observed difference is the result of intrinsic differences in the two adipose depots. This notion is further supported by the observation that nifedipine treatment resulted in a 24% reduction in subcutaneous adipose mass vs. a 13% reduction in visceral adipose mass.

Several studies have identified $Ca^{2+}$ regulatory elements that may mediate either negative or positive regulation of gene transcription by $Ca^{2+}$ (Collar et al., 1991; Lu et al., 1994). Therefore, similar mechanisms may be involved in regulation of FAS transcription by $Ca^{2+}$ and agouti. Alternatively, it is possible that $Ca^{2+}$ and agouti may affect FAS transcription in an indirect way, perhaps through stimulation or inhibition of other genes in their target tissues. For example, an accumulation of $[Ca^{2+}]_i$ inhibits the lipoprotein lipase expression in adipocytes (Barcellini-Couget et al., 1994), thereby decreasing fatty acid entry from triglyceride-rich lipoprotein. This may also result in loss of FAS suppression, as fatty acids are potent inhibitors of FAS gene expression (Odin et al., 1987; Nestel et al., 1984; Musch et al., 1974).

Example 19

Upregulation of Adipocyte Metabolism by Agouti Protein: Possible Paracrine Actions in Yellow Mouse Obesity If the yellow mouse phenotype involves paracrine actions of agouti, lipogenic tissues are likely targets for the agouti gene product. Both elevated rates of hepatic lipogenesis (Yen et al., 1976) and increased adipocyte size (Johnson and Hirsch, 1972) have been described in $A^{vy}$ mice relative to lean controls. These reports suggest that elevated rates of lipid synthesis and/or storage in liver and adipose tissue contribute to the obese phenotype of the yellow mouse. It is reasonable then to propose that regulatory enzymes in lipid metabolic pathways may be elevated in this model and may play a role in its obesity. Fatty acid synthase (FAS) and stearoyl-CoA desaturase (SCD) are two key enzymes in fatty acid metabolism. FAS is the principal enzyme in long-term regulation of de novo fatty acid synthesis, whereas SCD catalyzes the initial reaction in desaturation of saturated fatty acids. Both FAS (Shillabeer et al., 1992) and SCD (Enser, 1979, Jones et al., 1995) have been shown to be overexpressed in other genetic models of obesity. This example describes data that suggest that agouti-mediated increases in FAS activity and cellular triglyceride content in adipocytes may be mediated by an intracellular calcium ($[Ca^{2+}]_i$)-dependent mechanism.

Materials and Methods

Animals

Figure 36:
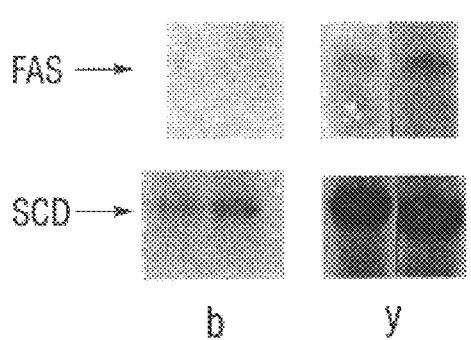
FIG. 36. Levels of stearoyl-CoA desaturase (SGD) and fatty acid synthase (FAS) mRNA in liver of lean ala (black) and obese A$^{vy}$ (yellow) mice. RNA was extracted from liver of lean black (b) and obese yellow (y) mice, age 5–8 mo, and analyzed by Northern blot as described. Equivalent amounts of total RNA (25 µg) were loaded into the gels for each sample; equivalency was confirmed by ethidium bromide staining of membranes after sample transfer. RNA from several animals was analyzed; autoradiogram signals shown here are from representative animals of each genotype. Levels of FAS and SCD mRNA shown are from the same animals in each genotype.
Figure 37:
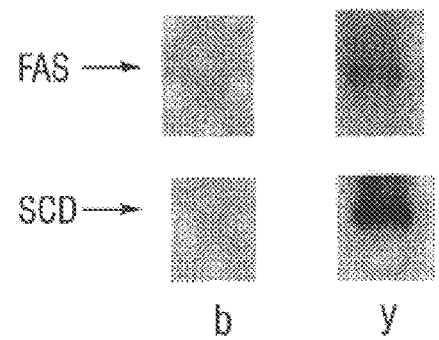
FIG. 37. Levels of FAS and SCD mRNA in adipose tissue of lean a/a (black, b) and obese A$^{vy}$ (yellow, y) mice. RNA was extracted and analyzed, and procedures were followed, as described in FIG. 36. Autoradiogram signals are from representative animals of each genotype; levels of FAS and SCD mRNA are from the same animal in each genotype.

C57BL/6J-$A^{vy}$ mice were purchased from the Jackson Laboratory and maintained at the Oak Ridge National Laboratory (Oak Ridge, Tenn.) by mating $A^{vy}$/a mice to nonagouti ala black siblings. Several male and female lean (black) and obese (yellow) mice, age 5–8 mo, were used in this study. Animals were killed by exsanguination while under pentobarbital anesthesia. Liver and adipose tissue were then snap-frozen into liquid nitrogen for subsequent RNA isolation. Representative Northern blot results from two or one animal(s) per genotype are shown in FIG. 36 and FIG. 37, respectively.

Northern Blot Analysis

RNA was isolated by the cesium chloride density gradient method. Equal amounts of total RNA (25 μg) for each sample were electrophoresed in agarose gels and transferred to nylon membranes [New England Nuclear (NEN)], as the inventors previously described (Moustaïd and Sul, 1991). Ethidium bromide staining of the membranes after transfer (mice tissue RNA) and hybridization with cDNA for the 18S ribosomal subunit (3T3-L1 adipocyte RNA) were used to confirm equivalency of sample loading cDNA probes for SCD (obtained from Dr. P. Smith) and FAS (pFAS7, cloned in Dr. J. W. Porter's laboratory and obtained from Dr. A. G. Goodridge) were radiolabeled by the random primer method, and hybridizations were carried out according to previously described procedures (Moustaïd and Sul, 1991). Hybridized blots were exposed to X-ray film (NEN), and signals were quantitated by scanning laser densitometry.

Expression of Murine Agouti cDNA

Full-length agouti cDNA was expressed in a baculovirus system, as the inventors previously described (Zemel et al., 1995b). Briefly, a 614-bp fragment containing the fill coding region of the agouti cDNA was subcloned into a baculovirus expression vector and expressed in T. ni cells. Medium was collected 48 h after infection, partially purified, then used to treat 3T3-L1 adipocytes for analysis of mRNA levels and enzyme activities. Western blot analysis and antagonism of α-MSH (Lu et al., 1994) were used to confirm the presence of agouti protein in the collected medium, as previously reported (Zemel et al., 1995b). Controls consisted of medium collected from T. ni cells infected with only the wild type baculovirus.

Cell Culture

3T3-L1 cells were grown and differentiated by standard methods, as the inventors previously described (Moustaïd and Sul, 1991). At day 5, cells were incubated in serum-free medium for 18 h, after which they were treated with recombinant agouti protein for 48 h (n=5) in the presence or absence of 30 $\mu$M nitrendipine (Research Biochemicals). In vitro studies were repeated twice; results shown are from a representative study.

FAS Activity

FAS activity was assayed spectophotometrically in crude cytosolic extracts of 3T3-L1 adipocytes by measuring the oxidation rate of NADPH, as the inventors previously described (Moustaïd et al., 1988). Data were expressed as nanomoles of NADPH oxidized per min per milligram of cytosolic protein, which was assayed by the method of Bradford (1976).

Triglyceride Assay

Cellular triglyceride content was measured spectrophotometrically using an enzyme-based assay kit (no. 336-10, Sigma Chemical Co., St. Louis, Mo.). Cells were washed once with phosphate-buffered saline and then scraped in 0.9% saline. Cell suspensions were homogenized by sonication. Data were expressed as milligrams of triglycerides per milligram of cellular protein.

Statistical Analysis

All data were expressed as means±for a minimum of three observations. One-way analysis of variance (ANOVA) was used to compare overall group means from treated 3T3-L1 adipocytes. Post hoc comparisons between groups were made using Student's t-test. All tests were conducted using a 95% confidence interval.

Results

Ectopic expression of the agouti gene leads to the obese phenotype of the yellow mouse, but the mechanisms linking this disregulated pattern of agouti expression to obesity have not been elucidated. Transgenic mice that are phenotypically similar to $A^{vy}$ have recently been generated by placing the agouti gene under the control of a constitutive promoter ($\beta$-actin), and the degree of agouti expression in these animals correlates directly with the onset of obesity (Klebig et al., 1995). These results suggest that expression of the agouti gene in a novel target tissue(s), perhaps in lipogenic tissues, triggers the development of obesity in this model. To gain further insight into this issue, the inventors first chose to determine whether mRNA levels of FAS and SCD in liver and adipose tissue were elevated in yellow mice relative to lean controls. FAS and SCD are two key enzymes in fatty acid biosynthesis and desaturation, respectively. Furthermore, levels of both enzymes have been shown to be elevated in lipogenic tissues of other genetically obese animal models (Guichard et al., 1992; Klebig et al., 1995; Klebig et al., 1994; Shillabeer et al., 1992). Both FAS and SCD genes are overexpressed in liver and adipose tissue of obese (yellow) compared with lean (black) mice (FIG. 36 and FIG. 37). In this regard the yellow mouse is similar to other genetic models of obesity.

Figure 38A:
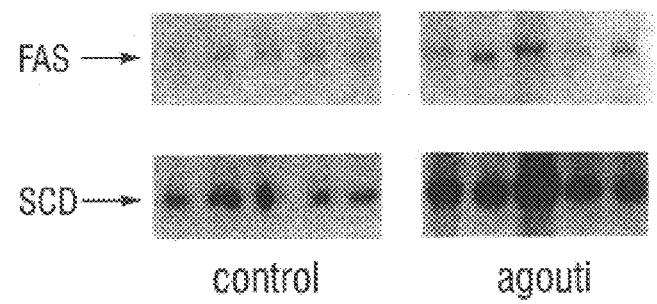
FIG. 38A. Effects of recombinant agouti protein on FAS and SCD mRNA levels in 3T3-L1 adipocytes. Recombinant agouti protein was produced in T. ni cells and partially purified as described. Differentiated 3T3-L1 adipocytes (day 6) were maintained overnight in serum-free medium and then treated for 48 h with the same medium supplemented or not with recombinant agouti protein. Autoradiograms from Northern blot analysis for FAS and SCD. Each lane represents RNA isolated from one culture dish. The 2 left lanes and the 3 right lanes were generated from two independent cultures. These studies were repeated twice.
Figure 38B:
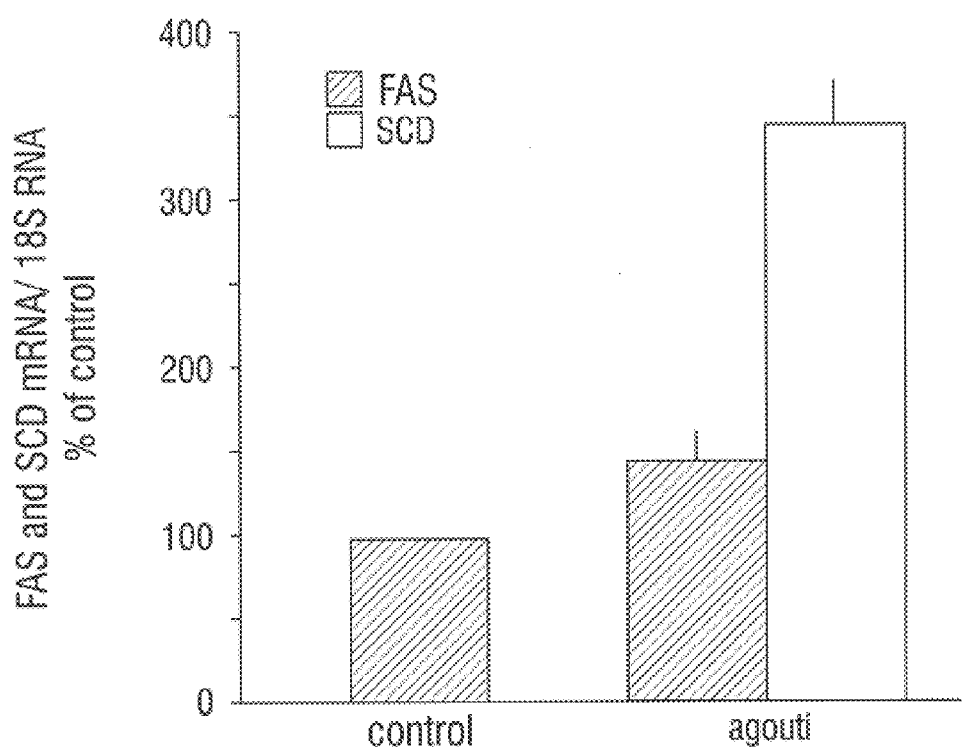
FIG. 38B. Effects of recombinant agouti protein on FAS and SCD mRNA levels in 3T3-L1 adipocytes. Recombinant agouti protein was produced in T. ni cells and partially purified as described. Differentiated 3T3-L1 adipocytes (day 6) were maintained overnight in serum-free medium and then treated for 48 h with the same medium supplemented or not with recombinant agouti protein. Data obtained from densitometric scanning of these autoradiograms, normalized to RNA levels for the 18S ribosomal subunit and presented as % of control.
Figure 39A:
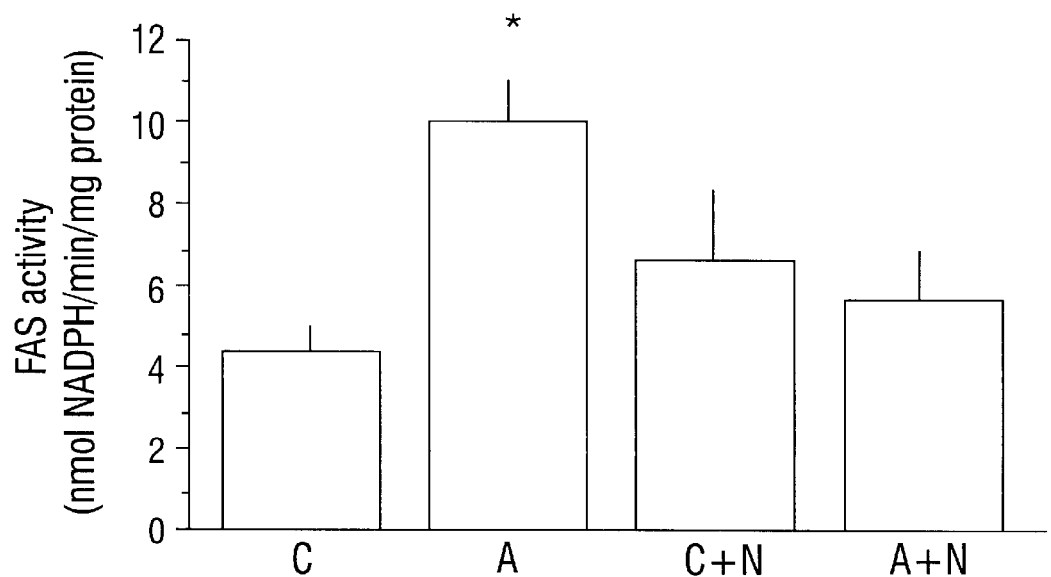
FIG. 39A. Effects of recombinant agouti protein and calcium channel blockade (nitrendipine) on lipogenesis in 3T3-L1 adipocytes. 3T3-L1 adipocytes were treated with agouti protein in absence or presence of nitrendipine (30 $\mu$M) for 48 h, as described in FIG. 38A. FAS activity was assayed as described. C, control; A, agouti; C+N, control 4-nitrendipine; A+N, agouti+nitrendipine. *vs. C; **vs. A; P<0.05.
Figure 39B:
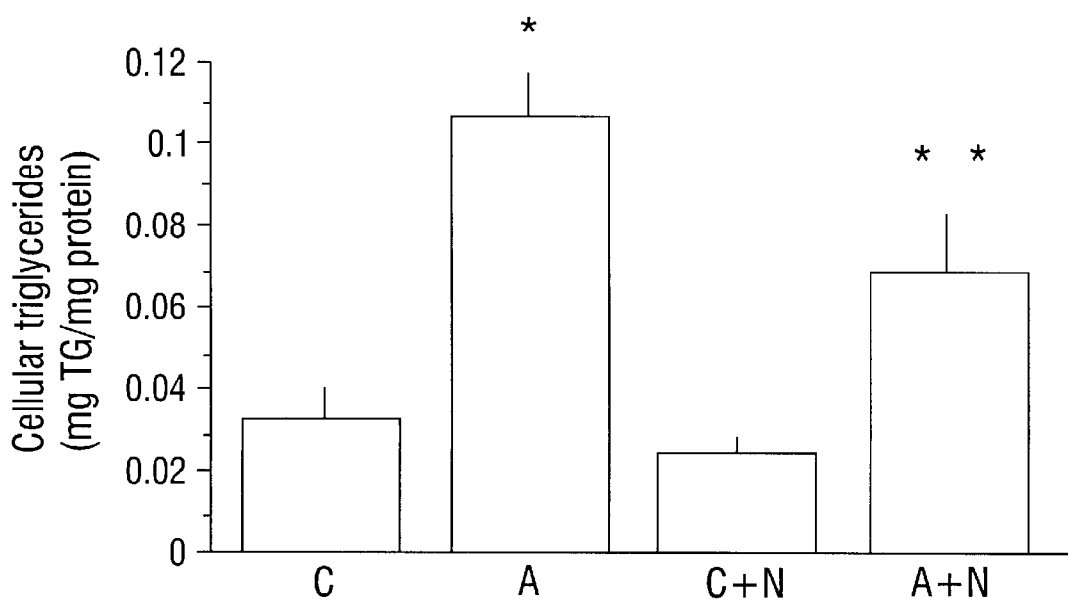
FIG. 39B. Effects of recombinant agouti protein and calcium channel blockade (nitrendipine) on lipogenesis in 3T3-L1 adipocytes. 3T3-L1 adipocytes were treated with agouti protein in absence or presence of nitrendipine (30 $\mu$M) for 48 h, as described in FIG. 39A. Cellular triglyceride content was assayed as described. C, control; A, agouti; C+N, control 4-nitrendipine; A+N, agouti+nitrendipine. *vs. C; **vs. A; P<0.05.

The agouti protein specifically stimulates 1.5- and 4-fold increases in FAS and SCD mRNA levels, respectively (FIG. 38A and FIG. 38B). In addition, agouti elicited significant increases in both FAS2 activity (4.38±0.67 vs. 10.05±0.96 nmol NADPH min$^{-1}$ mg protein$^{-1}$) and cellular triglyceride content (0.032±0.006 vs. 0.104±0.008 mg triglycerides/mg protein) relative to control-treated cells (FIG. 39A and FIG. 39B). The increase in cellular triglycerides is consistent with previous reports (Johnson and Hirsch, 1972) in which the elevated fat mass of obese yellow mice was attributed to adipose cell hypertrophy rather than hyperplasia. Taken together, these data demonstrate that agouti can act directly within adipose tissue to increase lipogenesis. Recent evidence demonstrates that in wild type mice agouti acts in a paracrine manner, because both its synthesis sites (various follicular cell types) and target cells (melanocytes) are found within the microenvironment of the hair follicle (Lu et al., 1994). The results from in vitro treatment of adipocytes with recombinant agouti protein (FIG. 38A, FIG. 38B, FIG. 39A, and FIG. 39B) are consistent with paracrine mechanisms of obesity in the yellow mouse. This concept is supported by parabiosis studies between obese $A^{vy}$ and lean mice, in which $A^{vy}$ obesity was not transmitted to the parabiosed partner (Klebig et al., 1994). Such a paracrine mode of agouti action is in sharp contrast to the recently cloned ob (Zhang et al., 1994), which apparently acts as an endocrine hormone (Halaas et al., 1995).

Previous studies using a variety of nutrients and hormones have shown that both FAS (Hillgartner et al., 1995) and SCD (Landschulz et al., 1994; Ntambi, 1992) mRNA levels are controlled primarily at the transcriptional level. Transcription of the FAS gene, for example, is tightly regulated by insulin through an insulin-response element localized in its proximal promoter region (Moustaïd et al., 1994). Given the direct effect of agouti on both FAS and SCD expression in vitro, it is then reasonable to postulate that agouti may also regulate transcription of FAS and SCD through an as yet unidentified agouti response element. This possibility is consistent with recent results obtained with the genetically obese Zucker (fa) rat, in which a fa response element was localized in the glyceraldehyde-3-phosphate dehydrogenase (GAPDH) gene (Rolland et al., 1995). A similar situation, in which the agouti gene product enhances transcription of FAS and SCD, may mediate overexpression of both genes in liver and adipose tissue of the obese yellow mouse. In such a scenario, agouti itself could act as a trans factor; alternatively, agouti could trigger the synthesis or activation of a second regulatory protein.

Agouti's signaling mechanisms within its wild type environment have been identified. Lu et al. (1994) demonstrated that, in the hair follicle, agouti functions as an antagonist of α-MSH at its melanocyte receptors; agouti affects pigment production by a resultant decrease in intracellular adenosine 3',5'-cyclic monophosphate (cAMP) levels. However, agouti may also act through other pathways outside the hair follicle. The inventors have recently reported that agouti induced a transient increase in $[Ca^2+]_i$ in various cell types, including $L_6$ skeletal muscle cells (Zemel et al., 1995b), human kidney cell lines and isolated human adipocytes), and 3T3-L1 adipocytes (Zemel et al., 1995a). Consistent with a $[Ca^2+]_i$-linked agouti transduction pathway, this example shows that simultaneous treatment with nitrendipine attenuated agouti effects on both FAS activity (10.05±0.96, agouti; 5.65±1.31, agouti+nitrendipine; $P<0.03$) and cellular triglyceride content (0.104±0.008, agouti; 0,067±0.011, agouti+ nitrendipine; $P<0.05$). There was no effect of nitrendipine alone on either FAS activity or triglyceride content. Similar effects of calcium channel blockade were obtained on SCD mRNA levels.

Example 20
Combined Effects of Insulin Treatment and Adipose Tissue-Specific Agouti Expression on the Development of Obesity To test the physiological significance of the expression of the agouti gene in adipose tissue in vivo, a mouse line that models the adipose-specific expression pattern of the agouti gene in humans was developed. Studies with a transgenic line that expresses the agouti gene under the influence of the aP2 promoter (Graves et al., 1991) reveal that these animals, like humans, express the agouti gene in adipose tissue and do not become obese or diabetic. However, when subjected to daily injections of insulin, they markedly increase their body weight compared with their insulin-treated, nontransgenic controls.

Materials and Methods
Mice

All mice were maintained at Oak Ridge National Laboratory. The FVB/N mice were obtained from random-bred stock. All mice were fed a diet containing 11% fat by weight (Mouse Diet 5015; Purina), weaned at 4 wk of age, and subsequently weighed monthly. Food and water were obtained from ad libitum. All data are from mice that are hemizygous for the transgene.

Agouti Expression Constructs

To generate the aP2 promoter-agouti expression construct, a HindIII-ClaI fragment containing the complete mouse agouti cDNA along with the simian virus 40 polyadenylylation signal sequence was isolated from BAPa (Klebig et al., 1995). This fragment was cloned downstream of the −5.4-kb to +21-bp fragment of the promoter for the adipocyte P2 (aP2) gene in the pSKII+ vector (Ross et al., 1990). All constructs were verified by DNA sequencing.

Transgenic Mice

One-cell FVB/N embryos were microinjected with the aP2a (6.6-kb KpnI-SacII fragment) construct (3 µg/ml in 10 mM Tris HCl, pH 7.5/0.1 mM EDTA), and transgenic mice were derived as previously described (Hogan et al., 1986). Some of the embryos were coinjected with the tyrosinase mini-gene (TyBS; Overbeck et al., 1991) to generate transgenic lines that could be visually genotyped on the albino FVB/N background. Southern and Northern blot hybridization analyses were performed as previously described (Sambrook et al., 1989).

Blood Analysis

Plasma and serum were obtained by retro-orbital sinus puncture from nonfasted mice between 9 am and 11 am. Plasma insulin levels were measured by radioimmunoassay (ICN) with porcine insulin as a standard. Blood glucose concentrations were determined by blood sampling from the tail vein followed by quantification via One-Touch™ glucose determination system (Johnson & Johnson).

Insulin Injections

Six- to ten-wk-old male mice were subcutaneously injected between 11 am and noon with Humulin U ultralente (Eli Lilly, Indianapolis, Ind.) at a daily dose of 0.5, 1, or 2 units/day per mouse. Insulin (100 units/ml) was diluted before injection with phosphate-buffered saline so that all mice received a 200-µl injection. A 1-ml syringe was filled with 700 µl of the diluted insulin solution. To keep the insulin suspension as uniform as possible, it was mixed between each injection via plunger action.

Statistical Analysis

All data are reported as mean±SEM. Statistical comparison between transgenic and controls was performed using an unpaired two-group t-test.

Results
Development and Testing of Transgenic Lines

To direct the expression of the normal agouti gene to adipose tissue, the inventors generated an expression cassette in which the full-length wildtype mouse agouti cDNA was placed under the transcriptional control of the aP2 promoter (Ross et al., 1990). The promoter element that was used for these studies was previously shown to direct expression of genes specifically to adipose tissue in transgenic mice (Ross et al., 1990). Eight transgenic founder mice were generated by pronuclear microinjection of the expression construct, and a total of five transgenic lines [FVB/N-TgN(aP2a)5373Rpw, -5374Rpw, -5409Rpw, -5412Rpw, and -5438Rpw] were established from these founder animals and will be abbreviated here as aP273, aP274, aP209, aP212, and aP238.

Figure 40:
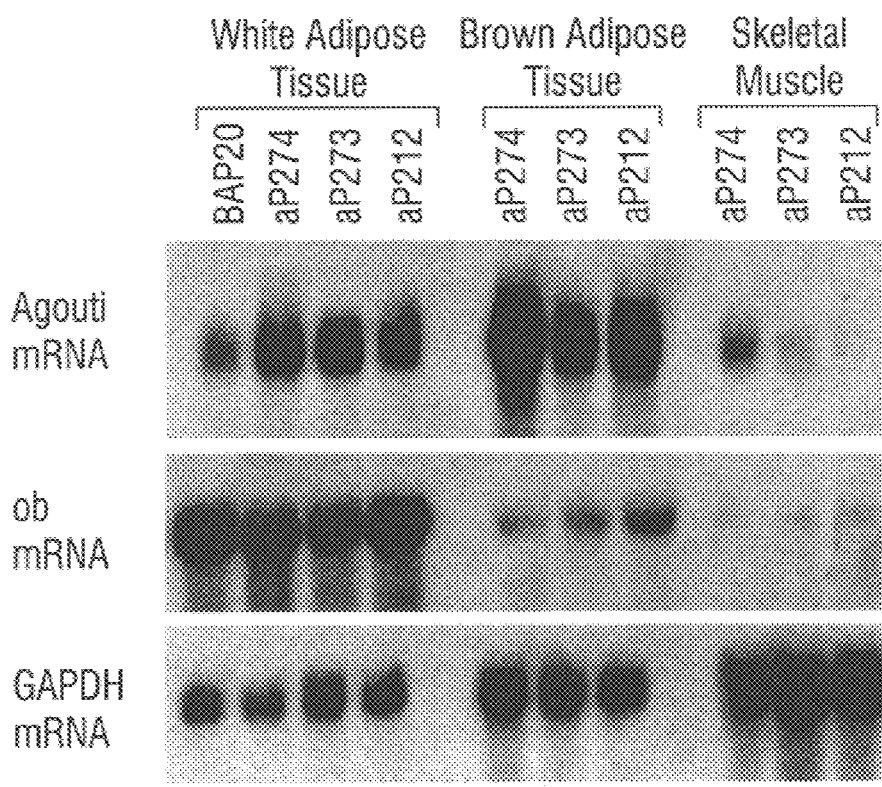
FIG. 40. Northern blot analysis of transgene expression in adipose tissue and muscle of the aP274, aP273, and aP212 lines. Samples from the $\beta$-actin promoter-agouti (BAP20) transgenic mice (Klebig et al., 1995) were also included in this analysis. (A) Total RNA (20 $\mu$g) from tissues of aP212, aP273, aP274, and BAP20 mice were hybridized with a radiolabeled full-length agouti cDNA probe and, subsequently, with a cDNA probe for glyceraldehyde phosphate dehydrogenase (GAPDH) as a loading control. The same blot was then probed with a cDNA probe for ob (Zhang et al., 1994) to check for adipose tissue contamination.

The tissue-specific expression of the transgene was examined in the aP212, aP273, and aP274 lines by Northern blotting (FIG. 40). All three lines exhibited comparable levels of agouti mRNA in white and brown adipose tissue and much greater levels of agouti mRNA in white adipose tissue than in the obese β-actin promoter-agouti transgenic line (BAP20) that the inventors studied previously (Klebig et al., 1995). Two of the three lines expressed the transgene primarily in adipose tissue, with only very low levels of expression elsewhere. This is comparable to results reported previously for the aP2 promoter element (Ross et al., 1990). One of the three lines (aP274) also expressed relatively high levels of the transgene in other tissues, particularly muscle, which was probably due to a chromosomal position effect, which can often influence the pattern of expression of the transgene. For this reason, the aP274 line was not used for the studies described below.

The low level of expression of the transgene that the inventors detected in other tissues of the aP212 and aP273 lines could be due to the presence of adipocytes in the tissue samples that were analyzed. To test this possibility, the inventors hybridized Northern blots from all three transgenic lines with a probe from the ob gene (Zhang et al., 1994), which is known to be expressed exclusively in adipocytes (FIG. 40). There was detectable ob expression in samples other than adipose tissue, most notably muscle. These results suggest that the low levels of agouti expression found in the samples other than adipose tissue are likely from the tissue-specific expression of the transgene in the adipocytes present within these tissues.

Physiological Effects of Transgene Expression

Figure 41A:
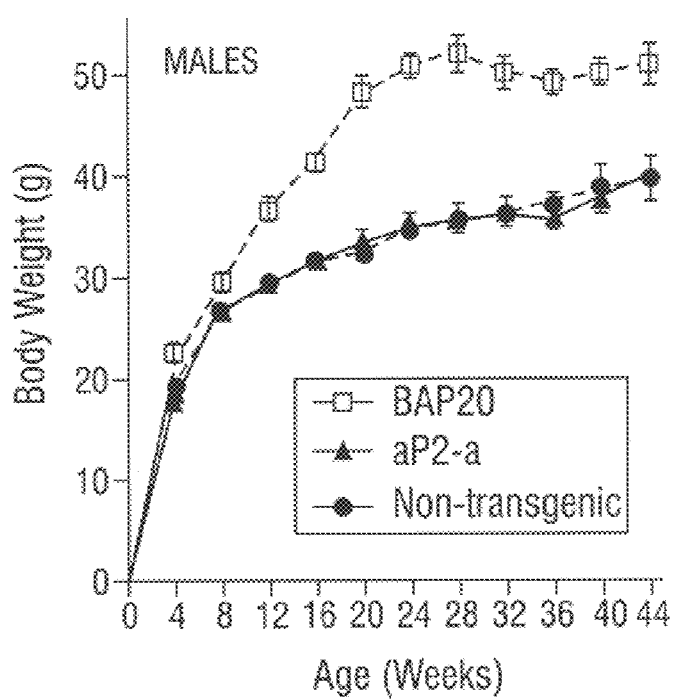
FIG. 41A and FIG. 41B. Comparison of body weight gain in male (FIG. 41A) and female (FIG. 41B) between transgenic lines expressing agouti in adipose tissue with the BAP20 line (Klebig et al., 1995), which expresses agouti ubiquitously. The aP2-a weight curve is the average body weight from four different transgenic lines (aP212, aP273, aP238, and aP209) using the aP2 promoter to express agouti in adipose tissue. There were between 16 and 91 mice per data point. Data are presented as mean±SEM.
Figure 41B:
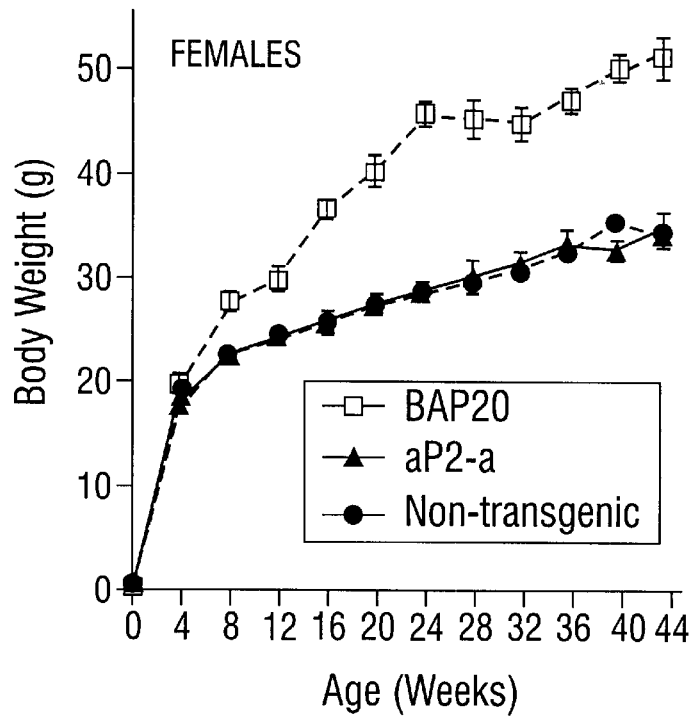

Since the aP212 and aP273 lines appeared to express the transgene in an adipose-specific manner, the inventors used these two lines for additional studies. Specifically, body weight was measured monthly from 4 to 44 wk of age. There was no significant difference between transgenic and nontransgenic littermates at any time point. Additionally, plasma insulin concentrations in 25- to 30-wk male mice were 29±8 microunits/ml for transgenic mice and 31±2 microunits/ml for nontransgenic littermates. Blood glucose concentrations were 120±7 and 122±11 mg/dl for transgenic and nontransgenic littermates, respectively. Body weight data was also obtained from the aP238 and aP209 lines, and there was no significant difference between transgenic and nontransgenic mice. The average body weight of the aP212, aP273, aP238, and aP209 transgenic mice and their nontransgenic littermates is compared with the body weight of the BAP20 transgenic mice, which do become obese with age (FIG. 41A and FIG. 41B). These data indicate that agouti expression in adipose tissue is not sufficient for the development of obesity and diabetes.

Effect of Daily Insulin Injections on Weight Gain

Figure 42A:
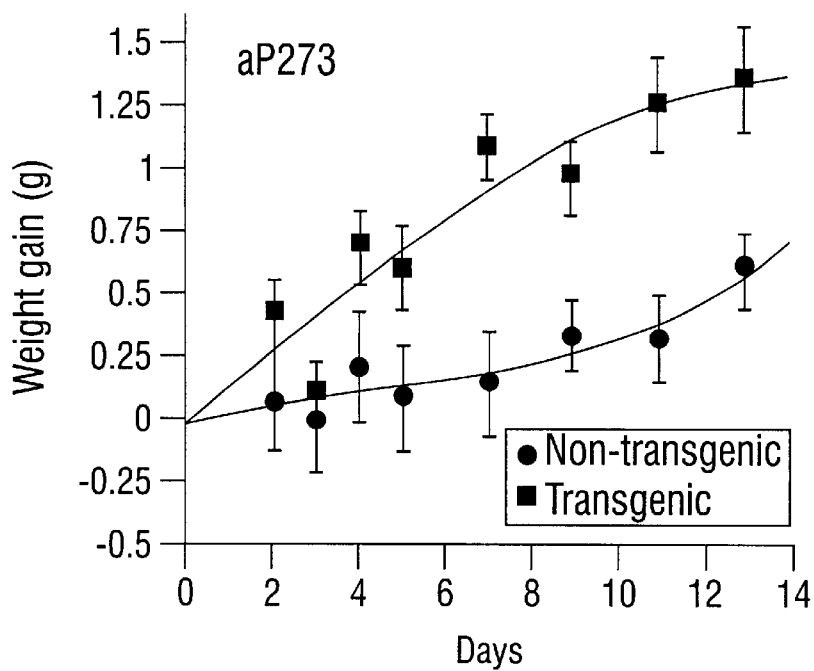
FIG. 42A and FIG. 42B. Effect of insulin on body weight Eight- to ten-wk-old nonobese aP273 (FIG. 42A) and aP212 (FIG. 42B) male mice and their nontransgenic male littermates were given daily subcutaneous injections of insulin (2 units per mouse per day) for 7 days. Body weight was measured daily. Data are presented as mean weight gain±SEM. *, Value significantly different (P$\leq$0.05) from nontransgenic mice. The number of mice was between 4 and 13 per group.
Figure 42B:
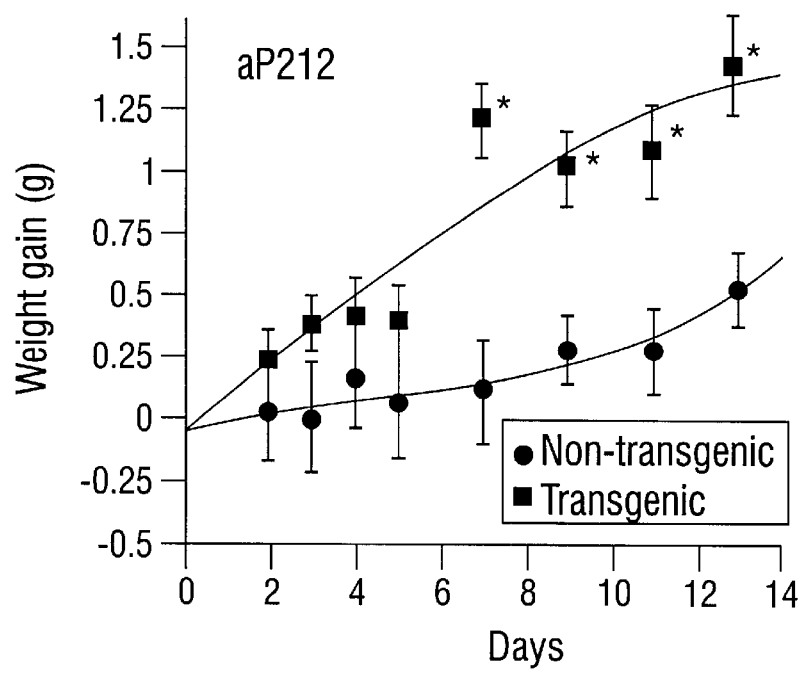
Figure 43:
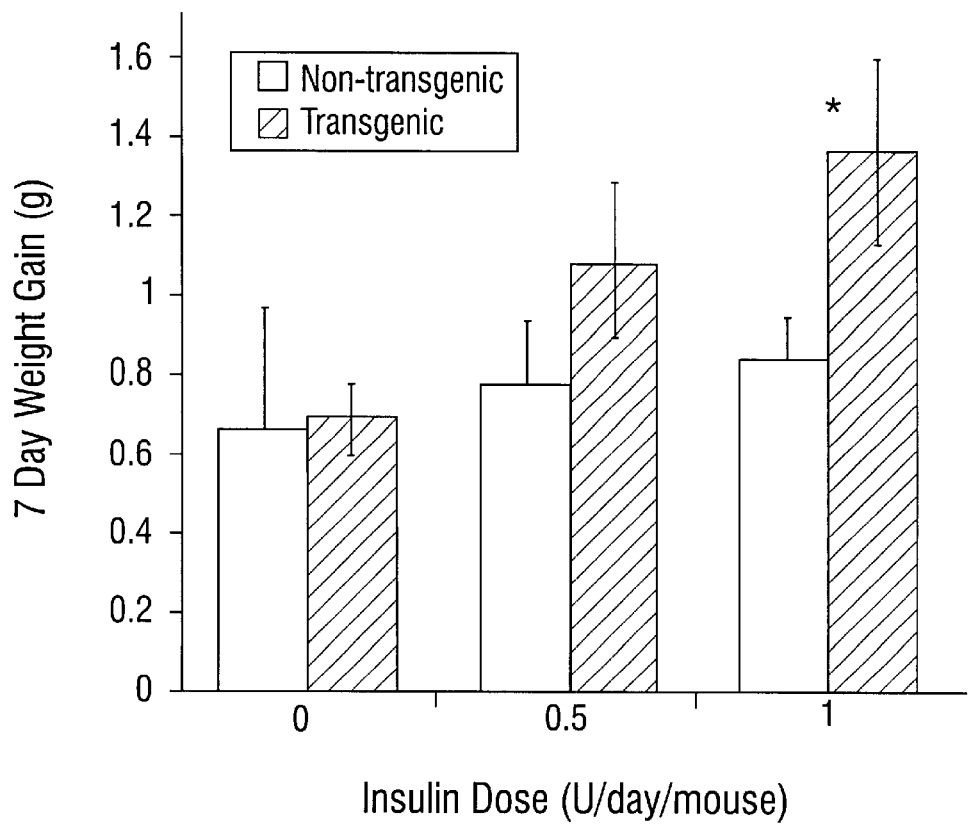
FIG. 43. Effect of insulin dose on body weight. Nonobese aP212 male mice and their nontransgenic male littermates at 6–8 wk of age were given daily subcutaneous injections of phosphate-buffered saline or insulin (0.5 or 1 unit per mouse per day) for 7 days. Body weight was measured on the morning of the day 8. Data are presented as mean weight gain±SEM. *, Value significantly different (P$\leq$0.05) from nontransgenic mice. The number of mice was between three and six per group.
Figure 44:
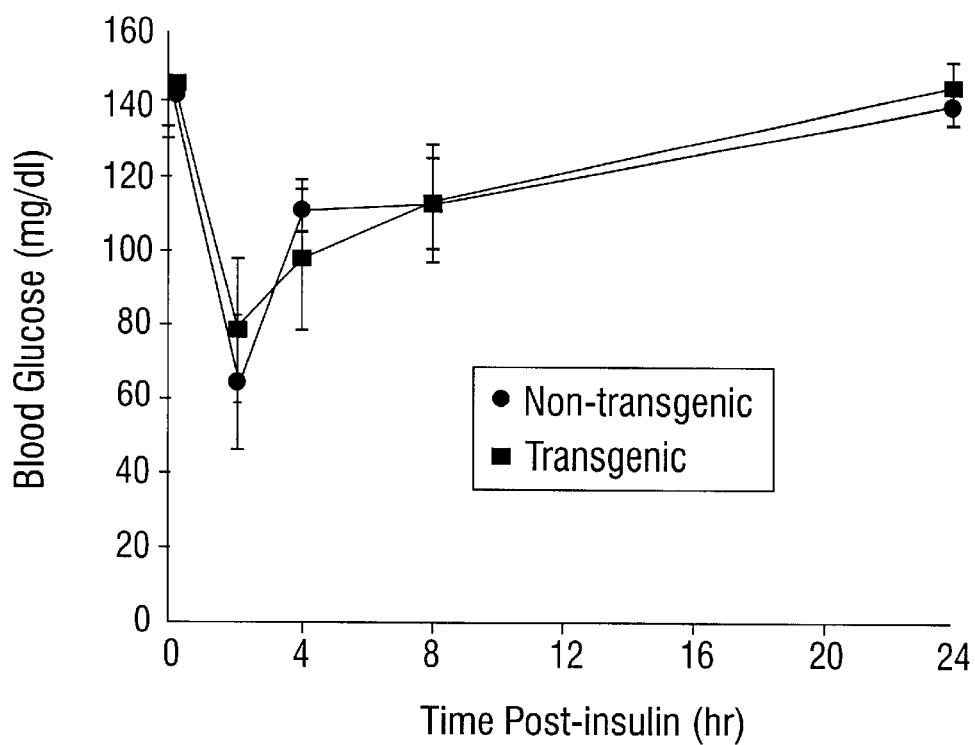
FIG. 44. Glucose values following insulin administration. Eight- to ten-wk-old nonobese aP212 male mice and their nontransgenic male littermates were given a subcutaneous injection of insulin (1 unit per mouse per day), and blood glucose was measured over a 24-h period. Data are presented as mean blood glucose±SEM. The number of mice was between three and five for each time point.

The fact that the aP212 and aP273 transgenic lines do not become obese while the BAP20 ubiquitously expressing line does suggests that another factor besides expression of agouti in adipose tissue is responsible for agouti-induced obesity. Plasma insulin concentrations are significantly elevated in 12-wk-old BAP20 transgenic mice (Klebig et al., 1995). The hyperinsulinemia in the BAP20 transgenic mice led the inventors to test whether insulin may act synergistically with agouti expression in adipose tissue to trigger the obesity. Consequently, the aP212 and aP273 transgenic animals were given daily subcutaneous injections of 2 units of insulin per day per mouse for the first 7 days of the study (FIG. 42A and FIG. 42B). The aP212 and aP273 animals injected with insulin exhibited a significantly greater weight gain compared with their nontransgenic, insulin-treated littermates, even over this relatively short period of time (FIG. 42A and FIG. 42B). The average rate of weight gain for the insulin-injected transgenic mice was 1.7-fold greater than control mice. After discontinuing insulin treatment, the aP212 and aP273 mice continued to gain weight more quickly than the control mice until day 10, when weight gain subsided. Additionally, the effect on weight gain was observed with lower doses of insulin per day (FIG. 43). Blood glucose levels were reduced by insulin injection to levels normally seen after an overnight fast, and they returned to normal within 24 h (FIG. 44). These results suggest that the combination of agouti expression in adipose tissue and insulin treatment induce physiological changes that result in weight gain.

Discussion

The agouti gene is expressed in adipose tissue in humans and has been shown to regulate lipid metabolism in cultured adipose cells in vitro (Jones et al., 1996). Although the agouti gene is not normally expressed in adipose tissue in the mouse, the inventors were able to induce the expression of high levels of agouti in white and brown adipose tissue by expressing the cloned mouse gene under the control of the aP2 promoter. While agouti expression in adipose tissue resulted in phenotypically normal mice, there was a clear interaction between transgene expression and insulin treatment. When the transgenic animals were treated with daily injections of insulin, they gained significantly more weight than their nontransgenic littermates. The inventors' hypothesis is that daily insulin treatments mimic the hyperinsulinemia that is normally observed in the obese transgenic lines that express agouti ubiquitously (Klebig et al., 1995). This result indicates that the ectopic expression of agouti specifically in adipose tissue may have a substantial metabolic effect on the animal. Accordingly, these data provide the first in vivo evidence that the expression of agouti in adipose tissue may be physiologically significant in humans, as humans exhibit agouti expression in adipose tissue.

The apparent synergistic effect of both agouti and insulin in the aP2-agouti transgenics is noteworthy, because both agouti and insulin can have similar effects on adipocytes. Insulin is well known to stimulate lipogenesis and inhibit lipolysis. Likewise, in vitro data demonstrate that agouti stimulates fatty acid synthetase activity and triglyceride accumulation in cultured adipocytes (Jones et al., 1996). It is possible that agouti modulates adipocyte metabolism by antagonizing adipocyte melanocortin receptor binding, similar to its antagonism of melanocyte melanocortin receptor binding in the regulation of coat color (Lu et al., 1994). Recently, it was demonstrated that mouse adipocytes ex-press high levels of melanocortin 2 (MC2) receptor (Boston and Cone, 1996). The ligand for the MC2 receptor is adrenocorticotropic hormone (ACTH), a potent lipolytic stimulant in rat adipocytes (White and Engel, 1958; Oelofsen and Ramachandrand, 1983). Therefore, agouti antagonism of ACTH binding to its adipocyte receptor may lead to an inhibition of ACTH-mediated lipolysis.

Data suggest that hyperinsulinemia in the agouti mutants is a critical component for the onset of obesity. Moreover, Warbritton et al. (1994) observed pancreatic 13 cell hyperplasia in the obese agouti mutants before any observed obesity, suggesting that the hyperinsulinemia precedes the obesity. Therefore, in addition to its role in adipose tissue, agouti could act directly on the pancreas to produce the hyperinsulinemia. The ability of agouti to increase intracellular calcium concentration ($[Ca^{2+}]_i$; Zemel et al., 1995) further suggests that it may play a physiological role in the pancreas. Glucose oxidation increases the ATP:ADP ratio and inhibits ATP-sensitive $K^+$ channels in 13 cells. Closing of the $K^+$ channels results in 13 cell depolarization and activation of voltage-gated $Ca^{2+}$ channels, which causes a net increase in $[Ca^{2+}]_i$. The increased $[Ca^{2+}]_i$ triggers insulin release from secretory granules (Newgard and McGarry, 1995). A reasonable prediction is that agouti may mimic these normal cellular events by increasing $[Ca^{2+}]_i$ and causing increased secretion of insulin from the pancreas.

Example 21

Role of Agouti in Yellow Obese Syndrome

Because of its role in regulating coat color, agouti has served as an important model of gene action and interaction for nearly a century. Over 25 different dominant and recessive agouti locus alleles have been identified (Green, 1989; Silvers, 1979; Siracusa, 1991), in which phaeomelanin (yellow-red pigment) synthesis is generally dominant over eumelanin (black-brown pigment) synthesis. At the top of the dominance hierarchy and perhaps the most notable of all agouti alleles are the lethal yellow ($A^y$) and viable yellow ($A^{vy}$) mutations that develop a dominant pleiotropic syndrome including obesity, insulin resistance, increased linear growth, increased susceptibility to certain neoplasms (reviewed in Wolff, 1987), as well as yellow fur (reviewed in Bray and York, 1979; Silvers, 1979; Wolff et al., 1986). These "yellow obese" mice have served as useful study models for obesity and diabetes research (Bray and York, 1979; Fan et al., 1997; Huszar et al., 1997; Mynatt et al., 1997; Wolff et al., 1986; Yen et al., 1994).

Agouti-Induced Obesity

Mice carrying the dominant agouti alleles $A^y$ or $A^{vy}$ develop the complex set of traits collectively referred to as the yellow obese or yellow mouse syndrome. The most apparent abnormality of $A^y$ and $A^{vy}$ mice, other than their yellow-to-orange colored fur, is a maturity-onset obesity that peaks between 8 and 17 mo of age (Dickie and Woolley, 1946; Roberts et al., 1984). Stored triacylglycerol levels increase significantly in adults, reaching ~25% of their body weight (Yen et al., 1976). Hepatic lipogenesis rates are sixfold greater in $A^{vy}$ adults than in age-matched controls, whereas the juvenile rate is only twice the normal value (Yen et al., 1976). Adipocyte hypertrophy, rather than hyperplasia (Johnson and Hirsch, 1972), and depressed basal lipolytic rates (reviewed in Yen et al., 1994) also contribute to the obesity trait. These and other features distinguish the yellow obese mutants from other obesity models. For example, the recessive obesity mutations $Lep^{ob}$ and $Lepr^{db}$ typify the juvenile-onset form of obesity. High levels of triacylglycerol accumulate in $Lep^{ob}$ and $Lepr^{db}$ mice as juveniles, not as adults, and reach 50% of their body weight (Yen et al., 1976). Rates of hepatic lipogenesis are much higher in young $Lep^{ob}$ and $Lepr^{db}$ homozygotes than in young lean controls or in the yellow obese mutants. Eventually lipogenesis rates normalize in $Lep^{ob}$ and $Lepr^{db}$ adults but remain elevated in yellow obese adults (Yen et al., 1976).

Body mass in both lean and obese individuals is generally determined by the balance between energy intake and expenditure, which are controlled by the central nervous system (reviewed in Bray and York, 1979, Spiegelman and Flier, 1996, Weigle and Kuijper, 1996). Excessive food intake promotes progressive weight gain if it is not accompanied by a compensating increase in energy expenditure. This is largely what happens in animals that carry the $Lep^{ob}$ or $Lepr^{db}$ mutations (reviewed in Spiegelman and Flier, 1996); both of these mutants exhibit an uncontrolled feeding behavior, a positive energy balance and early-onset obesity. Conversely, although the yellow agouti mutants have a stronger than normal motivation to consume food [they eat 10–36% more than their lean littermates (Frigeri et al., 1988; Yen et al., 1976; Yen et al., 1984)], their satiety mechanisms remain intact (Bray and York, 1979). Also, neither the moderate hyperphagia nor the decreased thermogenesis (Yen et al., 1984) observed in the $A^y$ and $A^{vy}$ mutants can account for the obesity (reviewed in Yen et al., 1994). Instead, it has been proposed that a major determinant of obesity in the yellow obese mutants is the enhanced efficiency with which they utilize calories (Yen et al., 1994). In other words, the dominant yellow agouti mutants seem more proficient at storing their consumed calories as fat rather than utilizing those calories for physical activity or for maintaining body heat. Measurement of mean body weight gain vs. number of calories consumed by female yellow $A^{vy}$ mice was used to verify a three- to fourfold higher caloric efficiency (Frigeri et al., 1988). This level of increased caloric efficiency is consistent with the degree of the adiposity observed in the mutant animals (Yen et al., 1976).

Hyperinsulinemia is evident in $A^{vy}$ mice at ~6 wk of age (compared with 10 and 15 d for $Lepr^{db}$ and $Lep^{ob}$ mutant mice, respectively) (Frigeri et al., 1983), and can become as high as 20-fold over lean controls by 6 mo of age (Gill and Yen, 1991). Because insulin promotes nutrient partitioning into adipose tissue and stimulates adipocyte growth and development (reviewed in Bray, 1996), the hyperinsulinemia in the yellow agouti mutants may contribute to their obesity and possibly to other traits of the pleiotropic syndrome (Wolff et al., 1986). A positive temporal relationship has been established between the hyperinsulinemia and the activity of hepatic lipogenic enzymes in yellow $A^{vy}$/a mice (Yen et al., 1976), and pancreatic β-cell hyperplasia is evident in $A^{vy}$ males at 21 d of age before any detectable weight gain or changes in insulin or glucagon levels (Warbritton et al., 1994). However, the relationships among hyperinsulinemia, insulin resistance and obesity are complex; currently, it is not possible to attribute the obesity in the yellow agouti mutants to the hyperinsulinemia alone (reviewed in Yen et al., 1994).

Endocrine abnormalities are commonly observed in many of the different mouse lines exhibiting obesity, with changes in adrenal corticoids being particularly noteworthy (reviewed in Bray, 1996). Adrenal corticoid levels are elevated in $Lep^{ob}$ and $Lepr^{db}$ homozygotes compared with their lean controls (Coleman and Burkart, 1977; Dubuc et al., 1975) but remain unchanged in the yellow agouti mutants (Wolff and Flack, 1971). Nevertheless, the adrenals are necessary for the full expression of the obesity syndrome in the yellow agouti mutants. Adrenalectomy normalizes hyperglycemia in $A^{vy}$/a mice (Shimizu, 1989) and reduces fat deposition in both yellow and lean agouti mice, but does not completely prevent the relative obesity of yellow vs. lean littermates (Jackson et al., 1976).

In addition, the pituitary gland is required for complete, manifestation of the yellow obese syndrome. Hypophysectomy offsets the hyperinsulinemia that normally develops in $A^{vy}$ mice (Salem et al., 1989) but only reduces and does not prevent the excess fat deposition or the unique "anabolic" effects of the dominant yellow agouti mutations (Plocher and Powley, 1976; Salem et al., 1989). Yellow obese mice typically exhibit mild increases (~10%) in skeletal length, lean muscle mass and fat-free dry weight, even in castrated males that lack endogenous testosterone (reviewed in Wolff et al., 1986). These observations have led to the hypothesis that agouti may somehow mimic the effects of growth hormone. Interestingly, the $Lep^{ob}/Lep^{ob}$ mice exhibit just the opposite effect on skeletal growth (Heston and Vlahakis, 1962), and it has been shown that the obese (fa/fa) Zucker rat expresses reduced levels of both growth hormone and growth hormone-releasing hormone (Ahmad et al., 1993; Ahmad et al., 1989). A causal relationship between growth hormone and obesity was ruled out over two decades ago when it was demonstrated that introducing a genetic deficiency of growth hormone does not prevent the excess adiposity and relative weight gain in $A^y$ mutants (Wolff, 1965a;b).

Parabiosis studies have been particularly useful in dissecting the hormonal contributions to obesity in several genetic models (reviewed in Yen et al., 1994). Surgical union of obese $A^y$/a and nonobese a/a mice had no effect on either partner's body weight or fat content, suggesting that circulating hormones are not directly involved in the development of agouti-induced obesity (Wolff, 1963). Because the agouti protein is normally secreted from the cell (see below), the results of the parabiosis studies may simply indicate that the agouti protein is not sufficiently stable to circulate between parabiotic partners, or that agouti acts in a localized manner.

Molecular Characterization of the Agouti Gene as it Relates to Obesity

Elucidation of the molecular nature of the dominant agouti mutations prompted the working hypothesis that the ectopic expression of the agouti gene causes the metabolic dysfunction that leads to obesity. However, because each of the dominant agouti mutations had a genomic rearrangement, it was possible that the structural changes in the DNA caused a deletion and/or dysregulation of a second gene in the vicinity of agouti that was itself responsible for the phenotype of the agouti mutants. To role out this possibility, transgenic mice were prepared with an expression construct that caused the ubiquitous expression of the wildtype agouti gene. For this purpose, the β-actin or phosphoglycerate kinase promoters (Klebig et al., 1995) were used to drive the expression of the wildtype agouti cDNA (BAPa and PGKPa, respectively). Examination of several lines prepared with each construct indicated that the transgene was expressed in multiple tissues at levels that were equal to or exceeded that observed in the $A^y$ mutant mice. When the BAPa or PGKPa transgene was crossed onto the C57BL1/6J inbred line, the transgenics developed yellow fur, and, as the animals aged, became obese. Transgenic males became 30–40% heavier and females 60–70% heavier than nontransgenic controls (Klebig et al., 1995). The analysis of fat pad masses indicated that ~80% of the body weight differences between transgenic and nontransgenic mice was attributable to increases in dissectable fat depots. A 2-wk feeding study in one line, BAPa20, indicated that hyperphagia is not necessary for the relative weight gain of transgenic vs. nontransgenic littermates. These findings lend direct support to the increased caloric efficiency hypothesis described in the previous section. Furthermore, the basal core temperature was measured in one line, BAPa20, and was found to be significantly depressed by 0.81° C. ($p<0.0005$) compared with nontransgenic controls (Kim et al., 1996), indicating that decreased thermogenesis contributes to a positive energy balance in these mice. With respect to insulin and glucose levels, both males (both BAPa and PGKPa) and females (BAPa only) become hyperinsulinemic within 12 wk of age, whereas only males developed overt hyperglycemia (Klebig et al., 1995). The ratio of insulin to glucose in the BAPa20 transgenic mice was twice that of the nontransgenic controls. This finding suggests that the mice produce higher levels of insulin to remain normoglycemic, which is a hallmark of noninsulin-dependent diabetes. Thus, the unambiguous parallels between the phenotype of these transgenic mice and the dominant yellow agouti mutants firmly established that the ectopic expression of agouti in a ubiquitous manner is sufficient to induce both obesity and diabetes.

Coupling agouti mutation analysis with ubiquitous expression of these mutations in transgenic mice revealed that the same structural features of agouti are generally important for both the production of yellow pigment and the development of obesity (Hustad et al., 1995; Perry et al., 1995; Perry et al., 1996). That agouti acts extracellularly to induce obesity was suggested by deletion of 10 residues of the hydrophobic core of the amino-terminal signal sequence. When expressed in transgenic founder mice (C57BL1/6J genetic background) under the control of the β-actin promoter, this signal peptide mutation re-suited in completely non-yellow mice that remained lean. Expression of agouti sequences containing an ENU-induced point mutation in the signal sequence (Hustad et al., 1995; Perry et al., 1995), or a mutation in the putative N-linked glycosylation site, resulted in only patchy yellow fur over the ventral surface of the animal but no obesity (Perry et al., 1996). Deletion of approximately half of the central basic region of agouti did not significantly impair the development of yellow pigmentation or obesity, suggesting that this region of agouti may be dispensable for either activity. In contrast, substitution of individual cysteines with serine residues at some positions in the agouti carboxy-terminus completely eliminated the potential for both yellow pigmentation and obesity. A mutation at cysteine 110 or 131, however, was only partially disabling because some mice expressing these mutations produced yellow fur (in the ventrum only) and a few became obese. It has been proposed that cysteine 110 and 131 form a disulfide bonded pair that is at least partially dispensable for either biological activity (Perry et al., 1996).

Molecular Models of Agouti-Induced Obesity

The molecular mechanism by which agouti influences pigmentation is known and has important implications for obesity. Genetic characterization of the extension (e) and agouti loci revealed that mutations at these two regions cause similar phenotypes, but that the dominance hierarchy for each is the opposite of the other (Silvers, 1979). The dominance hierarchy of the extension series of alleles ranges from dominant black mutations like tobacco ($E^{tob}$) and sombre ($E^{so}$) to recessive yellow (e). In contrast, most dominant agouti alleles are yellow and the recessive mutations are black. The extension locus mutations are epistatic to agouti mutations, meaning that animals carrying mutations at both loci exhibit the phenotype of the former (e/e) rather than the latter (o/a). Furthermore, unlike agouti, extension alleles function in a cell-autonomous fashion, suggesting that the gene product is expressed and acts within hair bulb melanocytes. The extension gene encodes the seven transmembrane-spanning receptor, melanocortin 1 (MCI-R) (Mountjoy et al., 1992), which is the receptor for the α-melanocyte stimulating hormone (αMSH). Eumelanin synthesis is stimulated by the binding of the αMSH ligand to MCI-R, resulting in a G-protein-mediated increase in intracellular cAMP levels that regulates melanogenic enzymes (reviewed in Jackson, 1994). The agouti gene product antagonizes the binding of αMSH to MC1-R and blocks the increase in cAMP, leading to the default synthesis of phaeomelanin. This antagonistic action of agouti was demonstrated directly in a heterologous system using recombinant agouti protein and the human embryonic kidney 293 cell line transfected with the MC1-R gene (Lu et al., 1994). Although the pigmentation effect of the dominant yellow agouti mutations correlates well with their effect on body weight, yellow pigment production per se is not critical for the development of obesity. $A^{vy}$ mice carrying the dominant black mutation $E^{so}$ have black fur and become obese (Wolff et al., 1978), indicating that the two phenotypes are separable and that agouti does not act through MCI receptors to induce obesity.

Targeted disruption of the MC4-R molecule in mice produced many of the hallmark features of the yellow obese syndrome, including increased skeletal length, but without producing yellow fur (Huszar et al., 1997). In this case, the magnitude of maturity-onset weight gain, hyperinsulinemia and hyperphagia were significantly higher than that observed in the BAPa transgenic mice or the yellow obese mutants of the same genetic background. The magnitude of the phenotypic differences may be explained by the complete absence of the receptor in the knock-out mice vs. partial (but chronic) antagonism of the receptor by the ectopically expressed agouti protein in the yellow obese mutants.

Although the tissue distribution of MC4-R has not yet been reported for the mouse, expression of MC4 receptors in the rat seems to be restricted to the brain (Mountjoy et al., 1994). Agouti antagonism of MC1-R is not significant with respect to obesity because chronic agouti expression in the skin results in yellow fur but no alterations in body weight or hyperglycemia (Kucera et al., 1996). The ubiquitously expressed MC5-R (Gantz et al., 1994; Griffon et al., 1994; Labbe et al., 1994) poses an unlikely target for the agouti protein because physiologically relevant concentrations of agouti do not antagonize this receptor in cell-based assays (Kiefer et al., 1997; Lu et al.; 1994). The MC3-R and MC2-R receptors remain potential targets for the agouti protein in peripheral tissues. In addition to its expression in the limbic system and hypothalamus, MC3-R is expressed in the placenta and gut (Gantz et al., 1993a); Roselli-Rehfuss et al., 1993), and agouti has been shown to be a high affinity antagonist of human, although not rat, MC3-R (Kiefer et al., 1997; Lu et al., 1994).

To test whether adipose tissue is a direct target for agouti action in vivo, transgenic mice were generated that express agouti from the transcriptional promoter of aP2 (aP2a), a gene that encodes the adipocyte fatty acid binding protein. Compared with the BAPa or PGKPa transgenic mice discussed above, the aP2a transgenic mice expressed extremely high levels of agouti in both white and brown adipose tissue, with negligible expression in other peripheral tissues or the brain. Even at a late age, the aP2a transgenic mice did not become overweight or hyperinsulinemic. This finding indicated that agouti expression in adipocytes alone is not sufficient to induce the metabolic changes that cause obesity and/or diabetes. How-ever, when the aP2a mice were given daily subcutaneous insulin injections for 1 wk, the transgenic mice gained significantly more weight (1.7-fold) than their nontransgenic controls. This finding strongly suggests that agouti and insulin act synergistically to promote weight gain in vivo, perhaps due to the combination of their similar lipogenic and antilipolytic effects in the animal (reviewed in Bray, 1996; Yen et al., 1994). Moreover, these findings establish a physiologically relevant role for agouti in adipose tissue in the yellow obese mutants.

Additional analysis of the yellow agouti mutants revealed that the expression of two key enzymes involved in de novo fatty acid synthesis and desaturation, fatty acid synthetase (FAS) and stearoyl-CoA desaturase were elevated in the liver and adipose tissue (Jones et al., 1996). Similarly, recombinant agouti protein stimulates both the expression and activity of FAS and causes an increase in triglyceride accumulation in 3T3-L1 adipocytes. This effect can either be completely prevented by $Ca^{2+}$ channel blockade (Jones et al., 1996) or mimicked with $Ca^{2+}$ agonists (Zemel et al., 1995a), suggesting that alterations in $Ca^{2+}$ influx, without complementary alterations in $Ca^{2+}$ efflux, may mediate these lipogenic effects of agouti. The soleus muscle of $A^{vy}$ mice also exhibited an elevation in steady-state levels of intracellular free $Ca^{2+}$ and increases in $Ca^{2+}$ influx rate (Zemel et al., 1995b). A similar effect has been observed in both primary and cultured skeletal myocytes after treatment with recombinant agouti protein. These findings suggest that perturbations in calcium signaling and calcium homeostasis by extracellular agouti protein may contribute substantially to the insulin resistance and lipogenic bias in the yellow obese mice. Possible mechanisms include a G-protein-mediated coupling between melanocortin receptors and $Ca^{2+}$ channels, direct stimulation of $Ca^{2+}$ channels by extracellular agouti protein, or an indirect effect on $Ca^{2+}$ channels by blocking voltage-gated or ATP-gated potassium channels.

Example 22

Obesity and the Adipocyte: Role of the Agouti Gene in Obesity

Dominant mutations in the mouse agouti gene confer a pleiotropic syndrome characterized by obesity, mild hyperphagia, decreased thermogenesis, hyperinsulinemia, peripheral insulin resistance, impaired glucose tolerance, hyperglycemia in males, increased susceptibility to cancer, and yellow hair (for review, see Wolff et al., 1986; Wolff, 1987; Yen et al., 1994; Klebig et al., 1996). Molecular analyses demonstrated that six dominant agouti alleles ($A^y$, $A^{sy}$, $A^{vy}$, $A^{iapy}$, $A^{hvy}$ and $A^{iy}$) are the result of regulatory mutations in which the normal agouti coding sequence is under the control of various ubiquitous promoters, resulting in the normal agouti protein being produced at high levels in all tissues of the body (Bultman et al., 1992; Miller et al., 1993; Michaud et al., 1994a,b; Duhl et al., 1994a; Duhl et al., 1994b; Argeson et al., 1996). The dominant obesity syndrome in these mice was recapitulated by expressing the wildtype agouti cDNA under the control of a ubiquitous promoter in transgenic mice, demonstrating that ectopic overexpression of the wildtype agouti gene is the cause of the obesity syndrome, not the deletion or the various insertions associated with the regulatory mutations (Klebig et al., 1995; Perry et al., 1995).

One hypothesis for the role of the agouti gene in the obesity syndrome is that, because of its ubiquitous expression in mutant mice, it may antagonize signal transduction cascades that are mediated by melanocortin receptors present in tissues other than the skin. The MC1-R is one of five recently cloned melanocortin receptors that are expressed in various tissues throughout the body: MC2-R is expressed in the adrenal cortex (Mountjoy et al., 1992) and adipose tissue (Boston and Cone, 1996), MC3-R is expressed in the hypothalamus and limbic systems in the brain, and in the placenta and gut (Gantz et al., 1993a; Roselli-Rehfuss et al., 1993), MC4-R is expressed throughout the brain (Gantz et al., 1993b; Mountjoy et al., 1994), and MC5-R is ubiquitously expressed (Gantz et al., 1994; Griffon et al., 1994; Labbe et al., 1994). To test the hypothesis that agouti protein may antagonize these other melanocortin receptors, the receptors were expressed in human embryonic kidney cells and the ability of recombinant agouti protein to antagonize the binding of α-MSH to the various receptors was determined by assaying for adenylyl cyclase activity (Lu et al., 1994). These studies demonstrated that the agouti protein is a high affinity antagonist of MC1-R and MC4-R, but agouti appeared to have no effect on MC3-R or MC5-R. At present, the effect of agouti on MC2-R is unknown. Interestingly, mice with a targeted disruption of MC4-R were recently generated and they exhibit an obesity syndrome that is remarkably similar to that seen in mice with dominant agouti locus mutations, suggesting that chronic antagonism of MC4-R by the agouti protein may be a central mechanism of the agouti-induced obesity syndrome (Huszar et al., 1997). In addition, a cyclic melanocortin analog that is an agonist of MC4-R was shown to inhibit feeding in $A^y$/a mice, whereas a melanocortin antagonist stimulated feeding (Fan et al., 1997). These recent studies clearly demonstrate a role for neural melanocortin receptor(s) in regulating nutrient intake and energy balance; however, it is unlikely that agouti antagonism of MC4-R in the brain completely explains the agouti obesity syndrome.

A second hypothesis for the mechanism of agouti action in inducing the obesity syndrome is that the agouti protein targets ion channels, causing an increase in intracellular free calcium ($[Ca^{2+}]_i$) in multiple target tissues. As a consequence, numerous cellular processes would be affected via calcium signaling. Ionized calcium ($Ca^{2+}$) is exquisitely regulated in cells and is the most common signal transduction factor, affecting a broad range of cellular processes (for review, see Clapham, 1995). The carboxyl-terminal end of the agouti protein is cysteine-rich, and the number and spacing of cysteine residues are extremely similar to those of toxins from snails (ω-conotoxins, Olivera et al., 1994) and spiders (plectoxins, Quistad and Skinner, 1994) that are known to function by targeting ion channels (for review, see Manne et al., 1995). The cysteines in the snail and spider venoms form intramolecular disulfide bonds that are critical for their three-dimensional structure and function. These observations suggest that the C-terminus of the agouti protein may form a three-dimensional structure that is functionally similar to the toxins. In this light, it is interesting to note that the C-terminal portion of the agouti protein retains equal functional activity found in the full-length protein in an in vitro assay (Willard et al., 1995). Importantly, recombinant agouti protein causes a significant increase in $[Ca^{2+}]_i$ in skeletal muscle myocytes and adipocytes by increasing $Ca^{2+}$ influx, with no complementary alterations in $Ca^{2+}$ efflux (Zemel et al., 1995a; Kim et al., 1997). At present it is unknown if agouti protein stimulates increases in $[Ca^{2+}]_i$ by signaling through melanocortin receptors or by directly targeting ion channels, or both. Because calcium is tightly regulated in cells and acts as a second messenger in a variety of signal transduction pathways, agouti-induced obesity may be partially mediated by alterations in $[Ca^{2+}]_i$ in peripheral tissues.

Humans also have an agouti gene, and the mouse and human proteins are 80% identical (87% over the cysteine-rich C-terminus), suggesting that agouti may be functionally similar in both species (Kwon et al., 1994; Wilson et al., 1995). Unlike the mouse, however, the human agouti gene is normally expressed in adipose tissue (Kwon et al., 1994). The presence of human agouti in adipose tissue is intriguing in light of the fact that recombinant murine agouti protein not only causes an increase in $[Ca^{2+}]_i$ in cultured adipocytes, but also increases fatty acid synthase expression and activity, and stimulates the accumulation of triglycerides in a $[Ca^{2+}]_i$-dependent manner (Jones et al., 1996). These results indicate that the agouti protein may regulate fatty acid metabolism by acting directly on adipose tissue. Furthermore, calcium channel inhibition results in significant decreases in adipose tissue mass and adipocyte lipogenesis in obese transgenic mice that express the agouti gene in a ubiquitous manner (Kim et al., 1996).

To model human agouti expression, transgenic mice were generated that express murine agouti at high levels in adipose tissue under the regulatory control of the aP2 promoter (Mynatt et al., 1997). These aP2-agouti transgenic mice are not obese or diabetic, but daily insulin injections for 7 days resulted in a significantly greater increase in their body weight (17-fold greater) than was produced in insulin-treated non-transgenic mice. The results from these studies suggest that agouti expression in adipose tissue, combined with insulin treatment, promotes obesity in mice and may have implications for human obesity. The hypothesis for the greater weight gain in the transgenic mice is that insulin-mediated changes in energy balance act synergistically with the agouti-conditioned adipocytes to stimulate weight gain. These in vivo data support the in vitro data on the effects of recombinant agouti protein on adipocytes and provide compelling evidence that agouti-induced obesity is mediated in part by its action on peripheral tissues.

Together, these findings suggest that the wildtype agouti protein acts on both the central nervous system (CNS) and tissues in the periphery to induce the obesity syndrome. In the CNS, agouti may antagonize neural melanocortin receptor(s), resulting in obesity, hyperphagia and hyperinsulinemia, as observed in the MC4-R. knock-out mice. In the periphery, agouti expression in adipose tissue, coupled with insulin treatment, results in significant weight gains in mice. Given that hyperinsulinemia appears to be an important aspect of the agouti-induced obesity syndrome, it is noteworthy that pancreatic β-cell hyperplasia precedes obesity in mutant agouti mice (Warbritton et al., 1994). In addition, increases in $[Ca^{2+}]_i$ in β cells stimulate insulin release (for review, see Newgard and McGarry, 1995). Therefore, it is possible that ectopic expression of the agouti gene in the pancreas may act directly on the β cells to trigger hyperinsulinemia.

Example 23

Agouti Regulation of Intracellular Calcium: Role of Melanocortin Receptors $A^{vy}$ mice exhibit a marked elevation of skeletal muscle $[Ca^{2+}]_i$, which is highly correlated with the degree of ectopic overexpression of agouti and obesity (Zemel et al., 1995). Incubation of cultured skeletal myocytes with medium containing the recombinant murine agouti protein caused an increase in steady-state $[Ca^{2+}]_i$ and that this may contribute to the insulin resistance characteristic of mutations at the mouse agouti locus (Zemel et al., 1995).

This example describes that the recombinant murine agouti protein induced elevation of $[Ca^{2+}]_i$ in L6 skeletal myocytes, A7r5 smooth muscle cells, and 3T3-L1 adipocytes and that this effect is sensitive to $Ca^{2+}$ channel blockade. Furthermore, agouti regulation of $[Ca^{2+}]_i$ appears to be modulated by melanocortin receptors in human embryonic kidney cells (HEK-293 cells). This suggests that agouti may regulate $[Ca^{2+}]_i$ in various tissue types via interaction with melanocortin receptors.

Materials and Methods

Cell Culture

The spontaneously fusing L6 skeletal muscle cells [American Type Culture Collection (ATCC), Bethesda, Md.] were grown in 75-cm² flasks in Dulbecco's modified Eagle's medium with 10% glucose (DMEM) supplemented with 5% fetal bovine serum (FBS, vol/vol), 5% calf serum supplemented iron enriched (CS, vol/vol, and antibiotics (50 U penicillin/ml and 5 μg of streptomycin/ml). Cultures were maintained in continuous passages (<20) by trypsinization (0.05% trypsin) of semiconfluent nonfused cells. A7r5 vascular smooth muscle cells (ATCC) were grown in the same conditions as for L6 cells. 3T3-L1 cells (ATCC) were grown in 100-mm dishes in DMEM containing 10% FBS and antibiotics. For differentiation of fibroblasts into adipocytes, confluent cells were incubated in DMEM-FBS containing 0.5 mM 3-isobutyl-1-methylxanthine (IBMX; Sigma, St. Louis, Mo.) and 0.25 μM dexamethasone (Dex; Sigma) for 60 h. IBMX and Dex were then removed, and cells remained in DMEM-FBS with 250 μg/ml geneticin and compared with nontransfected HEK-293 cells. All types of cells were maintained at 37° C. in an atmosphere containing 5% $CO_2$ and 100% humidity. Cell culture reagents, FBS, CS, and trypsin-EDTA were obtained from GIBCO/BRL (Grand Island, N.Y.).

Production and Purification of Recombinant Agouti Polypeptide

A 614-bp XbaI/PstI fragment of the full-length mouse agouti cDNA (Bultman et al., 1992; Miller et al., 1993) or human agouti cDNA (Kwon et al., 1994) was subcloned into an XbaI/PstI-digested baculovirus expression vector pAcMP3 (PharMingen, San Diego, Cailf.). Viruses incorporating this vector were produced by standard methods (Lu et al., 1994). *Spodoptera frugiperda* cells (Sf-9) were propagated in Grace's supplemented medium containing 10% CS and 0.1% Pluronic F68 and used to produce high-titer viral stocks. Fifteen-liter scale production runs of murine or human agouti were produced using T. ni cells adapted to suspension (JRH Biosciences, Woodland, Calif.). T. ni cells were infected 24 h postseeding at a density of $10^6$ cells/ml, and conditioned media from infected cells were harvested 48 h after infection filtered through a Whatman 3 filter and purified as recently described (Willard et al., 1995).

Transfection with Receptor Genes

The coding region of the human melanocortin 1, 3, and 5 receptor (hMC1R, hMC3R, and hMC5R) genes was amplified by polymerase chain reaction and subcloned into the vector pMT4, and the sequence was verified. HEK-293 cells, which appear to lack endogenous melanocortin receptors (Lu et al., 1994), were cotransfected with pMT4 and pRSV-Neo by either calcium phosphate coprecipitation method or the use of Transfectam reagent (Promega). Clones were selected using 600 μg geneticin/ml culture medium. By use of $^{125}$I-labeled Nle,D-Phe (NDP)-α-MSH, the inhibitor constant ($K_i$) for the clones ranged from 1.1 to $5.8 \times 10^{-10}$M. Of these clones, the receptor number per cell was for MC1R clone 10A and demonstrated to be ~18,000 receptors/cell.

Measurement of $[Ca^{2+}]_i$ $[Ca^{2+}]_i$ was measured in L6, A7r5, and HEK-293 cells (Zemel et al., 1995) as previously described and in 3T3-L1 cells as described by Klip and Ramlal (1987). Monolayers of nonfused L6 cells and confluent A7r5 cells after 14–16 h of starvation in a serum-free culture medium were rinsed with Hanks' balanced salt solution (HBSS), detached by incubation in 2 ml trypsin (0.05%) for 2–3 min at 37° C., and released by pipetting without trypsinization. Cells were harvested by centrifugation at 50 g and resuspended in 1 ml HBSS at a density of ~$10^6$ cells/ml. For 3T3-L1 cells, monolayers of differentiated adipocytes were rinsed with serum-free DMEM and exposed to 0.05% trypsin for 3 min. The solution was decanted, and the cells were incubated for 3 min in culture medium. Cells were detached by pipetting and collected by centrifugation at 50 g Cells were then incubated in culture medium to recover for 1 h followed by incubation in serum-free DMEM for 4 h at 37° C. in an atmosphere of 5% $CO_2$, collected by centrifugation, and resuspended in HBSS at a density of ~$10^6$ cells/ml. Cell suspensions were chilled on ice for 5 min and loaded with 10 mM (final concn) fura 2 acetoxymethyl ester (AM; Sigma) in the dark for 20 min at 37° C. For 3T3-L1 adipocytes, the chilling step was skipped. Extracellular fura 2-AM was washed three times with HBSS by centrifugation. For $[Ca^{2+}]_i$ measurements, L6, A7r5, HEK-293, and 3T3-L1 cells were resuspended in 1 ml HBSS and transferred to a 1-ml 37° C. cuvette; primary adipocytes were resuspended in 3–5 ml HBSS at the concentration of ~$20 \times 10^4$ cells//ml, and 2.4 ml of cell suspension were transferred to a 3-ml 37° C. cuvette. $[Ca^{2+}]_i$ levels were then measured fluorometrically in suspensions using dual excitation (340 and 380 nm)-single emission (510 nm) fluorometry as previously described (Zemel et al., 1995). $[Ca^{2+}]_i$ was then calculated by the computer in the fluorometer with the equation of Grynkiewicz et al. (1985). $[Ca^{2+}]_i$ response to the recombinant agouti protein or NDP-α-MSH was evaluated after establishing a stable baseline for each cell suspension. In studies with $Ca^{2+}$ channel blocker, after fura 2-AM was loaded, cells were pretreated with nitrendipine (Research Biochemicals International, Natick, Mass.; 30 μM final concn) for 10 min at 37° C. before addition of agonists.

Statistics

All data were analyzed in the Student's t-test or, where appropriate, analysis of variance.

Results

Figure 45A:
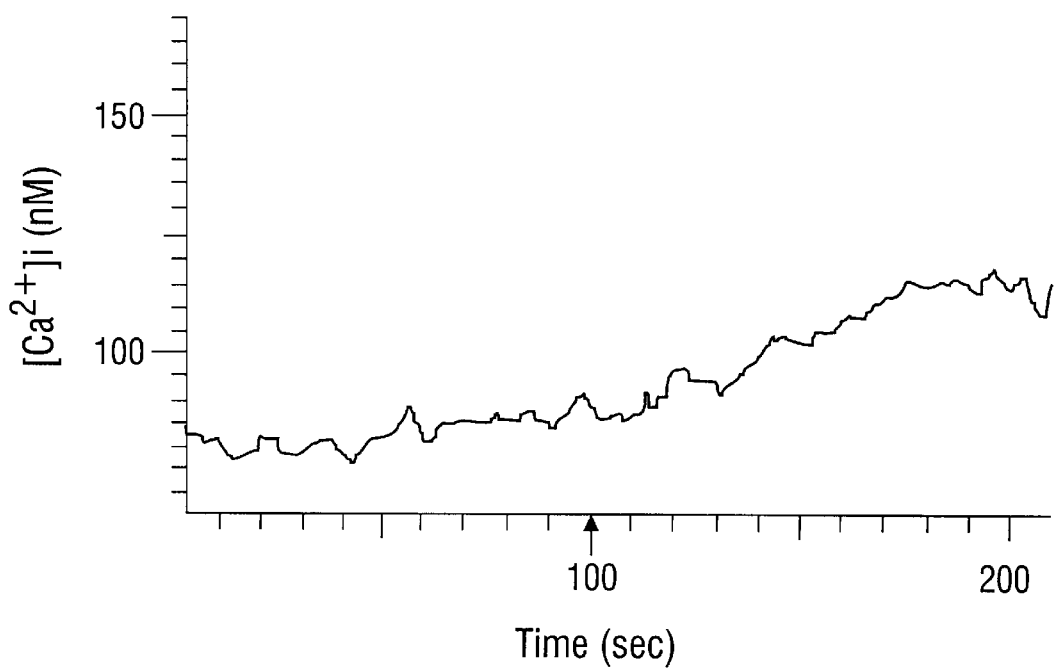
FIG. 45. Effects of murine agouti protein (50 nM) on cytosolic $Ca^{2+}$ levels ($[Ca^{2+}]_i$) in cultured L6 skeletal myocytes (A) and A7r5 vascular smooth cells (B). Agouti was added at times designated by arrows. $[Ca^{2+}]_i$ levels were measured as described in Materials and Methods.
Figure 45B:
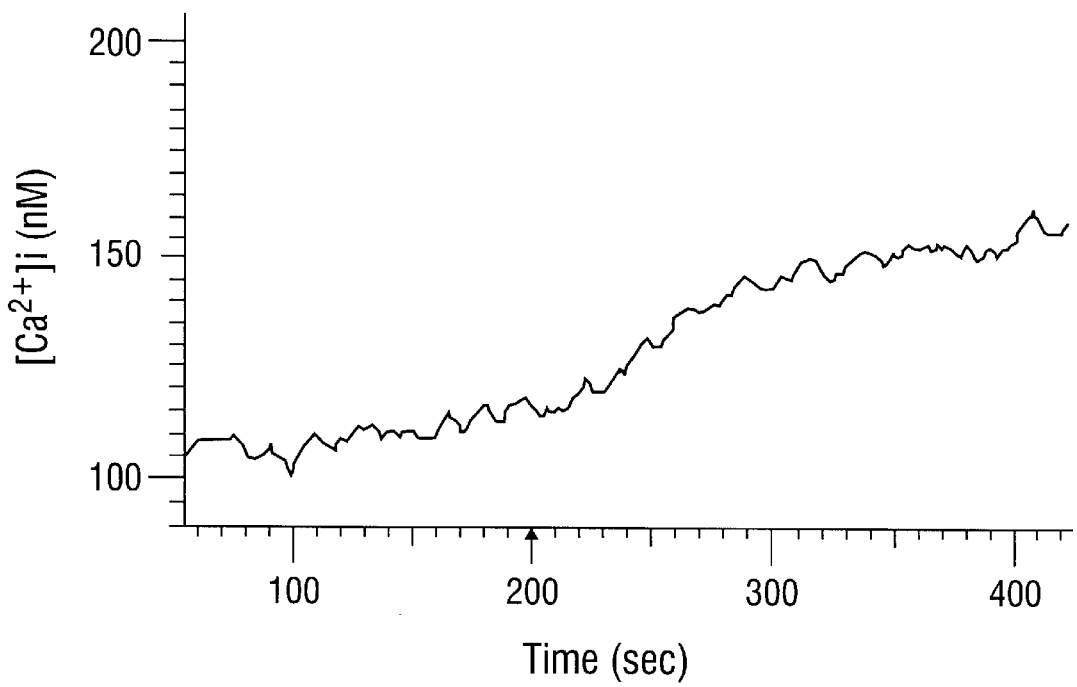

Purified recombinant murine agouti protein induced a slow, sustained increase in $[Ca^{2+}]_i$ (P<0.01) in L6 skeletal myocytes and A7r5 vascular smooth muscle cells (FIG. 45). Murine agouti also produced a slow, sustained increase in $[Ca^{2+}]_i$ in 3T3-L1 adipocytes. For example, 50 nM agouti increased $[Ca^{2+}]_i$ by 44±4 nM after 200 s and reached a plateau of 73±6 nM increase over baseline at 400 s after agouti addition (P<0.03 vs. vehicle and time controls). These data are summarized in Table 5.

TABLE 5

EFFECTS OF PURIFIED MURINE AGOUTI ON $[CA^{2+}]_i$ IN L6 SKELETAL MYOCYTES, A7R5 VSMC, AND 3T3-L1 ADIPOCYTES

| | $[Ca^{2+}]_i$ Increase over Baseline, nM | |
|---|---|---|
| | 25 nM Agouti | 5 nM Agouti |
| L6 myocytes | 32 ± 1* | 49 ± 8*† |
| A7r5 VSMC | 46 ± 9* | 74 ± 6*† |
| 3T3-L1 adipocytes | 33 ± 6* | 73 ± 6*† |

Values are means ± SE for 400 s after agouti addition; n = 8 for each treatment-cell combination. VSMC, vascular smooth muscle cells. *P<0.03 vs. vehicle control. †P<0.03 vs. 25 nM agouti.

Figure 46:
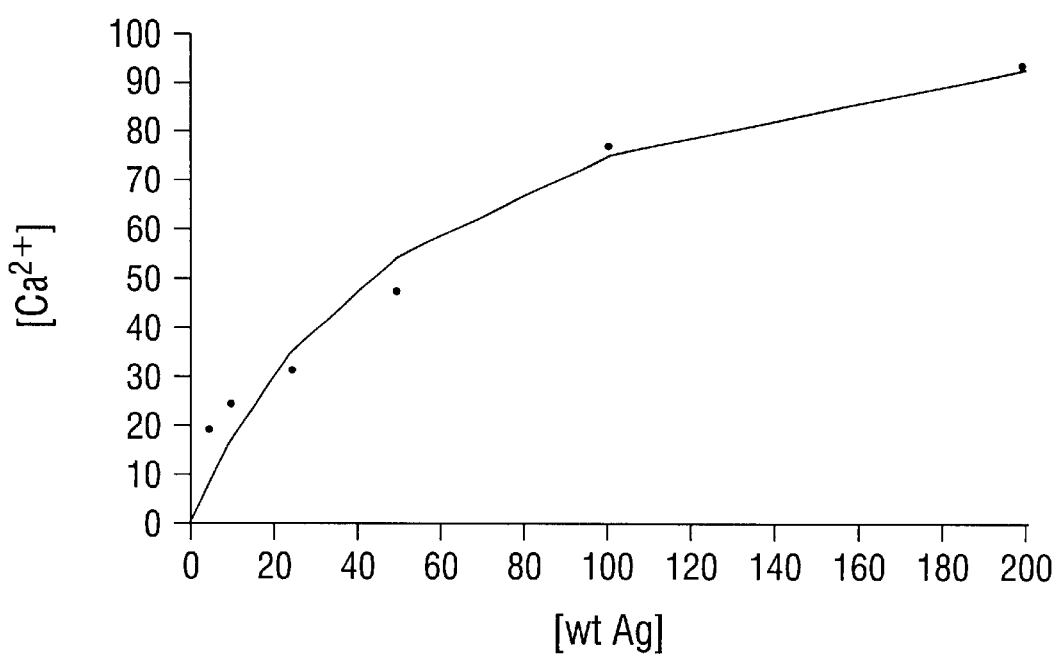
FIG. 46. Dose-response curve of effects of murine agouti (Ag) on $[Ca^{2+}]_i$ in cultured L6 skeletal myocytes. $[Ca^{2+}]_i$ responses were measured as described in Materials and Methods, and values reported are for response plateau at 400 s after agouti addition. Data were fitted by nonlinear least-squares analysis yielding a concentration inhibiting 50% of maximal response ($EC_{50}$) of 62±19. $y=(V_{max} \cdot x)/(K+x)$, where $V_{max}=123.036246 \pm 15.629815$ and $K=62.06378 \pm 19.361692$.

The agouti effect on $[Ca^{2+}]_i$ was further characterized in L6 myocytes. The $[Ca^{2+}]_i$ dose response to agouti is shown in FIG. 46; agouti stimulated $[Ca^{2+}]_i$, responses with an apparent $EC_{50}$ of 62±19 nM (FIG. 46). $Ca^{2+}$ channel blockade with 30 μM nitrendipine reduced the response to 50 nM agouti in these cells by ~50% (P<0.01), from 49±8 to 22±6 nM.

Figure 47A:
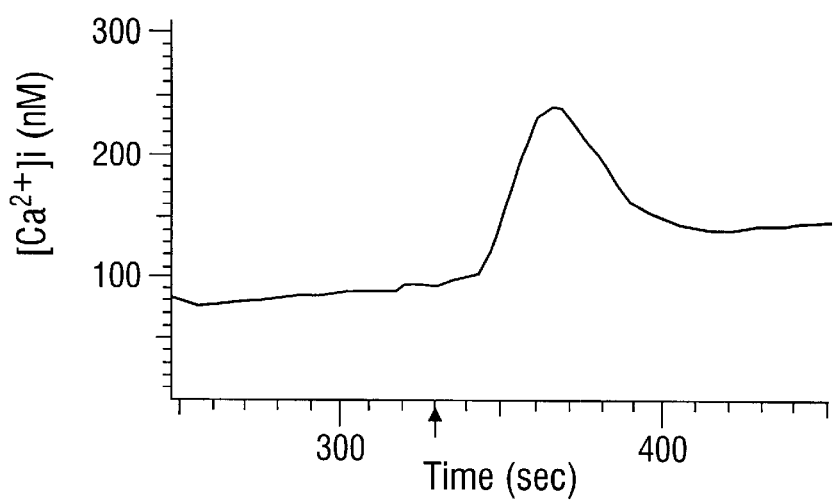
FIG. 47. Effects of Nle,D-Phe-$\alpha$-melanocortin-stimulating hormone (NDP-$\alpha$-MSH, 1–10 nM) on cytosolic $Ca^{2+}$ levels in human embryonic kidney cells (HEK-293 cells) transfected with human melanocortin 1, 3, or 5 receptor (hMC1R, 1 nM, A; hMC3R, 10 nM, B; or hMC5R, 10 nM, C). NDP-$\alpha$-MSH was added at times designated by arrows. Data were fitted by nonlinear least-squares analysis assuming a single binding site, yielding an $EC_{50}$ of 18±0.07.
Figure 47B:
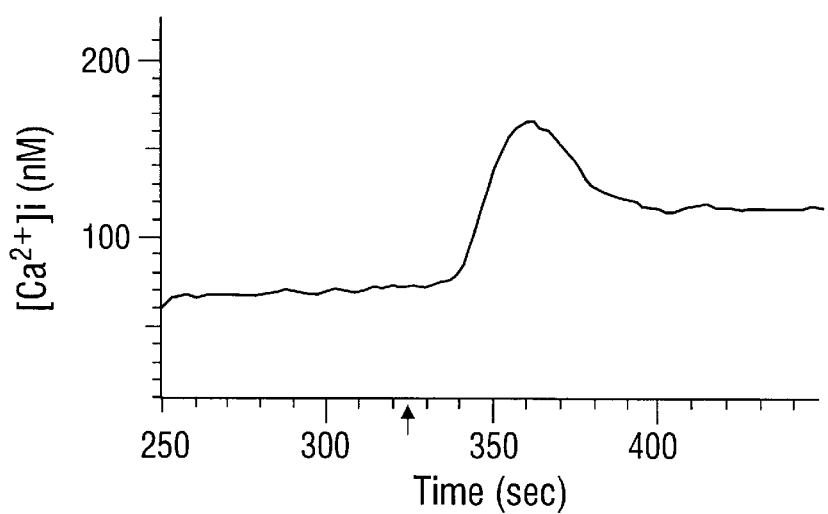
Figure 47C:
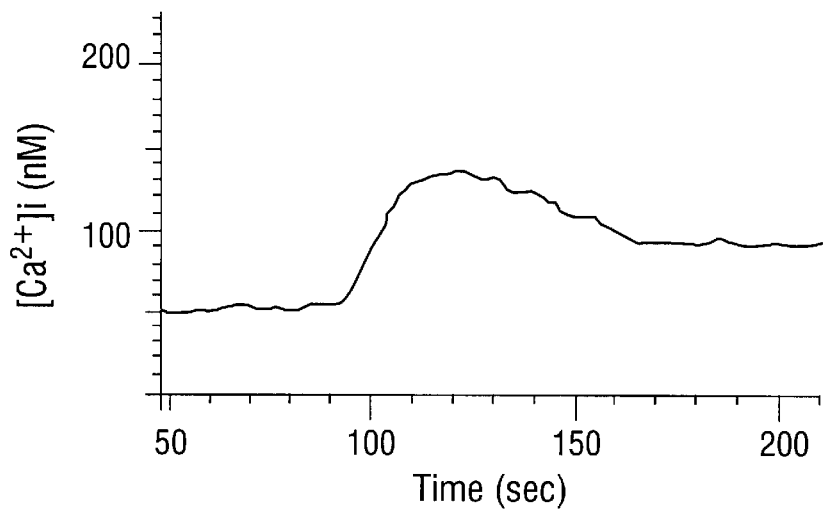

Agouti regulates coat color via antagonism of α-MSH binding to MC1R. Because melanocortin peptides also stimulate $[Ca^{2+}]_i$ increases, the inventors wanted to evaluate whether the effect of agouti on $[Ca^{2+}]_i$ was also mediated by melanocortin receptors; the inventors first measured the $[Ca^{2+}]_i$ response to NDP-α-MSH, a stable and potent analog of α-MSH, in HEK-293 cells stably transfected with hMC1R, hMC3R, and hMC5R and in nontransfected HEK-293 cells. NDP-α-MSH (1–10 nM) induced significant transient elevations in $[Ca^{2+}]_i$ in HEK-293 cells transfected with hMC1R, hMC3R, and hMC5R (P<0.01; FIG. 47) but not in nontransfected HEK-293 cells. Also, NDP-α-MSH in concentrations as high as 500 nM failed to stimulate an increase in $[Ca^{2+}]_i$ in L6 or A7r5 cells. Thus, as previously described, melanocortin peptides are capable of stimulating transient increases in $[Ca^{2+}]_i$ in a melanocortin receptor-dependent manner. In all HEK-293 cell lines except the nontransfected controls, NDP-α-MSH was able to cause an increase in adenosine 3',5'-cyclic monophosphate (cAMP) in a dose-dependent fashion, indicating that coupling to $G_s$ was functional.

As shown in Table 6, agouti (20 nM) provoked an increase in $[Ca^{2+}]_i$ in the MC1R and MC3R HEK-293 cell lines, whereas no response was observed in either the MC5R or nontransfected HEK-293 cells.

TABLE 6

EFFECTS OF PURIFIED HUMAN AGOUTI ON $[CA^{2+}]_i$ IN HEK-293 CELLS TRANSFECTED WITH MELANOCORTIN RECEPTORS

| | $[Ca^{2+}]_i$ Increase over Baseline |
|---|---|
| HEK-293 | ND |
| HEK-293-hMC1R | 57 ± 9* |
| HEK-293-hMC3R | 77 ± 14 |
| HEK-293-hMC3R | ND |

Values are means ± SE in response to 20 nM agouti; n = 8 for each cell line. HEK, human embryonic kidney; hMC1R, human melanocortin 1 receptor; hMC3R, human melanocortin 3 receptor; hMC5R, human melanocortin 5 receptor; ND, no detectable increase. *P<0.01.

Figure 48:
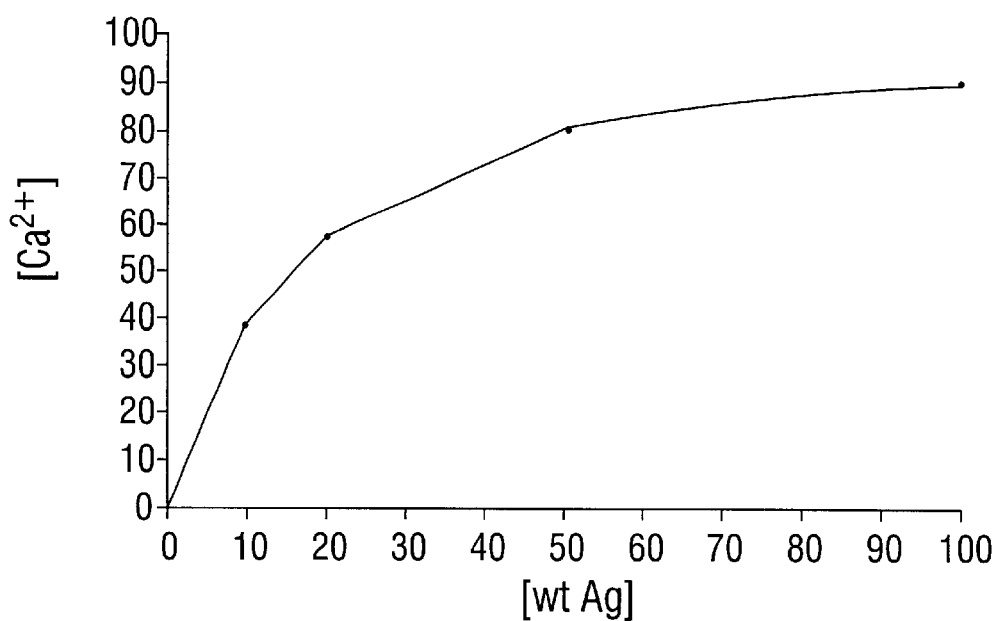
FIG. 48. Dose-response curve of effects of murine agouti on $[Ca^{2+}]$ levels in HEK-293 cells transfected with hMC1R $[Ca^{2+}]_i$ responses were measured as described in Materials and Methods, and values reported are for response plateau at 400 s after agouti addition. $y=(V_{max} \cdot x)/(K+x)$, where $V_{max}=108.22069 \pm 1.337041$ and $K=18.407786 \pm 0.706395$.

Further characterization of this response was per-formed using a dose response of human agouti on $[Ca^{2+}]_i$ in the MC1R line (FIG. 48). Agouti stimulated $[Ca^{2+}]_i$ with an approximate $EC_{50}$ of 18 nM. This $EC_{50}$ for human agouti is comparable to the $K_i$ for human agouti antagonism of $^{125}$I-NDP-α-MSH binding in the same cell line.

Discussion

Data from the present study directly demonstrate that recombinant murine and human agouti proteins elicit significant increases in $[Ca^{2+}]_i$ in several distinct cell types, including L6 skeletal myocytes, A7r5 vascular smooth muscle cells, and 3T3-L1 adipocytes. This effect on $[Ca^{2+}]_i$ was manifested as a gradual, sustained increase rather than a rapid transient and is in part dependent on $Ca^{2+}$ channel-mediated $Ca^{2+}$ influx, consistent with the report of increased skeletal muscle $Ca^{2+}$ influx in $A^{vy}$ mice (Zemel et al., 1995).

This is also consistent with other $Ca^{2+}$ agonists that inhibit insulin signaling. For example, Kelly et al. (1989) reported that treatment of adipocytes with agonists which either produced sustained increases in $[Ca^{2+}]_i$ or biphasic responses with a sustained component, such as norepinephrine or KCl, resulted in significant inhibition of insulin-stimulated glucose transport. In contrast, oxytocin in concentrations sufficient to cause three- to fivefold increases in $[Ca^{2+}]_i$ that were transient rather than sustained, similar to those found with NDP-α-MSH, were without effect on insulin action. Moreover, an additional common feature of those agonists that were able to inhibit insulin signaling was that they promoted $Ca^{2+}$ influx, and there was a high degree of correlation (r=0.92) between the sustained $[Ca^{2+}]_i$ response to these agonists and the degree of inhibition of insulin action. It was suggested that this correlation was related to $Ca^{2+}$ channel opening rather than to the actual increase in $[Ca^{2+}]_i$, since ionomycin, which also failed to inhibit insulin signaling, caused a sustained elevation in $[Ca^{2+}]_i$ that was derived from intracellular stores (Kelly et al., 1989). Accordingly, net elevations in $[Ca^{2+}]_i$ secondary to sustained agouti exposure may maintain a chronic excess in $Ca^{2+}$ channel-mediated $Ca^{2+}$ influx and thereby induce insulin resistance in $A^{vy}$ mice.

Agouti-induced increases in $[Ca^{2+}]_i$ in multiple cell types may result in tissue-specific consequences. For example, because increased $[Ca^{2+}]_i$ results in diminished insulin signaling (Draznin, 1993; Zemel, 1995), agouti-mediated elevations in skeletal muscle $[Ca^{2+}]_i$ are predicted to result in insulin resistance, as discussed above. In vascular smooth muscle cells, $Ca^{2+}$ plays a central role in both regulation of contraction and proliferation (Zemel, 1995). Consequently, agouti-induced increases in vascular smooth muscle $[Ca^{2+}]_i$ (as typified by A7r5 cells) may contribute to the hypertension that is characteristic of obese, insulin-resistant states. Indeed, the data indicate that vascular rings isolated from $A^{vy}$ mice exhibit exaggerated contractile responses to pressor agonists.

In addition to contributing to insulin resistance, increased $[Ca^{2+}]_i$ in adipocytes appears to stimulate lipogenesis. Incubation of 3T3-L1 adipocytes in an agouti-containing medium upregulates fatty acid synthase expression and activity (Jones et al., 1996). Moreover, these effects were reversed by $Ca^{2+}$ channel blockade with nitrendipine and could be replicated by depolarization with 50 mM KCl (Zemel et al., 1995). Thus agouti-induced increases in $[Ca^{2+}]_i$ appear to stimulate de novo lipogenesis and may thereby contribute to the obesity of $A^{vy}$ mice. This phenomenon maybe relevant to-human obesity as well, since the inventors have also found human agouti protein to stimulate an increase in $[Ca^{2+}]_i$ in isolated human adipocytes.

Although agouti regulation of $[Ca^{2+}]_i$ appears to be primarily via $Ca^{2+}$ channels, the mechanism of this $Ca^{2+}$ regulation is unknown. However, agouti has recently been demonstrated to have significant spatial cysteine homology to ω-conotoxins and plectoxins (Manne et al., 1995; Miller et al., 1993), both of which have high affinity for neuronal $Ca^{2+}$ channels. The action of ω-conotoxin GVIA, one of the ω-conotoxins from the venom of the marine snail *Conus geographus*, appears to be through direct interaction of the toxin with a receptor closely linked to an N-type $Ca^{2+}$ channel, without a second messenger, followed by a very slow dissociation (McCleskey et al., 1987). Plectoxins, contained in venom produced by the spider *Plectreurys tristis*, inhibit N-type $Ca^{2+}$ channels as well as unclassified $Ca^{2+}$ channels, although the underlying mechanisms are unclear (Lundy and Frew, 1993). The structural similarity of agouti protein with these two toxins suggests that agouti may act through a specific $Ca^{2+}$ channel subtype or a presently undefined $Ca^{2+}$ channel. Consistent with this, agouti-induced increases in $[Ca^{2+}]_i$ are abolished in the absence of extracellular $Ca^{2+}$ (Zemel et al., 1995) and have also demonstrated inhibition by nitrendipine.

Agouti regulation of $[Ca^{2+}]_i$ may also depend on an interaction with melanocortin receptors in HEK-293 cells. Several studies have demonstrated that melanocortin action is linked to $Ca^{2+}$ as well as cAMP signaling (Izawa et al., 1994; Konda et al., 1994). For example, adrenocorticotropic hormone (ACTH) binding to its receptor in adipocytes stimulates both adenylate cyclase and increased $[Ca^{2+}]_i$, and both are required for ACTH-induced lipolysis (Izawa et al., 1994). Moreover, (ω-conotoxin inhibits $Ca^{2+}$ channels and thereby inhibits ACTH action in several of its target tissues, including adrenal glomerulosa cells (Tremblay et al., 1991), lymphocytes (Clarke et al., 1994), and neuronal cells (Guarini et al., 1993). Consistent with this, all melanocortin receptor-transfected cells in the present study exhibited NDP-α-MSH-stimulated increases in $[Ca^{2+}]_i$, and these cells also respond to α-MSH with an increase in cAMP (Lu et al., 1994). However, coadministration of agouti failed to inhibit the independent effects of NDP-α-MSH on $[Ca^{2+}]_i$ in HEK-293 cells transfected with melanocortin receptors, similar to the previous report in which agouti did not antagonize cAMP Production in hMC3R- or hMC5R-transfected cells (Lu et al., 1994). Accordingly MC3R and MC5R do not appear to be direct targets for agouti antagonism with respect to $[Ca^{2+}]_i$ signaling. In contrast, nontransfected HEK-293 cells failed to respond to agouti, whereas HEK-293 cells transfected with either hMC1R or hMC3R exhibited significant $[Ca^{2+}]_i$ responses.

These data indicate that agouti regulation of $[Ca^{2+}]_i$ in HEK-293 cells is dependent on an interaction with receptors, although this interaction is clearly different from agouti regulation of coat color, which is dependent on a competitive antagonism with α-MSH (Lu et al., 1994). The only melanocortin receptor thus far reported to be expressed in muscle cells is MC5R (Labbe et al., 1994). Consistent with this, NDP-α-MSH failed to elicit an $[Ca^{2+}]_i$ response in either type of muscle cell (L6 or A7r5) examined. However, in the HEK-293 cells, the presence of MC5R was not sufficient to permit agouti regulation of $[Ca^{2+}]_i$, whereas MC1R and MC3R were sufficient.

Example 24
Sequence of Murine Agouti Gene and Polypeptide

TTCAAGGACAGGAAAGACATTCTGGCCTGGCTTCCCTTAGGGGAGCTGATGCGGAATAGAGTCAC (SEQ ID NO:1)

TTGTGCTGCTTCTCAGGATGGATGTCACCCGCCTACTCCTGGCCACCCTAGTGAGCTTCCTGTGC

TTCTTCACCGTCCACAGCCACCTGGCACTCGAGGAGACGCTTGGAGATGACAGGAGTCTGCGGAG

TAACTCCTCCATGAACTCGCTGGATTTCTCCTCTGTTTCTATCGTGGCACTGAACAAGAAATCCA

AGAAGATCAGCAGAAAAGAAGCCGAGAAGCGGAAGAGGTCTTCCAAGAAAAAGGCTTCGATGAAG

AAGGTGGCAAGGCCCCCGCCACCTTCGCCCTGCGTGGCCACCCGCGACAGCTGCAAGCCACCCGC

ACCCGCCTGCTGCGACCCGTGCGCCTCCTGCCAGTGCCGTTTCTTCGGCAGCGCCTGCACCTGTC

GAGTACTCAACCCCAACTGCTGACGCAGCTTCTTCGCTGCGCGCGCAGCTTCGGGAACGGGTGAT

TGGGCGGGGCTTCAGGGTCCCGCGCTTCTAGGCTGAGGGCGGGTCTCTGTGGGTGGGGCTTGTG

GGTGGGCGTGGTCAGTGGTTGTGACTTGTGGGCGCTTTCAAAAAACCGGTTTTCTAGGAAACCTA

GTGGAAGCTAAAATCAGAATACAATAATATTTTTAGGCTGCC

MDVTRLLLATLVSFLCFFTVHSHLALEETLGDDRSLRSNSSMNSLDFSSVSIVALN (SEQ ID NO:2)

KKSKKISRKEAEKRKRSSKKKASMKKVARPPPPSPCVATRDSCKPPAPACCDPCAS

CQCRFFGSACTCRVLNPNC

Example 25
Sequence of Human Agouti Gene and Polypeptide

1 GCAGAAGGAGGCTTCGATGAAGAAAGTGGTGCGGCCCCGGACCCCCCTATCTGCGCCCTG (SEQ ID NO:3)

61 CGTGGCCACCCGCAACAGCTGCAAGCCGCCGGCACCCGCCTGCTGCGACCCGTGCGCCTC

121 CTGCCAGTGCCGCTTCTTCCGCAGCGCCTGCTCCTGCCGCGTGCTCAGCCTCAACTGCTG

181 AGCGCCCCCACTCCCGGCCGCGAGCAGGCAGGGCTTCGGGGACGCGGGGCGCTTCTCGGG

241 CGGGTGATCCCTAACAGGGCGGCTTCCCAGGGCTGCAGGCGGGCGGAGGTTCCAGGAGAT

301 GGGACTTCAGGGAGACCTGGCTTGGGCTAAAATCGAAATACAATATATATAGGCTGCTCG

361 AAGGTGTGCGGCTGTTTCTGTAAAGGTCCCGAAAG

MDVTRLLLATLLVFLCFFTANSHLPPEEKLRDDRSLRSNSSVNLLDVPSVSIVALNKKSK (SEQ ID NO:4)

QIGRKAAEKKRSSKKEASMKKVVRPRTPLSAPCVATRNSCKPPAPACCDPCASCQCRFFR

SACSCRVLSLNC

References

The following references, to the extent that they provide exemplary procedural or other details supplementary to those set forth herein, are specifically incorporated herein by reference.

U.S. Pat. No. 3,791,932, issued February 1974.
U.S. Pat. No. 3,949,064, issued Apr. 6, 1976.
U.S. Pat. No. 4,174,384, issued Nov. 13, 1979.
U.S. Pat. No. 4,196,265, issued Apr. 1, 1980.
U.S. Pat. No. 4,237,224, issued Dec. 2, 1980.
U.S. Pat. No. 4,271,147, issued Jun. 2, 1981.
U.S. Pat. No. 4,329,332, issued May 11, 1982.
U.S. Pat. No. 4,358,535, issued Nov. 9, 1982.
U.S. Pat. No. 4,489,055, issued Dec. 18, 1984.
U.S. Pat. No. 4,514,498, issued Apr. 30, 1985.
U.S. Pat. No. 4,554,101, issued Nov. 19, 1985.
U.S. Pat. No. 4,578,770, issued Mar. 25, 1986.
U.S. Pat. No. 4,596,792, issued Jun. 24, 1986.
U.S. Pat. No. 4,599,230, issued Jul. 8, 1986.
U.S. Pat. No. 4,599,231, issued Jul. 8, 1986.
U.S. Pat. No. 4,601,903, issued Jul. 22, 1986.
U.S. Pat. No. 4,608,251, issued Aug. 26, 1986.
U.S. Pat. No. 4,683,195, issued Jul. 28, 1987.
U.S. Pat. No. 4,683,202, issued Jul. 28, 1987.
U.S. Pat. No. 4,740,467, issued Apr. 26, 1988.
U.S. Pat. No. 4,795,804, issued Jan. 3, 1989.
U.S. Pat. No. 4,800,159, issued Jan. 24, 1989.
U.S. Pat. No. 4,870,009, issued Sep. 26, 1989.
U.S. Pat. No. 4,873,191, issued Oct. 10, 1989.
U.S. Pat. No. 4,877,864, issued Oct. 31, 1989.
U.S. Pat. No. 4,883,750, issued Nov. 28, 1989.
U.S. Pat. No. 4,913,908, issued Apr. 3, 1990.
U.S. Pat. No. 4,935,496, issued Jun. 19, 1990.
U.S. Pat. No. 4,965,188, issued Oct. 23, 1990.

U.S. Pat. No. 4,968,590, issued Nov. 6, 1990.
U.S. Pat. No. 5,011,691, issued Apr. 30, 1991.
U.S. Pat. No. 5,013,649, issued May 7, 1991.
U.S. Pat. No. 5,106,748, issued Apr. 21, 1992.
U.S. Pat. No. 5,108,753, issued Apr. 28, 1992.
U.S. Pat. No. 5,108,922, issued Apr. 28, 1992.
U.S. Pat. No. 5,116,738, issued May 26, 1992.
U.S. Pat. No. 5,141,905, issued Aug. 25, 1992.
U.S. Pat. No. 5,166,058, issued Nov. 24, 1992.
U.S. Pat. No. 5,168,050, issued Dec. 1, 1992.
U.S. Pat. No. 5,174,986, issued Dec. 29, 1992.
U.S. Pat. No. 5,175,383, issued Dec. 29, 1992.
U.S. Pat. No. 5,175,384, issued Dec. 29, 1992.
U.S. Pat. No. 5,175,385, issued Dec. 29, 1992.
U.S. Pat. No. 5,176,995, issued Jan. 5, 1993.
U.S. Pat. No. 5,187,076, issued Feb. 16, 1993.
U.S. Pat. No. 5,279,721, issued Jan. 18, 1994.
U.S. Pat. No. 5,334,711, issued Aug. 2, 1994.
U.S. Pat. No. 5,354,855, issued Oct. 11, 1994.
U.S. Pat. No. 5,451,410, issued Sep. 19, 1995.
U.S. Pat. No. 5,500,224, issued Mar. 19, 1996.
U.S. Pat. No. 5,556,617, issued Sep. 17, 1996.
U.S. Pat. No. 5,620,708, issued Apr. 15, 1997.
U.S. Pat. No. 5,631,359, issued May 20, 1997.
U.S. Pat. No. 5,641,515, issued Jun. 24, 1997.
U.S. Pat. No. 5,698,515, issued Dec. 16, 1997.
Eur. Pat. Appl. Publ. No. EP 171,496.
Eur. Pat. Appl. Publ. No. EP 173,494.
Eur. Pat. Appl. Publ. No. EP 184,187.
Eur. Pat. Appl. Publ. No. EP 320,308.
Eur. Pat. Appl. Publ. No. EP 329,822.
Eur. Pat. Appl. Publ. No. EP 92110298.4.
Intl. Pat. Appl. Publ. No. WO 84/03564.
Intl. Pat. Appl. Publ. No. WO 86/01533.
Intl. Pat. Appl. Publ. No. WO 87/00880.
Intl. Pat. Appl. Publ. No. WO 88/10315.
Intl. Pat. Appl. Publ. No. WO 89/06700.
Intl. Pat. Appl. Publ. No. WO 90/14424.
Intl. Pat. Appl. Publ. No. WO 90/1443.
Intl. Pat. Appl. Publ. No. WO 91/03162.
Intl. Pat. Appl. Publ. No. WO 92/07065.
Intl. Pat. Appl. Publ. No. WO 93/23569.
Intl. Pat. Appl. Publ. No. WO 93/15187.
Intl. Pat. Appl. Publ. No. WO 93/23569.
Intl. Pat. Appl. Publ. No. WO 94/02595.
Intl. Pat. Appl. Publ. No. WO 94/13688.
Intl. Pat. Appl. Publ. No. WO 94/13688.
Intl. Pat. Appl. Publ. No. WO 94/02595.
Intl. Pat. Appl. Publ. No. WO 96/05309.
Intl. Pat. Appl. Publ. No. WO 97/00319.
Intl. Pat. Appl. Publ. No. WO 97/11192.
Intl. Pat. Appl. Publ. No. WO 97/26335.
Intl. Pat. Appl. Publ. No. WO 97/40280.
Intl. Pat. Appl. Publ. No. GB 2,202,328.
Intl. Pat. Appl. Publ. No. PCT/US89/01025.
Abel and Zemel, *Am. J. Hypertens.*, 6:500–504, 1993.
Adelman et al., *DNA*, 2/3:183–193, 1983.
Ahmad, Finkelstein, Downs, Frohman, "Obesity-associated decrease in growth hormone-releasing hormone gene expression: a mechanism for reduced growth hormone mRNA levels in genetically obese Zucker rats," *Neuroendocrinol.*, 58:332–337, 1993.
Ahmad, Steggles, Carrillo, Finkelstein, "Obesity-and sex-related alterations in growth hormone messenger RNA levels," *Mol. Cell. Endocrinol.*, 65:103–109, 1989.
Algate and McCubrey, "Autocrine transformation of hemopoietic cells resulting from cytokine message stabilization aker intracisternal A particle transposition," *Oncogene*, 8:1221–1232, 1993.
Allen and Choun, "Large unilamellar liposomes with low uptake into the reticuloendothelial system," *FEBS Lett.*, 223:42–46, 1987.
Altschul, Gish, Miller, Myers, Lipman, "Basic local alignment search tool," *J. Mol. Biol.*, 215:403–410, 1990.
Anceschi et al., *J. Virol. Methods*, 28:59–66, 1990.
Ansari-Lari, Jones, Timms, Gibbs, "Improved ligation-anchored PCR™ strategy for identification of 5' ends of transcripts," *Biotechniques*, 21:34–38, 1996.
Argeson, Nelson, Siracusa, "Molecular basis of the pleiotropic phenotype of mice carrying the hypervariable yellow ($A^{hvy}$) mutation at the agouti locus," *Genetics*, 142:557–567, 1996.
Ausubel et al., "Current Protocols in Molecular Biology," John Wiley & Sons, New York, 1997.
Ausubel, Brent, Kingston, Moore, Seidman, Smith, Struhl, In: *Current Protocols Molecular Biology*, Wiley, NY, 1988.
Aviv and Leder, "Purification of biologically active globin messenger RNA by chromatography on oligothymidylic acid-cellulose," *Proc. Natl. Acad. Sci.*, 69:1408–1412, 1972.
Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.
Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.
Balling, Mutter, Gruss, Kessel, *Cell*, 58:337–347, 1989.
Barcellini-Couget, Vassaux, Negrel, Ailhaud, "Rise in cytosolic $Ca^{2+}$ abolishes in preadipose cells the expression of lipoprotein lipase stimulated by growth hormone," *Biochem. Biophys. Res. Commun.*, 199:136–143, 1994.
Barsh and Epstein, "Physical and genetic characterization of a 75-kilobase deletion associated with a/, a recessive lethal allele at the mouse agouti locus," *Genetics*, 121:811–818, 1989a.
Barsh and Epstein, "The long-range restriction map surrounding the mouse agouti locus reveals a disparity between physical and genetic distances," *Genomics*, 5:9–18, 1989b.
Bates and Swift, *Gene*, 26:137–146, 1983.
Bayer and Wilchek, "The use of the avidin-biotin complex as a tool for molecular biology," In: *Methods of Biochemical Anaylsis*, Glick, D., John Wiley and Sons, New York, 1980.
Beam, Knudson, *J. Gen. Physiol.*, 91:781–798, 1988.
Beer, Jakubowicz, Beer, Arocha, Nestler, "Disparate effects of insulin reduction with diltiasem on serum dehydroeiandrosterone sulfate levels in obese hypertensive men and women," *J. Clin. Endocrinol. Metab.*, 79:1077–1081, 1994.
Beer, Jakubowicz, Beer, Arocha, Nestlet, "Effects of nitrendipine on glucose tolerance and serum insulin and dehydroepiandrosterone sulfate levels in insulin-resistant obese and hypertensive men," *J. Clin. Endocrinol. Metab.*, 76:178–183, 1993.
Begum, Sussman, Draznin, "Calcium-induced inhibition of phophoserine phosphatmse in insulin target cells is mediated by the phosphorylation and activation of inhibitor 1," *J. Biol. Chem.*, 267:5959–5963, 1992.
Begum, Sussman, Draznin, "High levels of cytosolic free calcium inhibit dephosphorylation of insulin receptor and glycogen synthase," *Cell Calcium*, 12:423–430, 1991.

Benvenisty and Neshif, "Direction introduction of genes into rats and expression of the genes," Proc. Nat. Acad. Sci. USA, 83:9551–9555, 1986.

Biedler et al., J. Immunol., 141:4053, 1988.

Blake and Clarke, "Suppression of rat hepatic fatty acid synthase and S14 gene transcription by dietary polyunsaturated fat," J. Nutr., 120:1727–1729, 1990.

Blanchard, Harris, Ittoop, Nichols, Parks, Truesdale, Wilkison, Biochem., 34:10406–10411, 1995.

Blatt, Abetdam, Schwartz, Sachs, "DNA rearrangement of a homeobox gene in myeloid leukaemic cells," EMBO J., 7:4283–4290, 1988.

Bolivar et al., Gene, 2:95, 1977.

Bollag, Roth, Beaudoir, Mochly-Rosen, Koshland, Jr., "Protein kinase C directly phosphorylates the insulin receptor in vitro and reduces its protein kinase activity," Proc. Natl. Acad. Sci. USA, 83:5822–5824, 1987.

Bonadonna and Defronzo, In: Obesity, (Björntorp and Brodoff, eds., Lippincott, Philadelphia, pp. 474–502, 1992.

Boston and Cone, "Characterization of melanocortin receptor subtype expression in murine adipose tissues and in the 3T3-L1 cell line," Endocrinol., 137:2043–2050, 1996.

Bradford, "A rapid and sensitive method for the quantitation of microgram quantities of protein utilizing the principle of protein-dye binding," Anal. Biochem., 72:248–254, 1976.

Bradley, Teratocarcinomas and Embryonic Stem Cells: A Practical Approach, (ed. Robinson, E. J.) 113–151, IRL, Oxford, 1987.

Bray and York, "Hypothalamic and genetic obesity in experimental animals: an autonomic and endocrine hypothesis," Physiol. Rev., 59:719–809, 1979.

Bray, "Mechanisms for development of genetic, hypothalamic and dietary obesity," In: Pennington Center Nutrition Series (Bray and Ryan, eds), 1st ed., Vol. 5, Molecular and Genetic Aspects of Obesity, Louisiana State University Press, Baton Rouge, La., pp. 3–66, 1996.

Brigle, Westre, Houghton, Goldman, "Insertion of an intracisternal A particle within the 5'-regulatory region of a gene encoding folate-binding protein in L1210 leukemia cells in response to low folate selection," J. Biol. Chem., 267:22351–22355, 1992.

Brinster et al., "Factors affecting the efficiency of introducing foreign DNA into mice by microinjecting eggs," Proc. Natl. Acad. Sci. U.S.A., 82(13):4438–4442, 1985.

Brown, "Southern blotting onto a nylon membrane with an alkaline buffer," In: Current Protocols in Molecular Biology, Boston, John Wiley and Sons, Ausubel et al. Eds., Vol. 1, p. 297, 1993.

Buffey, Edfeeombe MaeNeil, "Calcium plays a complex role in the regulation of melanogenesis in murine B16 melanoma cells, Pigm. Cell Res., 6:385–393, 1993.

Bultman, Klebig, Michaud, Sweet, Davisson, Woychik, "Molecular analysis of reverse mutations from nonagouti (a) to black-and-tan ($a^t$) and white-bellied agouti ($A^w$) reveals alternative forms of agouti transcripts," Genes Dev., 8:481–490, 1994.

Bultman, Michaud, Woychik, "Molecular characterization of the mouse agouti locus," Cell, Bultman, Russell, Gutierrez-Espeleta, Woychik, "Molecular characterization of a region of DNA associated with mutations at the agouti locus in the mouse," Proc. Natl. Acad. Sci. U.S.A., 88:8062–8066, 1991.

Byers and Steiner, Annu. Rev. Med, 43:269–289, 1992.

Byyny, LoVerde, Mitchell, Draznin, "Cytosolic calcium and insulin resistance in elderly patients," Am. J. Hypertension, 5:459–464, 1992.

Cabilly et al., Proc. Natl. Acad. Sci. U.S.A., 84:3439, 1987.

Calarco and Pederson, "Ultrastructural observations of lethal yellow ($A^y/A^y$) mouse embryos," J. Embryol. Exp. Morphol., 35:73–80, 1976.

Calvo, Vila-Jato, Alonso, "Effect of lysozyme on the stability of polyester nanocapsules and nanoparticles: stabilization approaches," Biomaterials, 18(19):1305–1310, 1997.

Calvo, Vila-Jato, Alonso, "Improved ocular bioavailability of indomethacin by novel ocular drug carriers," J. Pharm. Pharmacol., 48(11):1147–1152, 1996.

Campbell et al., Meth. Immunol., W. A. Benjamin, Inc., 1964.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, "High efficiency transformation by direct microinjection of DNA into cultured mammalian cells," Cell 22(2):479–488, 1980.

Carpenter and Mayer, "Physiologic observations on yellow obesity in the mouse," Am. J. Physiol., 193:499–504, 1958.

Carter et al., Biochim. Biophys. Acta, 951(1):130–138, 1988.

Castle and Little, "On a modified Mendelian ratio among yellow mice," Science, 32:868–870, 1910.

Chakrabarty and Leveille, "Acetyl CoA carboxylase and fatty acid synthetase activities in liver and adipose tissue of meal-fed rats," Proc. Soc. Exp. Biol. Med., 131:1051–1054, 1969.

Chang et al., Nature, 375:615, 1978.

Chee et al., Science, 274(5287):610–614, 1996.

Chen and Okayama, "High-efficiency transformation of mammalian cells by plasmid DNA," Mol. Cell. Biol., 7:2745–2752, 1987.

Chen et al., Nucl. Acids Res., 20:4581–9, 1992.

Chen, Charlat, Tartaglia, Woolf, Weng, Ellis, Lakey, Culpepper, Moore, Breitbart, Duyk, Tepper, Morgenstern, Cell, 84:491–495, 1996.

Chhajlani and Wikberg, FEBS Lett., 309:417–420, 1992.

Chhajlani, Muceniece, Wikberg, Biochem. Biophys. Res. Commun., 195:866–873, 1993.

Chou and Fasman, "Conformational Parameters for Amino Acides in Helical, β-Sheet, and Random Coil Regions Calculated from Proteins," Biochemistry, 13(2):211–222, 1974b.

Chou and Fasman, "Empirical Predictions of Protein Conformation," Ann. Rev. Biochem., 47:251–276, 1978b.

Chou and Fasman, "Prediction of β-Turns," Biophys. J., 26:367–384, 1979.

Chou and Fasman, "Prediction of Protein Conformation," Biochemistry, 13(2):222–245, 1974a.

Chou and Fasman, "Prediction of the Secondary Structure of Proteins from Their Amino Acid Sequence," Adv. Enzymol. Relat. Areas Mol. Biol., 47:45–148, 1978a.

Chowrira and Burke, Nucl. Acids Res., 20:2835–2840, 1992.

Christy and Huang, "Functional analysis of the long terminal repeats of intracisternal A-particle genes: Sequences within the U3 region determine both the efficiency and direction of promoter activity," Mol. Cell. Biol., 8:1093–1102, 1988.

Clapham, Cell, 80:259–268, 1992, 1995.

Clapp, "Somatic gene theraphy into hematopoietic cells. Current status and future implications," Clin. Perinatol., 20(1):155–168, 1993.

Clarke, Armstrong, Jump, "Nutritional control of rat liver fatty acid synthase and S14 mRNA abundance," J. Nutr., 120:218–224, 1990.

Clarke, Moore, Blalock, "Adrenocortico-tropic hormone stimulates a transient calcium uptake in rat lymphocytes," Endocrinol., 135:1780–1786, 1994.

Coffin, "Retroviridae and their replication," In: Fields B N, Knipe D M, ed. Virology. New York: Raven Press, pp. 1437–1500, 1990.

Coffman, Kirchhamer, Harrington, Davidson, "SpRunt-1, a new member of the runt domain family of transcription factors, is a positive regulator of the aboral ectoderm-specific CyIIIA gene in sea urchin embryos," Dev. Biol., 174:43–54, 1996.

Coleman and Burkart, "Plasma corticosterone concentrations in diabetic (db) mice," Diabetol., 13:25–26, 1977.

Coleman, In: The Mouse in Biomedical Research (Foster, Small, Fox, eds.), Academic, NY, Vol. 4, pp. 125–132, 1982.

Collar, Tourkine, Belin, Vassalli, Jeanteur, Blanchard, "c-fos gene transcription in murine macrophages is modulated by a calcium-dependent block to elongation in intron 1," Mol. Cell. Biol., 11:2826–2831, 1991.

Collins and Olive, Biochem., 32:2795–2799, 1993.

Conklin and Bourne, Nature, 364:110, 1993

Copeland, Jenkins, Lee, "Association of the lethal yellow ($A^y$) coat color mutation with an ecotropic murine leukemia virus genome," Proc. Natl. Acad. Sci. U.S.A., 80:247–249, 1983.

Couch et al., "Immunization with types 4 and 7 adenovirus by selective infection of the intestinal tract," Am. Rev. Resp. Dis., 88:394–403, 1963.

Coune, "Liposomes as drug delivery system in the treatment of infectious deseases: potential applications and clinical experience," Infection 16(3):141–147, 1988.

Coupar et al., "A general method for the construction of recombinant vaccinia virus expressing multiple foreign genes," Gene, 68:1–10, 1988.

Couvreur et al., "Nanocapsules, a new lysosomotropic carrier," FEBS Lett., 84:323–326, 1977.

Couvreur, "Polyalkyleyanoacrylates as colloidal drug carriers," Crit. Rev. Ther. Drug Carrier Syst., 5:1–20, 1988.

Cowman et al., Proc. Natl. Acad. Sci. U.S.A., 85:9109–9113, 1988.

Cuenot, "Les races pures et leurs combinaisons chez les souris," Arch. Zool. Exp. Gen., 3:123–132, 1905.

Culver et al., "In vivo gene transfer with retroviral vector-producer cells for treatment of experimental brain tumors," Science, 256:1550–1552, 1992.

Curiel, Agarwal, Wagner, Cotten, "Adenovirus enhancement of transferrin-polylysine-mediated gene delivery," Proc. Natl. Acad. Sci. U.S.A., 88(19):8850–8854, 1991.

Curiel, Wagner, Cotten, Birnstiel, Agarwal, Li, Loechel, Hu, "High-efficiency gene transfer mediated by adenovirus coupled to DNA-polylysine complexes," Hum. Gen. Ther., 3(2):147–154, 1992.

Damge, Vonderscher, Marback, Pinget, "Poly(alkyl cyanoacrylate) nanocapsules as a delivery system in the rate for octreotide, a long-acting somatostatin analogue," J. Pharm. Pharmacol., 49(10):949–954, 1997.

de Bergeyck et al., Eur. J. Immunol., 24(9):2203–2212, 1994.

Debois, Hogue, Karsenty, J. Biol. Chem., 269:1183–1190, 1994.

Deringer, "Influence of the lethal yellow ($A^y$) gene on development of reticular neoplasms," J. Nell. Cancer Inst., 45:1205–1210, 1970.

Desarnaud et al., Biochem. J., 299:367–373, 1994.

Desiderio and Campbell, "Liposome-encapsulated cephalotin in the treatment of experimental murine-salmonellosis," J. Reticuloendothel. Soc., 34:279–287, 1983.

Devereux, Haeberli, Smithies, "A comprehensive set of sequence analysis programs for the VAX," Nucl. Acids Res., 12:387–395, 1984.

Dexter and Moore, "In vitro duplication and cure of hematopoietic defects in genetically anaemic mice," Nature, 269:412–414, 1977.

Diamant, Gorin, Shafrir, "Enzyme activities related to fatty-acid synthesis in liver and adipose tissue of rats treated with triiodothyronine," Eur. J. Biochem., 26:553–559, 1972.

Dickerson and Gowen, "Hereditary obesity and efficient food utilization in mice," Science, 105:496–498, 1947.

Dickie and Woolley, "The age factor in weight of yellow mice," J. Hered., 37:365–368, 1946.

Dingwall and Laskey, "Nuclear targeting sequences—a consensus," Trends Biochem. Sci., 16:478–481, 1991.

Draznin, "Cytosolic calcium and insulin resistance," Am. J. Kidney Dis., 21(3):32–38, 1993.

Draznin, Sussman, Eckel, Kao, Yost, Sherman, "Possible role of cytosolic free calcium concentrations in mediating insulin resistance of obesity and hyperinsulinemia," J. Clin. Invest., 82:1848–1852, 1988.

Draznin, Sussman, Kao, Lewis, Sherman, "The existence of an optimal range of cytosolic free calcium for insulin-stimulated glucose transport in rat adipocytes," J. Biol. Chem., 262:14385–14388, 1987.

Dropulic et al., J. Virol., 66:1432–41, 1992.

Drwinga, Toji, Kim, Greene, Mulivor, Genomics, 16:311–314, 1993.

Dubensky et al., "Direct transfection of viral and plasmid DNA into the liver or spleen of mice," Proc. Nat. Acad. Sci. U.S.A., 81:7529–7533, 1984.

Dubuc, Mobley, Mahler, "Elevated glucocorticoids in obese-hyperglycemic mice.," Horm. Metab. Res., 7:102, 1975.

Ducy, Zhang, Geoffroy, Ridall, Karsenty, "Agouti: a transcriptional activator of osteoblast differentiation," Cell, 89:747–754, 1997.

Duhl, Stevens, Vrieling, Saxon, Miller, Epstein, Barsh, "Pleiotropic effects of the mouse lethal yellow ($A^y$) mu-tation explained by deletion of a maternally expressed gene and the simultaneous production of agouti fusion RNAs, " Develop., 120:1695–1708, 1994a.

Duhl, Vrieling, Miller, Wolff, Barsh, "Neomorphic agouti mutations in obese yellow mice," Nat. Genet., 8:59–65, 1994b.

Dunn, Proc. Natl. Acad. Sci. U.S.A., 14:816–819, 1928.

Dupressior and Heidmann, Mol. Cell. Biol., 16(8):4465–4503, 1996.

Dupressior and Heidmann, Oncogene, 14(24):2951–2958, 1997.

Dürkop et al., Cell, 68:421–427, 1992.

Eaton and Green, Genetica, 34:155–161, 1963.

Edmonson and Olson, "Helix-loop-helix proteins as regulators of muscle-specific transcription," J. Biol. Chem., 268:755–758, 1993.

Eglitis and Anderson, "Retroviral vectors for introduction of genes into mammalian cells," Biotechniques 6(7):608–614, 1988.

Eglitis, Kantoff, Kohn, Karson, Moen, Lothrop, Blaese, Anderson, "Retroviral-mediated gene transfer into hemopoietic cells," Avd. Exp. Med. Biol., 241:19–27, 1988.

Eichenlaub, J. Bacteriol., 138(2):559–566, 1979.

Eisenstein, J. Infectious Diseases, 161:595–602, 1990.

Eisenstein, New Engl. J. Med., 322:178–182, 1990.

Elroy-Stein and Moss, Proc. Natl. Acad. Sci. U.S.A., 87:6743–7, 1990.

Enser, "The role of insulin in the regulation of stearic acid desaturase activity in liver and adipose tissue from obese-hyperglycaemic (ob/ob) and lean mice," *Biochem. J.*, 180:551–558, 1979.

Epstein et al., *Cell*, 67:767–774, 1991

Erlebacher et al. "Toward a molecular understanding of skeletal development," *Cell* 80:371–378, 1995.

Fajans, Bell, Bowden, *J. Lab. Clin. Med.*, 119:206–210, 1992.

Fajans, Bell, Bowden, *J. Lab. Clin. Med.*, 119:206–210, 1992.

Faller and Baltimore, "Liposome encapsulation of retrovirus allows efficient super infection of resistant cell lines," *J. Virol.*, 49(1):269–272, 1984.

Falzon and Kuff, "Isolation and characterization of a protein fraction that binds to enhancer core sequences in intracisternal A-particle long terminal repeats," *J. Biol. Chem.*, 264:21915–21922, 1989.

Falzon and Kuff, "Binding of the transcription factor EBP-80 mediates the methylation response of an intracisternal A-particle long terminal repeat promoter," *Mol. Cell. Biol.*, 11:117–125, 1991.

Fan, Boston, Kesterson, Hruby, Cone, "Role of melanocortinergic neurons in feeding and the egouti obesity syndrome," *Nature* (Lond.), 385:165–168, 1997.

Fechheimer et al., "Transfection of mammalian cells with plasmid DNA by scrape loading and sonication loading," *Proc. Natl. Acad. Sci. U.S.A.*, 84:8463–8467, 1987.

Feenstra, Fewell, Lueders, Kuff, "In vitro methylation inhibits the promoter activity of a cloned intracisternal A-particle LTR," *Nucleic Acids Res.*, 14:4343–4352, 1986.

Feinberg and Vogelstein, "Addendum: A technique for radiolabeling DNA restriction endonuclease fragments to high specific activity," *Anal. Biochem.*, 137:266–267, 1984.

Fenton and Chase, "Effect of diet on obesity of yellow mice in inbred lines," *Proc. Soc. Exp. Biol. Med.*, 77:420–422, 1951.

Ferkol et al. *FASEB J.*, 7:1081–1091, 1993.

Fiers et al., *Nature*, 273:113, 1978.

Fodor et al., *Nature*, 364(6437):555–556, 1993.

Forster and Symons, "Self-cleavage of plus and minus RNAs of a virusoid and a structural model for the active sites," *Cell*, 49:211–220, 1987.

Fraley et al., "Entrapment of a bacterial plasmid in phospholipid vesicles: Potential for gene transfer," *Proc. Natl. Acad. Sci. U.S.A.*, 76:3348–3352, 1979.

Frazier et al., *Mol. Endocrinol.*, 4:1264–1276, 1990.

Freifelder et al., "Dialysis of small samples in agarose gels," *Anal. Biochem.*, 123(1):83–85, 1982.

Freifelder et al., "Studies on *Escherichia coli* sex factors. I. Specific labeling of F'Lac DNA," *J. Mol. Biol.*, 32(1):15–23, 1968a.

Freifelder et al., "Studies on *Escherichia coli* sex factors. II. Some physical properties of F'Lac and F DNA," *J. Mol. Biol.*, 32(1):15–23, 1968b.

Freshner, R. I. "Animal Cell Culture: a Practical Approach", Second Edition, Oxford/New York, IRL Press, Oxford University Press, 1992.

Friedman and Leibel, "Tackling a weighty problem," *Cell*, 69:217–220, 1992.

Friedmann, "Progress toward human gene therapy," *Science*, 244:1275–1281, 1989.

Frigeri, Wolff, Robel, "Impairment of glucose tolerance in yellow ($A^{vy}/A$) (BALB/c X VY) F-1 hybrid mice by hyperglycemic peptide(s) from human pituitary glands," *Endocrinol.*, 113:2097–2105, 1983.

Frigeri, Wolff, Teguh, "Differential responses of yellow $A^{vy}/A$ and agouti A/a (BALB/c X VY) F1 hybrid mice to the same diets: glucose tolerance, weight gain, and adipocyte cellularity," *Int. J. Obes.*, 12:305–320, 1988.

Frohman, M. A., In "PCR Protocols: A Guide to Methods and Applications," Academic Press, New York, 1990.

Furukawa, Yamaguchi, Ogawa, Shigesada, Satake, Ito, "A ubiquitous repressor interacting with an F9 cell-specific silencer and its functional suppression by differentiated cell-specific positive factors," *Cell Growth Diff.*, 1:135–147, 1990.

Fynan, Webster, Fuller, Haynes, Santoro, Robinson, "DNA vaccines: protective immunizations by parenteral, mucosal, and gene gun inoculations," *Proc. Natl. Acad Sci. USA* 90(24):11478–11482, 1993.

Gabizon and Papahadjopoulos, "Liposomes formulations with prolonged circulation time in blood and enhanced uptake by tumors," *Proc. Natl. Acad. Sci. USA*, 85:6949–6953, 1988.

Galbraith and Wolff, "Aberrant regulation of the agouti pigment pattern in the viable yellow mouse," *J. Hered.*, 65:137–140, 1974.

Gantz, Miwa, Konda, Shimoto, Tashiro, Watson, DelValle, Yamada, *J. Biol Chem.*, 268:15174–15179, 1993b.

Gantz, Konda, Tashiro, Shimoto, Miwa, Munzert, Watson, DelValle, Yamada, "Molecular cloning of a novel melanocortin receptor," *J. Biol Chem.*, 268:8246–8250, 1993a.

Gantz, Shimoto, Konda, Miwa, Dickinson, Yamada, "Molecular cloning, expression, and characterization of a fifth melanocortin receptor," *Biochem. Biophys. Res. Commun.*, 200:1214–1220, 1994.

Gao and Huang, *Nucl. Acids Res.*, 21:2867–72, 1993.

Gefter et a., *Somat. Cell Genet.*, 3:231–236, 1977.

Geissler et al., *Cell*, 55:185–192, 1988.

Gerber, Seipel, Georgiev, Hofferer, Hug, Rusconi, Schaffner, "Transcriptional activation modulated by homopolymeric glutamine and proline stretches," *Science*, 263:808–811, 1994.

Gergen and Wieschaus, "The localized requirements for a gene affecting segmentation in Drosophila: analysis of larvae mosaic for runt," *Dev. Biol.*, 109:321–335, 1985.

Gerlach et al., "Construction of a plant disease resistance gene from the satellite RNA of tobacco rinspot virus," *Nature* (London), 328:802–805, 1987.

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Ghosh-Choudhury, G., Y. Haj-Ahmad, and F. L. Graham, "Protein IX, a minor component of the human adenovirus capsid, is essential for the packaging of full-length genomes," *EMBO J.*, 6:1733–1739, 1987.

Gill and Yen, "Effects of ciglitazone on endogenous plasma islet amyloid polypeptide and insulin sensitivity in obese-diabetic viable yellow mice," *Life Sci.*, 48:703–710, 1991.

Girard, Perdereau, Foufelle, Prip-Buus, Ferre, "Regulation of lipogenic enzyme gene expression by nutrients and hormones," *FASEB J.*, 8:36–42, 1994.

Goding, "Monoclonal Antibodies: Principles and Practice," pp. 60–74. 2nd Edition, Academic Press, Orlando, Fla, 1986.

Goding, *Monoclonal Antibodies: Principles and Practice*, Academic Press, Inc., New York, N.Y., pp. 56–97, 1983.

Goeddel et al., *Nature*, 281:544, 1979.

Goeddel et al., *Nucl. Acids Res.*, 8:4057, 1980.

Gomez-Foix, A. M., W. S. Coats, S. Baque, T. Alam, R. D. Gerard, and C. B. Newgard, "Adenovirus-mediated transfer of the muscle glycogen phosphorylase gene into hepatocytes confers altered regulation of glycogen," J. Biol. Chem. 267:25129–25134, 1992.

Gopal, "Gene transfer method for transient gene expression, stable transfection, and cotransfection of suspension cell cultures," Mol. Cell Biol., 5:1188–1190, 1985.

Graham and Prevec, "Adenovirus-based expression vectors and recombinant vaccines," Biotechnology, 20:363–390, 1992.

Graham and Prevec, "Adenovirus-based expression vectors and recombinant vaccines," Biotechnology, 20:363–390, 1992.

Graham and Prevec, "Manipulation of adenovirus vector," In: E. J. Murray (ed.), Methods in Molecular Biology: Gene Transfer and Expression Protocol, Clifton, N.J.: Humana Press, 7:109–128, 1991.

Graham and van der Eb, A"Transformation of rat cells by DNA of human adenovirus 5," Virology, 54(2):536–539, 1973.

Graham et al., "Characteristics of a human cell line transformed by DNA from human adenovirus type 5", J. Gen. Virol., 36:59–72, 1977.

Granholm, Jeppesen, Japs, "Progressive infertility in female lethal yellow mice," J. Reprod. Fertil., 76:279–287, 1986.

Graves, Tontonoz, Ross, Spiegelman, Genes Dev., 5:428–437, 1991.

Green, "Catalogue of mutant genes and polymorphic loci," In: Genetic Variants and Strains of the Laboratory Mouse, M. F. Lyon and A. G. Searle, eds., Oxford, Oxford University Press, pp. 17–20, 1989.

Green, Nucl. Acids Res., 16(1):369, 1988.

Griffon, Mignon, Facchinetti, Diaz, Schwartz, Sokoloff, "Molecular cloning of the rat fifth melanocortin receptor," Biochem. Biophys. Res. Commun., 200:1007–1014, 1994.

Grunhaus and Horwitz, "Adenovirus as cloning vector," Seminar in Virology, 3:237–252, 1992.

Grynkiewicz, Poenie, Tsien, "A new generation of $Ca^{2+}$ indicators with greatly improved fluorescent properties," J. Biol. Chem., 260:3440–3450, 1985.

Guarini, Bazzani, Bertolini, "Role of neuronal and vascular $Ca^{2+}$ channels in the ACTH-induced reversal of haemorrhagic shock," Br. J. Pharmacol., 109:645–650, 1993.

Guerrier-Takada et al., Cell, 35:849, 1983.

Guichard, Dugail, Le Liepvre, Lavau, "Genetic regulation of fatty acid synthetase expression in adipose tissue: overtranscription of the gene in genetically obese rats," J. Lipid Res., 33:679–687, 1992.

Gundberg, Hauschka, Lian, Gallop, Methods Enzymol., 107:516–566, 1984.

Hacia et al., Nat. Genet., 14(4):441–447, 1996.

Hacia et al., Nat. Genet., 18(2):155–158, 1998.

Hahn, Vogel, Delling, Virchows Arch A. Pathol. Anat. Histopathol., 418:1–7, 1991.

Halaas, Gajiwala, Maffei, Cohen, Chait, Robinowitz, Lallone, Burley, Friedman," "Weight-reducing effects of the plasma protein encoded by the obese gene," Science, Washington D.C., 269:543–546, 1995.

Hampel and Tritz, Biochem., 28:4929, 1989.

Hampel et al., Nucl. Acids Res., 18:299, 1990.

Harland and Weintraub, "Translation of mammalian mRNA injected into Xenopus oocytes is specifically inhibited by antisense RNA," J. Cell Biol., 101:1094–1099, 1985.

Harlow. and Lane, "Antibodies: A Laboratory Manual," Cold Spring Harbor Laboratory, Cold Spring Harbor, N.Y., 1988.

Heath and Martin, "The development and application of protein-liposome conjugation techniques," Chem. Phys. Lipids 40:347–358, 1986.

Heath et al., "Liposome-mediated delivery of pteridine antifolates to cells: in vitro potency of methotrexate and its alpha and gamma substituents," Biochim. Biophys. Acta, 862:72–80, 1986.

Heldmann and Heldmann, "Retrotransposition of a mouse LAP sequence tagged with an indicator gene," Cell, 64:159–170, 1991.

Hellerström and Hellman, "The islets of Langerhans in yellow obese mice," Metabol., 12:527–536, 1963.

Henry-Michelland et al., "Attachment of antibiotics to nanoparticles; Preparation, drug-release and antimicrobial activity in vitro, Int. J. Pharm., 35:121–127, 1987.

Hermonat and Muzycska, "Use of adenoassociated virus as a mammalian DNA cloning vector: Transduction of neomycin resistance into mammalian tissue culture cells," Proc. Natl. Acad Sci. USA, 81:6466–6470, 1984.

Hersdorffer et al., "Efficient gene transfer in live mice using a unique retroviral packaging line," "DNA Cell Biol, 9:713–723, 1990.

Herz and Gerard, "Adenovirus-mediated transfer of low density lipoprotein receptor gene acutely accelerates cholesterol clearance in normal mice," Proc. Natl. Acad Sci. USA, 90:2812–2816, 1993.

Hess et al., J. Adv. Enzyme Reg., 7:149, 1968.

Heston and Deringer, "Relationship between the lethal yellow ($A^y$) gene of the mouse and susceptibility to spontaneous pulmonary tumors," J. Cancer Inst., 7:463–465, 1947.

Heston and Vlahakis, "Genetic obesity and neoplasia," J. Natl. Cancer Inst., 29:197–209, 1962.

Heston and Vlahakis, "Increase of induced skin tumors in the mouse by the lethal yellow gene ($A^y$)," J. Natl. Cancer Inst., 31:189–195, 1963.

Heston and Vlahakis, "Influence of the $A^y$ gene on mammary-gland tumors, hepatomas, and normal growth in mice," J. Natl. Cancer Inst., 26:969–983, 1961.

Heston, "Relationship between the lethal yellow ($A^y$) gene of the mouse and susceptibility to induced pulmonary tumors," J. Cancer Inst., 3:303–308, 1942.

Hillgartner, Salati, Goodridge, "Physiological and molecular mechanisms involved in nutritional regulation of fatty acid synthesis," Physiol. Rev., 75:47–76, 1995.

Hitzeman et al., J. Biol Chem., 255:2073, 1980.

Hogan, Costantini, Lacy, In: Manipulating the Mouse Embryo: A Laboratory Manual, Cold Spring Harbor Lab. Press, Plainview, N.Y., 1986.

Holland et al., Biochemistry, 17:4900, 1978.

Hollander and Gowen, J. Hered., 47:221–224, 1956.

Hoover et al., Ads.), "Remington's Pharmaceutical Sciences," 15th Edition, Mack Publishing Co., Easton, Pa., 1975.

Hopp, U. S. Pat. No. 4,554,101, Nov., 19, 1985.

Horowitz, Luria, Rechavi, Givol, "Mechanism of activation of the mouse c-mos oncogene by the LTR of an intracisternal A-particle gene," EMBO J., 3:2937–2941, 1984.

Horwich et al, "Synthesis of hepadnavirus particles that contain replication-defective duck hepatitis B virus genomes in cultured HuH7 cells," J. Virol, 64:642–650, 1990.

Hunt and Thody, J. Endocrinol., 147:R1–R4, 1995.

Huse et al., Science, 246:1275–1281, 1989.

Hustad, Perry, Siracusa, Rasberry, Cobb, Cattanach, Kovatch, Copeland, Jenkins, "Molecular genetic characterization of six recessive viable alleles of the mouse agouti locus," Genetics, 140:255–265, 1995.

Huszar, Lynch, Fairchild-Huntress, Dunmore, Fang, Berkemeier, Gu, Kesterson, Boston, Cone, Smith, Campfield, Bum, Lee, "Targeted disruption of the melanocortin-4 receptor results in obesity in mice," *Cell*, 88:131–141, 1997.

Imaizumi et al., "Liposome-entrapped superoxide dismutase reduces cerebral infarction in cerebral ischemia in rats," *Stroke*, 21(9):1312–1317, 1990a.

Itakura et al., *Science*, 198:1056, 1977.

Itakura et al., *Science*, 198:1056, 1977.

Izawa, Mochizuki, Komabayashi, Suda, Tsuboi, "Increase in cytosolic free $Ca^{2}$+ in corticotropin-stimulated white adipocytes. *Am. J. Physiol.*, 266 (*Endocrinol. Metab.* 29):E418–E426, 1994.

Jackson, "Molecular and developmental genetics of mouse coat color," *Annu. Rev. Genet.*, 28:189–217, 1994.

Jackson, "Mouse coat colour mutations: a molecular genetic resource which spans the centuries," *BioEssays*, 13:439446, 1991.

Jackson, *Nature*, 362:587–588, 1993.

Jackson, Stolz, Martin, "Effect of adrenalectomy on weight gain and body composition of yellow obese mice ($A^{y}$a), *Horm. Metab. Res.*, 8: 452–455, 1976.

Jaeger et al., *Proc. Natl. Acad. Sci. USA*, 86: 7706–7710, 1989.

Jameson and Wolf, "The Antigenic Index: A Novel Algorithm for Predicting Antigenic Determinants," *Compu. Appl Biosci.*, 4(1):181–6, 1988.

Jauch et al., *Hum Genet*, 85(2):145–150, 1990.

Johnson and Hirsch, "Cellularity of adipose depots in six stains of genetically obese mice," *J. Lipid Res.*, 13:2–11, 1972.

Johnson and Salomon, *Meth. Enzym.*, 195:3–21, 1991.

Johnson et al., "Peptide Turn Mimetics" in Biotechnology and Pharmacy, Pezzuto et al., eds., Chapman and Hall, New York, 1993.

Jones and Shenk, "Isolation of deletion and substitution mutants of adenovirus type 5," *Cell*, 13:181–188, 1978.

Jones et al., *Nature*, 321:552, 1986.

Jones, Banz, Abel, Zemel, Moustaïd, "Dietary polyunsaturated fatty acids suppress stearoyl-CoA desaturase gene expression in adipose tissue," Abstract, *FASEB J.*, 9:A1331, 1995.

Jones, Brynn, Kim, Zemel, Woychik, Michaud, Wilkison, Moustaid, "Upregulation of adipocyte metabolism by agouti protein: possible paracrine actions in obesity of the yellow mouse," *Am. J. Physiol.*, 270:E190–E192, 1996.

Jones, *Genetics*, 85:12, 1977.

Jones, Kim, Zemel, Woychik, Michaud, Wilkison, Moustaid, "Upregulation of adipocyte metabolism by agouti protein: possible paracrine actions in yellow mouse obesity," *Am. J. Physiol* 270(*Endocrinol Metab*. 33):E192–E196, 1996.

Joyce, "RNA evolution and the origins of life," *Nature*, 338:217–244, 1989.

Kaneda et al., "Increased expression of DNA cointroduced with nuclear protein in adult rat liver," *Science*, 243:375–378, 1989.

Kashani-Sabet et al., *Cancer Res.*, 48:5775–5778, 1988.

Kashani-Saber et al., *Antisense Res. Dev.*, 2:3–15, 1992.

Kato et al., "Expression of hepatitis B virus surface antigen in adult rat liver," *J. Biol. Chem*, 266:3361–3364, 1991.

Kawasaki, "Amplification of RNA," In: *PCR™ protocols: A guide to methods and applications*, Innis et al., eds., pp. 21–27, Academic Press, San Diego, 1990.

Kelly, Deeney, Corkey, "Cytosolic free calcium in adipocytes: distinct mechanisms of regulation and effects on insulin action," *J. Biol Chem.*, 264:12754–12757, 1989.

Kiefer, Ittop, Bunce, Truesdale, Willard, Nichols, Blanchard, Mountjoy, Chen, Wilkison, "Mutations in the carboxyl terminus of the agouti protein decrease agouti inhibition of ligand binding to the melanocortin receptors," *Biochem.*, 36:2084–2090, 1997.

Kim and Zemel, *Hypertension*, 22:74–77, 1993.

Kim, Kiefer, Woychik, Wilkison, Truesdale, Ittoop, Willard, Nichols, Zemel, *American J. Physiol*, 272:E379–E384, 1997.

Kim, Mynatt, Moore, Woychik, Moustaid, Zemel, "The effects of calcium channel blockade on agouti-induced obesity," *FASEB J.*, 10:1646–1652, 1996.

Kingsman et al., *Gene*, 7:141, 1979.

Klebig, Wilkinson, and Woychik, "Molecular analysis of the mouse agouti gene and the role of dominant agouti-locus mutations in obesity and insulin resistance," In: *Molecular and Genetic Aspects of Obesity*, ed. Bray, G., Baton Rouge, Louisiana State Univ. Press, Baton Rouge, La., 1994.

Klebig, Wilkinson, Geisier, Woychik, "Ectopic expression of the agouti gene in transgenic mice causes obesity, features of type II diabetes, and yellow fur," *Proc. Natl. Acad Sci. USA*, 92:4728–4732, 1995.

Klebig, Wilkinson, Woychik, In: *Molecular analysis of the mouse agouti gene and the role of dominant agouti-locus mutations in obesity and isulin resistance*, (Bray and Ryan, eds.), Baton Rouge, Louisiana State University Press, Vol.5, pp 120–160, 1996.

Klein et al., "High-velocity microprojectiles for delivering nucleic acids into living cells," *Nature*, 327:70–73, 1987.

Kleyn, Fan, Kovats, Lee, Pulido, et al., *Cell* 85:281–290, 1996.

Klip and Ramlal, "Cytoplasmic $Ca^{2+}$ during differentiation of 3T3-L1 adipocytes," *J. Biol. Chem.*, 262: 9141–9146, 1987.

Kobori, Strauss, Minard, Hood, "Molecular analysis of the hotspot of recombination in the murine major histocompatibility complex," *Sci.*, 234:173–179, 1986.

Kohler and Milstein, *Eur. J. Immunol*, 6:511–519, 1976.

Kohler and Milstein, *Nature*, 256:495–497, 1975.

Konda, Gantz, J. DelValle, Shimoto, Miwa, Yamadd, "Interaction of dual intracellular signaling pathways activated by the melanocortin-3 receptor," *J. Biol. Chem.*, 269:13162–13166, 1994.

Kongsuwan, Allen, Adams, "Expression of Hox-2.4 homeobox gene directed by proviral insertion m a myeloid leukemia," *Nucleic Acids Res.*, 17:1881–1892, 1989.

Kozak, "An analysis of 5'-noncoding sequences of 699 vertebrate messenger RNAs," *Nucleic Acids Res.*, 15:8125–8148, 1987.

Kozak, "The scanning model for translation: an update," *J. Cell Biol.*, 108:229–241, 1989.

Kuby, "Immunology" 2nd Edition. W. H. Freeman & Company, New York, 1994.

Kucera, Bortner, Rosenberg, "Overexpression of an agouti cDNA in the skin of transgenic mice recapitulates dominant coat color phenotypes of spontaneous mutants," *Dev. Biol.*, 173:162–173, 1996.

Kuff et al., *Chromosoma*, 93(3):213–219, 1986.

Kuff and Lueders, "The intracisternal A-particle gene family: structure and functional aspects," *Adv. Cancer Res.*, 51:183–276, 1988.

Kunkel et al, *Methods Enzymol*, 154:367–382, 1987.

Kuo, Conley, Chen, Sladek, Darnell Jr., Crabtree, "A transcriptional hierarchy involved in mammalian cell-type specification," *Nature*, 355:457–461, 1992.

Kwoh et al., *Proc. Natl. Acad. Sci, USA*, 86(4):1173–1177, 1989.

Kwon, Bultman, Loffler, Chen, Furdon, Powell, Usala, Wilkison, Hansmann, Woychik, "Molecular structure and chromosomal mapping of the human homolog of the agouti gene," *Proc. Natl. Acad Sci. USA,* 91:9760–9764, 1994.

Kyte and Doolite, *J. Mol. Biol,* 157:105–132, 1982.

L'Huillier et al., *EMBO J.,* 11:4411–8, 1992.

Labbe, Desamaud, Eggerickx, Vassart, Parmentier, "Molecular cloning of a mouse melanocortin 5 receptor gene widely expressed in peripheral tissues," *Biochem.,* 33:4543–4549, 1994.

Lakshmanan, Nepokroeff, Porter, "Control of the synthesis of fatty-acid synthetase in rat liver by insulin, glucagon, adenosine 3':5' cyclic monophosphate," *Proc. Natl. Acad Sci. USA,* 69:3516–3519, 1972.

Lamb, Satyamoorthy, Li, Solter, Howe, "CpG methylation of an endogenous retroviral enhancer inhibits transcription factor binding and activity," *Gene Expression,* 1:185–196, 1991.

Lamoreux and Mayer, *Dev. Biol.,* 46:160–166, 1975.

Landschulz, Jump, MacDougald, Lane, "Transcriptional control of the stearoyl-CoA desaturase-1 gene by polyunsaturated fatty acids," *Biochim. Biophys. Res. Commun.,* 200:763–768, 1994.

Larder et al., *Science,* 246:1155–1158, 1989.

Lawrence et al., *Science,* 249:938–932, 1990.

Lawrence Jr., Hiken, James, *J. Biol. Chem.,* 265:2324–2332, 1990.

Le Gal La Salle, G., J. J. Robert, S. Berrard, V. Ridoux, L. D. Stratford-Perricaudet, M. Perricaudet, and J. Mallet. 1993. An adenovirus vector for gene transfer into neurons and glia in the brain. *Science,* 259:988–990, 1993.

Le Gal La Salle, G., J. J. Robert, S. Berrard, V. Ridoux, L. D. Stratford-Perricaudet, M. Perricaudet, and J. Mallet. 1993. An adenovirus vector for gene transfer into neurons and glia in the brain. *Science,* 259:988–990, 1993.

Lebo, Chakravarti, Buetow, Cheung, Cann, Cordell, Goodman, "Recombination within and between the human insulin and β-globin gene loci," *Proc. Natl. Acad Sci. USA,* 80:4808–4812, 1963.

Leiter, Beamer, Coleman, Longcope, *Metabol.,* 36:863–869, 1987.

Lemaitre et al., *Proc. Natl. Acad. Sci. USA,* 84:648–652, 1989.

Levrero, M., V. Barban, S. Manteca, A. Ballay, C. Balsamo, M. L. Avantaggiati, G. Natoli, H. Skellekens, P. Tiollais, and M. Perricaudet, "Defective and nondefective adenovirus vectors for expressing foreign genes in vitro and in vivo," *Gene* 101:195–202, 1991.

Levy, Zemel, Sowers, *Am. J. Med,* 87(Suppl. 6A):75–165, 1989.

Lian et al., *Proc. Nat'l 7Acad. Sci. USA,* 86:1143–1147, 1989.

Lichter et al., *Proc. Natl. Acad. Sci. USA,* 87(17):6634–6638, 1990a.

Lichter, Cremer, Borden, Maneulidis, Ward, *Hum. Genet.,* 80:224–234, 1988.

Lichter, Tang, Call, Hermanson, Evans, Housman, Ward, *Science,* 247(4938):64–69, 1990b.

Liddell and Cryer, "A Practical Guide to: Monoclonal Antibodies," John Wiley & Sons, New York, 1991.

Lieber et al., *Methods EnzymoL,* 217:47–66, 1993.

Lifson et al., *J. Infect. Dis.,* 161 :436–439, 1990.

Lipshutz et al., *Biotechniques,* 19(3):442–447, 1995.

Lisziewicz et al., *Proc. Natl. Acad. Sci U.S.A.,* 90:8000–4, 1993.

Little, In: *The Inheritance of Coat Colors in Dogs,* Macmillian, N.Y., 1957.

Löffler, Rao, Schnittger, Pastuszak, Schuber, Hansmann, *Am. J. Hum. Genet.,* 53:S1324, 1993.

Lopez-Berestein et al., "Liposomal amphotericin B for the treatment of systemic fungal infections in patients with cancer: a preliminary study" *J. InfecL Dis.,* 2151:704, 1985a.

Lowry, Rosebrough, Farr, Randall, "Protein measurement with the Folin phenol reagent," *J. Biol. Chem.,* 193:265–275, 1951.

Lu, Rothnagel, Longley, Tsai, Roop, "Differentiation-specific expression of human keratin 1 is mediated by a composite AP-1/steroid hormone element," *J. Biol. Chem,* 269:7443–7449, 1994b.

Lu, Willard, Patel, Kadwell, Overton, Kost, Luther, Chen, Woychik, Wilkison, "Agouti protein is an antagonist of the melanocyte-stimulating-hormone receptor," *Nature* (Lond.), 371:799–802, 1994.

Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med,* 178(6):2089–2096, 1993.

Lueders and Kuff, "Intracisternal A-particle genes: Identification in the genome of *Mus musculus* and comparison of multiple isolates from a mouse gene library," *Proc. Natl. Acad. Sci.* 77:3571–3575, 1980.

Lundy and Frew, "Evidence of mammalian $Ca^{2+}$ channel inhibitors in venom of the spider *Plectreurys tristis,*" *Toxicon.,* 31:1249–1256, 1993.

Maas, et al., *Nature,* 346:853–855, 1990.

Macejak and Sarnow, *Nature,* 353(6339):90–94, 1991.

Macejak and Sarnow, *J. Virol.,* 66(3):1520–1527, 1992.

Malaisse and Sener, "Calcium antagonists and islet function. XII. Comparison between nifedipine and chemically related drugs," *Biochem. Pharmacol,* 30:1039–1041, 1981.

Malaisse, "Insulin secretion: multifactorial regulation for a single process of release," *Diabetologia,* 9:167–173, 1973.

Maloy et al., "Microbial Genetics" 2nd Edition. Jones and Barlett Publishers, Boston, Mass., 1994.

Maloy, "Experimental Techniques in Bacterial Genetics" Jones and Bartlett Publishers, Boston, Mass., 1990.

Maniatis et al., "Molecular Cloning: a Laboratory Manual," Cold Spring Harbor Laboratory, Cold Spring Harbor, N.Y., 1982.

Manipulating the Mouse Embryo: A Laboratory Manual," 2nd edition (eds., Hogan, Beddington, Costantimi and Long, Cold Spring Harbor Laboratory Press, 1994.

Mann et al., "Construction of a retrovirus packaging mutant and its use to produce helper-free defective retrovirus," *Cell,* 33:153–159, 1983.

Manne, Argeson, Siracusa, "Mechanisms for the pleitropic effects of the agouti gene," *Proc. Natl. Acad Sci. USA,* 92:4721–4724,1995.

Markowitz et al., "A safe packaging line for gene transfer: Separating viral genes on two different plasmids," *J. Virol.,* 62:1120–1124, 1988.

Mayer and Fishbane, "Mesoderm-ectoderm interaction in the production of the agouti pigmentation pattern in mice," *Genetics,* 71:297–303, 1972.

Mayer and Green, "An experimental analysis of the pigment defect caused by mutations at the W and SI loci in mice," *Dev. Bid.,* 18:62–75, 1989.

McBurney, Sutherland, Adra, Leclair, Rudnicki, Jardine, *Nucl. Acids Res.,* 19:5755–5761, 1991.

McCleskey, Fos, Foldman, Cruz, Olivera, Tsien, Yoshikami, ." ω-Conotoxin: direct and persistent blockade of specific types of calcium channels in neurons but not muscle," *Proc. Natl. Acad Sci. USA,* 84:4327–4331, 1987.

McCulloch, Siminovitch, Till, Russell, Berstein, "The cellular basis of the genetically determined hemopoietic defect in anemic mice of genotype SI/SI$^d$," *Blood,* 26:399–410, 1965.

McMahon and Bradley, *Cell,* 62:1073–1085, 1990.

Mercer et al., *Nature,* 349:709–713, 1991.

Meyuhas, Thompson, Jr., Perry, "Glucocorticoids selectively inhibit translation of ribosomal protein mRNAs in P1798 lymphosarcoma cells," *Mol. Cell. Biol.,* 7:2691–2699, 1987.

Michael, *Biotechniques,* 16:410–412, 1994.

Michaud et al., *Genes Dev.,* 8:1463–1472, 1994c.

Michaud, Bultman, Klebig, van Vugt, Stubbs, Russell, Woychik, "A molecular model for the genetic and phenotypic characteristics of the mouse lethal yellow (A$^y$) mutation," *Proc. Natl. Acad Sci. USA,*91: 2562–2566, 1994a.

Michaud, Bultman, Stubbs, Woychik, "The embryonic lethality of homozygous lethal yellow mice (A$^Y$/A$^Y$) is associated with the disruption of a novel RNA-binding protein," *Genes Dev.,* 7:1203–1213, 1993.

Michaud, van Vugt, Bultman, Sweot, Davisson, Woychik, "Differential expression of a new dominant agouti allele (A$^{iapy}$) is correlated with methylation state and is influenced by parental lineage," *Genes Dev.,* 8:1463–1472, 1994b.

Michel and Westhof, "Modeling of the three-dimensional architecture of group I catalytic introns based on comparative sequence analysis," *J. Mol. Biol.,* 216:585–610, 1990.

Millar, Miller, Stevens, Barsh, "Expression and transgenic studies of the mouse agouti gene provide insight into the mechanisms by which mammalian coat color patterns are generated," *Develop.,* 121:3223–3232, 1995.

Miller, Duhl, Vrieling, Cordes, Ollmann, Winkes, Barsh, "Cloning of the mouse agouti gene predicts a secreted protein ubiquitously expressed in mice carrying the lethal yellow mutation," *Genes Dev.,* 7:454–467, 1993.

Moller, In: *Insulin Resistance, Wiley, New York,* 1993.

Morgan and Huang, "Correlation of under-methylation of intracisternal A-particle genes with expression in murine plasmacytomas but not in NIH/3T3 embryo fibroblasts," *Cancer Res.,* 44:5234–5241, 1984.

Mori and Fukatsu, "Anticonvulsant effect of DN-1417 a derivative of thyrotropin-releasing hormone and liposome-entrapped DN-1417 on amygdaloid-kindled rats," *Epilepsia,* 33(6):994–1000, 1992.

Morrison, *Science,* 229:1202, 1985.

Mount, *Nucl. Acids Res.,* 10:459–472, 1982.

Mountjoy, Mortrud, Low, Simerly, Cone, "Localization of the melanocortin-4 receptor (MC4-R) in neuroendocrine and autonomic control circuits in the brain," *Mol. Endocrinol.,* 8:1298–1308, 1994.

Mountjoy, Robbins, Mortrud, Cone, "The cloning of a family of genes that encode the melanocortin receptors," *Sci. (Washington, D.C.),* 257:543–546. 1992.

Moustaïd and Sui, "Regulation of expression of the fatty acid synthase gene in 3T3-L1 cells by differentiation and triiodothyronine," *J. Biol. Chem.,* 266:18550–18554, 1991.

Moustaïd, Beyer, Sui, "Identification of an insulin response element in the fatty acid synthase promoter," *J. Biol. Chem.,* 269:5629–5634, 1994.

Moustaïd, Hainque, Quignard-Boulange, "Dexamethasone regulation of terminal differentiation in 3T'-F442A preadipocyte cell line," *Cytotechnology,* 1:285–293, 1988.

Musch, Ojakan, Williams, "Comparison of α-linolenate and oleate in lowering activity of lipogenic enzymes in rat liver evidence for a greater effect of dietary," linolenate independent of food and carbohydrate intake," *Biochim, Biophys. Acta,* 337:343–348, 1974.

Mynatt, Miltenberger, Klebig, Zemel, Wilkinson, Wilkison, Woychik, "Combined effects of insulin treatment and adipose tissue-specific agouti expression on the development of obesity," *Proc. Natl. Acad Sci. USA,* 94:919–922, 1997.

Naggert, Fricker, Varlamov, Nishina, Rouille, Steiner, Carroll, Paigen, Leiter, *Nat. Genet.,* 10:135–142, 1995.

Nakamura et al., "Enzyme Immunoassays: Heterogenous and Homogenous Systems," Chapter 27, 1987.

Nestel, Connor, Reardon, Connor, Wong, Boston, "Suppression by diets rich in fish oil of very low density lipoprotein production in man," *J. Clin. Invest.,* 74:82–89, 1984.

Newgard and McGarry, *Annu. Rev. Biochem.,* 64:689–719, 1995.

Nicolas and Rubenstein, "Retroviral vectors," In: Rodriguez R L, Denhardt D T, ed. Vectors: A survey of molecular cloning vectors and their uses. Stoneham: Butterworth, pp. 493–513, 1988.

Nicolau and Gersonde, "Incorporation of inositol hexaphosphate into intact red blood cells, I. fusion of effector-containing lipid vesicles with erythrocytes," *Naturwissenschaften* (Germany) 66(11):563–566, 1979.

Nicolau and Sene, "Liposome-mediated DNA transfer in eukaryotic cells," *Biochim. Biophys. Acta,* 721:185–190, 1982.

Nicolau et al., "Liposomes as carriers for in vivo gene transfer and expression," *Methods Enzymol.,* 149:157–176, 1987.

Nigg, "Nucleocytoplasmic transport: signals, mechanisms and regulation," *Nature,* 386:779–787, 1997.

Nishimura et al., *Canc. Res.,* 47:999, 1987.

Noben-Trauth, Naggert, North, Nishina, *Nature* (London), 380:534–538, 1996.

Ntambi, "Dietary regulation of stearoyl-CoA desaturase I gene expression in mouse liver," *J. Biol. Chem.,* 267:10925–10930, 1992.

Odin, Adikns-Finke, Blake, Phinney, Clarke, "Membrane phospholipid enrichment of cultured rat hepatocytes with omega-3 and -6 fatty acids is associated with decreased triglyceride production and secretion," *Biochim, Biophys. Acta,* 921:378–391, 1987.

Oellerich, *J. Clin. Chem. Biochem.,* 22: 895–904, 1984.

Oelofsen and Ramachandrand, *Arch. Biochem. Biophys.,* 225:414–421, 1983.

Ohara et al., *Proc. Natl. Acad. Sci USA,* 86(15):5673–5677, 1989.

Ohkawa et al., *Nucl. Acids Symp. Ser.,* 27:15–6, 1992.

Oi et al., *BioTechniques,* 4:214, 1986.

Ojwang et al., *Proc. Natl. Acad Sci. USA,* 89:10802–6, 1992.

Oldberg, Franzen, Heinegrad, *Proc. Natl. Acad Sci., USA,* 83:8819–8823, 1986.

Olivera, Miljanich, Ramachandran, Adams, "Calcium channel diversity and neurotransmitter release," *Annu. Rev. Biochem.,* 63:823–867, 1994.

Ono, Cole, White, Huang, "Sequence organization of cloned intracisternal A particle genes," *Cell,* 21:465–473, 1980.

Orkins, "Transcription factors and hematopoietic development," *J. Biol. Chem.,* 270:4955–4958, 1995.

Overbeek, Aguilar-Cordova, Hanteen, Schaffner, Patel, Lebovitz, Lieberman, *Transgenic Res.,* 1:31–37, 1991.

Palaparti, Baratz, Stifani, "The Groucho/Transducin-like Enhancer of split transcriptional repressors interact with the genetically defined amino-terminal silencing domain of Histone H3," *J. Biol. Chem.,* 272:26604–26610, 1997.

Papaioannou and Gardner, *J. Embryol. Exp. Morphol.,* 52:153–163, 1979.

Parfitt, Drezner, Glorieux, Kanis, Malluche, Meunier, Ott, Recker, *J. Bone Mineral Res.,* 2:595–610, 1987.

Parfitt, Mathews, Villanueva, Kleerekoper, M., Frame, B. and Rao, D. S., *J. Clin. Invest.,* 72:1396–1409, 1983.

Paskind et al., "Dependence of moloney murine leukemia virus production on cell growth," *Virology,* 67:242–248, 1975.

Pearson and Lipman, *Proc. Natl. Acad. Sci. USA,* 85:2444–2448, 1988.

Perales, J. C., Ferkol, T., Beegen, H., Ratnoff, O. D., and Hanson, R. W. *Proc. Natl. Acad. Sci. USA,* 91:4086–4090, 1994.

Pease et al., *Proc. Natl. Acad. Sci. USA,* 91(11):5022–5026, 1994.

Pelletier and Sonenberg, *Nature,* 334(6180):320–325, 1988a.

Pelletier et al, *J. Virol.,* 62(12):4486–4492, 1988b.

Perrault et al, *Nature,* 344:565, 1990.

Perrotta and Been, *Biochem.,* 31:16, 1992.

Perry, Hustad, Swing, Jenkins, Copeland, "A transgenic mouse assay for agouti protein activity," *Genetics,* 140:267–274, 1995.

Perry, Nakamura, Swing, Sacrest, Eagleson, Hustad, Copeland, Jenkins, "Couple site-directed mutagenesis/transgenesis identifies important functional domains of the mouse agouti protein," *Genetics,* 144:255–264, 1996.

Pieken et al., *Science,* 253:314, 1991.

Pieretti, Zhang, Fu, Warren, Oostra, Caskey, Nelson, "Absence of expression of the FMR-1 gene in fragile X syndrome," *Cell,* 66:817–822, 1991.

Pignon et al., "Exhaustive analysis of the P53 gene coding sequence by denaturing gradient gel electrophoresis: application to the detection of point mutations in acute leukemias," *Hum. Mutat.,* 3(2):126–132, 1994.

Pikul et al., "In vitro killing of melanoma by liposome-delivered intracellular irradiation, *Arch. Surg.* 122(12):1417–1420, 1987.

Pinkert et al., *Genes Dev.,* 1:268–276, 1987.

Plocher and Powley, "Effect of hypophysectomy on weight gain and body composition in the genetically obese yellow ($A^y$/a) mouse," *Metabol.,* 25:593–602, 1976.

Poli, Balena, Fattori, Markators, Yamamoto, Tanaka, Ciliberto, Rodan, Costantini, *EMBO J.,* 13:1189–1196, 1994.

Poole and Silvers, "The development of regional pigmentation patterns in black and tan ($a^t$) mice," *J. Exp. Zool.,* 197:115–119, 1976.

Poole, "Dermal-epidermal interactions and the site of action of the yellow ($A^y$) and nonagouti (a) coat color genes in the mouse," *Dev. Biol.,* 42:203–210, 1974.

Potter et al., "Enhancer-dependent expression of human k immunoglobulin genes introduced into mouse pre-B lymphocytes by electroporation," *Proc. Nat. Acad. Sci. USA,* 81:7161–7165, 1984.

Pravtcheva, Adra, Ruddle, Develop. (Cambridge, U.K.), 111:1109–1120, 1991.

Prockop, "Mutations that alter the primary structure of type I collagen. The perils of a system for generating large structures by the principle of nucleated growth," *J. Biol. Chem.,* 265:15349–15352, 1990.

Prokop and Bajpai, "Recombinant DNA Technology I" *Ann. N.Y. Acad Sci.* vol. 646, 1991.

Puech et al., *J. Biol. Chem.,* 272(9):5995–6003, 1997.

Quistad and Skinner, *J. Biolog. Chem.,* 269:11098–11101, 1994.

Radin, Chu, Hoepf, McCune, "Treatment of obese female and male SHHF/Mcc-fa$^{cp}$ rats with antihypertensive drugs, nifedipine and enalapril: effects on body weight, fat distribution, insulin resistance and systolic pressure," *Obesity Res.,* 1,433–442, 1993.

Ragot, T., N. Vincent, P. Chafey, E. Vigne, H. Gilgenkrantz, D. Couton, J. Cartaud, P. Briand, J.-C. Kaplan, M. Perricaudet, and A. Kahn. 1993. Efficient adenovirus-mediated transfer of a human minidystrophin gene to skeletal muscle of mdx mice. *Nature* 361:647–650, 1993.

Rainey, Viard, Saez, *J. Biol. Chem.,* 264:21474–21477, 1989.

Raisz and Kream, "Regulation of bone formation," *N Engl. J. Med.,* 309:29–35, 1983.

Ramirez-Solis, Davis, Bradley, *Methods Enzymol.,* 225:855–878, 1993.

Rao, Löffler, Wozney, Hansmann, *Hum. Genet.,* 90:299–302, 1992.

Rawn, "Biochemistry" Harper & Row Publishers, New York, 1983.

Ray, Higgins, Tan, Chu, Yee, Nguyen, Lacy, Besmer, *Genes Dev.,* 5:2265–2273, 1991.

Reaven, *Diabetes,* 37:1595–1607, 1988.

Reddi, "Bone and cartilage differentiation," *Curr. Opin. Genet. Dev.,* 4:737–744, 1994.

Reddy, Shehin, Sowers, Dardas, Zemel, *J. Vasc. Med. Biol.,* 2:47–51, 1990.

Reik, Collick, Norris, Barton, Surani, "Genomic imprinting determines methylation of parental alleles in transgenic mice," *Nature,* 328:248–251, 1987.

Reinhold-Hurek and Shub, "Self-splicing introns in tRNA genes of widely divergent bacteria," *Nature,* 357:173–176, 1992.

Renneisen et al., "Inhibition of expression of human immunodeficiency virus-1 in vitro by antibody-targeted liposomes containing antisense RNA to the env region," *J. Biol. Chem.,* 265(27):16337–16342, 1990.

Resnick, Gupta, Bhargava, Gruenspan, Alderman, Laragh, *Hypertension,* 17:951–957, 1991.

Reusch, Sussman, Draznin, "Inverse relationship between Glut-4 phosphorylation and its intrinsic activity," *J. Biol. Chem.,* 68:3348–3351, 1993.

Reynolds, "The effect of ascorbic acid on the growth of chick bone rudiments in vitro," *Exp. Cell. Res.,* 47:42–48, 1967.

Rhodes, DiMattia, Rosenfeld, "Transcriptional mechanisms in anterior pituitary cell differentiation," *Curr. Opin. Genet. Dev.,* 4:709–717, 1994.

Rich et al., "Development and analysis of recombinant adenoviruses for gene therapy of cystic fibrosis," *Hum. Gene Ther.,* 4:461–476, 1993.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.,* 10:689–695, 1990.

Robbins et al., *Cell,* 72:827–834, 1993.

Roberts, Wolff, Campbell, "Differential effects of the mottled yellow and pseudoagouti phenotypes on immunocompetence in $A^{vy}$/a mice," *Proc. Natl. Acad. Sci. USA,* 81:2152–2156, 1964.

Robertson, "An analysis of the development of homozygous yellow mouse embryos," *J. Exp. Zool.,* 89:197–231, 1942.

Rolland, Dugall, Le Liepvre, Lavau, "Evidence of increased glyceraldehyde-3-phosphate dehydrogenase and fatty acid synthetase promoter activities in transiently transfected adipocytes from genetically obese rats," *J. Biol. Chem.*, 270:1102–1106, 1995.

Rose and Bigazzi, eds., *Methods in Immunodiagnosis*, 2nd Edition, John Wiley and Sons, New York, 1980.

Roselli-Rehfuss, Mountjoy, Robbins, Mortrud, Low, Tatro, Entwistle, Simerly, Cone, "Identification of a receptor for gamma melanotropin and other proopiomelanocortin peptides in the hypothalamus and limbic system," *Proc. Natl. Acad. Sci. USA*, 90:8856–8860, 1993.

Rosenfeld, M. A., K. Yoshimura, B. C. Trapnell, K. Yoneyama, E. R. Rosenthal, W. Dalemans, M. Fukayama, J. Bargon, L. E. Stier, L. Stratford-Perricaudet, M. Perricaudet, W. B. Guggino, A. Pavirani, J.-P. Lecocq, and R. G. Crystal. "In vivo transfer of the human cystic fibrosis transmembrane conductance regulator gene to the airway epithelium," *Cell*, 68:143–155, 1992.

Rosenfeld, M. A., W. Siegfried, K. Yoshimura, K. Yoneyama, M. Fukayama, L. E. Stier, P. K. Paakko, P. Gilardi, L. Stratford-Perricaudet, M. Perricaudet, S. Jallat, A. Pavirani, J.-P. Lecocq, and R. G. Crystal, "Adenovirus-mediated transfer of a recombinant α1-antitrypsin gene to the lung epithelium in vivo," *Science*, 252:431–434, 1991.

Rosenthal et al, *Proc. Natl. Acad. Sci. USA*, 86:7780–7784, 1989.

Ross, Graves, Greenstein, Platt, Shyu, Mellovitz, Spiegelman, *Proc. Nad. Acad. Sci. USA*, 87:9590–9594, 1990.

Rossi et al., *Aids Res. Hum. Retrovir.*, 8:183, 1992.

Rothschild, Akots, Hayworth, Pettenati, Nagesh Rao, Wood, Stolz, Hansmann, Serino, Ketih, Fajans, Bowden, *Am. J. Hum. Genet.*, 52:110–123, 1993.

Roulston, Espinosa, Stoffel, LeBeau, *Am. J. Hum. Genet.*, 53:S352, 1993.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Russell, McDaniel, Woodel, "Crossing-over within the a "locus" of the mouse," *Genetics*, 48:907, 1963.

Rybak, Tharapel, Robinett, Garcia, Maniken, Freeman, *Hum. Genet.*, 60:328–333, 1982.

Sadowski and Ptashne, "A vector for expressing GAL4 (1–147) fusion in mammalian cells," *Nuc Acids Res.*, 17:7539, 1989.

Sakurai, Ochiai, Takeuchi, "Ultrastructural change of melanosomes associated with agouti pattern formation in mouse hair," *Dev. Biol.*, 47:466–471, 1975.

Salem and Wolff, *Proc. Soc. Exp. Biol. Med.*, 191:113–173, 1989.

Salem, Lewis, Haro, Kishi, McAllister, Seavey, Bee, Wolff, "Effects of hypophysectomy and the insulin-like and anti-insulin pituitary peptides on carbohydrate metabolism in yellow $A^{vy}$/A (BALB/c×VY)$F_1$, hybrid mice," *Proc. Soc. Exp. Biol. Med.*, 191:408–419, 1989.

Salomon, *Meth. Enzym.*, 195:22–28, 1991.

Sambrook, Fristch, Maniatis, "Molecular Cloning: A Laboratory Manual," C. Nolan, ed., New York: Cold Spring Harbor Laboratory Press, 1989.

Sanford, Clark, Chapman, Rossant, "Differences in DNA methylation during oogenesis and spermatogenesis and their persistence during early embryogenesis in the mouse," *Genes and Dev.*, 1:1039–1046, 1987.

Sanger, Nicklen, Coulson, "DNA sequencing with chain-terminating inhibitors," *Proc. Natl. Acad. Sci.*, 74:5463–5467, 1977.

Sapienza, Peterson, Rossant, Bailing, "Degree of methylation of transgenes is dependent on gamete of origin," *Nature*, 328:251–254, 1987.

Sarver et al., *Science*, 247:1222–1225, 1990.

Sasaki, Yagi, Bronson, Tominaga, Matsunashi, Deguchi, Tani, Kishimoto, Komori, "Absence of fetal liver hematopoiesis in mice deficient in transcriptional coactivator core binding factor β," *Proc. Natl. Acad. Sci. USA*, 93:12359–12363, 1996.

Satyamoorthy, Park, Atchison, Howe, "The intracisternal A-particle upstream element interacts with transcription factor YY1 on distinct DNA promoter elements," *Mol. Cell. Biol.*, 13:6621–6628, 1993.

Sauer, Hansen, Tjian, "Multiple $TAF_{IIS}$ directing synergistic activation of transcription," *Science*, 270:1783–1788, 1995.

Saville and Collins, *Cell*, 61:685–696, 1990.

Saville and Collins, *Proc. Natl. Acad. Sci. USA*, 88:8826–8830, 1991.

Scanlon, *J. Clin. Lab. Anal.*, 3:323–329, 1989.

Scaringe et al., *Nucl. Acids Res.*, 18:5433–5441, 1990.

Schochetman et al., *J. Infect. Dis.*, 158:1154–1157, 1988.

Sculier et al., "Pilot study of amphotericin B entrapped in sonicated liposomes in cancer patients with fungal infections," *J. Cancer Clin. Oncol.*, 24(3):527–538, 1988.

Sealey et al., *Nucl. Acids Res.*, 13:1905–1922, 1985.

Searle, In: *Comparative Genetics of Coat Color in Mammals*, Academic, New York, 1968.

Segal, "Biochemical Calculations" 2nd Edition. John Wiley & Sons, New York, 1976.

Segal, Lloyd, Sherman, Sussman, Draznin, "Postprandial changes in cytosolic free calcium and glucose uptake in adipocytes in obesity and non-insulin dependent diabetes mellitus, *Horm. Res. Basel.*, 34:39–44, 1990.'

Shaw et al., *J. Natl. Cancer Inst.*, 80:15553, 1988.

Sheets et al., *Nucl. Acids Res.*, 18:5799–5805, 1990.

Shehin, Sowers, Zemel, *J. Vasc. Med. Biol.*, 1:278–282, 1989.

Shih et al., *J. Med. Virol.*, 30:159–162 1990.

Shillabeer, Hornford, Forden, Wong, Russell, Lau, "Fatty acid synthase and adipsin mRNA levels in obese and lean JCR:LA-cp rats:effect of diet," *J. LipidRes.*, 33:31–39, 1992.

Shimizu, Shargill, Bray, "Adrenalectomy and response to corticosterone and MSH in the genetically obese yellow monse," *Am. J. Physiol.*, 256:R494–R500, 1989.

Shoemaker et al., *Nat. Genet.*, 14(4):450–456, 1996.

Siegrist et al., i J. Rec. Res., 8:323–343, 1988.

Sillence et al. "Animal model: skeletal abnormalities in mice with cleidocranial dysplasia," *Am. J. Med. Genet.*, 27:75–85, 1987.

Silvers and Russell, "An experimental approach to action of genes at the agouti locus in the mouse," *J. Exp. Zool.*, 130:199–220, 1955.

Silvers, "An experimental approach to action of genes at the agouti locus in the mouse. III. Transplants of newborn $A^w$-, A-, $a^t$-skin to $A^y$-, $A^w$-, A- and aa hosts," *J. Exp. Zool.*, 137:189–198, 1958b.

Silvers, "Genes and pigment cells of mammals," *Science*, 134:368–373, 1961.

Silvers, "The agouti and extension series of alleles, umbrous, and sable," In: *The Coat Colors of Mice: A Model for Mammalian Gene Action and Interaction,"* New York, N.Y., Springer-Verlag, pp. 6–44, 1979.

Silvers, In: The Coat Colors of Mice: *A Model for Mammalian Gene Action and Interaction*, Springer-Vedag, New York, N.Y., 1979.

Silvers, *J. Exp. Zool.,* 137:189–196, 1958.

Simeone, Daga, Calabi, "Expression of runt in the mouse embryo," *Dev. Dynamics,* 203:61–70, 1995.

Siracusa and Abbott, *Mamm. Genome,* 4:S31–S46, 1993.

Siracusa et al., "Genetic organization of the agouti region of the mouse," *Genetics,* 117:93–100, 1987.

Siracusa, "Genomic organization and molecular genetics of the agouti locus in the mouse," *Ann. N.Y. Acad. Sci.,* 642:419–430, 1991.

Siracusa, Buchberg, Copeland, Jenkins, "Recombinant inbred strain and interspecific backcross analysis of molecular markers flanking the murine agouti coat color locus," *Genetics,* 122:669–679, 1989.

Siracusa, Russell, Jenkins, Copeland, "Allelic variation within the Emv-15 locus defines genomic sequences closely linked to the agouti locus on mouse chromosome 2," *Genetics,* 117:85–92, 1987.

Smith, "The animal fatty acid synthase: one gene, one polypeptide, seven enzymes," *FASEB J.,* 8:1248–1259, 1994.

Soriano, Montgomery, Geske, Bradley, *Cell,* 64:693–702, 1991.

Sowers, Standley, Ram, Zemel, Resnick, *Am. J. Hypertens.,* 4:466S–472S, 1991.

Speck and Stacy, "A new transcription factor family associated with human leukemias," *Crit. Rev. Euk. Gene Exp.,* 5:337–364, 1995.

Spiegelman and Flier, "Adipogenesis and obesity: rounding out the big picture," *Cell,* 87:377–389, 1996.

Spoerel, *Methods Enzymol.* 152:588–597, 1987.

Steinmetz, Stephan, Lindahi, "Gene organization and recombinational hotspots in the murine major histocompatibility complex," *Cell,* 44:895–904, 1986.

Stinchcomb et al., *Nature,* 282:39, 1979.

Stråelfors, Björgell, Belfrage, *Proc. Natl. Acad. Sci USA,* 81:3317–3321.

Stratford-Perricaudet and Perricaudet," Gene transfer into animals: the promise of adenovirus," p. 51–61, In: *Human Gene Transfer,* Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.,* 1:241–256, 1990.

Strauss, "Preparation of genomic DNA from mammalian tissue," In: *Current Protocols in Molecular Biology,* Boston, John Wiley and Sons, Ausubel et al. Eds., Vol. 1, pp. 221–223, 1994.

Summers and Smith, *Tex Agric. Exp. Stn. Bull.,* 1555, 1987.

Swain, Stewart, Leder, "Parental legacy determines methylation and expression of an autosomal transgene: A molecular mechanism for parental imprinting," *Cell,* 50:719–727, 1987.

Tabor and Richardson, "DNA sequence analysis with a modified bacteriophage T7 DNA polymerase," *Proc. Natl. Acad. Sci. USA,* 84:4767–4771, 1987.

Taira et al., *Nucl. Acids Res.,* 19:5125–30, 1991.

Takeuchi, Kobunai, Yamamoto, "Genetic control of signal transduction in mouse melanocytes," *J. Invest. Dermatol.,* 92:239S–242S, 1989.

Tamate and Takeuchi, *Sci.,* 224:1241–1242, 1984.

Tanaka et al., *Molec. Biochem. Parasit.,* 39:127–134, 1990.

Tartaglia, Dembski, Weng, Deng, Culpepper, Devos, Richards, Campfield, Clark, Deeds, Muir, Sanker, Moriarty, Moore, Smutko, Mays, Woolf, Monroe, Tepper, *Cell,* 83:1263–1271, 1995.

Tartaglia, Dembski, Weng, Deng, Culpepper, Devos, Richards, Campfield, Clark, Deeds, Muir, Sanker, Moriarty, Moore, Smutko, Mays, Woolf, Monroe, Tepper, *Cell,* 83:1263–1271, 1995.

Temin, "Retrovirus vectors for gene transfer: Efficient integration into and expression of exogenous DNA in vertebrate cell genome," In: Kucherlapati R, ed. Gene transfer. New York: Plenum Press, pp. 149–188, 1986.

Tomic et al., *Nucl. Acids Res.,* 12:1656, 1990.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Treco, Thomas, Arnheim, "Recombination hot spot in the human β-globin gene duster: meiotic recombination of human DNA fragments in *Saccharomyces cerevisiae,*" *Mol. Cell. Biol.,* 5:2029–2038, 1985.

Tremblay, Payet, Gallo-Payet, "Effects of ACTH and angiotensin II on cytosolic calcium in cultured adrenal glomerulosa cells. Role of cAMp production in the ACTH effect," *Cell Calcium.,* 12:655–673, 1991.

Tschemper et al., *Gene,* 10:157, 1980.

Tur-Kaspa et al., "Use of electroporation to introduce biologically active foreign genes into primary rat hepatocytes," *Mol. Cell Biol.,* 6:716–718, 1986.

Upender et al., *Biotechniques,* 18:29–31, 1995.

Usman and Cedergren, *Trends in Biochem. Sci.,* 17:334, 1992.

Usman et al., *J. Am. Chem. Soc.,* 109:7845–7854, 1987.

Varmus et al., "Retroviruses as mutagens: Insertion and excision of a nontransforming provirus alter the expression of a resident transforming provirus," *Cell,* 25:23–36, 1981.

Ventura et al., *Nucl. Acids Res.,* 21:3249–55, 1993.

Verhoeyan et al., *Science,* 239:1534, 1988.

Vignery and Baron, *Anat. Rec.,* 196:191–200, 1980.

Volpe and Vagelos, "Mechanisms and regulation of biosynthesis of saturated fat," *Physiol. Rev.,* 56:339417, 1976.

Volpe and Vagelow, "Regulation of mammalian fatty acid synthetase," The role of carbohydrate and insulin," *Proc. Natl. Acad. Sci. USA,* 71:889–893, 1974.

von Heijne, *Nucl. Acids Res.,* 14:4683–4690, 1986.

Vrieling, Duhl, Miller, Miller, Barsh, *Proc. Natl. Acad. Sci. USA,* 91:5667–5671, 1994.

Wagner, E., Zenke, M., Cotten, M., Beug, H., and Birnstiel, M. L. Transferrin-polycation conjugates as carriers for DNA uptake into cells. *Proc. Nat'l Acad. Sci. USA* 87:3410–3414, 1990.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA,* 89(13):6099–6103, 1992.

Wakil, Stoops, Joshi, "Fatty acid synthesis and its regulation," *Annu. Rev. Biochem.,* 52:579–586, 1983.

Walker et al., *Proc. Natl. Acad. Sci. USA,* 89(1):392–396, 1992.

Wang, Wang, Crute, Melnikova, Keller, Speck, "Cloning and characterization of subunits of the T-cell receptor and murine leukemia virus enhancer core-binding factor," *Mol. Cell. Biol.,* 13:3324–3339, 1993.

Warbritton, Gill, Yen, Bucci, Wolff, "Pancreatic, islet cells in preobese yellow $A^{vy}/-$ mice: relation to adult hyperinsulinemia and obesity," *Proc. Soc. Exp. Biol. Mod.,* 206:145–151, 1994.

Watson, J. D. et al., *Molecular Biology of the Gene*, 4th Ed., W. A. Benjamin, Inc., Menlo Park, Calif., 1987.

Weerasinghe et al., *J. Virol.*, 65:5531–4, 1991.

Weigle and Kuijper, "Obesity genes and the regulation of body fat content," *BioEssays*, 18:867–874, 1996.

White and Engel, *J. Clin. Invest.*, 37:1556–1563, 1958.

Wilkinson, "In situ hybridization, In: In situ hybridization: A practical approach, New York, N.Y.: IRL Press at Oxford University, 11:257–263, 1992.

Willard, Bodnar, Harris, Kiefer, Nichols, Blanchard, Hoffman, Moyer, Burkhart, Weiel, Luther, Wilkison, Rocque, "Agouti structure and function: characterization of a potent alpha-melanocyte stimulating hormone receptor antagonist," *Biochem.*, 34:12341–12346, 1995.

Wilson, Ollmann, Kang, Stoffel, Bell, Barsh, "Structure and function of ASP, the human homolog of the mouse agouti gene," *Human Mol. Genet.*, 4:223–230, 1995.

Witte, *Cell,* 63:5–6, 1990.

Wolf et al., "An Integrated Family of Amino Acid Sequence Analysis Programs," *Compu. Appl. Biosci.*, 4(1):187–91, 1988.

Wolff and Flack, "Genetic regulation of plasma corticosterone concentration and its response to castration and allogeneic tumour growth in the mouse," *Nature N. Biol.*, 232:181–182, 1971.

Wolff and Pitot, *Genetics,* 73:109–123, 1973.

Wolff et al., *Carcinogen,* 8:1889–1894, 1987.

Wolff, "Body weight and cancer," *Am. J. Clin. Nutr.*, 45:168–180, 1987.

Wolff, "Genetic modification of homeostatic regulation in the mouse," *Am. Nat.*, 105:241–252, 1971.

Wolff, "Growth of inbred yellow ($A^{y/a}$) and non-yellow (a/a) mice in parabiosis," *Genetics,* 48:1041–1058, 1963.

Wolff, "Hereditary obesity and hormone deficiencies in yellow dwarf mice," *Am. J. Physiol.*, 209:632–636, 1965.

Wolff, "Influence of maternal phenotype on metabolic differentiation of agouti locus mutants in the mouse," *Genetics,* 88:529–539, 1978.

Wolff, Galbraith, Domon, Row, "Phaeomelanin synthesis and obesity in mice. Interaction of the viable yellow ($A^{vy}$) and sombre ($E^{so}$) mutations," *J. Hered.*, 69:295–298, 1978.

Wolff, Greenman, Frigeri, Morrissey, Suber, Felton, *Proc. Soc. Exp. Biol. Med.*, 193:155–163, 1990.

Wolff, Hofer, Beck, Roder, Schweizer, "Insulin-responsive regions of the rat fatty acid synthase gene promoter," *Biochem. Biophys. Res. Commun.*, 203:943–950, 1994.

Wolff, Roberts, Galbraith, "Prenatal determination of obesity, tumor susceptibility, and coat color pattern in viable yellow $A^{vy}$/a) mice. The yellow mouse syndrome," *J. Hered.*, 7:151–158, 1986.

Wolff, *Science,* 147:1145–1147, 1965a.

Wong and Neumann, "Electric field mediated gene transfer," *Biochim. Biophys. Res. Commun.*, 107(2):584–587, 1982.

Wong et al., "Appearance of β-lactamase activity in animal cells upon liposome mediated gene transfer," *Gene,* 10:87–94, 1980.

Wood et al., *Nature,* 314:446, 1985.

Woychik, Generoso, Russell, Cain, Cacheiro, Bultman, Selby, Dickinson, Hogan, Rutledge, "Molecular and genetic characterization of a radiation-induced structural rearrangement in mouse chromosome 2 causing mutations at the limb deformity and agouti loci," *Proc. Natl. Acad. Sci. USA,* 87:2588–2592, 1990.

Woychik, Maas, Zeller, Vogt, Leder, "'Formins': proteins deduced from the alternative transcripts of the limb deformity gene," *Nature,* 346:850–853, 1990b.

Woychik, Stewart, Davis, D'Eustachio, Leder, "An inherited limb deformity created by insertional mutagenesis in a transgenic mouse," *Nature* (Lond.), 318:36–40, 1985.

Wu and Wang, "Sequence-selective DNA binding to the regulatory subunit of cAMP-dependent protein kinase," *J. Biol. Chem.*, 264(17):9989–9993, 1989.

Wu and Wu, "Evidence for targeted gene delivery to HepG2 hepatoma cells in vitro," *Biochemistry,* 27:887–892, 1988.

Wu and Wu, "Receptor-mediated in vitro gene transfections by a soluble DNA carrier system," *J. Biol. Chem.*, 262:4429–4432, 1987.

Wu and Wu. *Adv. Drug Delivery Rev.* 12:159–167, 1993.

Wu, S.-J. and D. H. Dean, Functional significance of loops in the receptor binding domain of Bacillus thuringiensis CryIIIA δ-endotoxin. *J. Mol. Biol.* 255:628–640, 1996.

Yang et al., "In vivo and in vitro gene transfer to mammalian somatic cells by particle bombardment," *Proc. Natl. Acad. Sci. USA,* 87:9568–9572, 1990.

Yen, Allan, Yu, Acton, Pearson, "Triacylglycerol contents and in vivo lipogenesis of ob/ob, db/db, and $A^{vy/a}$ mice," *Biochim. Biophys. Acta,* 441:213–220, 1976.

Yen, Gill, Frigeri, Barsh, Wolff, "Obesity, diabetes, and neoplasia in yellow $A^{vy}$/– mice: ectopic expression of the agouti gene," *FASEB J.*, 8:479–488, 1994.

Yen, McKee, Stamm, "Thermogenesis and weight control," *Int. J. Obes.*, 8(1):65–78, 1984.

Yoshida, Umekawa, Wakabayashi, Sakane, Kondo, "Mechanism of anti-obesity action of benidipine hydrochloride in mice," *Int. J. Obesity,* 18:776–779, 1994.

Young and Davis, "Efficient Isolation of Genes by Using Antibody Probes," *Proc. Natl. Acad. Sci. USA,* 80:1194–1198, 1983.

Yu and Chang, "Submicron polymer membrane hemoglobin nanocapsules as potential blood substitutes: preparation and characterization," *Artif. Cells Blood Substit. Immobil. Biotechnol.*, 24(3):169–183, 1996.

Yu et al., *Proc. Natl. Acad. Sci. USA,* 90:6340–4, 1993.

Zatloukal, Wagner, Cotten, Phillips, Plank, Steinlein, Curiel, Birnstiel, "Transferrinfection: a highly efficient way to express gene constructs in eukaryotic cells," *Ann. N.Y Acad. Sci.*, 60:136–153, 1992.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

Zemel, "Insulin resistance vs. hyperinsulinemia in hypertension: insulin regulation of $Ca^{2+}$ transport and $Ca^{2+}$ regulation of insulin sensitivity, *J. Nutr.*, 125:17388–17438, 1995.

Zemel, Grunberger, Simpson, Zemel, Sowers, *Am. J. Hypertens.*, Abstract, 4:121, 1991.

Zemel, Iannucci, Moore, *J. Vasc. Biol. Med.*, 4:79–84, 1993.

Zemel, Kim, Jones, Moore, Woychik, Moustaid, Wilkison, "Agouti gene product regulation of adipocyte intracellular free calcium ($Ca^{2+}$) results in stimulation of fatty acid synthase," *Obes. Res.*, 3:338s, 1995a.

Zemel, Kim, Woychik, Michaud, Kadwell, Patel, Wilkison, "Agouti regulation of intracellular calcium: role in the insulin resistance of viable yellow mice," *Proc. Natl. Acad. Sci. USA,* 92:4733–4737, 1995b.

Zhang, Proenca, Maffei, Barone, Leopold, Friedman, "Positional cloning of the mouse obese gene and its human homologue," *Nature* (London), 372:425–432, 1994.

Zhou et al., *Mol. Cell Biol.*, 10:4529–37, 1990.

Zolg et al, "Point mutations in the dihydrofolate reductase-thymidylate synthase gene as the molecular basis for pyrimethamine resistance in Plasmodium falciparum," *Mol Biochem Parasitol.* 36(3):253–262, 1989.

Zolg et al., "Detection of pyrimethamine resistance in Plasmodium falciparum by mutation-specific polymerase chain reaction," *Mol Biochem Parasitol.* 39(2):257–265, 1990.

Zomely and Mayer. "Fat metabolism in experimental obesities," *Am. J. Physiol.,* 196:611–613, 1959.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated peptide or polypeptide, comprising an at least 5 contiguous amino acid antigenic fragment from SEQ ID NO:2 or an at least 6 contiguous amino acid sequence from SEQ ID NO:4.

2. The isolated peptide or polypeptide of claim 1, comprising an at least 8 contiguous amino acid antigenic fragment from SEQ ID NO:2 or SEQ ID NO:4.

3. The isolated or polypeptide of claim 2, comprising an at least 15 contiguous amino acid antigenic fragment from SEQ ID NO:2 or SEQ ID NO:4.

4. The isolated peptide or polypeptide of claim 3, comprising an at least 20 contiguous amino acid antigenic fragment from SEQ ID NO:2 or SEQ ID NO:4.

5. The isolated peptide or polypeptide of claim 4, comprising an at least 25 contiguous amino acid antigenic fragment from SEQ ID NO:2 or SEQ ID NO:4.

6. The isolated peptide or polypeptide of claim 5, comprising an at least 30 contiguous amino acid antigenic fragment from SEQ ID NO:2 or SEQ ID NO:4.

7. The isolated peptide or polypeptide of claim 6, comprising an at least 50 contiguous amino acid antigenic fragment from SEQ ID NO:2 or SEQ ID NO:4.

8. The isolated peptide of polypeptide of claim 7, comprising an at least 100 contiguous amino acid antigenic fragment from SEQ ID NO:2 or SEQ ID NO:4.

9. The isolated peptide or polypeptide of claim 8, comprising the amino acid sequence of SEQ ID NO:2 of SEQ ID NO:4.

10. The isolated peptide or polypeptide of claim 1, comprising an antigenic fragment that is encoded by an at least 17-basepair contiguous nucleotide sequence from SEQ ID NO:1 or SEQ ID NO:3.

11. The isolated peptide or polypeptide of claim 10, comprising an antigenic fragment that is encoded by an at least 21-basepair contiguous nucleotide sequence from SEQ ID NO:1 or SEQ ID NO:3.

12. The isolated peptide or polypeptide of claim 11, comprising an antigenic fragment that is encoded by an at least 25-basepair contiguous nucleotide sequence from SEQ ID NO:1 or SEQ ID NO:3.

13. The isolated peptide or polypeptide of claim 12, comprising an amino acid sequence that is encoded by the nucleotide sequence of SEQ ID NO:1 or SEQ ID NO:3.

14. The peptide of polypeptide of claim 1, wherein said polypeptide is of human origin.

15. The peptide or polypeptide of claim 1, further comprising a detectable label.

16. The peptide or polypeptide of claim 15, wherein said detectable label is selected from the group consisting of a radioisotope, a fluorescent compound, and enzyme, and an enzyme cofactor.

17. An isolated polypeptide comprising the amino acid sequence of SEQ ID NO:2.

18. An isolated polypeptide comprising the amino acid sequence of SEQ ID NO:4.

19. A substantially pure polypeptide comprising an amino acid sequence at least 85% identical to the sequence of SEQ ID NO.2 or SEQ ID NO:4, wherein said polypeptide has MSH or melanocortin-4 receptor antagonist activity.

20. The polypeptide of claim 19, comprising an amino acid sequence at least 90% identical to the sequence of SEQ ID NO:2 or SEQ ID NO:4.

21. The polypeptide of claim 20, comprising an amino acid sequence at least 95% identical to the sequence of SEQ ID NO:2 or SEQ ID NO:4.

22. The polypeptide of claim 21, comprising an amino acid sequence at least 99% identical to the sequence of SEQ ID NO:2 or SEQ ID NO:4.

23. The polypeptide of claim 22, comprising the amino acid sequence of SEQ ID NO:2 or SEQ ID NO:4.

24. An isolated mammalian agouti polypeptide comprising the amino acid sequence of SEQ ID NO:2 or SEQ ID NO:4.

25. An immunogen comprising the peptide or polypeptide of claim 1, in an immunogenic preparation, said immunogen being capable of eliciting an immune response in a mammal.

26. An immunogen comprising the peptide or polypeptide of claim 1, in an immunogenic preparation, wherein said immunogen is capable of eliciting antibodies that are specific for a mammalian agouti polypeptide.

27. A composition comprising the peptide or polypeptide of claim 1 or claim 19.

28. The composition of claim 27, further comprising a pharmaceutical excipient.

29. A composition comprising the immunogen of claim 25 or claim 26.

30. A kit comprising, in suitable container means, (a) the peptide or polypeptide of claim 1, (b) the polypeptide of claim 19, (c) the composition of claim 27, or (d) the composition of claim 29, and instructions for using said kit.

31. A kit comprising: (a) the peptide or polypeptide of claim 1, and (b) instructions for using said kit.

32. A kit comprising: (a) the polypeptide of claim 19, and (b) instructions for using said kit.

33. A kit comprising: (a) the composition of claim 27, and (b) instructions for using said kit.

34. A kit comprising: (a) the composition of claim 29, and (b) instructions for using said kit.

* * * * *